(12) United States Patent
Beatty et al.

(10) Patent No.: US 12,195,482 B1
(45) Date of Patent: Jan. 14, 2025

(54) COMPOUNDS AS INHIBITORS OF AXL

(71) Applicant: Arcus Biosciences, Inc., Hayward, CA (US)

(72) Inventors: Joel Worley Beatty, San Mateo, CA (US); Corinne Nicole Foley, San Carlos, CA (US); Balint Gal, Hayward, CA (US); Manjunath Lamani, Dublin, CA (US); Manmohan Reddy Leleti, Dublin, CA (US); Dillon Harding Miles, Berkeley, CA (US); Srinivas Paladugu, Hayward, CA (US); Jay Patrick Powers, Sisters, OR (US); Shiwei Qu, Alameda, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

(21) Appl. No.: 18/805,490

(22) Filed: Aug. 14, 2024

Related U.S. Application Data

(63) Continuation of application No. 18/341,844, filed on Jun. 27, 2023.

(60) Provisional application No. 63/356,421, filed on Jun. 28, 2022.

(51) Int. Cl.
*C07D 519/00* (2006.01)
*C07D 471/04* (2006.01)
*C07D 487/04* (2006.01)

(52) U.S. Cl.
CPC ......... *C07D 519/00* (2013.01); *C07D 471/04* (2013.01); *C07D 487/04* (2013.01)

(58) Field of Classification Search
CPC .................................................. C07D 519/00
USPC .................................................... 514/210.16
See application file for complete search history.

(56) References Cited

U.S. PATENT DOCUMENTS

| | | | |
|---|---|---|---|
| 2007/0010523 A1* | 1/2007 | Zhang | A61P 25/00 514/252.16 |
| 2009/0233955 A1 | 9/2009 | Frazee et al. | |
| 2023/0416277 A1 | 12/2023 | Beatty et al. | |
| 2024/0226115 A1 | 7/2024 | Foley et al. | |
| 2024/0246967 A1 | 7/2024 | Foley et al. | |

FOREIGN PATENT DOCUMENTS

| | | |
|---|---|---|
| EP | 4 163 278 A1 | 4/2023 |
| WO | WO-2007/106236 A2 | 9/2007 |
| WO | WO-2008/083354 A1 | 7/2008 |
| WO | WO-2008/083356 A1 | 7/2008 |
| WO | WO-2008/083367 A2 | 7/2008 |
| WO | WO-2010/005876 A2 | 1/2010 |
| WO | WO-2010/083465 A1 | 7/2010 |
| WO | WO-2016/193680 A1 | 12/2016 |
| WO | WO-2019/238067 A1 | 12/2019 |
| WO | WO-2020/103896 A1 | 5/2020 |
| WO | WO-2021/000925 A1 | 1/2021 |
| WO | WO-2021/013083 A1 | 1/2021 |
| WO | WO-2021/239133 A1 | 12/2021 |
| WO | WO-2022/184152 A1 | 9/2022 |
| WO | WO-2022/246177 A1 | 11/2022 |
| WO | WO-2022/268026 A1 | 12/2022 |

OTHER PUBLICATIONS

Feneyrolles, Clemence et al., "Discovering novel 7-azaindole-based series as potent AXL kinase inhibitors," Bioorganic & Medicinal Chemistry Letters (2017; available online Jan. 9, 2017); 27:862-866.

Holland, Sacha J. et al., "R428, a Selective Small Molecule Inhibitor of Axl Kinase Blocks Tumor 18. Spread and Prolongs Survival in Models of Metastatic Breast Cancer," Cancer Res (Feb. 15, 2010). 70(4):1544-1554.

International Search Report and Written Opinion mailed Sep. 2, 2022 in PCT/US2022/030227, filed May 20, 2022, 17 pages.

International Search Report and Written Opinion mailed Sep. 2, 2022 in PCT/US2022/030230, filed May 20, 2022, 15 pages.

International Search Report and the Written Opinion mailed Feb. 29, 2024 in corresponding PCT/US2023/069124, 11 pages.

Myers, Samuel H. et al., "AXL Inhibitors in Cancer: A Medicinal Chemistry Perspective," J. Med. Chem. (2016; published Nov. 10, 2015) 59:3593-3608.

Song, Xianzhou et al., "Hematopoietic progenitor kinase 1 down-regulates the oncogenic receptor tyrosine kinase AXL in pancreatic cancer," J. Biol. Chem. (Jan. 20, 2020) 295(8):2348-2358.

(Continued)

*Primary Examiner* — Niloofar Rahmani
(74) *Attorney, Agent, or Firm* — Foley & Lardner LLP; Brittany J. Perla

(57) ABSTRACT

Compounds of Formula I that inhibit AXL, and compositions containing the compound(s) and methods for synthesizing the compounds, are described herein. Also described are the use of such compounds and compositions for the treatment of a diverse array of diseases, disorders, and conditions, including cancer, that are mediated, at least in part, by AXL.

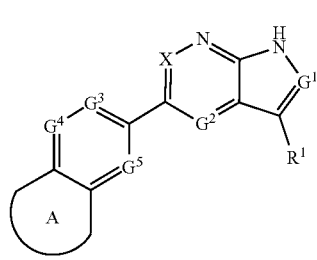

(Formula I)

2 Claims, No Drawings

(56) References Cited

OTHER PUBLICATIONS

Yule, Murray et al., "A Ph II study of the selective AXL inhibitor BGB324 in combination with 21. pembrolizumab in patients with previously treated, locally advanced and unresectable or metastatic triple negative breast cancer (TNBC) or triple negative inflammatory breast cancer (TN-IBC)," Poster presented at the San Antonio Breast Cancer Symposium 2017, San Antonia, TX (Dec. 5-9, 2017).

\* cited by examiner

COMPOUNDS AS INHIBITORS OF AXL

CROSS-REFERENCES TO RELATED APPLICATIONS

This application is a continuation of U.S. application Ser. No. 18/341,844, filed Jun. 27, 2023, which claims the benefit of priority under 35 U.S.C. § 119(e) to U.S. Provisional Application Ser. No. 63/356,421, filed Jun. 28, 2022, the disclosure of which is incorporated herein by reference in its entirety.

BACKGROUND OF THE DISCLOSURE

The following discussion is provided to aid the reader in understanding the disclosure and is not admitted to describe or constitute prior art thereto.

AXL is a receptor tyrosine kinase (RTK) that belongs to the TAM family. AXL regulates important processes such as cell growth, migration, aggregation, and apoptosis. AXL can be activated by a variety of mechanisms including ligand-dependent and ligand-independent mechanisms. Once activated AXL is involved in a variety of signaling pathways including the RAS-RAF-MEK-ERK pathway leading to cancer cell proliferation, and also the PI3K/AKT pathway responsible for several pro-survival proteins.

AXL has been shown to be overexpressed in a variety of malignancies. In cancer settings, AXL overexpression is associated with poor patient survival and resistance mechanisms (both targeted and non-targeted).

In view of the research linking AXL inhibition to diseases such as cancer, there is a need in the art for new AXL inhibitors. The present disclosure addresses this need and provides additional advantages over previous AXL inhibitors.

BRIEF SUMMARY OF THE DISCLOSURE

In one aspect, the present disclosure relates to compounds that inhibit the activity of AXL. The compounds are represented by Formula (I):

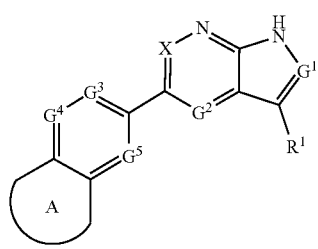

(I)

or a pharmaceutically acceptable salt thereof, wherein:
X is $CR^5$ or N;
$G^1$ is N or $CR^{G1}$;
$G^2$ is $CR^{G2}$ or N;
$G^3$ is $CR^{G3}$ or N;
$G^4$ is $CR^{G4}$ or N;
$G^5$ is $CR^{G5}$ or N;
$R^{G1}$ is selected from the group consisting of H, $C_{1-3}$ alkyl, halogen, $C_{1-3}$ haloalkyl, and CN;
each $R^{G2}$, $R^{G3}$, $R^{G4}$ and $R^{G5}$ is independently selected from the group consisting of H, halo, CN, $C_{1-7}$ alkyl, $C_{3-7}$ cycloalkyl, $C_{1-3}$ haloalkyl, —O—$C_{1-3}$ alkyl, —O—$C_{1-3}$ haloalkyl, —$NR^aR^b$, and 5- to 8-membered heterocycloalkyl having 1-3 heteroatom ring vertices selected from the group consisting of O, N, and S, and wherein cycloalkyl and heterocycloalkyl are substituted with 0-3 groups independently selected from halo, CN, $C_{1-4}$ alkyl, $C_{1-4}$ haloalkyl, $C_{1-4}$ hydroxyalkyl, —O—$C_{1-4}$ alkyl, and OH;
A is a fused ring selected from the group consisting of cycloheptane, cyclohexane, cyclopentane, azepane, 1,4-oxazepane, 1,4-diazepane, oxepane, tetrahydropyran, piperidine, bicyclo[4.2.1]nonane, bicyclo[4.1.1]octane, spiro[4.6]undecane, 1-azaspiro[4.6]undecane, and cyclooctane, each of which is substituted with from 1 to 4 $R^2$, and further substituted with 0 or 1 oxo (=O) which is on a carbon atom adjacent to a nitrogen atom;
$R^1$ is selected from the group consisting of phenyl and a 5 to 6-membered heteroaryl having 1-3 heteroatom ring vertices selected from the group consisting of O, N, and S, and wherein each phenyl and heteroaryl is substituted with one $R^{1a}$ and 0-3 $R^3$;
$R^{1a}$ is selected from the group consisting of phenyl and a 5 to 6-membered heteroaryl having 1-3 heteroatom ring vertices selected from the group consisting of O, N, and S, wherein the N atom, when present, is optionally oxidized, and wherein each phenyl and heteroaryl is substituted with 0-4 $R^4$;
each $R^2$ is independently selected from the group consisting of $C_{1-7}$ alkyl, $C_{3-7}$ alkenyl, $C_{3-7}$ alkynyl, $C_{3-7}$ cycloalkyl, —$Y^1$—O—$C_{1-7}$ alkyl, —$Y^1$—O—$C_{3-7}$ cycloalkyl, —$NR^aR^b$, —C(O)—$C_{1-7}$ alkyl, —C(O)—$C_{3-7}$ cycloalkyl, —$S(O)_2$—$C_{1-7}$ alkyl, —$S(O)_2$—$C_{3-7}$ cycloalkyl, —$C(O)NR^aR^b$, 5- to 8-membered heterocycloalkyl, —$NR^a$-(5- to 8-membered heterocycloalkyl), —C(O)-(5- to 8-membered heterocycloalkyl), —$X^1$-5- to 8-membered heterocycloalkyl, and —O—$X^1$-(5- to 8-membered heterocycloalkyl), wherein the heterocycloalkyl has 1-3 heteroatom ring vertices selected from the group consisting of O, N, and S, and wherein each cycloalkyl and heterocycloalkyl is substituted with from 0-3 groups independently selected from halo, CN, $C_{1-4}$ alkyl, $C_{1-4}$ haloalkyl, $C_{1-4}$ hydroxyalkyl, —O—$C_{1-4}$ alkyl, and OH;
each $R^3$ is independently selected from the group consisting of halogen, CN, $C_{1-7}$ alkyl, $C_{2-7}$ alkenyl, $C_{3-7}$ alkynyl, $C_{1-4}$haloalkyl, $C_{1-4}$hydroxyalkyl, $C_{1-4}$halohydroxyalkyl, —O—$C_{1-7}$ alkyl, —O—$C_{1-6}$ haloalkyl, —$NR^aR^b$, —C(O)—$NR^aR^b$, —$S(O)_2$—$NR^aR^b$, —S(O)(NH)—$C_{1-7}$ alkyl, —$S(O)_2$—$C_{1-7}$ alkyl, and —$S(O)_2$—$C_{1-7}$ haloalkyl;
each $R^4$ is independently selected from the group consisting of $C_{1-7}$ alkyl, halo, $C_{1-7}$ haloalkyl, —O—$C_{1-7}$ alkyl, —O—$C_{1-7}$ haloalkyl, CN, —$C_{1-7}$ alkylene-CN, hydroxy, $C_{1-7}$ hydroxyalkyl, —$C(O)NR^aR^b$, $C_{3-7}$ cycloalkyl, —$NR^a$—C(O)—$C_{1-7}$ alkyl, —$NR^a$—C(O)—$C_{3-7}$ cycloalkyl, —$NR^aR^b$, —O—$C_{1-4}$ alkylene-O—$C_{1-4}$ alkyl, —O-(5- to 8-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —$S(O)_2$—$C_{1-7}$ alkyl, —$S(O)_2$—$C_{3-7}$ cycloalkyl, —$S(O)_2$—$NR^aR^b$, —$NR^a$—$S(O)_2$—$C_{1-7}$ alkyl, and —$NR^a$—$S(O)_2$—$C_{3-7}$ cycloalkyl, wherein each cycloalkyl and heterocycloalkyl is substituted with 0 to 2 groups independently selected from the group consisting of $C_{1-4}$ alkyl, halo, and hydroxy;
alternatively, two $R^4$ groups on the same ring vertex combine to form an oxo (=O); or two R$^4$ groups on adjacent ring vertices combine to form a 5- to 6-membered heterocycloalkyl having from 1 to 2 heteroatom ring vertices selected from the group consisting of O, N, and S, wherein the 5- to 6-membered heterocycloalkyl is substituted with 0 to 2 groups independently selected from the group consisting of C$_{1-4}$ alkyl and halo;

R$^5$ is selected from the group consisting of H, C$_{1-4}$ alkyl, and —NH$_2$;

each X$^1$ is C$_{1-7}$ alkylene or C$_{3-7}$ cycloalkylene;

each Y$^1$ is C$_{2-7}$ alkylene or C$_{3-7}$ cycloalkylene;

each R$^a$ and R$^b$ are independently selected from group consisting of H, C$_{1-7}$ alkyl, C$_{1-7}$ haloalkyl, C$_{1-4}$ alkoxyC$_{1-4}$alkyl, C$_{3-7}$ cycloalkyl, wherein said cycloalkyl is optionally substituted with —O—C$_{1-3}$ alkyl; or R$^a$ and R$^b$ together with the nitrogen to which they are attached form a 4- to 8-membered heterocycloalkyl ring having 0-2 additional heteroatom ring vertices selected from the group consisting of O, N, and S, wherein the heterocycloalkyl ring is substituted with 0-3 groups, each group is independently selected from halo, CN, C$_{1-4}$ alkyl, C$_{1-4}$ haloalkyl, C$_{1-4}$ hydroxyalkyl, —O—C$_{1-4}$ alkyl, and X$^1$—O—C$_{1-3}$ alkyl, and OH; or two groups on the same ring vertex combine to form an oxo (=O).

In another aspect, this disclosure is directed to pharmaceutical compositions comprising the compounds of this disclosure, or pharmaceutically acceptable salts thereof.

In another aspect, this disclosure is directed to methods of inhibiting AXL in a subject comprising administering to the subject an effective amount of a compound described herein.

In yet another aspect, this disclosure provides methods for treating a disease, disorder, or condition mediated at least in part by AXL in a subject, comprising administering to the subject a therapeutically effective amount of a compound described herein, or a pharmaceutically acceptable salt thereof. Diseases, disorders, and conditions mediated by AXL include, e.g., cancer, viral infections, and fibrosis. Certain aspects of the present disclosure further comprise the administration of one or more additional therapeutic agents as set forth herein below.

DETAILED DESCRIPTION OF THE DISCLOSURE

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs.

Unless otherwise defined, all terms of art, notations and other scientific terms or terminology used herein are intended to have the meanings commonly understood by those of skill in the art to which this disclosure pertains.

The term "about" is used herein has its original meaning of approximately and is to provide literal support for the exact number that it precedes, as well as a number that is near to or approximately the number that the term precedes. In general, the term "about" refers to the usual error range for the respective value readily known to the skilled person in this technical field. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

Definitions

Unless otherwise indicated, the following terms are intended to have the meaning set forth below. Other terms are defined elsewhere throughout the specification.

The term "alkyl", by itself or as part of another substituent, means, unless otherwise stated, a saturated straight or branched chain hydrocarbon radical, having the number of carbon atoms designated (i.e. C$_{1-8}$ means one to eight carbons). Alkyl can include any number of carbons, such as C$_{1-2}$, C$_{1-3}$, C$_{1-4}$, C$_{1-5}$, C$_{1-6}$, C$_{1-7}$, C$_{1-8}$, C$_{1-9}$, C$_{1-10}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$ and C$_{5-6}$. Examples of alkyl groups include methyl (Me), ethyl (Et), n-propyl, isopropyl, n-butyl, t-butyl, isobutyl, sec-butyl, n-pentyl, n-hexyl, n-heptyl, n-octyl, and the like. In some embodiments, the alkyl groups are C$_{1-4}$ alkyl groups (e.g., methyl, ethyl, isopropyl, or t-butyl).

The term "hydroxyalkyl" refers to an alkyl group as defined herein having the indicated number of carbon atoms (e.g., C$_{1-6}$ or C$_{1-8}$) and which is substituted with one or two hydroxy (OH) groups.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, in some embodiments, can be substituted or unsubstituted. When a group comprising an alkylene is optionally substituted, it is understood that the optional substitutions may be on the alkylene portion of the moiety. In some embodiments, the alkylene groups are C$_{1-3}$ alkylene groups (e.g., methylene, ethylene, propylene, or isopropylene).

The term "cycloalkyl" refers to a monocyclic, bicyclic or polycyclic non-aromatic hydrocarbon ring system having the indicated number of ring atoms (e.g., a C$_{3-6}$ cycloalkyl has from 3 to 6 ring carbon atoms). Cycloalkyl groups can be saturated or partially unsaturated, i.e., cycloalkyl groups can be characterized by one or more points of unsaturation, provided the points of unsaturation do not result in an aromatic system. Examples of monocyclic cycloalkyl groups include, but are not limited to, cyclopropyl, cyclobutyl, cyclopentyl, cyclohexyl, cyclohexenyl, cycloheptyl, cyclooctyl, cyclooctenyl, cyclooctadienyl and the like. "Cycloalkyl" also refers to bicyclic and polycyclic hydrocarbon rings such as, for example, bicyclo[2.2.1]heptane, bicyclo[2.2.2]octane, etc. In some embodiments, the cycloalkyl groups of the present disclosure are monocyclic $C_{3-5}$ cycloalkyl moieties (e.g., cyclopropyl, cyclobutyl, or cyclopentyl).

The term "heterocycloalkyl" refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 3 to 8 members (e.g., 3- to 8-membered heterocycle), or 3 to 6 members (e.g., 3- to 6-membered heterocycle), or 5 to 6 members (e.g., 5- to 6-membered heterocycle), and having from one to five, one to four, one to three, one to two or one heteroatom selected from nitrogen (N), oxygen (O), and sulfur (S). In some embodiments, the nitrogen and sulfur atoms of the heterocycloalkyl group are optionally oxidized (e.g., N-oxide ($N^+$—$O^-$), sulfoxide (S=O), or sulfone ($S(=O)_2$)), and the nitrogen atom(s) are optionally quaternized. Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, pyrrolidine, imidazolidine, pyrazolidine, dioxolane, phthalimide, piperidine, 1,4-dioxane, morpholine, thiomorpholine, thiomorpholine-S-oxide, thiomorpholine-S,S-oxide, piperazine, 3,4,5,6-tetrahydropyridazine, pyran, decahydroisoquinoline, 3-pyrroline, thiopyran, tetrahydrofuran, tetrahydropyran, tetrahydrothiophene, quinuclidine, 2,6-diazaspiro[3.3]heptane, 2-azaspiro[3.3]heptane, 1-oxaspiro[3.3]heptane, 6-azaspiro[3.4]octane, 3-oxa-6-azabicyclo[3.1.1]heptane, 2-oxa-5-azabicyclo[2.2.1]heptane, 3-oxa-8-azabicyclo[3.2.1]octane, and the like. A heterocycloalkyl group can be attached to the remainder of the molecule through a ring carbon atom, or a ring heteroatom, when chemically permissible In some embodiments, the heterocycloalkyl groups of the present disclosure are monocyclic 5- to 8-membered heterocycloalkyl moieties having one or two heteroatom or heteroatom groups selected from N, and O (e.g., oxazolidine, piperidine, morpholine, pyrrolidine, tetrahydrofuran, tetrahydropyran, dioxane, 3-oxa-6-azabicyclo[3.1.1]heptane, or 2-oxa-5-azabicyclo[2.2.1]heptane).

As used herein, a wavy line, "⌇⌇",, that intersects a single, double or triple bond in any chemical structure depicted herein, represent the point of attachment of the single, double, or triple bond to the remainder of the molecule. Additionally, a bond extending from a substituent to the center of a ring (e.g., a phenyl ring) is meant to indicate attachment of that substituent to the ring at any of the available ring vertices, i.e., such that attachment of the substituent to the ring results in a chemically stable arrangement.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is meant to include trifluoromethyl, difluoromethyl, 2,2,2-trifluoroethyl, 4-chlorobutyl, 3-bromopropyl, and the like.

The term "aryl" refers to an aromatic ring system containing one ring, or two or three rings fused together, and having, in some embodiments, six to fourteen (i.e., $C_{6-14}$ aryl), or six to ten (i.e., $C_{6-10}$ aryl), or six (i.e., $C_6$ aryl) carbon atoms. Non-limiting examples of aryl groups include phenyl, naphthyl and anthracenyl. In some embodiments, aryl groups are phenyl.

The term "heteroaryl" refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two or one heteroatom selected from nitrogen (N), oxygen (O), and sulfur (S). In some embodiments, the nitrogen and sulfur atoms are optionally oxidized (e.g., N-oxide ($N^+$—$O^-$), sulfoxide (S=O), or sulfone ($S(=O)_2$)), and the nitrogen atom(s) are optionally quaternized. A heteroaryl group can be attached to the remainder of the molecule through a carbon atom or a heteroatom of the heteroaryl group, when chemically permissible. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolinyl, isoquinolinyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. When a heteroaryl is substituted, that substituent is connected to the heteroaryl through a ring carbon atom or a ring heteroatom when chemically permissible. In some embodiments, the heteroaryl groups of the present disclosure are monocyclic 5- to 6-membered heteroaryl moieties containing 1-3 heteroatoms independently selected from N, O and S, and wherein the N atom, when present, is optionally oxidized (e.g., pyridinyl, pyridyl N-oxide, pyrimidinyl, pyridazinyl, pyrazinyl, triazolyl, imidazolyl, pyrazolyl, oxazolyl, oxadiazolyl, or thiazolyl).

The compounds of the present disclosure can be present in their neutral form, or as a pharmaceutically acceptable salt, isomer, polymorph or solvate thereof, and may be present in a crystalline form, amorphous form or mixtures thereof.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

This disclosure also contemplates isomers of the compounds described herein (e.g., stereoisomers, and atropisomers). For example, certain compounds of the present disclosure possess asymmetric carbon atoms (chiral centers) or hindered rotation about a single bond; the racemates, diastereomers, enantiomers, and atropisomers (e.g., $R_a$, $S_a$, P and M isomers) of which are all intended to be encompassed within the scope of the present disclosure. Stereoisomeric forms may be defined, in terms of absolute stereochemistry, as (R) or (S), and/or depicted uses dashes and/or wedges. When a stereochemical depiction (e.g., using dashes, ·······, and/or wedges, ━━━) is shown in a chemical structure, or a stereochemical assignment (e.g., using (R) an (S) notation) is made in a chemical name, it is meant to indicate that the depicted isomer is present and substantially free of one or more other isomer(s) (e.g., enantiomers and diastereomers, when present). "Substantially free of" other isomer(s) indicates at least an 70/30 ratio of the indicated isomer to the other isomer(s), more preferably 80/20, 90/10, or 95/5 or more. In some embodiments, the indicated isomer will be present in an amount of at least 99%. A chemical bond to an asymmetric carbon that is depicted as a solid line ( ─── ) indicates that all possible stereoisomers (e.g., enantiomers, diastereomers, racemic mixtures, etc.) at that carbon atom are included. In such instances, the compound may be present as a racemic mixture, scalemic mixture, or a mixture of diastereomers.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere herein. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure. In some embodiments, the compounds according to this disclosure are characterized by one or more deuterium atoms.

The terms "patient" or "subject" are used interchangeably to refer to a human or a non-human animal (e.g., a mammal).

The terms "treat", "treating", treatment" and the like refer to a course of action that eliminates, reduces, suppresses, mitigates, ameliorates, or prevents the worsening of, either temporarily or permanently, a disease, disorder or condition to which the term applies, or at least one of the symptoms associated therewith. Treatment includes alleviation of symptoms, diminishment of extent of disease, inhibiting (e.g., arresting the development or further development of the disease, disorder or condition or clinical symptoms association therewith) an active disease, delaying or slowing of disease progression, improving the quality of life, and/or prolonging survival of a subject as compared to expected survival if not receiving treatment or as compared to a published standard of care therapy for a particular disease.

The term "in need of treatment" as used herein refers to a judgment made by a physician or similar professional that a subject requires or will benefit from treatment. This judgment is made based on a variety of factors that are in the realm of the physician's expertise, which may include a positive diagnosis of a disease, disorder or condition.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom.

The term "in need of prevention" as used herein refers to a judgment made by a physician or other caregiver that a subject requires or will benefit from preventative care. This judgment is made based on a variety of factors that are in the realm of a physician's or caregiver's expertise.

"Substantially pure" indicates that a component (e.g., a compound according to this disclosure) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

Compounds that are selective may be particularly useful in the treatment of certain disorders or may offer a reduced likelihood of undesired side effects. In some embodiments, the compounds of the present disclosure are selective over other tyrosine kinases. Specific examples include TYRO3 and MER. Selectivity may be determined, for example, by comparing the inhibition of a compound as described herein against AXL against the inhibition of a compound as described herein against another protein. In one embodiment, the selective inhibition of AXL is at least 1000 times greater, 500 times greater, or 100 times greater, or 75 times greater, or 50 times greater, or 40 times greater, or 30 times greater, or 25 times greater, or 20 times greater than inhibition of another kinase (e.g., TYRO3 and/or MER).

Compounds provided herein may have advantageous pharmacokinetic profiles including, for example, inhibition against CYP, bioavailability, and/or inhibition of the human Ether-a-go-go Related Gene (hERG) potassium channel.

Compounds of the Disclosure

In some aspects, provided herein are compounds represented by Formula (I)

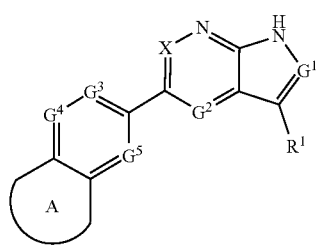

or a pharmaceutically acceptable salt thereof, wherein:
X is $CR^5$ or N;
$G^1$ is N or $CR^{G1}$;
$G^2$ is $CR^{G2}$ or N;
$G^3$ is $CR^{G3}$ or N;
$G^4$ is $CR^{G4}$ or N;
$G^5$ is $CR^{G5}$ or N;
$R^{G1}$ is selected from the group consisting of H, $C_{1-3}$ alkyl, halogen, $C_{1-3}$ haloalkyl, and CN;
each $R^{G2}$, $R^{G3}$, $R^{G4}$ and $R^{G5}$ is independently selected from the group consisting of H, halo, CN, $C_{1-7}$ alkyl, $C_{3-7}$ cycloalkyl, $C_{1-3}$ haloalkyl, —O—$C_{1-3}$ alkyl, —O—$C_{1-3}$ haloalkyl, —$NR^aR^b$, and 5- to 8-membered heterocycloalkyl having 1-3 heteroatom ring vertices selected from the group consisting of O, N, and S, and wherein cycloalkyl and heterocycloalkyl are substituted with 0-3 groups independently selected from halo, CN, $C_{1-4}$ alkyl, $C_{1-4}$ haloalkyl, $C_{1-4}$ hydroxyalkyl, —O—$C_{1-4}$ alkyl, and OH;
A is a fused ring selected from the group consisting of cycloheptane, cyclohexane, cyclopentane, azepane, 1,4-oxazepane, 1,4-diazepane, oxepane, tetrahydropyran, piperidine, bicyclo[4.2.1]nonane, bicyclo[4.1.1] octane, spiro[4.6]undecane, 1-azaspiro[4.6]undecane, and cyclooctane, each of which is substituted with from 1 to 4 $R^2$, and further substituted with 0 or 1 oxo (=O) which is on a carbon atom adjacent to a nitrogen atom;

$R^1$ is selected from the group consisting of phenyl and a 5 to 6-membered heteroaryl having 1-3 heteroatom ring vertices selected from the group consisting of O, N, and S, and wherein each phenyl and heteroaryl is substituted with one $R^{1a}$ and 0-3 $R^3$;

$R^{1a}$ is selected from the group consisting of phenyl and a 5 to 6-membered heteroaryl having 1-3 heteroatom ring vertices selected from the group consisting of O, N, and S, wherein the N atom, when present, is optionally oxidized, and wherein each phenyl and heteroaryl is substituted with 0-4 $R^4$;

each $R^2$ is independently selected from the group consisting of $C_{1-7}$ alkyl, $C_{3-7}$ alkenyl, $C_{3-7}$ alkynyl, $C_{3-7}$ cycloalkyl, —$Y^1$—O—$C_{1-7}$ alkyl, —$Y^1$—O—$C_{3-7}$ cycloalkyl, —$NR^aR^b$, —C(O)—$C_{1-7}$ alkyl, —C(O)—$C_{3-7}$ cycloalkyl, —$S(O)_2$—$C_{1-7}$ alkyl, —$S(O)_2$—$C_{3-7}$ cycloalkyl, —$C(O)NR^aR^b$, 5- to 8-membered heterocycloalkyl, —$NR^a$-(5- to 8-membered heterocycloalkyl), —C(O)-(5- to 8-membered heterocycloalkyl), —$X^1$-5- to 8-membered heterocycloalkyl, and —O—$X^1$-(5- to 8-membered heterocycloalkyl), wherein the heterocycloalkyl has 1-3 heteroatom ring vertices selected from the group consisting of O, N, and S, and wherein each cycloalkyl and heterocycloalkyl is substituted with from 0-3 groups independently selected from halo, CN, $C_{1-4}$ alkyl, $C_{1-4}$ haloalkyl, $C_{1-4}$ hydroxyalkyl, —O—$C_{1-4}$ alkyl, and OH;

each $R^3$ is independently selected from the group consisting of halogen, CN, $C_{1-7}$ alkyl, $C_{2-7}$ alkenyl, $C_{3-7}$ alkynyl, $C_{1-4}$haloalkyl, $C_{1-4}$hydroxyalkyl, $C_{1-4}$halohydroxyalkyl, —O—$C_{1-7}$ alkyl, —O—$C_{1-6}$ haloalkyl, —$NR^aR^b$, —C(O)—$NR^aR^b$, —$S(O)_2$—$NR^aR^b$, —S(O)(NH)—$C_{1-7}$ alkyl, —$S(O)_2$—$C_{1-7}$ alkyl, and —$S(O)_2$—$C_{1-7}$ haloalkyl;

each $R^4$ is independently selected from the group consisting of $C_{1-7}$ alkyl, halo, $C_{1-7}$ haloalkyl, —O—$C_{1-7}$ alkyl, —O—$C_{1-7}$ haloalkyl, CN, —$C_{1-7}$ alkylene-CN, hydroxy, $C_{1-7}$ hydroxyalkyl, —$C(O)NR^aR^b$, $C_{3-7}$ cycloalkyl, —$NR^a$—C(O)—$C_{1-7}$ alkyl, —$NR^a$—C(O)—$C_{3-7}$ cycloalkyl, —$NR^aR^b$, —O—$C_{1-4}$ alkylene-O—$C_{1-4}$ alkyl, —O-(5- to 8-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —$S(O)_2$—$C_{1-7}$ alkyl, —$S(O)_2$—$C_{3-7}$ cycloalkyl, —$S(O)_2$—$NR^aR^b$, —$NR^a$—$S(O)_2$—$C_{1-7}$ alkyl, and —$NR^a$—$S(O)_2$—$C_{3-7}$ cycloalkyl, wherein each cycloalkyl and heterocycloalkyl is substituted with 0 to 2 groups independently selected from the group consisting of $C_{1-4}$ alkyl, halo, and hydroxy;

alternatively, two $R^4$ groups on the same ring vertex combine to form an oxo (=O); or two $R^4$ groups on adjacent ring vertices combine to form a 5- to 6-membered heterocycloalkyl having from 1 to 2 heteroatom ring vertices selected from the group consisting of O, N, and S, wherein the 5- to 6-membered heterocycloalkyl is substituted with 0 to 2 groups independently selected from the group consisting of $C_{1-4}$ alkyl and halo;

$R^5$ is selected from the group consisting of H, $C_{1-4}$ alkyl and —$NH_2$;

each $X^1$ is $C_{1-7}$ alkylene or $C_{3-7}$ cycloalkylene;
each $Y^1$ is $C_{2-7}$ alkylene or $C_{3-7}$ cycloalkylene;
each $R^a$ and $R^b$ are independently selected from group consisting of H, $C_{1-7}$ alkyl, $C_{1-7}$ haloalkyl, $C_{1-4}$ alkoxy$C_{1-4}$alkyl, and $C_{3-7}$ cycloalkyl, wherein said cycloalkyl is optionally substituted with —O—$C_{1-3}$ alkyl; or
$R^a$ and $R^b$ together with the nitrogen to which they are attached form a 4- to 8-membered heterocycloalkyl ring having 0-2 additional heteroatom ring vertices selected from the group consisting of O, N, and S, wherein the heterocycloalkyl ring is substituted with 0-3 groups, each group is independently selected from halo, CN, $C_{1-4}$ alkyl, $C_{1-4}$ haloalkyl, $C_{1-4}$ hydroxyalkyl, —O—$C_{1-4}$ alkyl, and $X^1$—O—$C_{1-3}$ alkyl, and OH; or two groups on the same ring vertex combine to form an oxo (=O).

In some embodiments, the compound of Formula (I) or a pharmaceutically acceptable salt, hydrate, or solvate thereof, is a compound wherein $G^1$ is N or $CR^{G1}$ wherein $R^{G1}$ is H. In some embodiments, the compound of Formula (I) or a pharmaceutically acceptable salt, hydrate, or solvate thereof, is a compound wherein $G^1$ is N. In some embodiments, the compound of Formula (I) or a pharmaceutically acceptable salt, hydrate, or solvate thereof, is a compound wherein $G^1$ is $CR^{G1}$ wherein $R^{G1}$ is H.

In some embodiments, the compound of Formula (I) or a pharmaceutically acceptable salt, hydrate, or solvate thereof, is a compound wherein $G^2$ is $CR^{G2}$ wherein $R^{G2}$ is H or F. In some embodiments, the compound of Formula (I) or a pharmaceutically acceptable salt, hydrate, or solvate thereof, is a compound wherein $G^2$ is $CR^{G2}$ wherein $R^{G2}$ is H. In some embodiments, the compound of Formula (I) or a pharmaceutically acceptable salt, hydrate, or solvate thereof, is a compound wherein $G^2$ is N.

In some embodiments, the compound of Formula (I) or a pharmaceutically acceptable salt, hydrate, or solvate thereof, is a compound wherein $G^3$ is N or $CR^{G3}$, and $R^{G3}$ is H, or $CH_3$.

In some embodiments, the compound of Formula (I) or a pharmaceutically acceptable salt, hydrate, or solvate thereof, is a compound wherein $G^4$ is N or $CR^{G4}$ wherein $R^{G4}$ is H.

In some embodiments, the compound of Formula (I) or a pharmaceutically acceptable salt, hydrate, or solvate thereof, is a compound wherein $G^5$ is N or $CR^{G5}$ wherein $R^{G5}$ is H.

In some embodiments, the compound of Formula (I) or a pharmaceutically acceptable salt, hydrate, or solvate thereof, is a compound wherein $G^1$ is N, and $G^2$ is $CR^{G2}$ wherein $R^{G2}$ is H.

In some embodiments, the compound of Formula (I) or a pharmaceutically acceptable salt, hydrate, or solvate thereof, is a compound wherein $G^3$ is $CR^{G3}$ wherein $R^{G3}$ is H.

In some embodiments, the compound of Formula (I) or a pharmaceutically acceptable salt, hydrate, or solvate thereof, is a compound wherein $G^4$ is $CR^{G4}$ wherein $R^{G4}$ is H.

In some embodiments, the compound of Formula (I) or a pharmaceutically acceptable salt, hydrate, or solvate thereof, is a compound wherein $G^5$ is $CR^{G5}$ wherein $R^{G5}$ is H.

In some embodiments, the compound of Formula (I) or a pharmaceutically acceptable salt, hydrate, or solvate thereof, is a compound wherein X is N or $CR^5$ wherein $R^5$ is H. In some embodiments, the compound of Formula (I) or a pharmaceutically acceptable salt, hydrate, or solvate thereof, is a compound wherein X is $CR^5$ wherein $R^5$ is H.

With reference to A, it is understood from the formula as shown above that A is fused to an aromatic ring comprising $G^3$, $G^4$ and $G^5$, and that the presence of A does not destroy the aromaticity of the aromatic ring comprising $G^3$, $G^4$ and $G^5$. Specifically, the ring vertices that fuse the two rings together are $sp^2$ hybridized carbon atoms. Therefore, each of these ring vertices have a p orbital that participates in the conjugated pi system of the aromatic ring. Accordingly, it is understood from the formula as shown above A moieties have a point of unsaturation at the fusion point to the remainder of the molecule. For example, cyclopentane at A refers to cyclopentene, where the double bond is between the two carbon atoms that fuse to the remainder of the compound as further illustrated and detailed throughout.

In some embodiments, the compound of Formula (I) or a pharmaceutically acceptable salt, hydrate, or solvate thereof, is a compound wherein A has a formula selected from the group consisting of

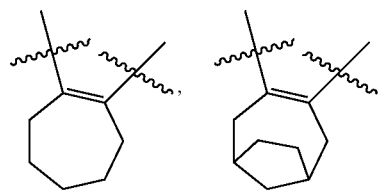 [SMILES: *C1=C(*)CCCCC1 ; *C1=C(*)CC2CCC(C1)C2]

and

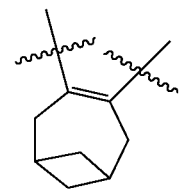 [SMILES: *C1=C(*)CC2CC(C1)C2]

each of which is substituted with from 1 to 4 $R^2$.

In some embodiments, the compound of Formula (I) or a pharmaceutically acceptable salt, hydrate, or solvate thereof, is a compound wherein A has a formula selected from the group consisting of

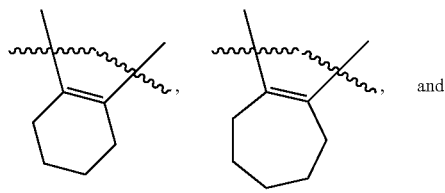

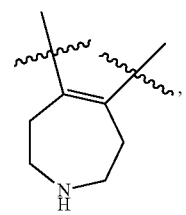

each of which is substituted with from 1 to 4 $R^2$.

In some embodiments, the compound of Formula (I) or a pharmaceutically acceptable salt, hydrate, or solvate thereof, is a compound wherein A has a formula

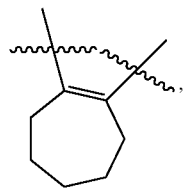 [SMILES: *C1=C(*)CCCCC1]

which is substituted with from 1 to 4 R².

In some embodiments, the compound of Formula (I) or a pharmaceutically acceptable salt, hydrate, or solvate thereof, is a compound wherein A has a formula

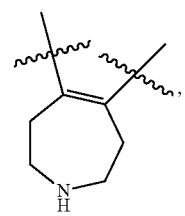

wherein A is substituted with from 1 to 4 R².

In some embodiments, the compound of Formula (I) or a pharmaceutically acceptable salt, hydrate, or solvate thereof, is a compound wherein A is substituted with at least one R² selected from —C$_{2-7}$ alkylene-O—C$_{1-4}$ alkyl and C$_{3-7}$ cycloalkyl. In some embodiments, the compound of Formula (I) or a pharmaceutically acceptable salt, hydrate, or solvate thereof, is a compound wherein A is substituted with at least one R² selected from

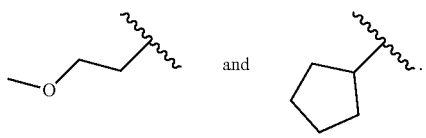

In some embodiments, the compound of Formula (I) or a pharmaceutically acceptable salt, hydrate, or solvate thereof, is a compound wherein A has the formula:

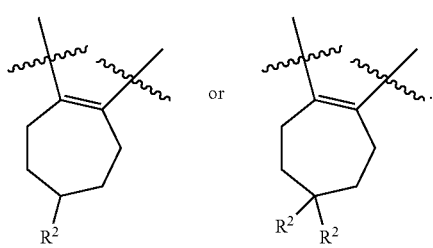

In some embodiments, the compound of Formula (I) or a pharmaceutically acceptable salt, hydrate, or solvate thereof, is a compound wherein A has the formula:

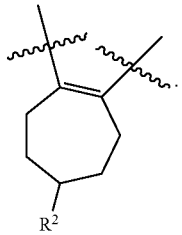

In some embodiments, the compound of Formula (I) or a pharmaceutically acceptable salt, hydrate, or solvate thereof, is a compound wherein A has the formula:

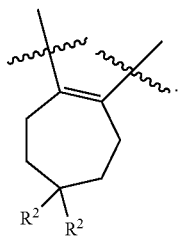

In some embodiments, the compound of Formula (I) or a pharmaceutically acceptable salt, hydrate, or solvate thereof, is a compound wherein each R² is independently selected from the group consisting of C$_{1-7}$ alkyl, C$_{3-7}$ alkenyl, C$_{3-7}$ alkynyl, C$_{3-7}$ cycloalkyl, —Y¹—O—C$_{1-7}$ alkyl, —Y¹—O—C$_{3-7}$ cycloalkyl, —NR$^a$R$^b$, —C(O)—C$_{1-7}$ alkyl, —C(O)—C$_{3-7}$ cycloalkyl, —S(O)$_2$—C$_{1-7}$ alkyl, —S(O)$_2$—C$_{3-7}$ cycloalkyl, —C(O)NR$^a$R$^b$, 5- to 8-membered heterocycloalkyl, —NR$^a$-(5- to 8-membered heterocycloalkyl), —C(O)-(5- to 8-membered heterocycloalkyl), —X¹-5- to 8-membered heterocycloalkyl, and —O—X¹-(5- to 8-membered heterocycloalkyl), wherein said 5- to 8-membered heterocycloalkyl, —NR$^a$-(5- to 8-membered heterocycloalkyl), —C(O)-(5- to 8-membered heterocycloalkyl), —X¹-5- to 8-membered heterocycloalkyl, and —O—X¹-(5- to 8-membered heterocycloalkyl) has 1-3 heteroatom ring vertices selected from the group consisting of O, N, and S, and wherein each of said C$_{3-7}$ cycloalkyl, —Y¹—O—C$_{3-7}$ cycloalkyl, —C(O)—C$_{3-7}$ cycloalkyl, —S(O)$_2$—C$_{3-7}$ cycloalkyl, 5- to 8-membered heterocycloalkyl, —NR$^a$-(5- to 8-membered heterocycloalkyl), —C(O)-(5- to 8-membered heterocycloalkyl), —X¹-5- to 8-membered heterocycloalkyl, and —O—X¹-(5- to 8-membered heterocycloalkyl) is substituted with from 0-3 groups independently selected from halo, CN, C$_{1-4}$ alkyl, C$_{1-4}$ haloalkyl, C$_{1-4}$ hydroxyalkyl, —O—C$_{1-4}$ alkyl, and OH. In some embodiments, the compound of Formula (I) or a pharmaceutically acceptable salt, hydrate, or solvate thereof, is a compound wherein one R² is —NR$^a$R$^b$.

In some embodiments, the compound of Formula (I) or a pharmaceutically acceptable salt, hydrate, or solvate thereof, is a compound wherein one R² is selected from the group consisting of

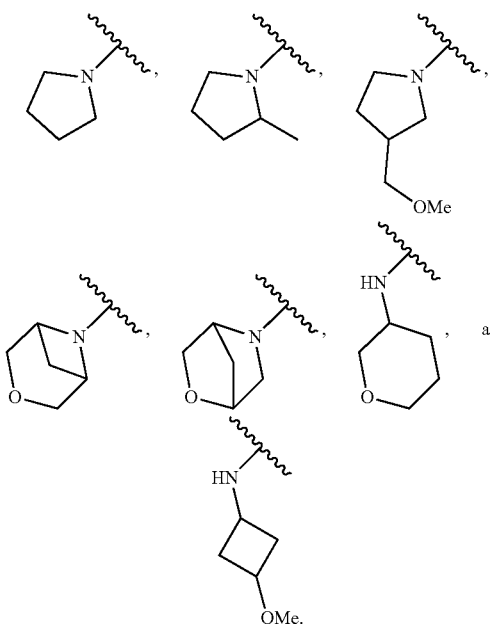

In some embodiments, the compound of Formula (I) or a pharmaceutically acceptable salt, hydrate, or solvate thereof, is a compound wherein one R² is

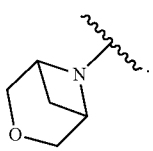 [SMILES: *N1C2COCC1C2]

In some embodiments, the compound of Formula (I) or a pharmaceutically acceptable salt, hydrate, or solvate thereof, is a compound wherein R¹ is selected from the group consisting of phenyl, pyridyl, pyridazinyl, pyrimidinyl, pyrazinyl, oxadiazolyl, and pyrazolyl, wherein R¹ is substituted with one R¹ᵃ and 0-2 R³. In some embodiments, the compound of Formula (I) or a pharmaceutically acceptable salt, hydrate, or solvate thereof, is a compound wherein R¹ is selected from the group consisting of phenyl, pyridyl, pyridazinyl, and pyrazolyl, wherein R¹ is substituted with one R¹ᵃ and 0-2 R³. In some embodiments, the compound of Formula (I) or a pharmaceutically acceptable salt, hydrate, or solvate thereof, is a compound wherein R¹ is selected from the group consisting of pyrimidinyl, pyrazinyl, and oxadiazolyl, wherein R¹ is substituted with one R¹ᵃ and 0-2 R³. In some embodiments, the compound of Formula (I) or a pharmaceutically acceptable salt, hydrate, or solvate thereof, is a compound wherein R¹ is phenyl or pyridyl, wherein R¹ is substituted with one R¹ᵃ and 0-2 R³. In some embodiments, the compound of Formula (I) or a pharmaceutically acceptable salt, hydrate, or solvate thereof, is a compound wherein R¹ is pyridyl substituted with one R¹ᵃ and 0-2 R³. In some embodiments, the compound of Formula (I) or a pharmaceutically acceptable salt, hydrate, or solvate thereof, is a compound wherein R¹ is phenyl substituted with one R¹ᵃ and 0-2 R³.

In some embodiments, the compound of Formula (I) or a pharmaceutically acceptable salt, hydrate, or solvate thereof, is a compound wherein R¹ is selected from the group consisting of

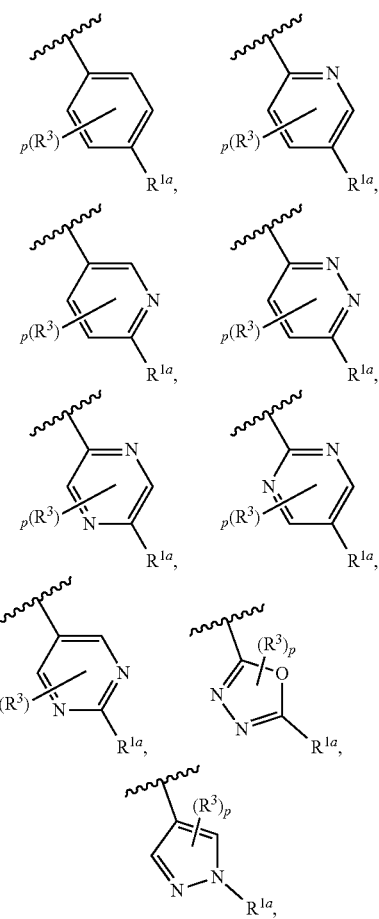

wherein the subscript p is 0 or 1.

In some embodiments, the compound of Formula (I) or a pharmaceutically acceptable salt, hydrate, or solvate thereof, is a compound wherein R¹ is selected from the group consisting of

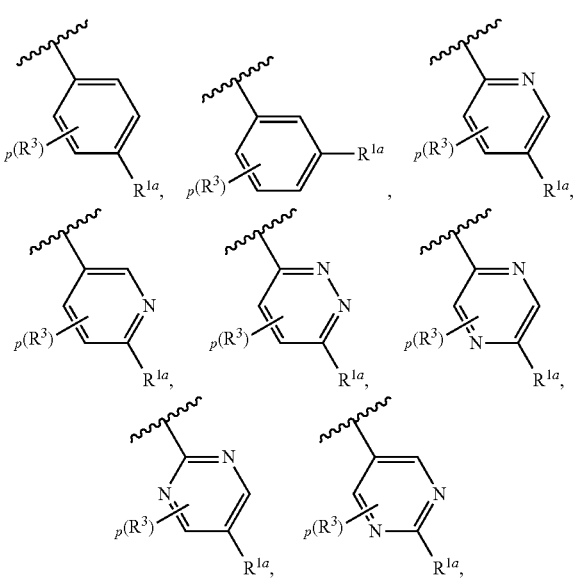

-continued

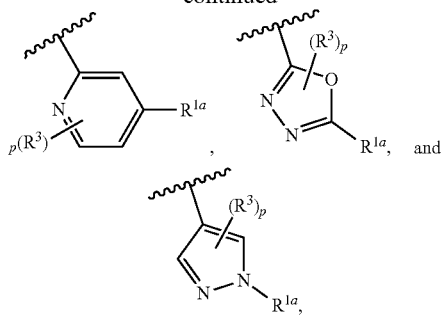

wherein the subscript p is 0 or 1.

In some embodiments, the compound of Formula (I) or a pharmaceutically acceptable salt, hydrate, or solvate thereof, is a compound wherein $R^1$ is selected from the group consisting of

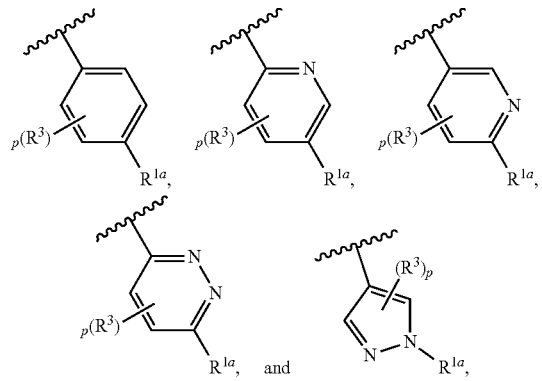

wherein the subscript p is 0 or 1.

In some embodiments, the compound of Formula (I) or a pharmaceutically acceptable salt, hydrate, or solvate thereof, is a compound wherein $R^1$ is selected from the group consisting of

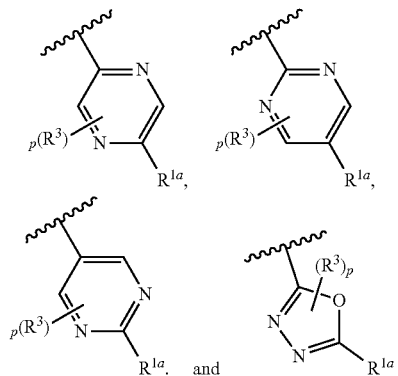

wherein the subscript p is 0 or 1.

In some embodiments, the compound of Formula (I) or a pharmaceutically acceptable salt, hydrate, or solvate thereof, is a compound wherein $R^1$ is selected from the group consisting of

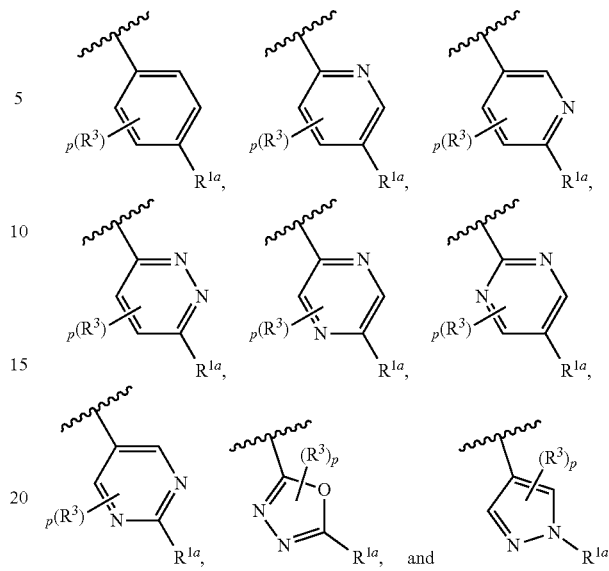

wherein the subscript p is 0 or 1.

In some embodiments, the compound of Formula (I) or a pharmaceutically acceptable salt, hydrate, or solvate thereof, is a compound wherein $R^1$ is

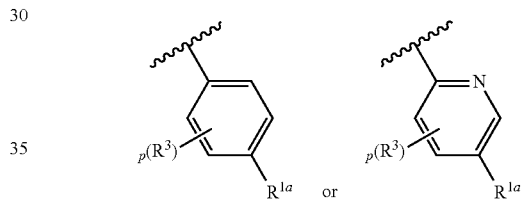

wherein the subscript p is 0 or 1.

In some embodiments, the compound of Formula (I) or a pharmaceutically acceptable salt, hydrate, or solvate thereof, is a compound wherein $R^1$ is

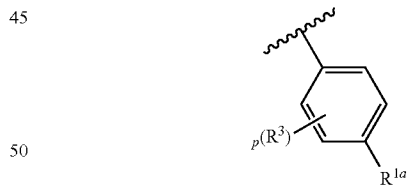

wherein the subscript p is 0 or 1.

In some embodiments, the compound of Formula (I) or a pharmaceutically acceptable salt, hydrate, or solvate thereof, is a compound wherein $R^1$ is

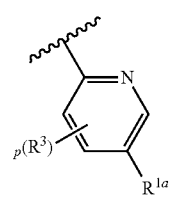

wherein the subscript p is 0 or 1.

In some embodiments, the compound of Formula (I) or a pharmaceutically acceptable salt, hydrate, or solvate thereof, is a compound wherein $R^1$ is substituted with 0 $R^3$ groups. In some embodiments, the compound of Formula (I) or a pharmaceutically acceptable salt, hydrate, or solvate thereof, is a compound wherein $R^1$ is substituted with 1 $R^3$ group.

In some embodiments, the compound of Formula (I) or a pharmaceutically acceptable salt, hydrate, or solvate thereof, is a compound wherein each $R^3$, when present, is independently selected from the group consisting of halogen, CN, $C_{1-4}$ alkyl, $C_{1-4}$haloalkyl, $C_{1-4}$ hydroxyalkyl, $C_{1-4}$halohydroxyalkyl, —O—$C_{1-4}$ alkyl, —O—$C_{1-4}$ haloalkyl, —$NR^aR^b$, —C(O)—$NR^aR^b$, —$S(O)_2$—$NR^aR^b$, —$S(O)(NH)$—$C_{1-4}$ alkyl, —$S(O)_2$—$C_{1-4}$ alkyl, and —$S(O)_2$—$C_{1-4}$haloalkyl.

In some embodiments, the compound of Formula (I) or a pharmaceutically acceptable salt, hydrate, or solvate thereof, is a compound wherein each $R^3$, when present, is independently selected from the group consisting of halogen, $C_{1-4}$ alkyl, and —O—$C_{1-4}$ alkyl.

In some embodiments, the compound of Formula (I) or a pharmaceutically acceptable salt, hydrate, or solvate thereof, is a compound wherein each $R^3$, when present, is independently selected from the group consisting of chloro, fluoro, methyl, and methoxy.

In some embodiments, the compound of Formula (I) or a pharmaceutically acceptable salt, hydrate, or solvate thereof, is a compound wherein each $R^3$, when present, is independently selected from the group consisting of fluoro, methyl, and methoxy.

In some embodiments, the compound of Formula (I) or a pharmaceutically acceptable salt, hydrate, or solvate thereof, is a compound wherein $R^{1a}$ is selected from the group consisting of, pyrazolyl, imidazolyl, triazolyl, thiazolyl, oxazolyl, pyridyl, pyrazinyl, pyridazinyl, pyrimidinyl, pyridyl N-oxide, and phenyl, wherein $R^{1a}$ is substituted with and 0-3 $R^4$. In some embodiments, the compound of Formula (I) or a pharmaceutically acceptable salt, hydrate, or solvate thereof, is a compound wherein $R^{1a}$ is selected from the group consisting of, pyrazolyl, imidazolyl, triazolyl, thiazolyl, oxazolyl, pyridyl, pyrazinyl, pyridazinyl, pyrimidinyl, and phenyl, wherein $R^{1a}$ is substituted with and 0-3 $R^4$.

In some embodiments, the compound of Formula (I) or a pharmaceutically acceptable salt, hydrate, or solvate thereof, is a compound wherein $R^{1a}$ is selected from the group consisting of

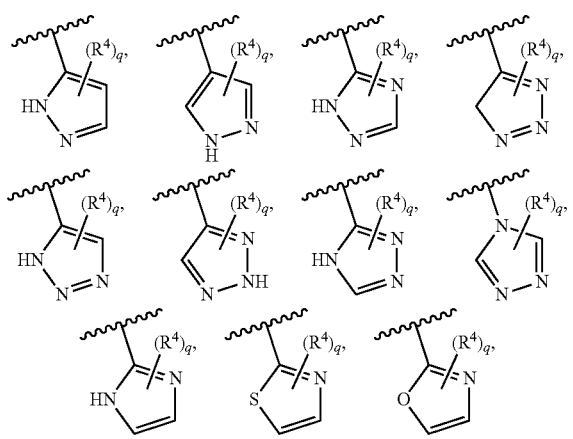

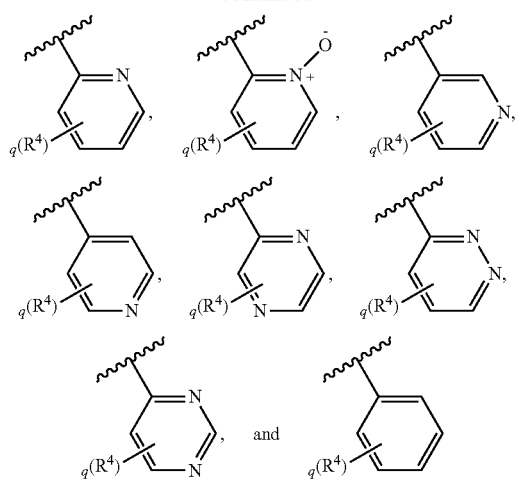

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

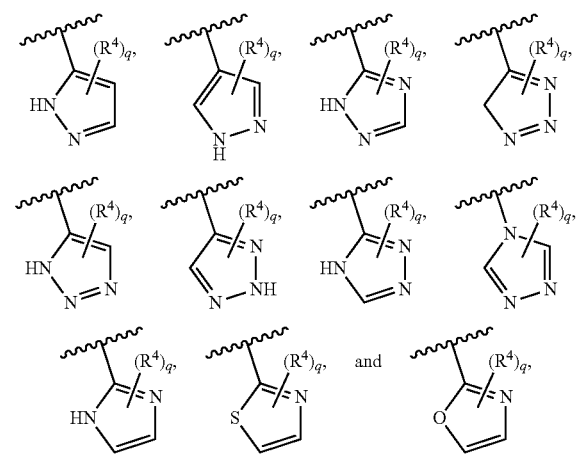

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

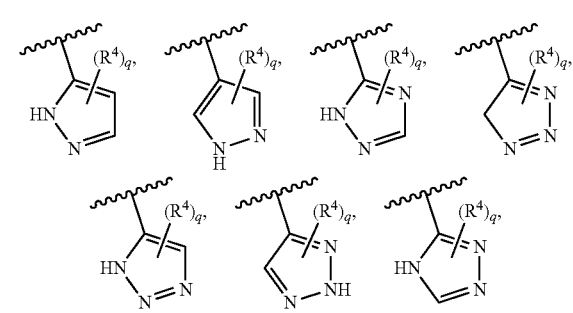

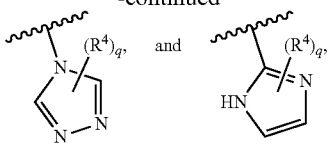

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

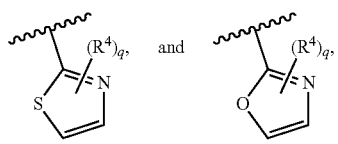

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

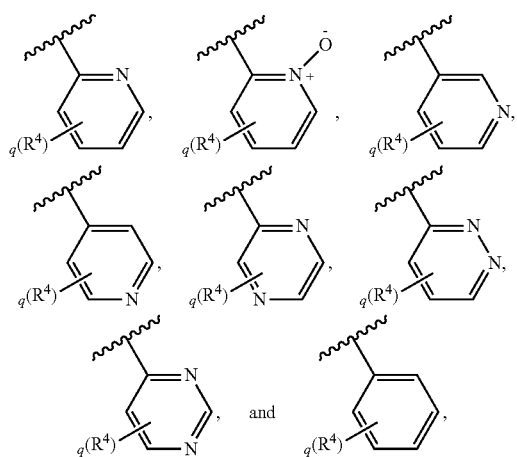

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

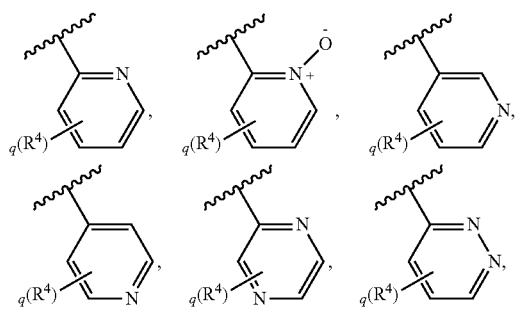

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

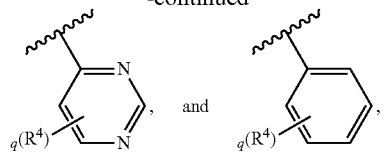

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

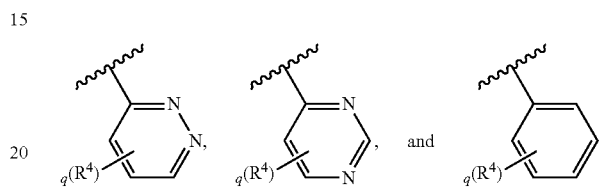

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

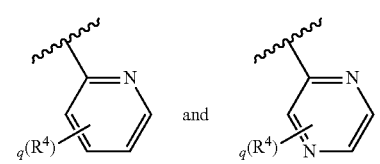

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

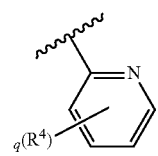

wherein the subscript q is 0, 1, or 2.

In some embodiments, the compound of Formula (I) or a pharmaceutically acceptable salt, hydrate, or solvate thereof, is a compound wherein $R^{1a}$ is selected from the group consisting of

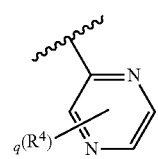

wherein the subscript q is 0, 1, or 2.

In some embodiments, the compound of Formula (I), or a pharmaceutically acceptable salt, hydrate, or solvate thereof, is a compound wherein $R^{1a}$ is selected from the group consisting of:

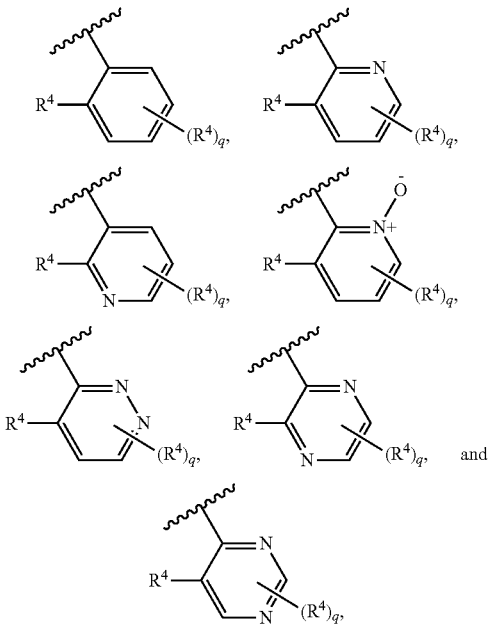

wherein q is 0 or 1.

In some embodiments, the compound of Formula (I), or a pharmaceutically acceptable salt, hydrate, or solvate thereof, is a compound wherein $R^{1a}$ is selected from the group consisting of

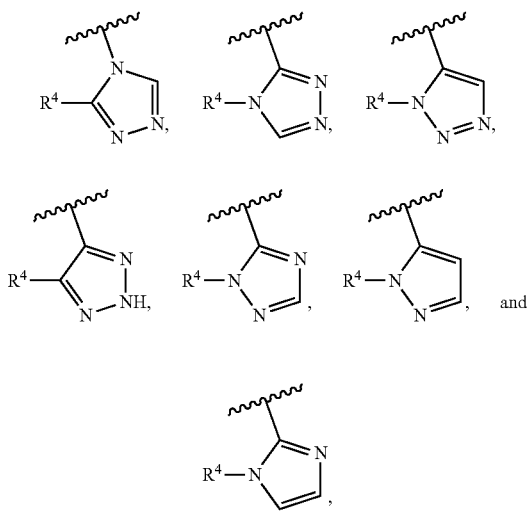

each of which is optionally substituted with one additional $R^4$.

In some embodiments, the compound of Formula (I) or a pharmaceutically acceptable salt, hydrate, or solvate thereof, is a compound wherein $R^{1a}$ is selected from the group consisting of

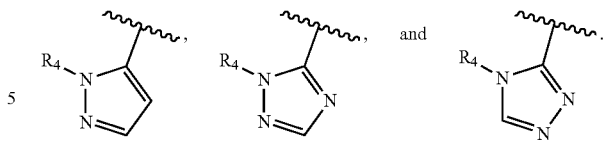

In some embodiments, heteroaryl moieties in $R^{1a}$ include groups substituted with one or more oxo substituents that abide by Huckel's rule. Accordingly, in some embodiments, the compound of Formula (I) or a pharmaceutically acceptable salt, hydrate, or solvate thereof, is a compound wherein heteroaryl groups of $R^{1a}$ include two $R^4$ groups on the same ring vertex that combine to form an oxo (=O). Exemplary groups include, but are not limited to pyridazinonyl and pyridinonyl. Therefore, in some embodiments, the compound of Formula (I) or a pharmaceutically acceptable salt, hydrate, or solvate thereof, is a compound wherein $R^{1a}$ together with two $R^4$ groups on the same ring vertex that combine to form an oxo (=O) form a heteroaryl moiety selected from the group consisting of pyridazinonyl, and pyridinonyl, wherein $R^{1a}$ is substituted with 0-2 additional $R^4$ groups.

In some embodiments, the compound of Formula (I) or a pharmaceutically acceptable salt, hydrate, or solvate thereof, is a compound wherein $R^{1a}$ includes 2-4 $R^4$ moieties and is selected from the group consisting of

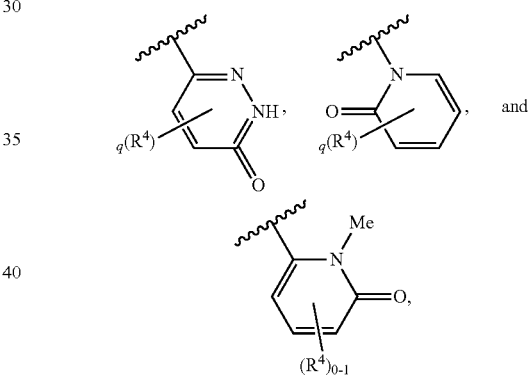

wherein the subscript q is 0, 1, or 2.

In some embodiments, the compound of Formula (I) or a pharmaceutically acceptable salt, hydrate or solvate thereof, is a compound wherein $R^4$ is independently selected from the group consisting of $C_{1-7}$ alkyl, halo, $C_{1-7}$ haloalkyl, —O—$C_{1-7}$ alkyl, —O—$C_{1-7}$ haloalkyl, CN, —$C_{1-7}$ alkylene-CN, hydroxy, $C_{1-7}$ hydroxyalkyl, —C(O)NR$^a$R$^b$, $C_{3-7}$ cycloalkyl, —NR$^a$—C(O)—$C_{1-7}$ alkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 8-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —S(O)$_2$—$C_{1-7}$ alkyl, —S(O)$_2$—$C_{3-7}$ cycloalkyl, —S(O)$_2$—NR$^a$R$^b$, —NR$^a$—S(O)$_2$—$C_{1-7}$ alkyl, and —NR$^a$—S(O)$_2$—$C_{3-7}$ cycloalkyl, wherein each $C_{3-7}$ cycloalkyl, —NR$^a$—C(O)—$C_{3-7}$ cycloalkyl, —S(O)$_2$—$C_{3-7}$ cycloalkyl, —NR$^a$—S(O)$_2$—$C_{3-7}$ cycloalkyl, —O-(5- to 8-membered heterocycloalkyl), and -5- to 8-membered heterocycloalkyl is substituted with 0 to 2 groups independently selected from the group consisting of $C_{1-4}$ alkyl, halo, and hydroxy.

In some embodiments, the compound of Formula (I) or a pharmaceutically acceptable salt, hydrate, or solvate thereof, is a compound wherein each $R^4$, when present, is independently selected from the group consisting of $C_{1-4}$ alkyl, halo, $C_{1-4}$ haloalkyl, —O—$C_{1-4}$ alkyl, —O—$C_{1-4}$ haloalkyl, CN, —$C_{1-4}$ alkylene-CN, $C_{1-4}$ hydroxyalkyl, —C(O)NR$^a$R$^b$, $C_{3-7}$ cycloalkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 6-membered heterocycloalkyl) having 1-3 heteroatom ring vertices selected from the group consisting of O, N, and S, —S(O)$_2$—$C_{1-4}$ alkyl, and —S(O)$_2$—NR$^a$R$^b$, wherein each cycloalkyl and heterocycloalkyl is substituted with 0 to 2 groups selected from the group consisting of $C_{1-4}$ alkyl, halo, and hydroxy; or alternatively, two $R^4$ groups on the same ring vertex combine to form an oxo (=O).

In some embodiments, the compound of Formula (I) or a pharmaceutically acceptable salt, hydrate, or solvate thereof, is a compound wherein each $R^4$, when present, is independently selected from the group consisting of $C_{1-4}$ alkyl, halo, $C_{1-4}$ haloalkyl, —O—$C_{1-4}$ alkyl, —O—$C_{1-4}$ haloalkyl, CN, —$C_{1-4}$ alkylene-CN, $C_{1-4}$ hydroxyalkyl, —C(O)NR$^a$R$^b$, $C_{3-7}$ cycloalkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 6-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —S(O)$_2$—$C_{1-4}$ alkyl, and —S(O)$_2$—NR$^a$R$^b$, wherein each cycloalkyl and heterocycloalkyl is substituted with 0 to 2 groups selected from the group consisting of $C_{1-4}$ alkyl, halo, and hydroxy; or alternatively, two $R^4$ groups on the same ring vertex combine to form an oxo (=O).

In some embodiments, the compound of Formula (I) or a pharmaceutically acceptable salt, hydrate, or solvate thereof, is a compound wherein each $R^4$, when present, is independently selected from the group consisting of $C_{1-4}$ alkyl, halo, $C_{1-4}$ haloalkyl, —O—$C_{1-4}$ alkyl, —O—$C_{1-4}$ haloalkyl, CN, —$C_{1-4}$ alkylene-CN, $C_{1-4}$ hydroxyalkyl, —C(O)NR$^a$R$^b$, $C_{3-7}$ cycloalkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 6-membered heterocycloalkyl) having 1-3 heteroatom ring vertices selected from the group consisting of O, N, and S, —S(O)$_2$—$C_{1-4}$ alkyl, —S(O)$_2$—NR$^a$R$^b$, wherein each cycloalkyl and heterocycloalkyl is substituted with 0 to 2 groups selected from the group consisting of $C_{1-4}$ alkyl, halo, and hydroxy.

In some embodiments, the compound of Formula (I) or a pharmaceutically acceptable salt, hydrate, or solvate thereof, is a compound wherein each $R^4$, when present, is independently selected from the group consisting of $C_{1-4}$ alkyl, halo, $C_{1-4}$ haloalkyl, —O—$C_{1-4}$ alkyl, —O—$C_{1-4}$ haloalkyl, CN, —$C_{1-4}$ alkylene-CN, $C_{1-4}$ hydroxyalkyl, —C(O)NR$^a$R$^b$, $C_{3-7}$ cycloalkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 6-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —S(O)$_2$—$C_{1-4}$ alkyl, —S(O)$_2$—NR$^a$R$^b$, wherein each cycloalkyl and heterocycloalkyl is substituted with 0 to 2 groups selected from the group consisting of $C_{1-4}$ alkyl, halo, and hydroxy.

In some embodiments, the compound of Formula (I) or a pharmaceutically acceptable salt, hydrate, or solvate thereof, is a compound wherein each $R^4$, when present, is independently selected from the group consisting of methyl, ethyl, fluoro, chloro, difluoromethyl, trifluoromethyl, CN, methoxy, ethoxy, difluoromethoxy, trifluoromethoxy,

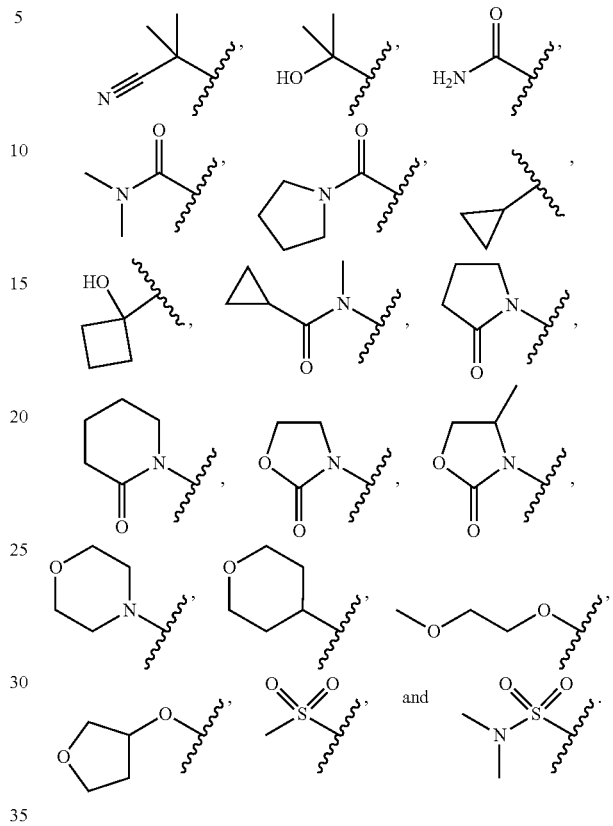

In some embodiments, the compound of Formula (I) or a pharmaceutically acceptable salt, hydrate, or solvate thereof, is a compound wherein each $R^4$, when present, is independently methyl. In some embodiments, the compound of Formula (I) or a pharmaceutically acceptable salt, hydrate, or solvate thereof, is a compound wherein each $R^4$, when present, is independently ethyl. In some embodiments, the compound of Formula (I) or a pharmaceutically acceptable salt, hydrate, or solvate thereof, is a compound wherein each $R^4$, when present, is independently fluoro. In some embodiments, the compound of Formula (I) or a pharmaceutically acceptable salt, hydrate, or solvate thereof, is a compound wherein each $R^4$, when present, is independently chloro. In some embodiments, the compound of Formula (I) or a pharmaceutically acceptable salt, hydrate, or solvate thereof, is a compound wherein each $R^4$, when present, is independently CN.

In some embodiments, the compound of Formula (I) or a pharmaceutically acceptable salt, hydrate, or solvate thereof, is a compound wherein two $R^4$ groups on adjacent ring vertices combine to form a 5- to 6-membered heterocycloalkyl having from 1 to 2 heteroatom ring vertices selected from the group consisting of O, N, and S, wherein the 5- to 6-membered heterocycloalkyl is substituted with 0 to 2 groups independently selected from the group consisting of $C_{1-4}$ alkyl and halo.

In some embodiments, the compound of Formula (I) or a pharmaceutically acceptable salt, hydrate, or solvate thereof, is a compound wherein two $R^4$ groups on adjacent ring vertices combine to form a heterocycloalkyl selected from:

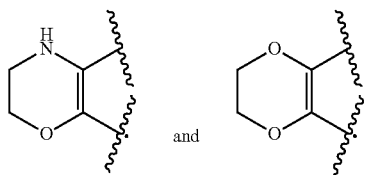

wherein said heterocycloalkyl is substituted with 0 to 2 groups independently selected from the group consisting of $C_{1-4}$ alkyl and halo. In some embodiments, the hyterocycloalkyl is substituted with one $C_{1-4}$ alkyl.

In some embodiments, the compound of Formula (I) or a pharmaceutically acceptable salt, hydrate, or solvate thereof, is a compound wherein A has a formula selected from the group consisting of:

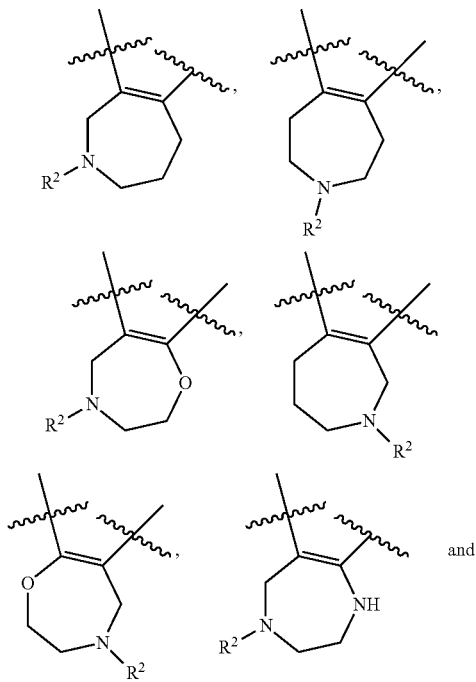

each of which is further substituted with 0 to 2 independently selected $R^2$ groups.

In some embodiments, the compound of Formula (I) or a pharmaceutically acceptable salt, hydrate, or solvate thereof, is a compound wherein A has the formula:

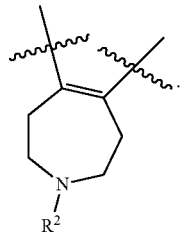

In some embodiments, the compound of Formula (I) or a pharmaceutically acceptable salt, hydrate, or solvate thereof, is a compound wherein the $R^2$, attached to nitrogen is selected from the group consisting of $C_{1-7}$ alkyl, $C_{3-6}$ cycloalkyl, —$Y^1$—O—$C_{1-4}$ alkyl, —$Y^1$—O—$C_{3-7}$ cycloalkyl, —C(O)—$C_{1-7}$ alkyl, —C(O)—$C_{3-7}$ cycloalkyl, 5- to 8-membered heterocycloalkyl, —C(O)—(5- to 8-membered heterocycloalkyl) and —$X^1$-(5- to 8-membered heterocycloalkyl), wherein the heterocycloalkyl has 1-3 heteroatom ring vertices selected from the group consisting of O, N, and S, and wherein cycloalkyl and heterocycloalkyl are substituted with from 0-3 groups independently selected from halo, CN, $C_{1-4}$ alkyl, $C_{1-4}$ haloalkyl, $C_{1-4}$ hydroxyalkyl, —O—$C_{1-4}$ alkyl, and OH.

In some embodiments, the compound of Formula (I) or a pharmaceutically acceptable salt, hydrate, or solvate thereof, is a compound having Formula (Ia):

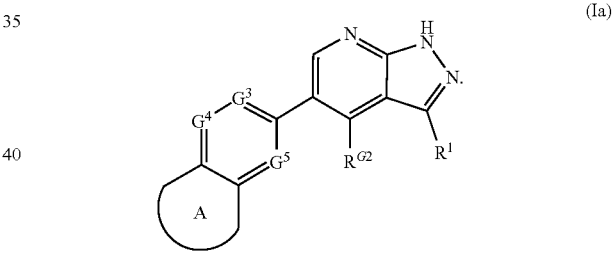

(Ia)

In some embodiments, the compound of Formula (I) or a pharmaceutically acceptable salt, hydrate, or solvate thereof, is a compound having Formula (Ia1):

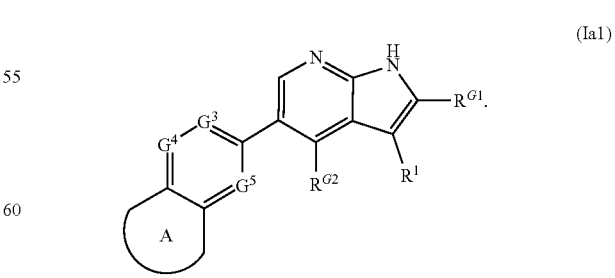

(Ia1)

In some embodiments, the compound of Formula (I) or a pharmaceutically acceptable salt, hydrate, or solvate thereof, is a compound having Formula (Ib):

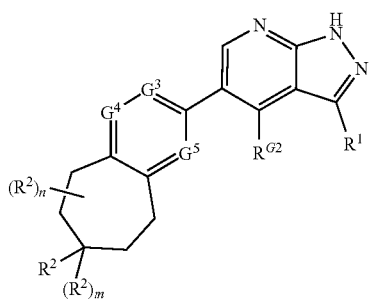
(Ib)

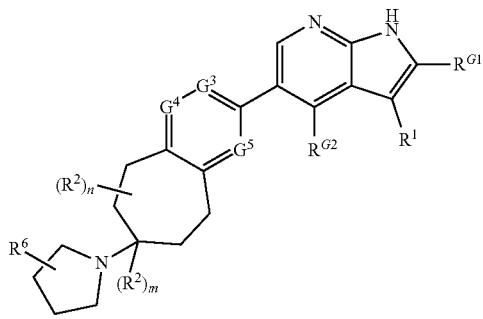
(Ic1)

wherein the subscript m is 0 or 1; and n is 0, 1 or 2, and each $R^2$ can be the same or different.

In some embodiments, the compound of Formula (I) or a pharmaceutically acceptable salt, hydrate, or solvate thereof, is a compound having Formula (Ib1):

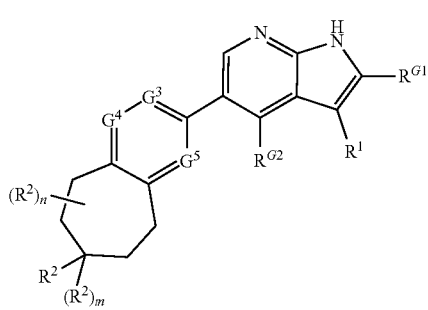
(Ib1)

wherein the subscript m is 0 or 1; and n is 0, 1 or 2, and each $R^2$ can be the same or different.

In some embodiments, the compound of Formula (I) or a pharmaceutically acceptable salt, hydrate, or solvate thereof, is a compound having Formula (Ic):

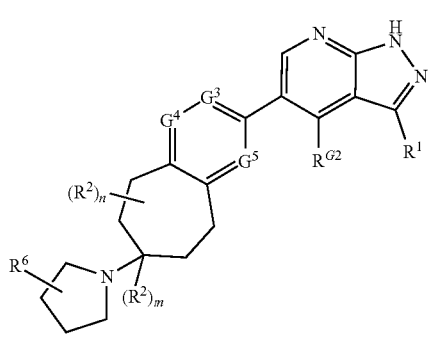
(Ic)

wherein $R^6$ is selected from the group consisting of halo, CN, $C_{1-4}$ alkyl, $C_{1-4}$ haloalkyl, $C_{1-4}$ hydroxyalkyl, —O—$C_{1-4}$ alkyl, oxo and OH.

In some embodiments, the compound of Formula (I) or a pharmaceutically acceptable salt, hydrate, or solvate thereof, is a compound having Formula (Ic1):

wherein $R^6$ is selected from the group consisting of halo, CN, $C_{1-4}$ alkyl, $C_{1-4}$ haloalkyl, $C_{1-4}$ hydroxyalkyl, —O—$C_{1-4}$ alkyl, oxo and OH.

In some embodiments, the compound of Formula (I) or a pharmaceutically acceptable salt, hydrate, or solvate thereof, is a compound having Formula (Id):

(Id)

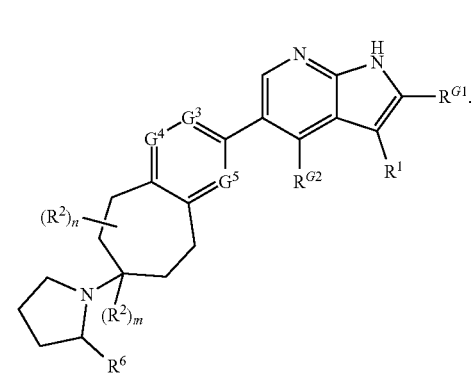

In some embodiments, the compound of Formula (I) or a pharmaceutically acceptable salt, hydrate, or solvate thereof, is a compound having Formula (Id1):

(Id1)

In some embodiments, the compound of Formula (I) or a pharmaceutically acceptable salt, hydrate, or solvate thereof, is a compound having Formula (Ie):

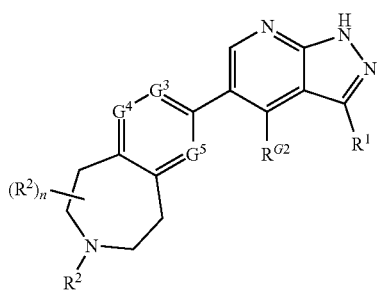

(Ie)

wherein the subscript n is 0, 1 or 2, and each R² can be the same or different.

In some embodiments, the compound of Formula (I) or a pharmaceutically acceptable salt, hydrate, or solvate thereof, is a compound having Formula (Ie1):

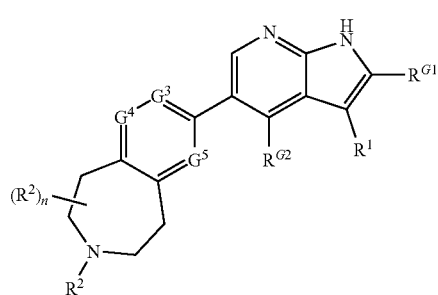

(Ie1)

wherein the subscript n is 0, 1 or 2, and each R² can be the same or different.

In some embodiments, the compound of Formula (I) or a pharmaceutically acceptable salt, hydrate, or solvate thereof, is a compound having Formula (If):

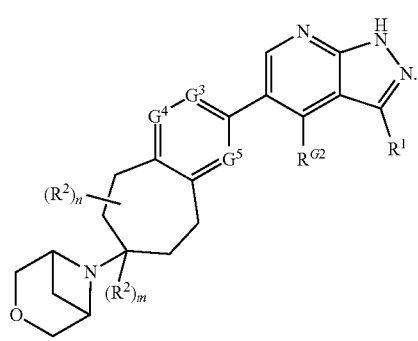

(If)

In some embodiments, the compound of Formula (I) or a pharmaceutically acceptable salt, hydrate, or solvate thereof, is a compound having Formula (If1):

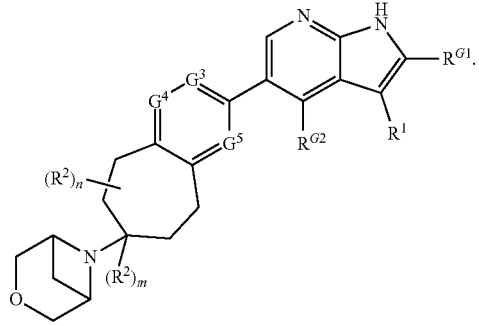

(If1)

In some embodiments, the compound of Formula (I) or a pharmaceutically acceptable salt, hydrate, or solvate thereof, is a compound wherein m is 0.

In some embodiments, the compound of Formula (I) or a pharmaceutically acceptable salt, hydrate, or solvate thereof, is a compound wherein n is 0.

In some embodiments, the compound of Formula (I) or a pharmaceutically acceptable salt, hydrate, or solvate thereof, is a compound having Formula (II):

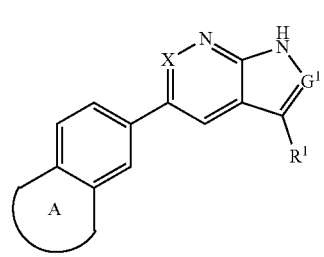

(II)

or a pharmaceutically acceptable salt thereof, wherein:
X is CH or N;
G¹ is N or CH;
A is a fused ring selected from the group consisting of cycloheptane, cyclohexane, and azepane, each of which is substituted with from 1 to 4 R²;
R¹ is selected from the group consisting of phenyl and a 5 to 6-membered heteroaryl having 1-3 heteroatom ring vertices selected from the group consisting of O, N, and S, and wherein each phenyl and heteroaryl is substituted with one $R^{1a}$ and 0-3 R³;
$R^{1a}$ is selected from the group consisting of phenyl and a 5 to 6-membered heteroaryl having 1-3 heteroatom ring vertices selected from the group consisting of O, N, and S, wherein the N atom, when present, is optionally oxidized, and wherein each phenyl and heteroaryl is substituted with 0-4 R⁴;
each R² is independently selected from the group consisting of $C_{1-7}$ alkyl, $C_{3-7}$ cycloalkyl, —Y¹—O—$C_{1-7}$ alkyl, —NR$^a$R$^b$, 5- to 8-membered heterocycloalkyl, and —NR$^a$-(5- to 8-membered heterocycloalkyl), wherein the heterocycloalkyl has 1-3 heteroatom ring vertices selected from the group consisting of O, N, and S, and wherein each cycloalkyl and heterocycloalkyl is substituted with from 0-3 groups independently selected from $C_{1-4}$ alkyl, and —O—$C_{1-4}$ alkyl;
each R³ is independently selected from the group consisting of halo, $C_{1-7}$ alkyl, and —O—$C_{1-7}$ alkyl;

each $R^4$ is independently selected from the group consisting of $C_{1-7}$ alkyl, halo, $C_{1-7}$ haloalkyl, —O—$C_{1-7}$ alkyl, —O—$C_{1-7}$ haloalkyl, CN, —$C_{1-7}$ alkylene-CN, $C_{1-7}$ hydroxyalkyl, —C(O)NR$^a$R$^b$, $C_{3-7}$ cycloalkyl, —NR$^a$—C(O)—$C_{3-7}$ cycloalkyl, —NR$^a$R$^b$, —O—$C_{1-4}$ alkylene-O—$C_{1-4}$ alkyl, —O-(5- to 8-membered heterocycloalkyl) having 1-3 heteroatom ring vertices selected from the group consisting of O, N, and S, -5- to 8-membered heterocycloalkyl having 1-3 heteroatom ring vertices selected from the group consisting of O, N, and S, —S(O)$_2$—$C_{1-7}$ alkyl, and —S(O)$_2$—NR$^a$R$^b$, wherein each cycloalkyl and heterocycloalkyl is substituted with 0 to 2 groups independently selected from the group consisting of $C_{1-4}$ alkyl, and hydroxy;

alternatively, two $R^4$ groups on adjacent ring vertices combine to form a 5- to 6-membered heterocycloalkyl having from 1 to 2 heteroatom ring vertices selected from the group consisting of O, N, and S, wherein the 5- to 6-membered heterocycloalkyl is substituted with 0 to 2 $C_{1-4}$ alkyl;

each $X^1$ is $C_{1-7}$ alkylene;
each $Y^1$ is $C_{2-7}$ alkylene;
each $R^a$ and $R^b$ are independently selected from group consisting of H, $C_{1-7}$ alkyl, $C_{3-7}$ cycloalkyl, wherein said cycloalkyl is optionally substituted with —O—$C_{1-3}$ alkyl; or $R^a$ and $R^b$ together with the nitrogen to which they are attached form a 4- to 8-membered heterocycloalkyl ring having 0-2 additional heteroatom ring vertices selected from the group consisting of O, N, and S, wherein the heterocycloalkyl ring is substituted with 0-3 groups, each group is independently selected from $C_{1-4}$ alkyl, —O—$C_{1-4}$ alkyl, and $X^1$—O—$C_{1-3}$ alkyl; or two groups on the same ring vertex combine to form an oxo (=O).

In some selected embodiments, any one compound described in the examples, or a pharmaceutically acceptable salt, solvate or hydrate thereof is provided. In some embodiments, any one compound described in the examples, or a pharmaceutically acceptable salt thereof is provided. In further embodiments, any one compound described in the examples is provided.

Processes for Preparing the Compounds of the Disclosure

In some aspects, this disclosure is directed to methods for preparing compounds that inhibit the activity of AXL.

In some embodiments, this disclosure is directed to a method comprising:
a) contacting a compound of Formula (A) with a compound of Formula (B) in the presence of a first palladium catalyst to form a compound of Formula (C):

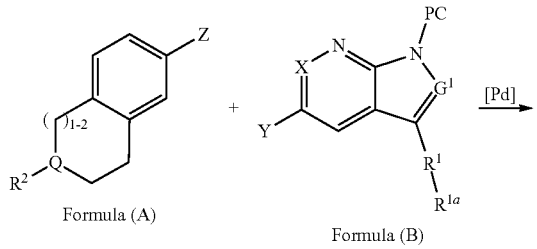

Formula (A)

Formula (B)

and b) contacting the compound of Formula (C) with a deprotecting agent to form a compound of Formula (D):

Formula (C)

Formula (D)

wherein X, $G^1$, $R^1$, $R^{1a}$, and $R^2$ are as defined herein; Q is N, CH, or $CR^2$; PG is a protecting group; and one of Y and Z is Cl, Br, I, or OTf, and the other is a boronate ester.

In another embodiment, this disclosure is directed to a method comprising:
a) contacting a compound of Formula (E) with a compound of Formula (B-2) in the presence of a first palladium catalyst to form a compound of Formula (C):

Formula (E)

Formula (B-2)

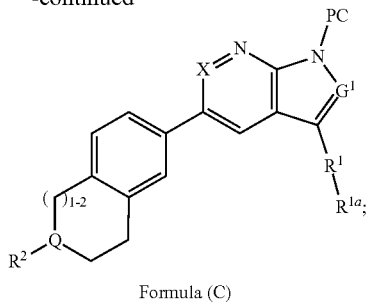

Formula (C)

and
b) contacting the compound of Formula (C) with a deprotecting agent to form a compound of Formula (D):

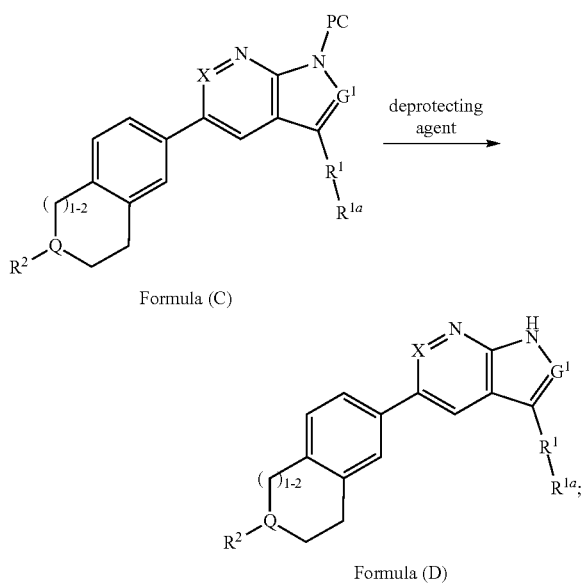

wherein X, $G^1$, $R^1$, $R^{1a}$, and $R^2$ are as defined herein; Q is N, CH, or $CR^2$; PG is a protecting group; and one of Y' and Z' is Cl, Br, I, or OTf, and the other is a boronate ester.

Any suitable boronate ester can be utilized. Exemplary boronate esters include, but are not limited to, pinacolborane (Bpin), catecholborane, and N-methyliminodiacetic acid boronate (MIDA boronate). In some embodiments, the boronate ester is a moiety having the formula —$B(OR^x)_2$, wherein each $R^x$ is H, or $C_1$-$C_3$ alkyl, or two —$OR^x$ groups taken with the boron atom to which they are attached form pinacol borane (Bpin). In one embodiment, the boronate ester is Bpin.

The term "protecting group" refers to a moiety of a compound that masks or alters the properties of a functional moiety. The protecting group can be removed so as to restore the functional moiety to its original state. Chemical protecting groups and strategies for protection/deprotection are well known in the art. See also *Protective Groups in Organic Chemistry*, Peter G. M. Wuts and Theodora W. Greene, 4th Ed., 2006. Protecting groups are often utilized to mask the reactivity of certain functional moieties, to assist in the efficiency of desired chemical reactions, e.g., making and breaking chemical bonds in an ordered and planned fashion. For example, a nitrogen protecting group refers to a protecting group useful for masking nitrogen atoms, e.g., to render amines or nitrogen containing heteroarenes unreactive during intermediate steps. Exemplary nitrogen protecting groups include, but are not limited to, allyloxycarbonyl (Alloc), benzolylcarbonyl (Cbz), benzyl (Bz), allyl (All), 2,2,2-trichloroethoxycarbonyl (Troc), 2-(trimethylsilyl) ethoxycarbonyl (Teoc), trityl (Tr), tetrahydropyranyl ether (THP), and sulfonyl (e.g., mesyl (Ms), tosyl (Ts), nosyl (Ns), trifulyl (Tf), and phenyl sulfone (—$S(O)_2Ph$)) groups. In some embodiments, the protecting group is phenyl sulfone (—$S(O)_2Ph$), tosyl (Ts), trityl (Tr), 2-(trimethylsilyl) ethoxymethyl (SEM), or tetrahydropyranyl ether (THP).

A "deprotecting agent" is a chemical reactant that is capable of effecting removal of a protecting group. The deprotecting agent used will depend on, for example, the identity of the protecting group that is to be removed, and the reactivity of other functional groups present on the molecule. Typical deprotecting agents include reducing agents, oxidizing agents, acids, Lewis acids, bases, fluoride reagents, and enzymes. In general, ether protecting groups can be removed under acidic conditions; alkyl protecting groups can be removed under reductive conditions, or by treatment with a Lewis acid; trityl protecting groups can be removed under acidic conditions, or by treatment with a Lewis acid; acyl protecting groups can be removed under reductive conditions, under basic conditions, or by treatment with an enzyme; and benzyl protecting groups can be removed under reductive conditions, or by treatment with a Lewis acid. Exemplary reducing agents include, but are not limited to, hydrogen, metal hydrides (e.g., diisobutylaluminum hydride (DIBAL), and lithium aluminum hydride (LAH)), or borohydrides (e.g., sodium borohydride). Exemplary bases include, but are not limited to, ammonia, methylamine, sodium methoxide, metal hydroxides (e.g., LiGH, NaOH, and KOH), and the like. Exemplary acids include, but are not limited to HCl, formic acid, acetic acid, trifluoroacetic acid, methanesulfonic acid, and the like. Exemplary Lewis acids include, but are not limited to $ZnCl_2$, ZnBr2, $TiCl_4$, $BF_3$, trimethylsilyl iodide (TMSI), and the like. Exemplary oxidizing agents include, but are not limited to dicyanodichloroquinone (DDQ), triethylenediamine (DABCO), poly(4-vinylpyridinium tribromide), hydrogen peroxide, and the like. Exemplary enzymes include, but are not limited to, ester hydrolases, or lipases.

In some embodiments, the protecting group is —$S(O)_2Ph$, or tosyl (Ts), and the deprotecting agent is a base (e.g., NaOH). In another embodiment, the protecting group is tetrahydropyranyl ether (THP), trityl (Tr), or 2-(trimethylsilyl)ethoxymethyl (SEM), and the deprotecting agent is an acid (e.g., trifluoroacetic acid). In some embodiments, the deprotecting agent further comprises a silane (e.g., triethylsilane or trimethylsilane), or an amine (e.g., $NH_3$, or N,N-dimethylethylenediamine).

Any suitable palladium catalyst may be utilized in the preparation of the compound of Formula (C). Exemplary palladium catalysts that may be used include, but are not limited to, [1,1'-bis(diphenylphosphine)ferrocene]palladium (II) dichloride ($PdCl_2$(dppf)), palladium(II) acetate (Pd$(OAc)_2$), tetrakis(triphenylphosphine) palladium(0) (Pd$(PPh_3)_4$), dichloro(1,5-cyclooctadiene)palladium(II) ((COD)$PdCl_2$), bis[1,2-bis(diphenylphosphino)ethane]palladium(0) (Pd(dppe)$_2$), bis(triphenylphosphine)palladium (II) dichloride ((PPh3)$_2$$PdCl_2$), (2-dicyclohexylphosphino-2',6'-dimethoxybiphenyl) [2-(2'-amino-1,1'-biphenyl)]palladium(II) methanesulfonate (SPhos Pd G3), (2-dicyclohexylphosphino-2',4',6'-triisopropyl-1,1'-biphenyl)[2-(2'-amino-1,1'-biphenyl)]palladium(II) methanesulfonate (XPhos Pd G3), tris(dibenzylideneacetone)dipalladium(0) (Pd$_2$(dba)$_3$), and the like. In one embodiment, the palladium catalyst is PdCl$_2$(dppf).

In some embodiments, the process further comprises contacting the compound of Formula (A) with the compound of Formula (B) in the presence of the first palladium catalyst and a base. Any suitable base made be used. Exemplary bases include, but are not limited to, sodium carbonate, potassium carbonate, potassium acetate, sodium acetate, sodium hydroxide, potassium hydroxide, potassium tert-butoxide, sodium tert-butoxide, and the like. In some embodiments, the base is sodium carbonate, potassium carbonate, or potassium acetate.

In one or more embodiments, the compound of Formula (B) is formed by contacting a compound of Formula (B-1) with a compound of Formula (B-2) in the presence of a second palladium catalyst:

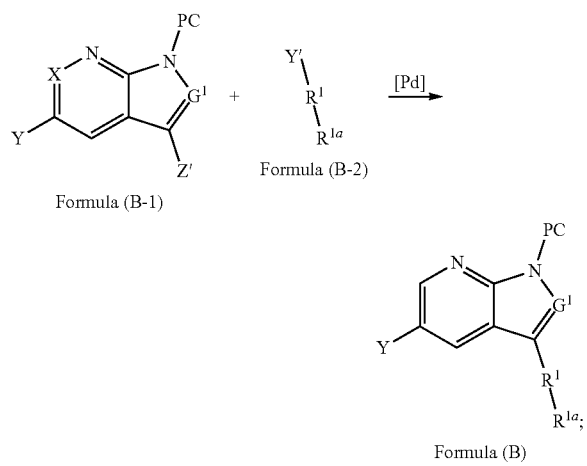

Formula (B-1)

Formula (B-2)

Formula (B)

wherein one of Y' and Z' is Cl, Br, I, or OTf, and the other is a boronate ester; and PG is a protecting group. The remaining variables have the identities described above.

In general, Y, Y' and Z' are selected such that Y' and Z' are better coupling partners than Y' and Y. For example, when Y' is a boronate ester, and each of Y and Z' are Cl, Br, I, or OTf, it is preferable that Z' is more reactive than Y. In some embodiments, Y' is a boronate ester; Z' is I or OTf; and Y is Cl or Br. In one embodiment, Y' is a boronate ester; Z' is I; and Y is Br.

In other embodiments, the compound of Formula (E) is formed by contacting a compound of Formula (A) with a compound of Formula (B-1) in the presence of a second palladium catalyst:

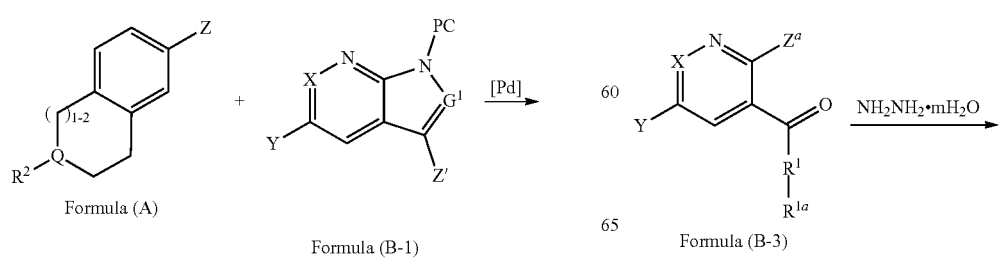

Formula (A)

Formula (B-1)

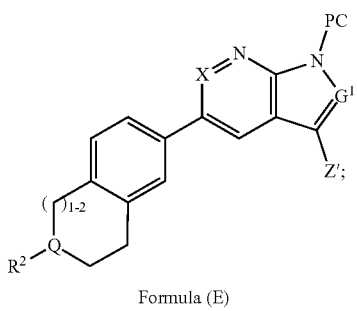

Formula (E)

wherein one of Y and Z is Cl, Br, I, or OTf, and the other is a boronate ester; and PG is a protecting group. The remaining variables have the identities described above.

In general, Y, Z and Z' are selected such that Y and Z are better coupling partners than Z and Z'. For example, when Z is a boronate ester, and each of Y and Z' are Cl, Br, I, or OTf, it is preferable that Y is more reactive than Z'. In some embodiments, Z is a boronate ester, Y is I or OTf, and Z' is Cl or Br. In one embodiment, Z is a boronate ester; Y is I; and Z' is Br.

In one or more embodiments, the boronate ester is a moiety having the formula —B(OR$^x$)$_2$, wherein each R$^x$ is H, or —C$_1$-C$_3$ alkyl, or two —OR$^x$ groups taken with the boron atom to which they are attached form pinacol borane (Bpin). In one embodiment, the boronate ester is Bpin.

Any suitable palladium catalyst may be utilized in the preparation of the compound of Formula (B). Exemplary palladium catalysts that may be used include, but are not limited to, [1,1'-bis(diphenylphosphine)ferrocene]palladium (II) dichloride (PdCl$_2$(dppf)), palladium(II) acetate (Pd (OAc)$_2$), tetrakis(triphenylphosphine) palladium(0) (Pd (PPh$_3$)$_4$), dichloro(1,5-cyclooctadiene)palladium(II) ((COD)PdCl$_2$), bis[1,2-bis(diphenylphosphino)ethane]palladium(0) (Pd(dppe)$_2$), bis(triphenylphosphine)palladium (II) dichloride ((PPh3)$_2$PdCl$_2$), (2-dicyclohexylphosphino-2',6'-dimethoxybiphenyl) [2-(2'-amino-1,1'-biphenyl)] palladium(II) methanesulfonate (SPhos Pd G$^3$), (2-dicyclohexylphosphino-2',4',6'-triisopropyl-1,1'-biphenyl)[2-(2'-amino-1,1'-biphenyl)]palladium(II) methanesulfonate (XPhos Pd G3), tris(dibenzylideneacetone)dipalladium(0) (Pd$_2$(dba)$_3$), and the like. In one embodiment, the palladium catalyst is PdCl$_2$(dppf).

In one or more embodiments, G$^1$ is N. In certain such embodiments, the compound of Formula (B) may be formed by contacting a compound of Formula (B-3) with hydrazine, or a hydrate thereof:

Formula (B-3)

-continued

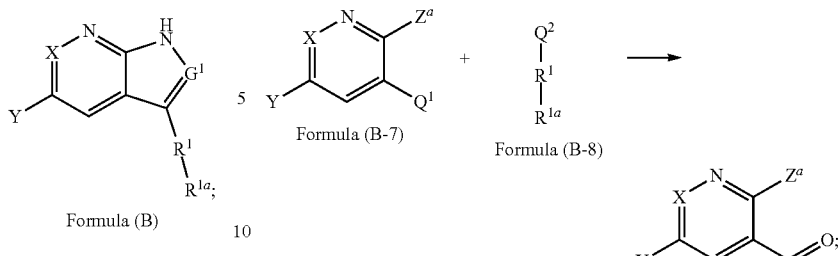

Formula (B)

wherein $Z^a$ is halo; and m is 0 or 1. In some embodiments, $Z^a$ is F. The remaining variables have the identities defined above.

In one or more embodiments, the compound of Formula (B-3) is prepared by:

a) contacting a compound of Formula (B-4) with a lithiation reagent to form a compound of Formula (B-5):

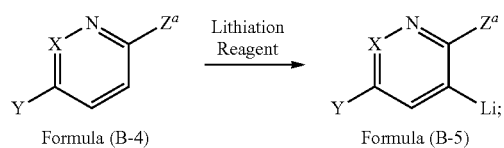

Formula (B-4)  Formula (B-5)

and b) contacting the compound of Formula (B-5) with a compound of Formula (B-6):

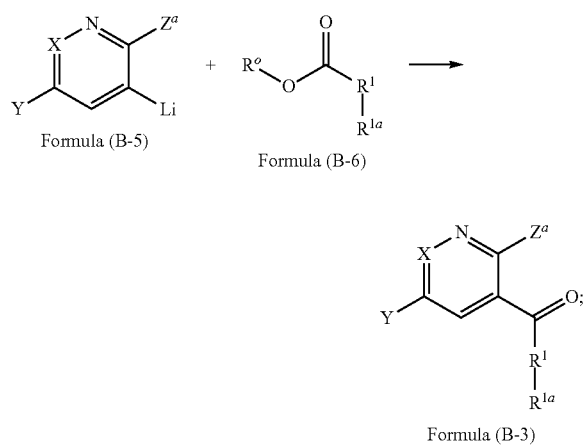

Formula (B-5)  Formula (B-6)

Formula (B-3)

wherein $R^o$ is H or $C_1$-$C_3$ alkyl. The remaining variables have the identities defined above.

Any suitable lithiation reagent may be used. Exemplary lithiation reagents include, but are not limited to, lithium diisopropylamide (LDA), 2,2,6,6-tetramethylpiperidine lithium (LTMP), lithium dicyclohexylamide, lithium dimethylamide, lithium diethylamide, lithium amide, lithium bis(trimethylsilyl)amide, and the like. In some embodiment, the lithiation reagent is LDA.

In further embodiments, the compound of Formula (B-3) is prepared by: contacting a compound of Formula (B-7) with a compound of Formula (B-8):

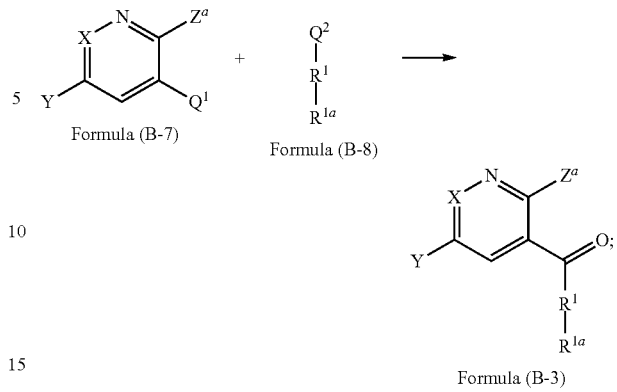

Formula (B-7)  Formula (B-8)

Formula (B-3)

wherein $Q^1$ is halo, —CN, —C(O)OH, —C(O)O—($C_1$-$C_3$ alkyl), —C(O)Cl, or —C(O)N($C_1$-$C_3$ alkyl)-O—($C_1$-$C_3$ alkyl); $Q^2$ is —Li, —Mg-halo, or —B(OR$^x$)$_2$; and each $R^x$ is H, or $C_1$-$C_3$ alkyl, or two —OR$^x$ groups taken with the boron atom to which they are attached form pinacol borane (Bpin). The remaining variables have the identities defined above.

In some embodiments, $Q^1$ is —Cl, —Br, —I, —CN, —C(O)OH, —C(O)OCH$_3$, —C(O)Cl, or —C(O)N(CH$_3$)OCH$_3$. In some embodiments, $Q^2$ is —Li, —MgCl, —MgBr, —B(OH)$_2$, or —Bpin.

In further embodiments, $Q^1$ is —CN, —C(O)OH, —C(O)OCH$_3$, —C(O)Cl, or —C(O)N(CH$_3$)O(CH$_3$), and $Q^2$ is —Li, —MgCl, or —MgBr. In certain embodiments, $Q^1$ is —CN, $Q^2$ is —MgCl or —MgBr, and the process further comprises the addition of water.

In further embodiments, $Q^1$ is —C(O)Cl, $Q^2$ is —B(OR$^x$)$_2$ (e.g., B(OH)$_2$, or —Bpin), and the process further comprises the addition of a palladium catalyst such as those described elsewhere herein.

In still further embodiments, $Q^1$ is halo (e.g., —Cl, —Br, or —I), $Q^2$ is —Li, —MgCl, or —MgBr, and the process further comprises the addition of CO, and a palladium catalyst such as those described elsewhere herein.

For the most efficient preparation of any particular compound of the disclosure, the timing and order of connection of the fragments and modification of the functionality present in any of the fragments may vary and will be dependent on the functionality present. A variety of the methods described above have been used to prepare compounds of this disclosure, and are exemplified in the examples below. Deuterated forms of the below examples can be synthesized using appropriate deuterated intermediates.

Therapeutic and Prophylactic Uses

The present disclosure provides methods for using the compounds described herein in the preparation of a medicament for the inhibition of AXL. As used herein, the terms "inhibit", 'inhibition" and the like refer to the ability of an antagonist to decrease the function or activity of a particular target, e.g., AXL. The decrease is preferably at least a 50% and may be, for example, at least about 55%, at least about 60%, at least about 65%, at least about 70%, at least about 75%, at least about 80%, at least about 85%, at least about 90%, or at least about 95%. The present disclosure also encompasses the use of compounds described herein in the preparation of a medicament for the treatment or prevention of diseases, disorders, and/or conditions that would benefit from inhibition of AXL. As one example, the present disclosure encompasses the use of the compounds described herein in the preparation of a medicament for the treatment of cancer. In another embodiment, the present disclosure encompasses the use of the compounds described herein in the preparation of a medicament for the treatment of fibrotic diseases. In another embodiment, the present disclosure encompasses the use of the compounds described herein in the preparation of a medicament for the treatment of viral infections. In some embodiments of the aforementioned methods, the compounds described herein are used in combination with at least one additional therapy, examples of which are set forth elsewhere herein.

AXL is expressed in cancer, select immune cells, and stromal cells and has been implicated in the development of resistance/relapse to chemotherapy, radiotherapy, targeted therapies, and immunotherapies. Activation of AXL by its ligand, growth arrest specific protein 6 (GAS6), or ligand-independent dimerization facilitates AXL phosphorylation, and initiates signaling cascades that promote cancer cell proliferation, survival, and an immunosuppressive microenvironment. Accordingly, inhibition of AXL is a promising therapeutic strategy to overcome resistance to chemotherapy, radiotherapy, targeted therapy, and/or immunotherapy.

As demonstrated herein, the compounds according to this disclosure potently inhibit AXL. Diseases, disorders, and/or conditions that would benefit from AXL inhibition may include those characterized by overexpression of AXL.

Accordingly, in some embodiments, the compounds described herein are administered to a subject in need thereof in an amount effective to inhibit AXL. AXL inhibition may be assessed measuring soluble AXL (sAXL) levels in plasma or AXL expression, or phospho-AXL (pAXL) levels in a peripheral blood sample or a tissue sample (e.g., a tumor sample) obtained from the subject. Activity may be determined, for example, by comparison to a previous sample obtained from the subject (i.e., prior to administration of the AXL inhibitor), or by comparison to a reference value for a control group (e.g., standard of care, a placebo, etc.).

Alternatively or in addition, in some embodiments, the compounds described herein are administered to a subject in need thereof in an amount effective to inhibit AXL phosphorylation. Inhibition of AXL phosphorylation (pAXL) may be assessed by measuring pAXL expression in a peripheral blood sample or a tissue sample (e.g., a tumor sample) obtained from the subject. Activity may be determined, for example, by comparison to a previous sample obtained from the subject (i.e., prior to administration of the compound according to this disclosure) or by comparison to a reference value for a control group (e.g., standard of care, a placebo, etc.). Inhibition of pAXL may also be assessed by measuring levels of sAXL, GAS6, or other factors in serum or plasma obtained from the subject.

Alternatively or in addition, in some embodiments, the compounds described herein are administered to a subject in need thereof to treat and/or prevent cancer or a cancer-related disease, disorder or condition. In some embodiments, the compounds described herein are administered to a subject in need thereof to treat cancer, optionally in combination with at least one additional therapy, examples of which are set forth elsewhere herein.

Alternatively or in addition, in some embodiments, the compounds described herein are administered to a subject in need thereof to treat and/or prevent a viral infection, as described in further detail below.

Alternatively or in addition, in some embodiments, the compounds described herein are administered to a subject in need thereof to treat and/or prevent a fibrotic disease, disorder or condition, as described in further detail below.

Alternatively or in addition, in some embodiments, the compounds described herein are administered to a subject in need thereof to treat and/or prevent pain, as described in further detail below.

Alternatively or in addition, in some embodiments, the compounds described herein are administered to a subject in need thereof to treat and/or prevent immune-related disease, disorder or condition.

In particular embodiments of the present disclosure, the compounds are used to increase or enhance an immune response to a tumor or a viral infection. In a particular embodiment, at least one antigen or vaccine is administered to a subject in combination with at least one compound of the present disclosure to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one compound of the present disclosure.

Oncology and Oncology-related Disorders. In one or more embodiments, the compounds described herein are useful in the treatment and/or prophylaxis of cancer (e.g., carcinomas, sarcomas, leukemias, lymphomas, myelomas, etc.). In certain embodiments, the cancer may be locally advanced and/or unresectable, metastatic, or at risk of becoming metastatic. Alternatively, or in addition, the cancer may be recurrent or no longer responding to a treatment, such as a standard of care treatment known to one of skill in the art. Exemplary types of cancer contemplated by this disclosure include cancer of the genitourinary tract (e.g., bladder, kidney, renal cell, penile, prostate, testicular, ovary, cervix, uterus, Von Hippel-Lindau disease, etc.), breast, gastrointestinal tract (e.g., esophagus, oropharynx, stomach, small or large intestines, colon, or rectum), bone, bone marrow, skin (e.g., melanoma, squamous cell carcinoma, or basal cell carcinoma), head and neck, liver, gall bladder, bile ducts, heart, lung, pancreas, salivary gland, adrenal gland, thyroid, brain (e.g., gliomas), ganglia, central nervous system (CNS), peripheral nervous system (PNS), the hematopoietic system (i.e., hematological malignancies), and the immune system (e.g., spleen or thymus). In some embodiments, the patient having cancer is determined to have an STK11 mutation.

In some embodiments, the compounds according to this disclosure are useful in the treatment and/or prophylaxis of hematological malignancies. Exemplary types of cancer affecting the hematopoietic system include leukemias, lymphomas and myelomas, including acute myeloid leukemia, adult T-cell leukemia, T-cell large granular lymphocyte leukemia, acute lymphoblastic leukemia, chronic lymphocytic leukemia, chronic myelogenous leukemia, acute monocytic leukemia, Hodgkin's and Non-Hodgkin's lymphoma, Diffuse large B Cell lymphoma, and multiple myeloma. In some embodiments, the hematological malignancy is acute myeloid leukemia.

In another embodiment, the compounds according to this disclosure are useful in the treatment and/or prophylaxis of solid tumors. The solid tumor may be, for example, ovarian cancer, fallopian tube cancer, primary peritoneal cancer, endometrial cancer, breast cancer, lung cancer (small cell or non-small cell), colon cancer, prostate cancer, cervical cancer, biliary cancer, pancreatic cancer, gastric cancer, esophageal cancer, liver cancer (hepatocellular carcinoma), kidney cancer (renal cell carcinoma), head-and-neck tumors, mesothelioma, melanoma, sarcomas, central nervous system (CNS) hemangioblastomas, and brain tumors (e.g., gliomas, such as astrocytoma, oligodendroglioma and glioblastomas).

In some embodiments, the compounds according to this disclosure are useful in the treatment lung cancer (e.g., non-small cell lung cancer (NSCLC)), pancreatic cancer (e.g., pancreatic ductal adenocarcinoma (PDAC)), ovarian cancer (e.g., epithelial ovarian cancer (EOC), high grade serous ovarian cancer (HSOC), or platinum resistant ovarian cancer (PROC)), breast cancer (e.g., triple negative breast cancer (TNBC)), bladder cancer, head and neck cancer (e.g., head and neck squamous cell carcinoma (HNSCC)), kidney cancer (e.g., clear cell renal cell carcinoma (ccRCC)), liver cancer, glioblastoma, mesothelioma, melanoma, or leukemia (e.g., acute myeloid leukemia (AML), or myelodysplastic syndrome). In some embodiments, the cancer is lung cancer, pancreatic cancer, ovarian cancer, breast cancer, head and neck cancer, kidney cancer, leukemia, or myelodysplastic syndrome. In one embodiment, the cancer is NSCLC, PDAC, ccRCC, or AML.

In some embodiments, the compounds according to this disclosure are useful in the treatment of kidney cancer. In further embodiments, the kidney cancer is renal cell carcinoma. In still further embodiments, the renal cell carcinoma is clear cell renal carcinoma (ccRCC).

In some embodiments, the compounds according to this disclosure are useful in the treatment of lung cancer. In further embodiments, the lung cancer is non-small cell lung cancer (NSCLC). In still further embodiments, the NSCLC is lung squamous cell carcinoma or lung adenocarcinoma. In some embodiments the NSCLC is EGFR mutant NSCLC. In some embodiments, the NSCLC is STK11 mutant NSCLC. In some embodiments, the NSCLC has relapsed to therapeutics, including, but not limited to, anti-PD-Li or other immunotherapies, targeted therapy, or chemotherapy. In some embodiments, the lung cancer is squamous cell carcinoma (SCC).

In some embodiments, the compounds according to this disclosure are useful in the treatment of head and neck cancer. In further embodiments, the head and neck cancer is head and neck squamous cell carcinoma (HNSCC). In some embodiments, the HNSCC is relapsed or resistant to radiation, chemotherapy, or immunotherapy.

In some embodiments, the compound according to this disclosure are useful in the treatment of leukemia or myelodysplastic syndrome (MDS). In further embodiments, the leukemia is acute myeloid leukemia (AML). In still further embodiments the AML or MDS is relapsed or refractory AML or MDS. In some embodiments, the AML is FLT-3 mutant AML.

In some embodiments, the compounds according to this disclosure are useful in the treatment of breast cancer. In further embodiments, the breast cancer is hormone receptor positive (e.g., ERα-positive breast cancer, PR-positive breast cancer, ERα-positive and PR-positive breast cancer), HER2 positive breast cancer, HER2 over-expressing breast cancer, or any combination thereof. In still further embodiments, the breast cancer is triple negative breast cancer (TNBC).

In some embodiments, the compounds according to this disclosure are useful in the treatment of pancreatic cancer. In further embodiments, the pancreatic cancer is pancreatic neuroendocrine tumor (PNET) or pancreatic adenocarcinoma (i.e., pancreatic ductal adenocarcinoma (PDAC)).

In some embodiments, the compounds according to this disclosure are useful in the treatment of ovarian cancer. In further embodiments the ovarian cancer is metastatic. In further embodiments, the ovarian cancer is epithelial ovarian cancer (EOC). In some embodiments, the ovarian cancer is high grade serous ovarian cancer (HGSOC). In some embodiments, the ovarian cancer is characterized by a mesenchymal (MES) molecular subtype. In some embodiments, the ovarian cancer is resistant to therapy, including but not limited to platinum- or taxane-based therapies (e.g., platinum-resistant ovarian cancer (PROC)).

In one or more embodiments, the cancer is an oncogene addicted cancer. Oncogene addicted cancers are those that rely on a dominant oncogene for growth and survival, such as, for example, ALK, ABL, AURORA, AKT, PDGFR, KIT, EGFR, VEGFR, FGFR3, FLT-3, MYC, RET, BRAF, PI3K, NF-κB, JAK, STAT, BCL-2, MCL-1, KRAS, HRAS, MEK, ERK, HER-2, HER-3 or MET. In one embodiment, the oncogene is KRAS.

In the aforementioned embodiments, the methods of the present disclosure may be practiced in an adjuvant setting or neoadjuvant setting. The methods described herein may be indicated as a first line, second line, third line, or greater line of treatment.

In some embodiments, the methods of the present disclosure may be indicated as a first line therapy in subjects identified as having a STK11 mutant cancer. In another embodiment, the methods of the present disclosure may be indicated as a second line therapy in subjects identified as having a cancer resistant to therapy (e.g., resistance to chemotherapy, radiation, etc.). In one embodiment, standard therapy is ineffective, intolerable, or considered inappropriate for treatment of the patient's cancer.

The present disclosure also provides methods of treating or preventing other cancer-related diseases, disorders or conditions. The use of the term(s) cancer-related diseases, disorders and conditions is meant to refer broadly to conditions that are associated, directly or indirectly, with cancer and non-cancerous proliferative disease, and includes, e.g., angiogenesis, precancerous conditions such as dysplasia, and non-cancerous proliferative diseases disorders or conditions, such as benign proliferative breast disease and papillomas. For clarity, the term(s) cancer-related disease, disorder and condition do not include cancer per se.

In general, the disclosed methods for treating or preventing cancer, or a cancer-related disease, disorder or condition, in a subject in need thereof comprise administering to the subject a compound disclosed here. In some embodiments, the present disclosure provides methods for treating or preventing cancer, or a cancer-related disease, disorder or condition with a compound disclosed herein and at least one additional therapy, examples of which are set forth elsewhere herein.

Viral Infections. AXL has been found to promote the infection of a wide range of enveloped viruses, including, for example, coronavirus, poxvirus, retrovirus, flavivirus, arenavirus, filovirus, and alphavirus. In particular, enveloped viruses display phosphatidylserine. AXL's ligand, GAS6 bridges envelope phosphatidylserine to cell surface receptor AXL, thereby facilitating entry of the enveloped virus into the cell. For SARS-CoV-2 in particular, AXL is a co-receptor to ACE2, to which the spike protein of the virus attaches, allowing for subsequent entry into the host cell. Further, AXL signaling suppresses viral-induced type I interferon (IFN) responses, resulting in increased viral replication in infected cells, and decreased anti-viral defenses of neighboring cells. Accordingly, inhibition of AXL is a useful strategy to treat viral infections.

In some embodiments, the compounds according to this disclosure are useful in the treatment of a viral infection. In some embodiments, the viral infection is caused by an enveloped virus. Exemplary viral infections include those caused by a coronavirus, poxvirus, retrovirus, flavivirus, arenavirus, filovirus, or alphavirus. In some embodiments, the viral infection is caused by a coronavirus (e.g., MERS-CoV, SARS-CoV, SARS-CoV-2, 229E, NL63, OC43, or HKU1). In some embodiments, the viral infection is caused by a poxvirus (e.g., orthopox, parapox, molluscipox, yatapox, capripox, suipox, leporipox, monkeypox, or avipox). In some embodiments, the viral infection is caused by a retrovirus (e.g., human immunodeficiency virus (HIV), human T-lymphotropic virus type 1 (HTLV-1), or human T-lymphotropic virus type 2 (HTLV-II)). In some embodiments, the viral infection is caused by a flavivirus (e.g., west nile, dengue, tick-borne encephalitis, yellow fever, Zika, classical swine fever, hepatitis C, or Japanese encephalitis). In some embodiments, the viral infection is caused by an arenavirus (e.g., Chapare, Guanarito, Junin, Lassa, Machupo, Sabia, Whitewater Arroyo or Lujo). In some embodiments, the viral infection is caused by a filovirus (e.g., Ebola, Marburg, Cueva, Dianlo, Stria, or Thamno). In some embodiments, the viral infection is caused by an alphavirus (e.g., Aura, Barmah Forest, Bebaru, Caaingua, Cabassou, Chikungunya, Eastern equine encephalitis, Eilat, Everglades, Fort Morgan, Getah, Highlands J, Madariaga, Mayaro, Middelburg, Mosso das Pedras, Mucambo, Ndumu, O'nyong'nyong, Pixuna, Rio Negro, Ross River, Salmon pancreas disease, Semliki Forest, Sindbis, Southern elephant seal, Tonate, Trocara, Una, Venezuelan equine encephalitis, Western equine encephalitis, or Whataroa).

In some embodiments, the compounds according to this disclosure are useful in the treatment of an infection caused by SARS-CoV-2, Ebolavirus, monkeypox, or Zika virus. In some embodiments, the compounds according to this disclosure are useful in the treatment of an infection caused by SARS-CoV-2, Ebolavirus, or Zika virus. In one embodiment, the infection is caused by SARS-CoV-2.

Fibrosis. AXL is expressed on fibroblasts and has been implicated in the activation of myofibroblasts. Activated myofibroblasts are key effector cells associated with fibrosis in multiple organ systems. Accordingly, inhibition of AXL is a promising approach for antifibrotic therapy.

In some embodiments, the compounds according to this disclosure are useful in the treatment of fibrosis. In some embodiments, the fibrosis is renal fibrosis (e.g., chronic kidney disease), intestinal fibrosis (e.g., Chron's disease), liver fibrosis, or lung fibrosis (e.g., asthma, or idiopathic pulmonary fibrosis (IPF)). In some embodiments, the fibrosis is associated with cancer and tumor growth. In some embodiments, the fibrosis is tumor related tissue fibrosis. In some embodiments, the tumor related tissue fibrosis is associated with pancreatic cancer.

In one embodiment, the compounds are useful in the treatment of renal fibrosis. In some embodiments, the renal fibrosis is associated with chronic kidney disease. In further embodiments, the compound is useful in treating renal fibrosis following unilateral ureteral obstruction (UUO). In one embodiment, the renal fibrosis is associated with IgA nephropathy (i.e., Berger's disease).

In some embodiments, the compounds are useful in the treatment of intestinal fibrosis. In one embodiment, the intestinal fibrosis is associated with Chron's disease.

In some embodiments, the compounds are useful in the treatment of liver fibrosis. In some embodiments, the liver fibrosis is associated with chronic liver disease. In one embodiment, the liver fibrosis is associated with non-alcoholic fatty liver disease (NAFLD).

In some embodiments, the compounds are useful in the treatment of lung fibrosis. In some embodiments, the lung fibrosis is associated with chronic lung disease. In further embodiments, the lung fibrosis is idiopathic pulmonary fibrosis (IPF). In another embodiment, the lung fibrosis is associated with asthma.

Pain. AXL is upregulated in injured dorsal root ganglion, and has been implicated in neuropathic pain. Accordingly, inhibition of AXL is a promising strategy for the treatment of pain.

In one embodiment, the compounds according to this disclosure are useful in the treatment of pain. In some embodiment, the pain is neuropathic pain.

Selection of oncology patients. In some instances, the methods according to this disclosure may be provided in selected patients, for example subjects identified as having, e.g., elevated AXL expression, or AXL pathway activation, or having high microsatellite instability or high tumor mutational burden in a relevant tissue or sample. In some embodiments, patients are selected by assessing AXL expression (e.g., soluble AXL (sAXL), cell surface AXL, or total AXL) in a relevant tissue or sample. In some embodiments, patients are selected by assessing phospho-AXL levels. In some embodiments, patients are selected by assessing an AXL gene signature. In some embodiments, patients are selected by further assessing GAS6 expression in a relevant tissue or sample. In some embodiments, the disclosure provides a method of treating cancer in a patient having elevated AXL expression, phospho-AXL levels, or AXL gene signature with a compound as described herein. In one embodiment, the disclosure provides a method of treating cancer in a patient having elevated cell surface AXL expression with a compound as described herein. In another embodiment, the disclosure provides a method of treating cancer in a patient having elevated sAXL expression with a compound as described herein. In another embodiment, the disclosure provides a method of treating cancer in a patient having elevated phospho-AXL levels with a compound as described herein. In another embodiment, the disclosure provides a method of treating cancer in a patient having an elevated AXL gene signature with a compound as described herein. In still another embodiment, the disclosure provides a method of treating cancer in a patient having an elevated ratio of sAXL expression to GAS6 expression with a compound as described herein. In some embodiments, the disclosure provides a method of administering a therapeutically effective amount of an AXL inhibitor to an individual for the treatment of cancer based on a determination of the relative amount of AXL expression. In another embodiment, the disclosure provides a method of administering an effective amount of an AXL inhibitor to an individual for the treatment of cancer based on a determination of the relative amount of cell surface AXL expression. In another embodiment, the disclosure provides a method of administering an effective amount of an AXL inhibitor to an individual for the treatment of cancer based on a determination of the relative amount of sAXL expression or by composite AXL (cAXL) levels. In another embodiment, the disclosure provides a method of administering an effective amount of an AXL inhibitor to an individual for the treatment of cancer based on a determination of the relative amount of phospho-AXL levels. In another embodiment, the disclosure provides a method of administering an effective amount of an AXL inhibitor to an individual for the treatment of cancer based on a determination of the relative strength of an AXL gene signature. In still another embodiment, the disclosure provides a method of administering an effective amount of an AXL inhibitor to an individual for the treatment of cancer based on a determination of the relative ratio of sAXL expression to GAS6 expression. In another embodiment, the disclosure provides a method of administering an effective amount of an AXL inhibitor to a subject for the treatment of cancer based on the determination of the presence of a mutation in, or deletion of STK11. In certain such embodiments, such subjects can be identified by evaluating a suitable sample (e.g., blood or plasma) in a suitable assay (e.g., the Foundation I liquid CDx) by sequencing such as next generation sequencing or by IHC for LKB1 protein detection in the sample. In certain instances, the subject is identified as having an oncogene driven cancer that has a mutation or overexpression in at least one gene associated with cancer, e.g., ALK, ABL, AURORA, AKT, PDGFR, KIT, EGFR, VEGFR, FGFR3, FLT-3, MYC, RET, BRAF, PI3K, NF-κB, JAK, STAT, BCL-2, MCL-1, KRAS, HRAS, MEK, ERK, HER-2, HER-3 or MET. In some embodiments, the subject is identified as having resistance to a prior line of treatment (e.g., chemotherapy, radiation, etc.).

Routes of Administration

In some embodiments, pharmaceutical compositions containing a compound according to this disclosure may be in a form suitable for oral administration. Oral administration may involve swallowing the formulation thereby allowing the compound to be absorbed into the bloodstream in the gastrointestinal tract. Alternatively, oral administration may involve buccal, lingual or sublingual administration, thereby allowing the compound to be absorbed into the blood stream through oral mucosa.

In another embodiment, the pharmaceutical compositions containing a compound according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers. Depot injections, which are generally administered subcutaneously or intramuscularly, may also be utilized to release the compounds disclosed herein over a defined period of time.

Other routes of administration are also contemplated by this disclosure, including, but not limited to, nasal, vaginal, intraocular, rectal, topical (e.g., transdermal), and inhalation.

Particular embodiments of the present disclosure contemplate oral administration or parenteral administration.

Combination Therapy

The present disclosure contemplates the use of the AXL inhibitors described herein alone or in combination with one or more additional therapy. Each additional therapy can be a therapeutic agent or another treatment modality. In embodiments comprising one or more additional therapeutic agents, each agent may target a different, but complementary, mechanism of action. The use of the compounds of this disclosure in combination with one or more additional therapies may have a synergistic therapeutic or prophylactic effect on the underlying disease, disorder, or condition. In addition or alternatively, the combination therapy may allow for a dose reduction of one or more of the therapies, thereby ameliorating, reducing or eliminating adverse effects associated with one or more of the agents.

In embodiments comprising one or more additional treatment modality, the AXL inhibitor can be administered before, after or during treatment with the additional treatment modality. In embodiments comprising one or more additional therapeutic agent, the therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

Cancer Therapies

The present disclosure contemplates the use of the AXL inhibitors described herein in combination with one or more additional therapies useful in the treatment of cancer.

In some embodiments, one or more of the additional therapies is an additional treatment modality. Exemplary treatment modalities include but are not limited to surgical resection of a tumor, bone marrow transplant, radiation therapy, and photodynamic therapy.

In some embodiments, one or more of the additional therapies is a therapeutic agent. Exemplary therapeutic agents include chemotherapeutic agents, radiopharmaceuticals, hormone therapies, epigenetic modulators, ATP-adenosine axis-targeting agents, targeted therapies, signal transduction inhibitors, RAS signaling inhibitors, PI3K inhibitors, arginase inhibitors, HIF inhibitors, PAK4 inhibitors, immunotherapeutic agents, cellular therapies, gene therapies, immune checkpoint inhibitors, and agonists of stimulatory or co-stimulatory immune checkpoints. In one or more embodiments, one or more of the additional therapies is selected from the groups consisting of inhibitors of CD47-SIRPα pathway, kinase inhibitors, inhibitors of HIF, inhibitors of PARP, RAS signaling inhibitors, immune checkpoint inhibitors, agents that target the extracellular production of adenosine, radiation therapy, and chemotherapeutic agents.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising one or more of FOLFOX (folinic acid, fluorouracil, and oxaliplatin), FOLFIRI (e.g., folinic acid, fluorouracil, and irinotecan), a taxoid (e.g., docetaxel, paclitaxel, nab-paclitaxel, etc.), low-dose cytarabine (LDAC), and/or gemcitabine. In one embodiment, combination therapy comprises a chemotherapeutic regimen comprising one or more of FOLFOX (folinic acid, fluorouracil, and oxaliplatin), FOLFIRI (e.g., folinic acid, fluorouracil, and irinotecan), a taxoid (e.g., docetaxel, paclitaxel, nab-paclitaxel, etc.), low-dose cytarabine (LDAC), gemcitabine, and/or platinum based therapies (e.g., cisplatin, carboplatin, and oxaliplatin).

In some embodiments, one or more of the additional therapeutic agents is a radiopharmaceutical. A radiopharmaceutical is a form of internal radiation therapy in which a source of radiation (i.e., one or more radionuclide) is put inside a subject's body. The radiation source can be in solid or liquid form. Non-limiting examples of radiopharmaceuticals include sodium iodide I-131, radium-223 dichloride, lobenguane iodine-131, radioiodinated vesicles (e.g., saposin C-dioleoylphosphatidylserine (SapC-DOPS) nanovesicles), various forms of brachytherapy, and various forms of targeted radionuclides. Targeted radionuclides comprise a radionuclide associated (e.g., by covalent or ionic interactions) with a molecule ("a targeting agent") that specifically binds to a target on a cell, typically a cancer cell or an immune cell. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (i.e., an antigen enriched but not specific to a cancer cell), a tumor-specific antigen (i.e., an antigen with minimal to no expression in normal tissue), or a neo-antigen (i.e., an antigen specific to the genome of a cancer cell generated by non-synonymous mutations in the tumor cell genome). Non-limiting examples of targeted radionuclides include radionuclides attached to: somatostatin or peptide analogs thereof (e.g., 177Lu-Dotatate, etc.); prostate specific membrane antigen or peptide analogs thereof (e.g., 177Lu-PSMA-617, 225Ac-PSMA-617, 177Lu-PSMA-I&T, 177Lu-MIP-1095, etc.); a receptor's cognate ligand, peptide derived from the ligand, or variants thereof (e.g., 188Re-labeled $VEGF_{125-136}$ or variants thereof with higher affinity to VEGF receptor, etc.); antibodies targeting tumor antigens (e.g., 131I-tositumomab, 90Y-ibritumomab tiuxetan, CAM-H2-I131 (Precirix NV), I131-omburtamab, etc.).

In some embodiments, one or more of the additional therapeutic agents is a hormone therapy. Hormone therapies act to regulate or inhibit hormonal action on tumors. Examples of hormone therapies include, but are not limited to: selective estrogen receptor degraders such as fulvestrant, giredestrant, SAR439859, $R^{G6171}$, AZD9833, rintodestrant, ZN-c5, LSZ102, D-0502, LY3484356, SHR9549; selective estrogen receptor modulators such as tamoxifen, raloxifene, 4-hydroxytamoxifen, trioxifene, keoxifene, toremifene; aromatase inhibitors such as anastrozole, exemestane, letrozole and other aromatase inhibiting 4(5)-imidazoles; gonadotropin-releasing hormone agonists such as nafarelin, triptorehin, goserelin: gonadotropin-releasing hormone antagonists such as degarelix: antiandrogens such as abiraterone, enzalutamide, apalutamide, darolutamide, flutamide, nilutamide, bicalutamide, leuprolide; 5α-reductase inhibitors such as finasteride, dutasteride; and the like. In certain embodiments, combination therapy comprises administration of a hormone or related hormonal agent. In one embodiment, combination therapy comprises administration of enzalutamide.

In some embodiments, one or more of the additional therapeutic agents is an epigenetic modulator. An epigenetic modulator alters an epigenetic mechanism controlling gene expression, and may be, for example, an inhibitor or activator of an epigenetic enzyme. Non-limiting examples of epigenetic modulators include DNA methyltransferase (DNMT) inhibitors, hypomethylating agents, and histone deacetylase (HDAC) inhibitors. In one or more embodiments, the AXL inhibitors according to this disclosure are combined with DNA methyltransferase (DNMT) inhibitors or hypomethylating agents. Exemplary DNMT inhibitors include decitabine, zebularine and azacitadine. In one or more embodiments, combinations of the compounds according to this disclosure with a histone deacetylase (HDAC) inhibitor is also contemplated. Exemplary HDAC inhibitors include vorinostat, givinostat, abexinostat, panobinostat, belinostat and trichostatin A.

In some embodiments, one or more of the additional therapeutic agents is an ATP-adenosine axis-targeting agent. ATP-adenosine axis-targeting agents alter signaling mediated by adenine nucleosides and nucleotides (e.g., adenosine, AMP, ADP, ATP), for example by modulating the level of adenosine or targeting adenosine receptors. Adenosine and ATP, acting at different classes of receptors, often have opposite effects on inflammation, cell proliferation and cell death. For instance, ATP and other adenine nucleotides have antitumor effects via activation of the PS2Y1 receptor subtype, while accumulation of adenosine in the tumor microenvironment has been shown to inhibit the antitumor function of various immune cells and to augment the immunosuppressive activity of myeloid and regulatory T cells by binding to cell surface adenosine receptors. In certain embodiments, an ATP-adenosine axis-targeting agent is an inhibitor of an ectonucleotidase involved in the conversion of ATP to adenosine or an antagonist of adenosine receptor. Ectonucleotidases involved in the conversion of ATP to adenosine include the ectonucleoside triphosphate diphosphohydrolase 1 (ENTPD1, also known as CD39 or Cluster of Differentiation 39) and the ecto-5'-nucleotidase (NT5E or 5NT, also known as CD73 or Cluster of Differentiation 73). Exemplary small molecule CD73 inhibitors include CB-708, ORIC-533, LY3475070 and quemliclustat (AB680). Exemplary anti-CD39 and anti-CD73 antibodies include ES002023, TTX-030, IPH-5201, SRF-617, CPI-006, oleclumab (MEDI9447), NZV930, IPH5301, GS-1423, uliledlimab (TJD5, TJ004309), AB598, and BMS-986179. In one embodiment, the present disclosure contemplates combination of the AXL inhibitors described herein with a CD73 inhibitor such as those described in WO 2017/120508, WO 2018/067424, WO 2018/094148, and WO 2020/046813. In further embodiments, the CD73 inhibitor is quemliclustat. Adenosine can bind to and activate four different G-protein coupled receptors: $A_1R$, $A_{2A}R$, $A_{2B}R$, and $A_3R$. $A_2R$ antagonists include etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005. In some embodiments, the present disclosure contemplates the combination of the AXL inhibitors described herein with an $A_{2A}R$ antagonist, an $A_{2B}R$ antagonist, or an antagonist of $A_{2A}R$ and $A_{2B}R$. In some embodiments, the present disclosure contemplates the combination of the compounds described herein with the adenosine receptor antagonists described in WO 2018/136700, WO 2018/204661, WO 2018/213377, or WO 2020/023846. In one embodiment, the adenosine receptor antagonist is etrumadenant.

In some embodiments, one or more of the additional therapeutic agents is a targeted therapy. In one aspect, a targeted therapy may comprise a chemotherapeutic agent, a radionuclide, a hormone therapy, or another small molecule drug attached to a targeting agent. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). Specific examples include but are not limited to patritumab deruxtecan and telisotuzumab vedotin. In other aspects, a targeted therapy may inhibit or interfere with a specific protein that helps a tumor grow and/or spread. Non-limiting examples of such targeted therapies include signal transduction inhibitors, RAS signaling inhibitors, inhibitors of oncogenic transcription factors, activators of oncogenic transcription factor repressors, angiogenesis inhibitors, immunotherapeutic agents, kinase inhibitors, ATP-adenosine axis-targeting agents, PARP inhibitors, PAK4 inhibitors, PI3K inhibitors, HIF-2a inhibitors, CD39 inhibitors, CD73 inhibitors, A2R antagonists, TIGIT antagonists, and PD-1 antagonists. ATP-adenosine axis-targeting agents are described above, while other agents are described in further detail below.

In some embodiments, one or more of the additional therapeutic agents is a signal transduction inhibitor. Signal transduction inhibitors are agents that selectively inhibit one or more steps in a signaling pathway. Signal transduction inhibitors (STIs) contemplated by the present disclosure include but are not limited to: (i) BCR-ABL kinase inhibitors (e.g., imatinib); (ii) epidermal growth factor receptor tyrosine kinase inhibitors (EGFR TKIs), including small molecule inhibitors (e.g., CLN-081, gefitinib, erlotinib, afatinib, icotinib, and osimertinib), and anti-EGFR antibodies; (iii) inhibitors of the human epidermal growth factor (HER) family of transmembrane tyrosine kinases, e.g., HER-2/neu receptor inhibitors (e.g., trastuzumab) and HER-3 receptor inhibitors; (iv) vascular endothelial growth factor receptor (VEGFR) inhibitors including small molecule inhibitors (e.g., axitinib, sunitinib and sorafenib), VEGF kinase inhibitors (e.g., lenvatinib, cabozantinib, pazopanib, tivozanib, XL092, etc.) and anti-VEGF antibodies (e.g., bevacizumab); (v) inhibitors of AKT family kinases or the AKT pathway (e.g., rapamycin); (vi) inhibitors of serine/threonine-protein kinase B-Raf (BRAF), such as, for example, vemurafenib, dabrafenib and encorafenib; (vii) inhibitors of rearranged during transfection (RET), including, for example, selpercatinib and pralsetinib; (viii) tyrosine-protein kinase Met (c-MET) inhibitors (e.g., tepotinib, tivantinib, cabozantinib and crizotinib); (ix) anaplastic lymphoma kinase (ALK) inhibitors (e.g., ensartinib, ceritinib, lorlatinib, crizotinib, and brigatinib); (x) inhibitors of the RAS signaling pathway (e.g., inhibitors of KRAS, HRAS, RAF, MEK, ERK) as described elsewhere herein; (xi) FLT-3 inhibitors (e.g., gilteritinib); (xii) inhibitors of Trop-2, such as, for example, the antibody drug conjugate sacituzumab govitecan-hziy; (xiii) inhibitors of the JAK/STAT pathway, e.g., JAK inhibitors including tofacitinib and ruxolitinib, or STAT inhibitors such as napabucasin; (xiv) inhibitors of NF-κB; (xv) cell cycle kinase inhibitors (e.g., flavopiridol); (xvi) phosphatidyl inositol kinase (PI3K) inhibitors; (xix) protein kinase B (AKT) inhibitors (e.g., capivasertib, miransertib); (xx) platelet-derived growth factor receptor (PDGFR) inhibitors (e.g., imatinib, sunitinib, regorafenib, avapritinib, Lenvatinib, nintedanib, famitinib, ponatinib, axitinib, repretinib, etc.); and (xxi) insulin-like growth factor receptor (IGFR) inhibitors (e.g., erlotinib, afatinib, gefitinib, osimertinib, dacomitinib). In one or more embodiments, the additional therapeutic agent comprises an inhibitor of EGFR, VEGFR, PDGFR, IGFR, HER-2, HER-3, BRAF, RET, MET, ALK, RAS (e.g., KRAS, MEK, ERK), FLT-3, JAK, STAT, NF-κB, PI3K, and/or AKT, or any combinations thereof. In one embodiment, the additional therapeutic agent comprises a kinase inhibitor that inhibits of one or more of EGFR, VEGFR, HER-2, HER-3, BRAF, PDGFR, c-MET, MEK, ERK, ALK, RET, KIT, IGFR, TRK, and/or FGFR. In some embodiments, the additional therapeutic agent comprises a kinase inhibitor that inhibits one or more of EGFR, VEGFR, and/or c-MET.

In some embodiments, one or more of the additional therapeutic agents is an agent that prevents, inhibits, or slows autophagy. Autophagy is increased in various tumor settings, and drives the downregulation of major histocompatibility complex class I molecules (MHC-I) and associated antigen presentation machinery. Downregulation of antigen presentation can reduce the sensitivity of cancer cells to T cell-mediated killing. One strategy of preventing, inhibiting, or slowing autophagy is to target Unc-51 Like Autophagy Activating Kinase 1/2 (ULK1, and/or ULK2). Exemplary inhibitors of ULK1 and/or ULK2 include DC-3116, ERAS-5, and ENV-201. In some embodiments, one or more of the additional therapeutic agents is an inhibitor of ULK1, ULK2, or both ULK1 and ULK2.

In some embodiments, one or more of the additional therapeutic agents is a RAS signaling inhibitor. Oncogenic mutations in the RAS family of genes, e.g., HRAS, KRAS, and NRAS, are associated with a variety of cancers. For example, mutations of G12C, G12D, G12V, $G^{12}A$, $G^{13}D$, Q61H, $G^{13}C$ and $G^{12}S$, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963, everolimus. Direct inhibitors of RAS mutants have also been explored, and generally target the KRAS-GTP complex or the KRAS-GDP complex. Exemplary direct RAS inhibitors under development include, but are not limited to, sotorasib (AMG510), adagrasib (MRTX849), mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments one or more of the additional therapeutic agents is an inhibitor of a phosphatidylinositol 3-kinase (PI3K), particularly an inhibitor of the PI3Kγ and/or the PI3Kδ isoforms. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T cell responses thereby decreasing cancer development and spread. Exemplary PI3Kγ inhibitors include copanlisib, duvelisib, AT-104, ZX-101, tenalisib, eganelisib, SF-1126, AZD3458, and pictilisib. In some embodiments, the AXL inhibitors according to this disclosure are combined with one or more PI3Kγ inhibitors described in WO 2020/0247496A1. Additionally, PI3Kδ is expressed on malignant B cells, and plays a role in promoting B-cell activation, differentiation, proliferation and survival. Exemplary PI3Kδ inhibitors include duvelisib, leniolisib, idelalisib, parsaclisib, copanlisib, umbralisib, zandelisib, eganelisib, linperlisib, pilaralisib, and tenalisib, In some embodiments, one or more of the additional therapeutic agents is an inhibitor of arginase. Arginase has been shown to be either responsible for or participate in inflammation-triggered immune dysfunction, tumor immune escape, immunosuppression and immunopathology of infectious disease. Exemplary arginase compounds include CB-1158 and OAT-1746. In some embodiments, the AXL inhibitors according to this disclosure are combined with one or more arginase inhibitors described in WO/2019/173188 and WO 2020/102646.

In some embodiments, one or more of the additional therapeutic agents is an inhibitor of an oncogenic transcription factor or an activator of an oncogenic transcription factor repressor. Suitable agents may act at the expression level (e.g., RNAi, siRNA, etc.), through physical degradation, at the protein/protein level, at the protein/DNA level, or by binding in an activation/inhibition pocket. Non-limiting examples include inhibitors of one or more subunit of the MLL complex (e.g., HDAC, DOT1L, BRD4, Menin, LEDGF, WDR5, KDM4C (JMJD2C) and PRMT1), inhibitors of hypoxia-inducible factor (HIF) transcription factor, and the like.

In some embodiments, one or more of the additional therapeutic agents is an inhibitor of a hypoxia-inducible factor (HIF) transcription factor, particularly HIF-2α. Exemplary HIF-2α inhibitors include belzutifan, ARO-HIF2, PT-2385, and those described in WO 2021113436 and WO 2021188769. In some embodiments, the compounds according to this disclosure are combined with one or more HIF-2α inhibitors described in WO 2021188769. In one embodiment, the HIF-2α inhibitor is AB521.

In some embodiments, one or more of the additional therapeutic agents is an inhibitor of p21-activated kinase 4 (PAK4). PAK4 overexpression has been shown across a variety of cancer types, notably including those resistant to PD-1 therapies. While no PAK4 inhibitors have been approved, some are in development, and exhibit dual PAK4/NAMPT inhibitor activity, e.g., ATG-019 and KPT-9274. In some embodiments, the compounds according to this disclosure are combined with a PAK4 selective inhibitor. In some embodiments, the compounds according to this disclosure are combined with a PAK4/NAMPT dual inhibitor, e.g., ATG-019 or KPT-9274.

In some embodiments, one or more of the additional therapeutic agents is (i) an agent that inhibits the enzyme poly (ADP-ribose) polymerase (e.g., olaparib, niraparib and rucaparib, etc.); (ii) an inhibitor of the Bcl-2 family of proteins (e.g., venetoclax, navitoclax, etc.); (iii) an inhibitor of MCL-1; (iv) an inhibitor of the CD47-SIRPα pathway (e.g., the anti-CD47 antibody, magrolimab, etc.); (v) an isocitrate dehydrogenase (IDH) inhibitor, e.g., IDH-1 or IDH-2 inhibitor (e.g., ivosidenib, enasidenib, etc.).

In some embodiments, one or more of the additional therapeutic agents is an immunotherapeutic agent. Immunotherapeutic agents treat a disease by stimulating or suppressing the immune system. Immunotherapeutic agents useful in the treatment of cancers typically elicit or amplify an immune response to cancer cells. Non-limiting examples of suitable immunotherapeutic agents include: immunomodulators; cellular immunotherapies; vaccines; gene therapies; ATP-adenosine axis-targeting agents; immune checkpoint modulators; and certain signal transduction inhibitors. ATP-adenosine axis-targeting agents and signal transduction inhibitors are described above. Immunomodulators, cellular immunotherapies, vaccines, gene therapies, and immune checkpoint modulators are described further below.

In some embodiments, one or more of the additional therapeutic agents is an immunotherapeutic agent, more specifically a cytokine or chemokine, such as, IL-1, IL-2, IL-12, IL-18, ELC/CCL19, SLC/CCL21, MCP-1, IL-4, TNF, IL-15, MDC, IFNa/b, M-CSF, IL-3, GM-CSF, IL-13, and anti-IL-10; bacterial lipopolysaccharides (LPS); an organic or inorganic adjuvant that activates antigen-presenting cells and promote the presentation of antigen epitopes on major histocompatibility complex molecules agonists including, but not limited to Toll-like receptor (TLR) agonists, antagonists of the mevalonate pathway, agonists of STING; indoleamine 2,3-dioxygenase 1 (IDO1) inhibitors and immune-stimulatory oligonucleotides, as well as other T cell adjuvants.

In some embodiments, one or more of the additional therapeutic agents is an immunotherapeutic agent, more specifically a cellular therapy. Cellular therapies are a form of treatment in which viable cells are administered to a subject. In certain embodiments, one or more of the additional therapeutic agents is a cellular immunotherapy that activates or suppresses the immune system. Cellular immunotherapies useful in the treatment of cancers typically elicit or amplify an immune response. The cells can be autologous or allogenic immune cells (e.g., monocytes, macrophages, dendritic cells, NK cells, T cells, etc.) collected from one or more subject. Alternatively, the cells can be "(re)programmed" allogenic immune cells produced from immune precursor cells (e.g., lymphoid progenitor cells, myeloid progenitor cells, common dendritic cell precursor cells, stem cells, induced pluripotent stem cells, etc.). In some embodiments, such cells may be an expanded subset of cells with distinct effector functions and/or maturation markers (e.g., adaptive memory NK cells, tumor infiltrating lymphocytes, immature dendritic cells, monocyte-derived dendritic cells, plasmacytoid dendritic cells, conventional dendritic cells (sometimes referred to as classical dendritic cells), M1 macrophages, M2 macrophages, etc.), may be genetically modified to target the cells to a specific antigen and/or enhance the cells' anti-tumor effects (e.g., engineered T cell receptor (TCR) cellular therapies, chimeric antigen receptor (CAR) cellular therapies, lymph node homing of antigen-loaded dendritic cells, etc.), may be engineered to express of have increased expression of a tumor-associated antigen, or may be any combination thereof. Non-limiting types of cellular therapies include CAR-T cell therapy, CAR-NK cell therapy, TCR therapy, and dendritic cell vaccines. Exemplary cellular immunotherapies include sipuleucel-T, tisagenlecleucel, lisocabtagene maraleucel, idecabtagene vicleucel, brexucabtagene autoleucel, and axicabtagene ciloleucel, as well as CTX110, JCAR015, JCAR017, MB-CART19.1, MB-CART20.1, MB-CART2019.1, Uni-CAR02-T-CD123, BMCA-CAR-T, JNJ-68284528, BNT211, and NK-92/5.28.z.

In some embodiments, one or more of the additional therapeutic agents is an immunotherapeutic agent, more specifically a gene therapy. Gene therapies comprise recombinant nucleic acids administered to a subject or to a subject's cells ex vivo in order to modify the expression of an endogenous gene or to result in heterologous expression of a protein (e.g., small interfering RNA (siRNA) agents, double-stranded RNA (dsRNA) agents, micro RNA (miRNA) agents, viral or bacterial gene delivery, etc.), as well as gene editing therapies that may or may not comprise a nucleic acid component (e.g., meganucleases, zinc finger nucleases, TAL nucleases, CRISPR/Cas nucleases, etc.), oncolytic viruses, and the like. Non-limiting examples of gene therapies that may be useful in cancer treatment include Gendicine® (rAd-p53), Oncorine® (rAD5-H101), talimogene laherparepvec, Mx-dnG1, ARO-HIF2 (Arrowhead), quaratusugene ozeplasmid (Immunogene), CTX110 (CRISPR Therapeutics), CTX120 (CRISPR Therapeutics), and CTX130 (CRISPR Therapeutics).

In some embodiments, one or more of the additional therapeutic agent is an immunotherapeutic agent, more specifically an agent that modulates an immune checkpoint. Immune checkpoints are a set of inhibitory and stimulatory pathways that directly affect the function of immune cells (e.g., B cells, T cells, NK cells, etc.). Immune checkpoints engage when proteins on the surface of immune cells recognize and bind to their cognate ligands. The present invention contemplates the use of AXL inhibitors described herein in combination with agonists of stimulatory or co-stimulatory pathways and/or antagonists of inhibitory pathways. Agonists of stimulatory or co-stimulatory pathways and antagonists of inhibitory pathways may have utility as agents to overcome distinct immune suppressive pathways within the tumor microenvironment, inhibit T regulatory cells, reverse/prevent T cell anergy or exhaustion, trigger innate immune activation and/or inflammation at tumor sites, or combinations thereof.

In some embodiments, one or more of the additional therapeutic agents is an immune checkpoint inhibitor. As used herein, the term "immune checkpoint inhibitor" refers to an antagonist of an inhibitory or co-inhibitory immune checkpoint. The terms "immune checkpoint inhibitor", "checkpoint inhibitor" and "CPI" may be used herein interchangeably. Immune checkpoint inhibitors may antagonize an inhibitory or co-inhibitory immune checkpoint by interfering with receptor-ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD1 ligand); BTLA (B and T lymphocyte attenuator); CTLA-4 (cytotoxic T-lymphocyte associated antigen 4); TIM-3 (Tcell immunoglobulin and mucin domain containing protein 3); LAG-3 (lymphocyte activation gene 3); TIGIT (T cell immunoreceptor with Ig and ITIM domains); CD276 (B7-H3), PD-L2, Galectin 9, CEACAM-1, CD69, Galectin-1, CD113, GPR56, VISTA, 2B4, CD48, GARP, PD1H, LAIR1, TIM-1, and TIM-4, and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

In some embodiments, an immune checkpoint inhibitor is a CTLA-4 antagonist. In further embodiments, the CTLA-4 antagonist can be an antagonistic CTLA-4 antibody. Suitable antagonistic CTLA-4 antibodies include, for example, monospecific antibodies such as ipilimumab or tremelimumab, as well as bispecific antibodies such as MEDI5752 and KN046.

In some embodiments, an immune checkpoint inhibitor is a PD-1 antagonist. In further embodiments, the PD-1 antagonist can be an antagonistic PD-1 antibody, small molecule or peptide. Suitable antagonistic PD-1 antibodies include, for example, monospecific antibodies such as balstilimab, budigalimab, camrelizumab, cosibelimab, dostarlimab, cemiplimab, ezabenlimab (BI-754091), MEDI-0680 (AMP-514; WO2012/145493), nivolumab, pembrolizumab, pidilizumab (CT-011), pimivalimab, retifanlimab, sasanlimab, spartalizumab, sintilimab, tislelizumab, toripalimab, and zimberelimab; as well as bi-specific antibodies such as LY3434172. In still further embodiments, the PD-1 antagonist can be a recombinant protein composed of the extracellular domain of PD-L2 (B7-DC) fused to the Fc portion of IgGl (AMP-224). In certain embodiments, an immune checkpoint inhibitor is zimberelimab.

In some embodiments, the immune checkpoint inhibitor is a PD-L1 antagonist. In further embodiments, the PD-L1 antagonist can be an antagonistic PD-L1 antibody. Suitable antagonistic PD-L1 antibodies include, for example, monospecific antibodies such as avelumab, atezolizumab, durvalumab, BMS-936559, and envafolimab as well as bi-specific antibodies such as LY3434172 and KN046.

In some embodiments, an immune checkpoint inhibitor is a TIGIT antagonist. In further embodiments, the TIGIT antagonist can be an antagonistic TIGIT antibody. Suitable antagonistic anti-TIGIT antibodies include monospecific antibodies such as AGEN1327, AB308 (WO2021247591), BMS 986207, COM902, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936. In certain embodiments, an immune checkpoint inhibitor is an antagonistic anti-TIGIT antibody disclosed in WO2017152088 or WO2021247591. In certain embodiments, an immune checkpoint inhibitor is domvanalimab or AB308.

In some embodiments, an immune checkpoint inhibitor is a LAG-3 antagonist. In further embodiments, the LAG-3 antagonist can be an antagonistic LAG-3 antibody. Suitable antagonistic LAG-3 antibodies include, for example, BMS-986016 (WO10/19570, WO14/08218), or IMP-731 or IMP-321 (WO08/132601, WO09/44273).

In certain embodiments, an immune checkpoint inhibitor is a B7-H3 antagonist. In further embodiments, the B7-H3 antagonist is an antagonistic B7-H3 antibody. Suitable antagonist B7-H3 antibodies include, for example, enoblituzumab (MGA271; WO11/109400), omburtumab, DS-7300a, ABBV-155, and SHR-A1811.

In some embodiments, one or more of the additional therapeutic agents activates a stimulatory or co-stimulatory immune checkpoint. Examples of stimulatory or co-stimulatory immune checkpoints (ligands and receptors) include B7-1, B7-2, CD28, 4-1BB (CD137), 4-1BBL, ICOS, ICOS-L, OX40, OX40L, GITR, GITRL, CD70, CD27, CD40, DR3 and CD2.

In some embodiments, an agent that activates a stimulatory or co-stimulatory immune checkpoint is a CD137 (4-1BB) agonist. In further embodiments, the CD137 agonist can be an agonistic CD137 antibody. Suitable CD137 antibodies include, for example, urelumab and utomilumab (PF-05082566; WO12/32433). In some embodiments, an agent that activates a stimulatory or co-stimulatory immune checkpoint is a GITR agonist. In further embodiments, the GITR agonist can be an agonistic GITR antibody. Suitable GITR antibodies include, for example, BMS-986153, BMS-986156, TRX-518 (WO06/105021, WO09/009116) and MK-4166 (WO11/028683). In some embodiments, an agent that activates a stimulatory or co-stimulatory immune checkpoint is an OX40 agonist. In further embodiments, the OX40 agonist can be an agonistic OX40 antibody. Suitable OX40 antibodies include, for example, MEDI-6383, MEDI-6469, MEDI-0562, PF-04518600, GSK3174998, BMS-986178, and MOXR0916. In some embodiments, an agent that activates a stimulatory or co-stimulatory immune checkpoint is a CD40 agonist. In further embodiments, the CD40 agonist can be an agonistic CD40 antibody. In some embodiments, an agent that activates a stimulatory or co-stimulatory immune checkpoint is a CD27 agonist. In further embodiments, the CD27 agonist can be an agonistic CD27 antibody. Suitable CD27 antibodies include, for example, varlilumab.

In some embodiments, one or more of the additional therapeutic agents is an agent that inhibits or depletes immune-suppressive immune cells. For example, to inhibit or deplete immunosuppressive macrophages or monocytes the agent may be CSF-1R antagonists such as CSF-1R antagonist antibodies including $R^{G7155}$ (WO11/70024, WO11/107553, WO11/131407, WO13/87699, WO13/119716, WO13/132044) or FPA-008 (WO11/140249; WO13169264). As another example WO14/036357), ex vivo anti-CD25 bead depletion of Tregs.

In some embodiments, each additional therapeutic agent can independently be a chemotherapeutic agent, a radiopharmaceutical, a hormone therapy, an epigenetic modulator, a targeted agent, an immunotherapeutic agent, a cellular therapy, or a gene therapy. For example, in one embodiment, the present disclosure contemplates the use of the AXL inhibitors described herein in combination with one or more chemotherapeutic agent and optionally one or more additional therapeutic agents, wherein each additional therapeutic agent is independently a radiopharmaceutical, a hormone therapy, a targeted agent, an immunotherapeutic agent, a cellular therapy, or a gene therapy. In another embodiment, the present disclosure contemplates the use of the AXL inhibitors described herein in combination with one or more chemotherapeutic agent and optionally one or more additional therapeutic agents, wherein each additional therapeutic agent is independently a targeted agent, an immunotherapeutic agent, or a cellular therapy. In another embodiment, the present disclosure contemplates the use of the AXL inhibitors described herein in combination with one or more immunotherapeutic agents and optionally one or more additional therapeutic agent, wherein each additional therapeutic agent is independently a radiopharmaceutical, a hormone therapy, a targeted agent, a chemotherapeutic agent, a cellular therapy, or a gene therapy. In another embodiment, the present disclosure contemplates the use of the AXL inhibitors described herein in combination with one or more immunotherapeutic agents and optionally one or more additional therapeutic agents, wherein each additional therapeutic agent is independently a chemotherapeutic agent, a targeted agent, or a cellular therapy. In another embodiment, the present disclosure contemplates the use of the AXL inhibitors described herein in combination with one or more immune checkpoint inhibitors and/or one or more ATP-adenosine axis-targeting agents, and optionally one or more additional therapeutic agents, wherein each additional therapeutic agent is independently a chemotherapeutic agent, a targeted agent, an immunotherapeutic agent, or a cellular therapy. In further embodiments of the above (a) the targeted agent can be a PI3K inhibitor, an arginase inhibitor, a HIF2α inhibitor, an inhibitor of CD47-SIRPα pathway, a kinase inhibitor, a PARP inhibitor, or a PAK4 inhibitor; (b) the kinase inhibitor can inhibit one or more of EGFR, VEGF, HER-2, HER-3, BRAF, PDGFR, MET, MEK, ERK, ALK, RET, KIT, IGFR, TRK, and/or FGFR; (c) the kinase inhibitor can inhibit one or more of EGFR, VEGFR, and/or c-MET; (d) the immunotherapeutic agent is an ATP-adenosine axis-targeting agent or an immune checkpoint inhibitor; (e) the ATP-adenosine axis-targeting agent is an $A2_AR$ and/or $A2_BR$ antagonist, a CD73 inhibitor, or a CD39 inhibitor; (f) the ATP-adenosine axis-targeting agent is etrumadenant, quemliclustat, or AB598; (g) the immunotherapeutic agent is an anti-PD-1 antagonist antibody or an anti-TIGIT antagonist antibody; (h) the immunotherapeutic agent is zimberelimab, domvanalimab, or AB308; or (i) any combination thereof. In still further embodiments of the above, the present disclosure contemplates the use of the AXL inhibitors described herein in combination with domvanalimab, etrumadenant, quemliclustat, zimberelimab, AB308, AB598, AB521, or any combination thereof.

In one or more embodiments, one or more of the additional therapies is selected from the groups consisting of inhibitors of CD47-SIRPα pathway, kinase inhibitors, inhibitors of HIF, inhibitors of PARP, RAS signaling inhibitors, immune checkpoint inhibitors, agents that target the extracellular production of adenosine, radiation therapy, and chemotherapeutic agents. In some embodiments, the inhibitor of the CD47-SIRPα pathway is an anti-CD47 antibody. In some embodiments, the kinase inhibitors inhibit one or more of EGFR, VEGF, HER-2, HER-3, BRAF, PDGFR, MET, MEK, ERK, ALK, RET, KIT, IGFR, TRK, and/or FGFR. In some embodiments, the kinase inhibitor is an inhibitor of EGFR, VEGF, and/or c-MET. In some embodiments, the kinase inhibitor is osimertinib, lenvatinib, axitinib, sunitinib, cabozantinib, XL092, or bevacizumab. In some embodiments, the inhibitors of HIF comprise an inhibitor of HIF-2α. In certain embodiments, the HIF-2α inhibitor is AB521. In some embodiments, the PARP inhibitor is olaparib, rucaparib, or niraparib. In some embodiments, the RAS signaling inhibitor is an inhibitor of KRAS. In some embodiments, the immune checkpoint inhibitor inhibits one or more of PD-1, PD-L1, CTLA-4, LAG-3, TIM-3, and/or TIGIT. In certain embodiments, the immune checkpoint inhibitor inhibits one or more of PD-1, PD-L1, or TIGIT. In some embodiments, the immune checkpoint inhibitor comprises one or more of zimberelimab, domvanalimab, and/or AB308. In some embodiments, the agent that target the extracellular production of adenosine comprise one or more of a CD73 inhibitor, a CD39 inhibitor, an A2AR inhibitor, an $A_{2B}R$ inhibitor, and/or an inhibitor of $A_{2A}R$ and $A_{2B}R$. In certain embodiments, the agent that targets the extracellular production of adenosine comprises one or more of etrumadenant, quemliclustat, and/or AB598. In some embodiments, the chemotherapeutic agent comprises one or more of a platinum-based, taxoid-based, anthracycline-based chemotherapeutic agent, low-dose cytarabine (LDAC), or gemcitabine. In certain embodiments, the chemotherapeutic agent is selected from cisplatin, carboplatin, oxaliplatin, doxorubicin, docetaxel, paclitaxel, nab-paclitaxel, low-dose cytarabine (LDAC), and gemcitabine. In yet another embodiment, the AXL inhibitor described herein is administered with docetaxel. In still another embodiment, the AXL inhibitor is administered with a checkpoint inhibitor. In still another embodiment, the AXL inhibitor is administered in combination with docetaxel and checkpoint inhibitor, for example, zimberelimab.

Selection of the additional therapeutic agent(s) may be informed by current standard of care for a particular cancer and/or mutational status of a subject's cancer and/or stage of disease. Detailed standard of care guidelines are published, for example, by National Comprehensive Cancer Network (NCCN). See, for instance, NCCN Acute Myeloid Leukemia v1.2022, NCCN Squamous Cell Skin Cancer v.2.2022, NCCN Head and Neck Cancers v.2.2022, NCCN Ovarian Cancer/Fallopian Tube Cancer/Primary Peritoneal Cancer v.1.2022, NCCN Pancreatic Adenocarcinoma v.1.2022, NCCN Bladder Cancer v.1.2022, NCCN Malignant Peritoneal Mesothelioma v.1.2022, NCCN Malignant Pleural Mesothelioma v.1.2022, NCCN Melanoma: Cutaneous v.2.2022, NCCN Melanoma: Uveal v2.2022, NCCN Non-Small Cell Lung Cancer v.3.2022, NCCN Kidney Cancer v.4.2022.

Pharmaceutical Compositions

The AXL inhibitors of the present disclosure may be in the form of compositions suitable for administration to a subject. In general, such compositions are pharmaceutical compositions comprising a compound according to this disclosure or a pharmaceutically acceptable salt thereof and one or more pharmaceutically acceptable excipients. In certain embodiments, the AXL inhibitor may be present in an effective amount. The pharmaceutical compositions may be used in the methods of the present disclosure; thus, for example, the pharmaceutical compositions comprising a compound according to this disclosure can be administered to a subject in order to practice the therapeutic and prophylactic methods and uses described herein.

In one or more embodiments, the pharmaceutical composition comprises the AXL inhibitor according to the present disclosure in an amount of between about 10 mg to about 1,000 mg. In one or more embodiments, the pharmaceutical composition comprises the AXL inhibitor according to the present disclosure in an amount of between about 10 mg to about 500 mg. In some embodiments, the AXL inhibitor according to the present disclosure is present in an amount of between about 10 mg to about 300 mg, such as, for example, 10 mg, 15 mg, 20 mg, 25 mg, 30 mg, 35, mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, or 500 mg. In some embodiments, the AXL inhibitor according to the present disclosure is present in an amount of between about 10 mg and about 50 mg. In some embodiments, the AXL inhibitor according to the present disclosure is present in an amount of between about 25 mg to about 75 mg. In some embodiments, the AXL inhibitor according to the present disclosure is present in an amount of between about 25 mg to about 50 mg. In some embodiments, the AXL inhibitor according to the present disclosure is present in an amount of between about 50 mg to about 100 mg. In some embodiments, the AXL inhibitor according to the present disclosure is present in an amount of between about 100 mg to about 200 mg. In some embodiments, the AXL inhibitor according to the present disclosure is present in an amount of between about 100 mg to about 150 mg. In some embodiments, the AXL inhibitor according to the present disclosure is present in an amount of between about 150 mg to about 200 mg. In some embodiments, the AXL inhibitor according to the present disclosure is present in an amount of between about 200 mg to about 300 mg. In some embodiments, the AXL inhibitor according to the present disclosure is present in an amount of between about 200 mg to about 250 mg. In some embodiments, the AXL inhibitor according to the present disclosure is present in an amount of between about 250 mg to about 300 mg. In some embodiments, the AXL inhibitor according to the present disclosure is present in an amount of between about 300 mg to about 400 mg. In some embodiments, the AXL inhibitor according to the present disclosure is present in an amount of between about 300 mg to about 350 mg. In some embodiments, the AXL inhibitor according to the present disclosure is present in an amount of between about 350 mg to about 400 mg. In some embodiments, the AXL inhibitor according to the present disclosure is present in an amount of between about 400 mg to about 500 mg. In some embodiments, the AXL inhibitor according to the present disclosure is present in an amount of between about 400 mg to about 450 mg. In some embodiments, the AXL inhibitor according to the present disclosure is present in an amount of between about 450 mg to about 500 mg.

The pharmaceutical compositions of the present disclosure can be formulated to be compatible with the intended method or route of administration. Routes of administration may include those known in the art. Exemplary routes of administration are oral and parenteral. Furthermore, the pharmaceutical compositions may be used in combination with one or more other therapies described herein in order to treat or prevent the diseases, disorders and conditions as contemplated by the present disclosure. In one embodiment, one or more other therapeutic agents contemplated by this disclosure are included in the same pharmaceutical composition that comprises the AXL inhibitor according to this disclosure. In another embodiment, the one or more other therapeutic agents are in a composition that is separate from the pharmaceutical composition comprising the AXL inhibitor according to this disclosure.

In one aspect, the compounds described herein may be administered orally. Oral administration may be via, for example, capsule or tablets. In making the pharmaceutical compositions that include the compound of Formula (I), or a pharmaceutically acceptable salt thereof, the tablet or capsule typically includes at least one pharmaceutically acceptable excipient. Non-limiting examples of pharmaceutically acceptable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, sterile water, syrup, and methyl cellulose. Additional pharmaceutically acceptable excipients include lubricating agents such as talc, magnesium stearate, and mineral oil; wetting agents; emulsifying and suspending agents; preserving agents such as methyl and propylhydroxy-benzoates.

In another aspect, the compounds described herein may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

The pharmaceutical compositions described herein may be stored in an appropriate sterile container or containers. In some embodiments, the container is designed to maintain stability for the pharmaceutical composition over a given period of time.

Administering

In general, the disclosed methods comprise administering a AXL inhibitor described herein, or a composition thereof, in an effective amount to a subject in need thereof. An "effective amount" with reference to a AXL inhibitor of the present disclosure means an amount of the compound that is sufficient to engage the target (by inhibiting or antagonizing the target) at a level that is indicative of the potency of the compound. For AXL, target engagement can be determined by one or more biochemical or cellular assays resulting in an EC50, ED50, EC90, IC50, or similar value which can be used as one assessment of the potency of the compound. Assays for determining target engagement include, but are not limited to, those described in the Examples. The effective amount may be administered as a single quantity or as multiple, smaller quantities (e.g., as one tablet with "x" amount, as two tablets each with "x/2" amount, etc.).

In some embodiments, the disclosed methods comprise administering a therapeutically effective amount of a compound described herein to a subject in need thereof. As used herein, the phrase "therapeutically effective amount" with reference to AXL means a dose regimen (i.e., amount and interval) of the compound that provides the specific pharmacological effect for which the compound is administered to a subject in need of such treatment. For prophylactic use, a therapeutically effective amount may be effective to eliminate or reduce the risk, lessen the severity, or delay the onset of the disease, including biochemical, histological and/or behavioral signs or symptoms of the disease. For treatment, a therapeutically effective amount may be effective to reduce, ameliorate, or eliminate one or more signs or symptoms associated with a disease, delay disease progression, prolong survival, decrease the dose of other medication(s) required to treat the disease, or a combination thereof. With respect to cancer specifically, a therapeutically effective amount may, for example, result in the killing of cancer cells, reduce cancer cell counts, reduce tumor burden, reduce tumor volume, eliminate tumors or metastasis, or reduce metastatic spread. A therapeutically effective amount may vary based on, for example, one or more of the following: the age and weight of the subject, the subject's overall health, the stage of the subject's disease, the route of administration, and prior or concomitant treatments.

Administration may comprise one or more (e.g., one, two, or three or more) dosing cycles.

In certain embodiments, the AXL inhibitor contemplated by the present disclosure may be administered (e.g., orally, parenterally, etc.) at about 0.01 mg/kg to about 100 mg/kg, or about 0.1 mg/kg to about 50 mg/kg, or about 0.1 mg/kg to about 25 mg/kg, or about 0.1 mg/kg to about 15 mg/kg, or about 0.1 mg/kg to about 10 mg/kg, or about 0.1 mg/kg to about 5 mg/kg of subject's body weight per day, one or more times a day, a week, or a month, to obtain the desired effect. In some embodiments, a suitable weight-based dose of a compound contemplated by the present disclosure is used to determine a dose that is administered independent of a subject's body weight. In certain embodiments, the AXL inhibitors of the present disclosure are administered (e.g., orally, parenterally, etc.) at fixed dosage levels of about 1 mg to about 1000 mg one or more times a day, a week, or a month, to obtain the desired effect. In some embodiments, the AXL inhibitor according to the present disclosure is administered at a fixed dosage level of between about 10 mg to about 500 mg one or more times a day, a week, or a month, to obtain the desired effect. In some embodiments, the AXL inhibitor according to the present disclosure is administered at a fixed dosage level of between about 10 mg to about 300 mg, particularly 10 mg, 15 mg, 20 mg, 25 mg, 30 mg, 35, mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg, one or more times a day, a week, or a month, to obtain the desired effect. In some embodiments, the AXL inhibitor according to the present disclosure is administered in an amount of between about 10 mg and about 50 mg one or more times a day, a week, or a month, to obtain the desired effect. In some embodiments, the AXL inhibitor according to the present disclosure is administered in an amount of between about 25 mg to about 75 mg one or more times a day, a week, or a month, to obtain the desired effect. In some embodiments, the AXL inhibitor according to the present disclosure is administered in an amount of between about 50 mg to about 100 mg one or more times a day, a week, or a month, to obtain the desired effect. In some embodiments, the AXL inhibitor according to the present disclosure is administered in an amount of between about 100 mg to about 200 mg one or more times a day, a week, or a month, to obtain the desired effect. In some embodiments, the AXL inhibitor according to the present disclosure is administered in an amount of between about 100 mg to about 150 mg one or more times a day, a week, or a month, to obtain the desired effect. In some embodiments, the AXL inhibitor according to the present disclosure is administered in an amount of between about 200 mg to about 300 mg one or more times a day, a week, or a month, to obtain the desired effect. In some embodiments, the AXL inhibitor according to the present disclosure is administered in an amount of between about 250 mg to about 300 mg one or more times a day, a week, or a month, to obtain the desired effect.

In some embodiments, the AXL inhibitor according to the present disclosure is administered one or more times a day, a week, or a month to obtain a desired effect. In some embodiments, the AXL inhibitor is administered once or twice a day. In one embodiment, the AXL inhibitor is administered twice daily. In another embodiment, the AXL inhibitor is administered once daily.

In certain embodiments, the AXL inhibitor is contained in a "unit dosage form". The phrase "unit dosage form" refers to physically discrete units, each unit containing a predetermined amount of the AXL inhibitor, either alone or in combination with one or more additional agents, sufficient to produce the desired effect. It will be appreciated that the parameters of a unit dosage form will depend on the particular agent and the effect to be achieved.

EXPERIMENTAL

The following examples are put forth so as to provide those of ordinary skill in the art with a complete disclosure and description of how to make and use the present disclosure, and are not intended to limit the scope of what the inventors regard as their invention. Additional compounds within the scope of this disclosure may be made using methods based on those illustrated in these examples, or based on other methods known in the art. Efforts have been made to ensure accuracy with respect to numbers used (e.g., amounts, temperature, etc.), but some experimental errors and deviations should be accounted for.

All reactions were performed using a Teflon-coated magnetic stir bar at the indicated temperature and were conducted under an inert atmosphere when stated. All chemicals were used as received. Reactions were monitored by TLC (silica gel 60 with fluorescence F254, visualized with a short wave/long wave UV lamp) and/or LCMS (Agilent 1100 or 1200 series LCMS with UV detection at 254 or 220 nm using a binary solvent system [0.1% formic acid in MeCN/0.1% formic acid in H$_2$O] using one of the following columns: Agilent Eclipse Plus C18 [3.5 µm, 4.6 mm i.d.×100 mm], Waters XSelect HSS C18 [3.5 µm, 2.1 mm i.d.×75 mm]). Flash chromatography was conducted on silica gel using an automated system (CombiFlash RF+ manufactured by Teledyne ISCO), with detection wavelengths of 254 and 280 nm, and optionally equipped with an evaporative light scattering detector. Reverse phase preparative HPLC was conducted on an Agilent 1260 or 1290 Infinity series HPLC. Samples were eluted using a binary solvent system (MeCN/H$_2$O with an acid modifier as needed—for example 0.1% TFA or 0.1% formic acid) with gradient elution on a Gemini C18 110 Å column (21.2 mm i.d.×x250 mm) with variable wavelength detection. Final compounds obtained through preparative HPLC were concentrated through lyophilization. All reported yields are isolated yields. All assayed compounds were purified to ≥95% purity as determined by $^1$H NMR or LCMS (Agilent 1100 or 1200 series LCMS with UV detection at 254 or 220 nm using a binary solvent system [0.1% formic acid in MeCN/0.1% formic acid in H$_2$O] using one of the following columns: Agilent Eclipse Plus C18 [3.5 [µm, 4.6 mm i.d.×100 mm], Waters XSelect HSS C18 [3.5 µm, 2.1 mm i.d.×75 mm]). $^1$H NMR spectra were recorded on a Varian 400 MHz NMR spectrometer equipped with an Oxford AS400 magnet or a Bruker AVANCE NEO 400 MHz NMR. Chemical shifts (δ) are reported as parts per million (ppm) relative to residual undeuterated solvent or tetramethylsilane as an internal reference. The abbreviations s, br s, d, t, q, dd, dt, ddd, dddt, and m stand for singlet, broad singlet, doublet, triplet, quartet, doublet of doublets, doublet of triplets, doublet of doublet of doublets, and multiplet, respectively.

Unless indicated otherwise, temperature is in degrees Celsius (° C.), and pressure is at or near atmospheric. Standard abbreviations are used, including the following: rt or r.t.=room temperature; min=minute(s); h or hr=hour(s); t=elapsed time; mg=milligram; g=gram; µl or µL=microliter; ml or mL=milliliter; l or L=liter; mM=millimolar; M=molar; mol=mole; mmol=millimole; aq.=aqueous; calcd=calculated; sat.=saturated; DCM or CH$_2$Cl$_2$=dichloromethane; DCE=1,2-dichloroethane; MTBE=methyl tert-butyl ether; THF=tetrahydrofuran; Et$_2$O=diethylether; EtOAc=ethyl acetate; ACN=acetonitrile; AcOH=acetic acid; TFA=trifluoroacetic acid; NMP=N-methyl-2-pyrrolidone; DMF=N,N-dimethylformamide; DMSO=dimethyl sulfoxide; IPA=isopropanol; EtOH=ethanol; MeOH=methanol; m-CPBA=meta-chloroperoxybenzoic acid; H$_2$=hydrogen gas; N$_2$=nitrogen gas; NH$_3$=ammonia; Cs$_2$CO$_3$=cesium carbonate; NaH=sodium hydride; NaBH(OAc)$_3$=sodium triacetoxyborohydride; NaOH=sodium hydroxide; Na$_2$SO4=sodium sulfate; MgSO4=magnesium sulfate; Na$_2$CO$_3$=sodium carbonate; NaHCO$_3$=sodium bicarbonate; Et$_3$N=triethylamine; MeMgBr=methylmagnesium bromide; LDA=lithium diisopropylamide; DIPEA=N,N-diisopropylethylamine; DMEDA=N,N-dimethylethane-1,2-diamine; SEMC1=2-(trimethylsilyl)ethoxymethyl chloride; HATU=N-[(Dimethylamino)-1H-1,2,3-triazolo-[4,5-b]pyridin-1-ylmethylene]-N-methylmethanaminium hexafluorophosphate N-oxide; EDC=1-ethyl-3-(3-dimethylaminopropyl)carbodiimide; HOBt=hydroxybenzotriazole; NBS=N-bromosuccinimide; KOAc=potassium acetate; K$_3$PO$_4$=potassium phosphate; K$_2$CO$_3$=potassium carbonate; TFA=trifluoroacetic acid; MeI=iodomethane; PdCl$_2$(dppf) or (dppf)PdCl$_2$=[1,1'-bis(diphenylphosphino)ferrocene]palladium(II) dichloride; XPhos Pd G$^3$=(2-Dicyclohexylphosphino-2',4',6'-triisopropyl-1,1'-biphenyl)[2-(2'-amino-1,1'-biphenyl)]palladium(II) methanesulfonate; Xantphos=(9,9-Dimethyl-9H-xanthene-4,5-diyl)bis(diphenylphosphane); Pd$_2$dba$_3$=Tris(dibenzylideneacetone)dipalladium(0); Pd(PPh$_3$)$_4$=tetrakis(triphenylphospine)palladium(0); B2pin2=bis(pinacolato) diboron; MHz=megahertz; Hz=hertz; ppm=parts per million; ESI-MS=electrospray ionization mass spectrometry; NMR=nuclear magnetic resonance.

EXAMPLES

Example 1: 6-[(7S)-2-{3-[4-(3-Methylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

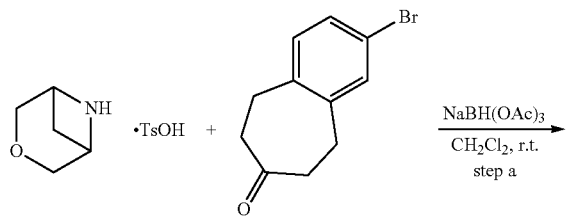

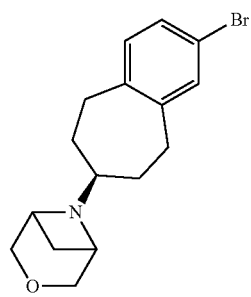

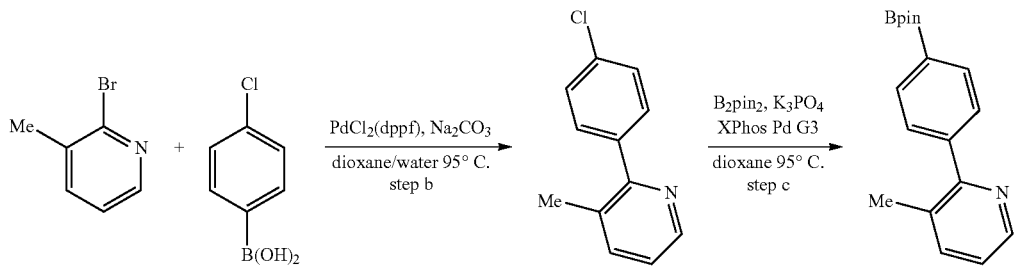

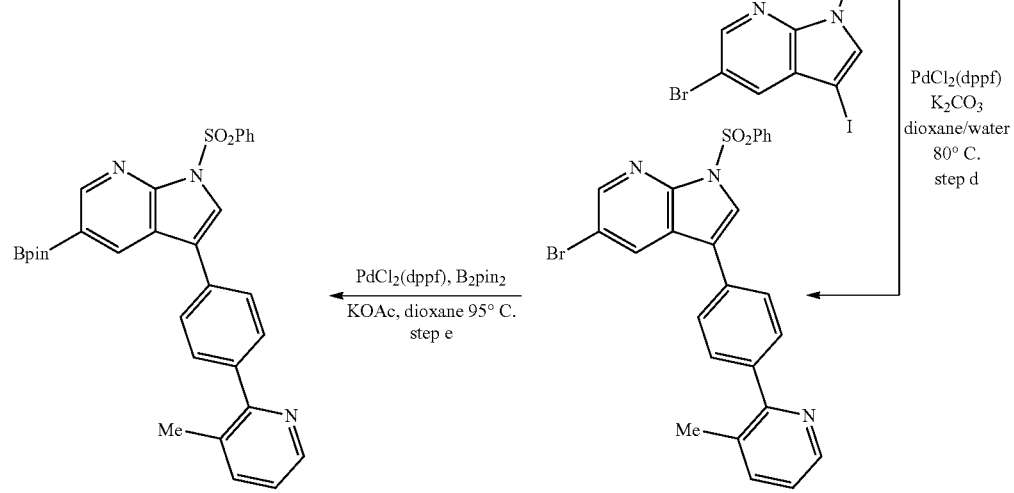

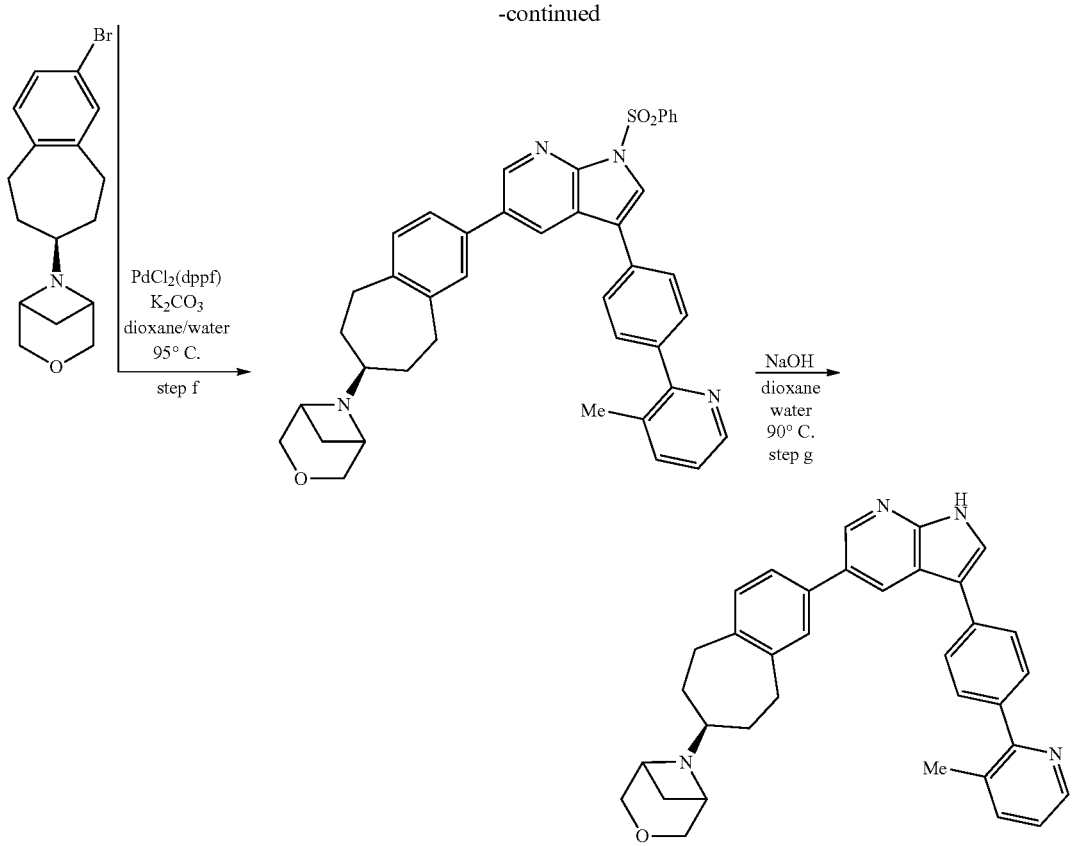

Step a: To a mixture of 3-oxa-6-aza-bicyclo[3.1.1]heptane 4-methylbenzenesulfonic acid (5.00 g, 18.4 mmol) in CH$_2$Cl$_2$ (92 mL) at room temperature was added 2-bromo-5,6,8,9-tetrahydro-benzocyclohepten-7-one (4.63 g, 19.4 mmol) followed by NaBH(OAc)$_3$ (4.69 g, 22.1 mmol). The reaction mixture was then stirred at room temperature for 4 hours. Additional NaBH(OAc)$_3$ (4.69 g each) was added at t=4 hours and t=8 hours. After the final addition, the reaction mixture was stirred at room temperature for an additional 4 hours. The reaction mixture was diluted with CH$_2$Cl$_2$ (250 mL), water (250 mL), and 2 M NaOH$_{(aq)}$ (100 mL, or until pH>12), and agitated. The organic phase was washed with 4:1:1 water:brine:2 M NaOH$_{(aq)}$ (300 mL), dried over Na$_2$SO4, and concentrated. The crude material was purified by silica gel chromatography (hexanes:(EtOAc+1% Et$_3$N) 0 to 100% gradient) to afford the racemic product as a white solid (5.13 g, 86%). The racemic mixture was resolved using chiral HPLC (Daicel CHIRALPAK IA; MeOH/DEA 100/0.1 v/v; 1.0 mL/min; UV 230 nm; 5.3 minutes (desired isomer), 7.0 minutes (other isomer)).

Step b: To a mixture of 2-bromo-3-methylpyridine (2.0 g, 12 mmol), (4-chlorophenyl)boronic acid (1.82 g, 11.6 mmol), and Na$_2$CO$_3$ (2.46 g, 23.2 mmol) was added dioxane (64 mL) and water (14 mL). The suspension was degassed with nitrogen for 10 min and PdCl$_2$(dppf) (425 mg, 0.581 mmol) was added. The reaction mixture was stirred at 95° C. for 16 hours, cooled, diluted with EtOAc (15 mL), dried over MgSO$_4$, filtered through celite, and concentrated. The crude material was purified by silica gel chromatography (hexanes:EtOAc 0 to 100% gradient) to afford the desired product as an off-white solid (2.0 g, 86%).

Step c: To a mixture of the product from step b (2.0 g, 9.8 mmol), B$_2$pin$_2$ (5 g, 20 mmol), and K$_3$PO$_4$ (5.22 g, 24.6 mmol) was added dioxane (100 mL). The suspension was degassed with nitrogen for 10 minutes and XPhos Pd G3 (834 mg, 0.985 mmol) was added. The reaction mixture was stirred at 95° C. for 16 hours, cooled, diluted with EtOAc (15 mL), filtered through celite, and concentrated to afford the desired product which was used crude in step d.

Step d: To a mixture of the product of step c (4.9 mmol), 1-(benzenesulfonyl)-5-bromo-3-iodopyrrolo[2,3-b]pyridine (2.26 g, 4.88 mmol), and K$_2$CO$_3$ (1.35 g, 9.77 mmol) was added dioxane (30 mL) and water (5 mL). The suspension was degassed with nitrogen for 10 minutes and PdCl$_2$(dppf) (180 mg, 0.245 mmol) was added. The reaction mixture was stirred at 80° C. for 4 hours, cooled, diluted with CH$_2$Cl$_2$ (15 mL), dried over MgSO$_4$, filtered through celite, and concentrated. The crude material was purified by silica gel chromatography (hexanes:EtOAc 0 to 100% gradient) to afford the desired product as an off-white solid (1.8 g, 73%, two steps).

Step e: To a mixture of the product from step d (350 mg, 0.694 mmol), B$_2$pin$_2$ (353 mg, 1.39 mmol), and KOAc (136 mg, 1.39 mmol) was added dioxane (7 mL). The suspension was degassed with nitrogen for 10 minutes and PdCl$_2$(dppf) (26 mg, 0.035 mmol) was added. The reaction mixture was stirred at 95° C. for 16 hours, cooled, diluted with EtOAc, filtered through celite and concentrated to afford the desired product which was used crude in step f.

Step f: To a mixture of the product of step e (0.694 mmol), 6-[(7S)-3-bromo-6,7,8,9-tetrahydro-5H-benzo[7]annulen-7-yl]-3-oxa-6-azabicyclo[3.1.1]heptane (222 mg, 0.689 mmol), and K$_2$CO$_3$ (192 mg, 1.39 mmol) was added dioxane (5.8 mL) and water (1.2 mL). The suspension was degassed with nitrogen for 10 minutes and PdCl$_2$(dppf) (26 mg, 0.035 mmol) was added. The reaction mixture was stirred at 95° C. for 3 hours, cooled, diluted with CH$_2$Cl$_2$ (15 mL), dried over MgSO$_4$, filtered through celite, and concentrated. The crude material was purified by silica gel chromatography ((CH$_2$Cl$_2$:MeOH)+1% NH$_{3(aq, 28\% \, wt.)}$ 0 to 10% gradient) to afford the desired product as a white solid (302 mg, 65%, two steps).

Step g: To a solution of the product from step f (280 mg, 0.420 mmol) in dioxane (4 mL) was added 6 M NaOH$_{(aq)}$ (84 mg, 2.1 mmol). The reaction mixture was stirred for 2 hours at 90° C., cooled, diluted with water, and extracted with CH$_2$Cl$_2$ (3×50 mL). The combined organic phases were dried over MgSO$_4$ and concentrated. The crude material was purified by C18 reverse phase chromatography ((water: ACN)+1% TFA 0 to 70% gradient) followed by partial concentration and addition of K$_2$CO$_3$. The mixture was extracted with CH$_2$Cl$_2$ (3×50 mL). The combined organic phases were dried over MgSO$_4$ and concentrated to afford the desired product as a white solid (199 mg, 90%). $^1$H NMR (400 MHz, Chloroform-d) δ 10.78 (s, 1H), 8.61 (d, J=2.0 Hz, 1H), 8.55 (ddd, J=4.7, 1.7, 0.7 Hz, 1H), 8.43 (d, J=2.0 Hz, 1H), 7.79-7.71 (m, 2H), 7.67-7.55 (m, 4H), 7.39 (d, J=6.5 Hz, 2H), 7.22-7.15 (m, 2H), 4.30 (d, J=10.8 Hz, 2H), 3.74 (d, J=10.8 Hz, 2H), 3.70 (d, J=6.0 Hz, 2H), 3.27 (dd, J=11.1, 7.8 Hz, 1H), 2.97 (m, 2H), 2.83 (q, J=12.9 Hz, 2H), 2.65-2.56 (m, 1H), 2.43 (s, 3H), 1.93 (d, J=8.1 Hz, 2H), 1.85 (d, J=8.4 Hz, 1H), 1.37 (m, 2H). ESI MS [M+H]$^+$ for C$_{35}$H$_{35}$N$_4$O, calcd. 527.3, found 527.3.

Example 2: 6-[(7S)-2-{3-[4-(3-Methylpyridin-2-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

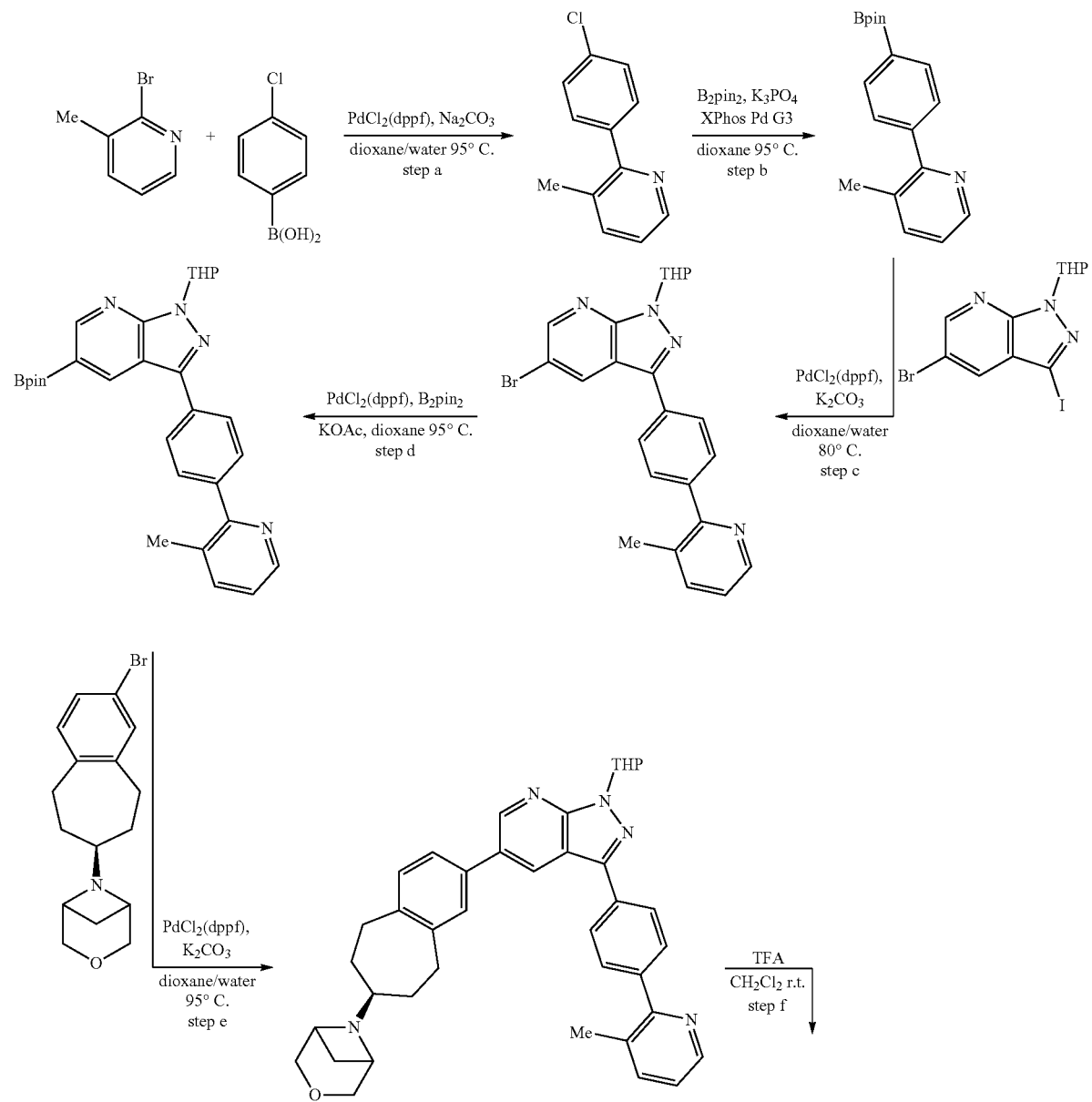

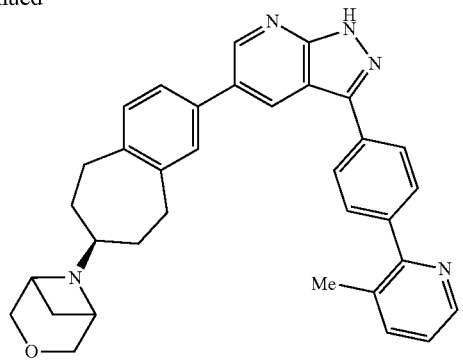

Steps a and b: The compound formed from step b was prepared in a similar manner to that described for steps b and c of example 1.

Step c: To a mixture of the product from step b (4.9 mmol), 5-bromo-3-iodo-1-(oxan-2-yl)pyrazolo[3,4-b]pyridine (2.0 g, 4.9 mmol), and $K_2CO_3$ (1.35 g, 9.8 mmol) was added dioxane (30 mL) and water (5 mL). The suspension was degassed with nitrogen for 10 minutes and $PdCl_2(dppf)$ (180 mg, 0.245 mmol) was added. The reaction mixture was stirred at 80° C. for 4 hours, cooled, diluted with $CH_2Cl_2$ (15 mL), dried over $MgSO_4$, filtered through celite, and concentrated. The crude material was purified by silica gel chromatography (hexanes:EtOAc 0 to 100% gradient) to afford the desired product as an off-white solid (1.5 g, 68%, two steps).

Step d: To a mixture of the product from step c (250 mg, 0.556 mmol), $B_2pin_2$ (283 mg, 1.11 mmol), and KOAc (110 mg, 1.11 mmol) was added dioxane (6 mL). The suspension was degassed with nitrogen for 10 minutes and $PdCl_2(dppf)$ (20 mg, 0.027 mmol) was added. The reaction mixture was stirred at 95° C. for 16 hours, cooled, diluted with EtOAc (10 mL), filtered through celite, and concentrated to afford the desired product which was used crude in step c. Step e: To a mixture of the product from step d (0.556 mmol), 6-[(7S)-3-bromo-6,7,8,9-tetrahydro-5H-benzo[7]annulen-7-yl]-3-oxa-6-azabicyclo[3.1.1]heptane (177 mg, 0.549 mmol), and $K_2CO_3$ (153 mg, 1.11 mmol) was added dioxane (5 mL) and water (1 mL). The suspension was degassed with nitrogen for 10 minutes and $PdCl_2(dppf)$ (20 mg, 0.027 mmol) was added. The reaction mixture was stirred at 95° C. for 3 hours, cooled, diluted with $CH_2Cl_2$ (15 mL), dried over $MgSO_4$, filtered through celite, and concentrated. The crude material was purified by silica gel chromatography $((CH_2Cl_2:MeOH)+1\% NH_{3(aq, 28\% wt.)}$ 0 to 10% gradient) to afford the desired product as a white solid (218 mg, 65%, two steps).

Step f: To a solution of the product from step e (200 mg, 0.327 mmol) in $CH_2Cl_2$ (4 mL) was added TFA (2 mL). The reaction mixture was stirred at room temperature for 16 hours and concentrated. The crude material was purified by C18 reverse phase chromatography ((water:ACN)+1% TFA 0 to 70% gradient) followed by partial concentration and addition of $K_2CO_3$. The mixture was extracted with $CH_2Cl_2$ (3×50 mL). The combined organic phases were dried over $MgSO_4$ and concentrated to afford the desired product as a white solid (152 mg, 88%). $^1$H NMR (400 MHz, Chloroform-d) δ 12.87 (s, 1H), 8.85 (d, J=2.1 Hz, 1H), 8.55 (ddd, J=4.8, 1.7, 0.7 Hz, 1H), 8.51 (d, J=2.1 Hz, 1H), 8.12-8.04 (m, 2H), 7.74-7.66 (m, 2H), 7.60 (ddt, J=7.7, 1.8, 0.8 Hz, 1H), 7.38 (d, J=6.3 Hz, 2H), 7.24-7.17 (m, 2H), 4.31 (d, J=10.7 Hz, 2H), 3.73 (d, J=10.7 Hz, 2H), 3.67 (d, J=6.1 Hz, 2H), 3.31-3.21 (m, 1H), 3.04-2.91 (m, 2H), 2.85 (q, J=12.2 Hz, 2H), 2.56 (q, J=6.7 Hz, 1H), 2.42 (s, 3H), 1.96 (d, J=12.2 Hz, 2H), 1.84 (d, J=8.3 Hz, 1H), 1.37 (q, J=11.3 Hz, 2H). ESI MS [M+H]$^+$ for $C_{34}H_{34}N_5O$, calcd. 528.3, found 528.2.

Example 3: 6-[(7S)-2-(3-{4-[3-(2-Methoxyethoxy) pyridin-2-yl]phenyl}-1H-pyrrolo[2,3-b]pyridin-5-yl)-6,7,8,9-tetrahydro-5H-benzo[7]annulen-7-yl]-3-oxa-6-azabicyclo[3.1.1]heptane

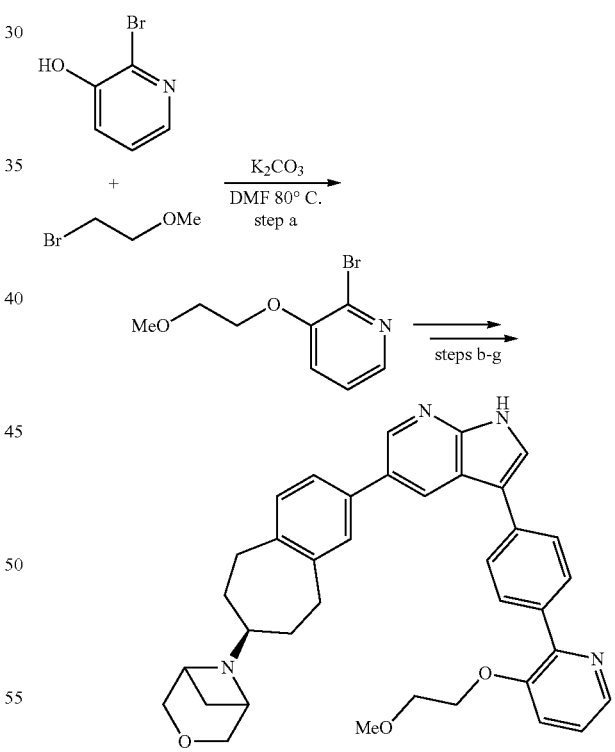

Step a: To a solution of 2-bromopyridin-3-ol (2.0 g, 11 mmol) in DMF (25 mL) at room temperature was added $K_2CO_3$ (3.17 g, 22.9 mmol) and 1-bromo-2-methoxyethane (2.4 g, 17 mmol). The reaction mixture was stirred at 80° C. for 16 hours, cooled, diluted with MTBE, filtered through celite, washed with water twice, dried over $MgSO_4$, and concentrated to afford the desired product which was used in the next step without any further purification (11 mmol assumed).

Steps b-g: The title compound was prepared in a similar manner to example 1 using steps b-g. $^1$H NMR (400 MHz, Chloroform-d) δ 10.55 (d, J=2.4 Hz, 1H), 8.61 (d, J=2.0 Hz, 1H), 8.44 (d, J=2.0 Hz, 1H), 8.34 (dd, J=4.6, 1.4 Hz, 1H), 8.15-8.07 (m, 2H), 7.79-7.70 (m, 2H), 7.61 (d, J=2.4 Hz, 1H), 7.39 (dq, J=3.4, 2.0 Hz, 2H), 7.32 (dd, J=8.3, 1.4 Hz, 1H), 7.23-7.18 (m, 2H), 4.30 (d, J=10.7 Hz, 2H), 4.22-4.15 (m, 2H), 3.81-3.68 (m, 4H), 3.65 (d, J=6.1 Hz, 2H), 3.43 (s, 3H), 3.24 (d, J=9.8 Hz, 1H), 2.98 (m, 2H), 2.84 (q, J=13.1 Hz, 2H), 2.56 (q, J=6.8 Hz, 1H), 1.98 (d, J=5.0 Hz, 2H), 1.83 (d, J=8.3 Hz, 1H), 1.34 (p, J=10.0 Hz, 2H). ESI MS [M+H]$^+$ for $C_{37}H_{39}N_4O_3$, calcd. 587.3, found 587.3.

Example 4: 6-[(7S)-2-(3-{4-[3-(Pyrrolidine-1-carbonyl)pyridin-2-yl]phenyl}-1H-pyrazolo[3,4-b]pyridin-5-yl)-6,7,8,9-tetrahydro-5H-benzo[7]annulen-7-yl]-3-oxa-6-azabicyclo[3.1.1]heptane

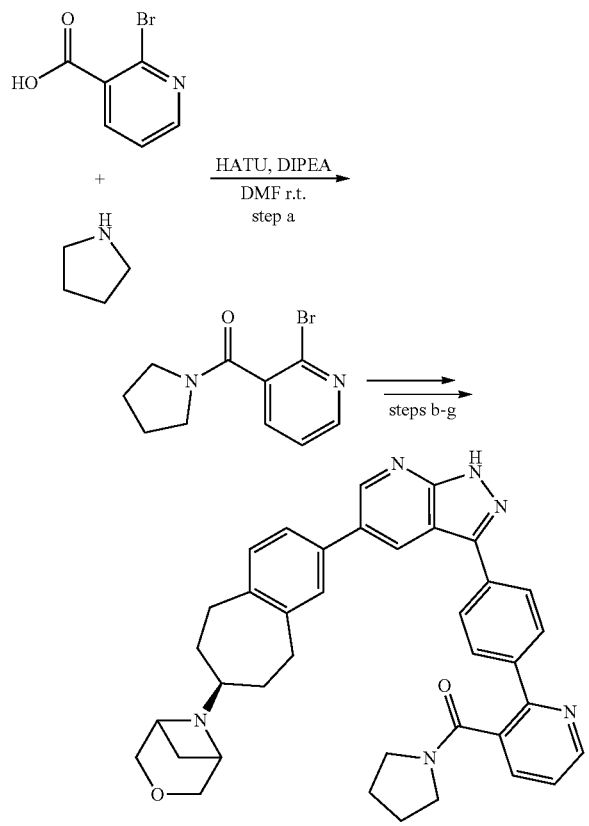

Step a: To a stirred solution of 2-bromopyridine-3-carboxylic acid (1.0 g, 5.0 mmol) in DMF (10 mL) at room temperature was added HATU (2.48 g, 6.52 mmol), diisopropylethylamine (1.3 mL, 7.5 mmol), and pyrrolidine (0.45 mL, 5.5 mmol). The reaction mixture was stirred at room temperature for 16 hours, diluted with water (50 mL), and extracted with EtOAc (3×50 mL). The combined organic phases were dried over MgSO$_4$ and concentrated. The crude material was purified by silica gel chromatography (hexanes:EtOAc 0 to 100% gradient) to afford the desired product as a white solid (755 mg, 60%).

Steps b-g: The title compound was prepared in a similar manner to example 2. $^1$H NMR (400 MHz, Chloroform-d) δ 12.15 (s, 1H), 8.85 (d, J=2.0 Hz, 1H), 8.76 (dd, J=4.8, 1.7 Hz, 1H), 8.51 (d, J=2.0 Hz, 1H), 8.15-8.07 (m, 2H), 8.01- 7.93 (m, 2H), 7.80 (dd, J=7.7, 1.7 Hz, 1H), 7.43-7.30 (m, 3H), 7.24 (m, 1H), 4.34-4.26 (m, 2H), 3.73 (d, J=10.7 Hz, 2H), 3.65 (d, J=6.1 Hz, 2H), 3.51 (bs, 1H), 3.31-3.22 (m, 1H), 3.07-2.73 (m, 5H), 2.57 (q, J=6.7 Hz, 1H), 1.96 (d, J=11.6 Hz, 2H), 1.84 (d, J=8.3 Hz, 1H), 1.79-1.63 (m, 5H), 1.54 (bs, 1H), 1.36 (d, J=12.3 Hz, 2H). ESI MS [M+H]$^+$ for $C_{38}H_{39}N_6O_2$, calcd. 611.3, found 611.3.

Example 5: 6-[(7S)-2-(3-{4-[3-(Morpholin-4-yl)pyridin-2-yl]phenyl}-1H-pyrrolo[2,3-b]pyridin-5-yl)-6,7,8,9-tetrahydro-5H-benzo[7]annulen-7-yl]-3-oxa-6-azabicyclo[3.1.1]heptane

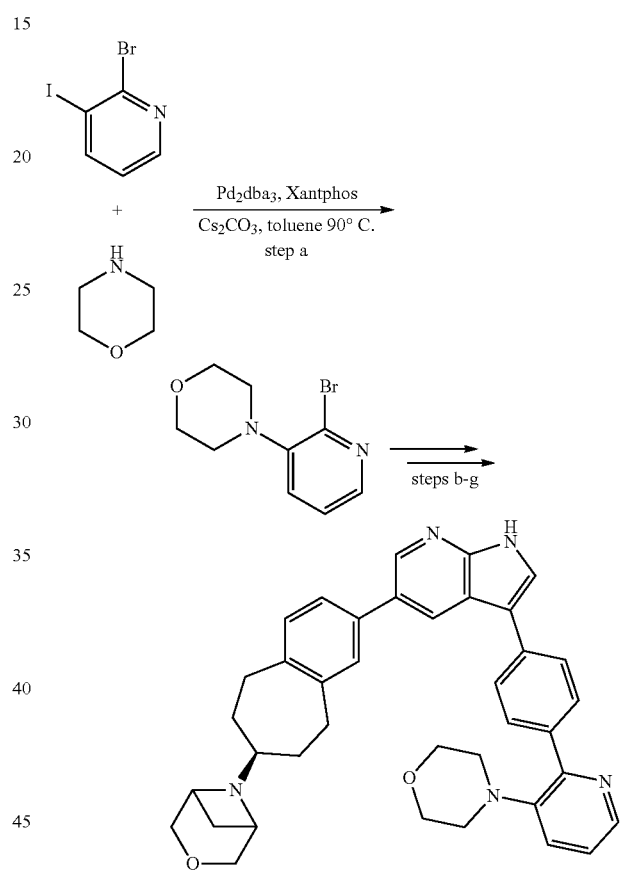

Step a: To a mixture of 2-bromo-3-iodopyridine (2.0 g, 7.0 mmol), morpholine (668 µL, 7.75 mmol), and Cs$_2$CO$_3$ (2.52 g, 7.75 mmol) was added toluene (20 mL). The suspension was degassed with nitrogen for 10 minutes and Xantphos (611 mg, 1.06 mmol) and Pd$_2$dba$_3$ (322 mg, 0.352 mmol) were added. The reaction mixture was stirred at 90° C. for 16 hours, cooled, diluted with EtOAc (10 mL), filtered through celite, and concentrated. The crude material was purified by silica gel chromatography (hexanes:EtOAc 0 to 100% gradient) to afford the desired product (342 mg, 20%).

Steps b-g: The title compound was prepared in a similar manner to example 1 using steps b-g. $^1$H NMR (400 MHz, Chloroform-d) δ 11.37 (d, J=2.4 Hz, 1H), 8.65-8.60 (m, 1H), 8.44 (d, J=2.0 Hz, 1H), 8.38 (dd, J=4.6, 1.4 Hz, 1H), 8.14-8.06 (m, 2H), 7.79-7.71 (m, 2H), 7.64 (d, J=2.3 Hz, 1H), 7.39 (dq, J=3.9, 2.0 Hz, 2H), 7.33 (dd, J=8.2, 1.5 Hz, 1H), 7.27-7.14 (m, 2H), 4.30 (d, J=10.7 Hz, 2H), 3.76-3.67 (m, 6H), 3.67-3.61 (m, 2H), 3.29-3.19 (m, 1H), 3.05-2.78 (m, 8H), 2.54 (q, J=6.7 Hz, 1H), 1.93 (bs, 2H), 1.83 (d, J=8.2

Hz, 1H), 1.33 (p, J=10.0 Hz, 2H). ESI MS [M+H]+ for C38H40N5O2, calcd. 598.3, found 598.3.

Example 6: N,N-Dimethyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-3-sulfonamide

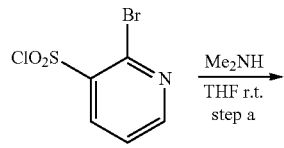

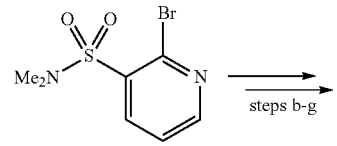

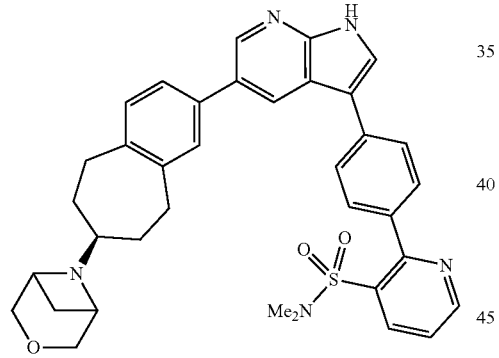

Step a: To a stirred solution of 2-bromopyridine-3-sulfonyl chloride (2.5 g, 9.7 mmol) in THF (50 mL) at 0° C. was added N,N-dimethylamine (5.89 mL, 11.8 mmol, 2 M in THF). The reaction mixture was stirred at room temperature for 16 hours and concentrated. The crude material was purified by silica gel chromatography (hexanes:EtOAc 0 to 70% gradient) to afford the desired product as an off-white solid (1.1 g, 35%).

Steps b-g: The title compound was prepared in a similar manner to example 1 using steps b-g. 1H NMR (400 MHz, Chloroform-d) δ 11.52 (s, 1H), 8.82 (dd, J=4.8, 1.7 Hz, 1H), 8.61 (d, J=2.1 Hz, 1H), 8.47-8.39 (m, 2H), 7.81-7.73 (m, 2H), 7.73-7.65 (m, 2H), 7.62 (d, J=1.3 Hz, 1H), 7.48-7.35 (m, 3H), 7.24-7.17 (m, 1H), 4.30 (d, J=10.7 Hz, 2H), 3.78-3.65 (m, 4H), 3.31-3.21 (m, 1H), 3.05-2.76 (m, 4H), 2.60 (dd, J=9.4, 4.8 Hz, 1H), 2.39 (s, 6H), 1.99-1.91 (m, 2H), 1.84 (d, J=8.4 Hz, 1H), 1.36 (p, J=10.6 Hz, 2H). ESI MS [M+H]+ for C36H38N5O3S, calcd. 620.3, found 620.3.

Example 7: 1-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridin-3-yl]pyrrolidin-2-one

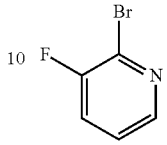

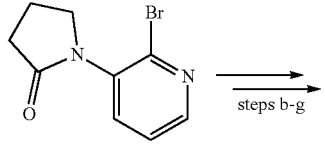

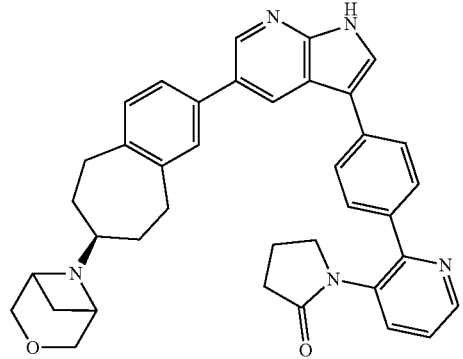

Step a: To a stirred solution of 2-bromo-3-fluoropyridine (5.0 g, 28 mmol) in DMF (60 mL) at 0° C. was added 2-pyrrolidone (3.62 g, 42.5 mmol) and NaH (1.5 g, 38 mmol, 60% wt. in oil). The reaction mixture was stirred at 0° C. for 15 minutes, stirred at 85° C. for 16 hours, cooled, carefully diluted with water (50 mL), and extracted with EtOAc (3×50 mL). The combined organic phases were dried over MgSO4 and concentrated. The crude material was purified by silica gel chromatography (hexanes:EtOAc 0 to 100% gradient) to afford the desired product (3.8 g, 55%).

Steps b-g: The title compound was prepared in a similar manner to example 1 using steps b-g. 1H NMR (400 MHz, Chloroform-d) δ 11.17 (s, 1H), 8.64 (dd, J=4.7, 1.6 Hz, 1H), 8.56 (d, J=2.0 Hz, 1H), 8.38 (d, J=2.0 Hz, 1H), 7.77-7.66 (m, 5H), 7.62 (s, 1H), 7.39-7.30 (m, 2H), 7.22-7.13 (m, 2H), 4.34 (d, J=11.8 Hz, 2H), 4.12 (s, 2H), 3.90 (d, J=11.7 Hz, 2H), 3.35 (t, J=7.0 Hz, 3H), 3.01-2.70 (m, 5H), 2.50 (t, J=8.1 Hz, 2H), 1.97 (m, 5H), 1.52 (s, 2H). ESI MS [M+H]+ for C38H38N5O2, calcd. 596.3, found 596.3.

Example 8: 2-[5-Methyl-6-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridin-2-yl]propan-2-ol

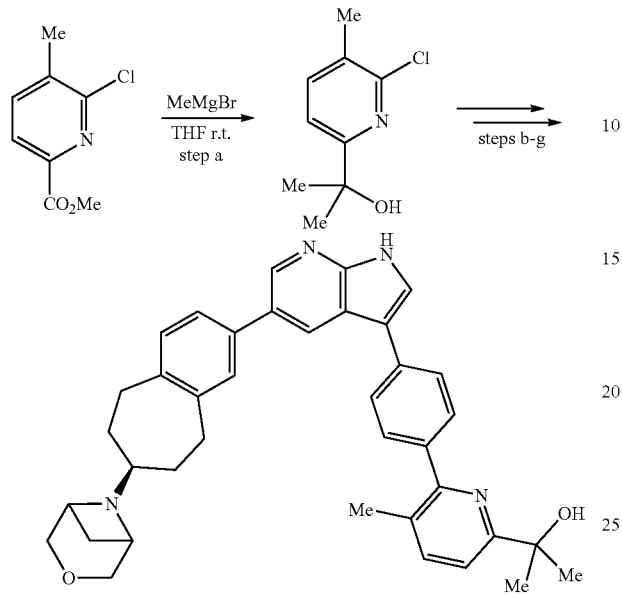

Step a: To a stirred solution of methyl 6-chloro-5-methylpyridine-2-carboxylate (1.0 g, 5.4 mmol) in THF (20 mL) at −15° C. was added methyl magnesium bromide (8.9 mL, 27 mmol, 3 M in diethyl ether). The reaction mixture was stirred at −15° C. for 15 minutes, stirred at room temperature for 16 hours, quenched with sat. $NH_4Cl_{(aq)}$ (50 mL), and extracted with EtOAc (3×50 mL). The combined organic phases were dried over $MgSO_4$ and concentrated to afford the desired product which was used in the next step without any further purification (5.4 mmol assumed).

Steps b-g: The title compound was prepared in a similar manner to example 1 using steps b-g. $^1$H NMR (400 MHz, Chloroform-d) δ 10.88 (s, 1H), 8.58-8.53 (m, 1H), 8.46-8.40 (m, 1H), 7.79-7.63 (m, 4H), 7.63-7.54 (m, 2H), 7.42-7.32 (m, 2H), 7.27-7.14 (m, 2H), 5.66 (s, 1H), 4.33 (d, J=11.3 Hz, 2H), 3.93 (d, J=5.7 Hz, 2H), 3.84 (d, J=11.4 Hz, 2H), 3.37-3.27 (m, 1H), 2.99-2.75 (m, 5H), 2.43 (s, 3H), 2.02-1.88 (m, 3H), 1.56 (s, 6H), 1.46 (bs, 2H). ESI MS [M+H]$^+$ for $C_{38}H_{41}N_4O_2$, calcd. 585.3, found 585.3.

Example 9: 3,6-Dimethyl-6'-{5-[(7S)-7-[(1R)-3-oxa-6-azabicyclo[3.1.1]heptan-6-yl]-6,7,8,9-tetrahydro-5H-benzo[7]annulen-2-yl]-1H-pyrazolo[3,4-b]pyridin-3-yl}-2,3'-bipyridine

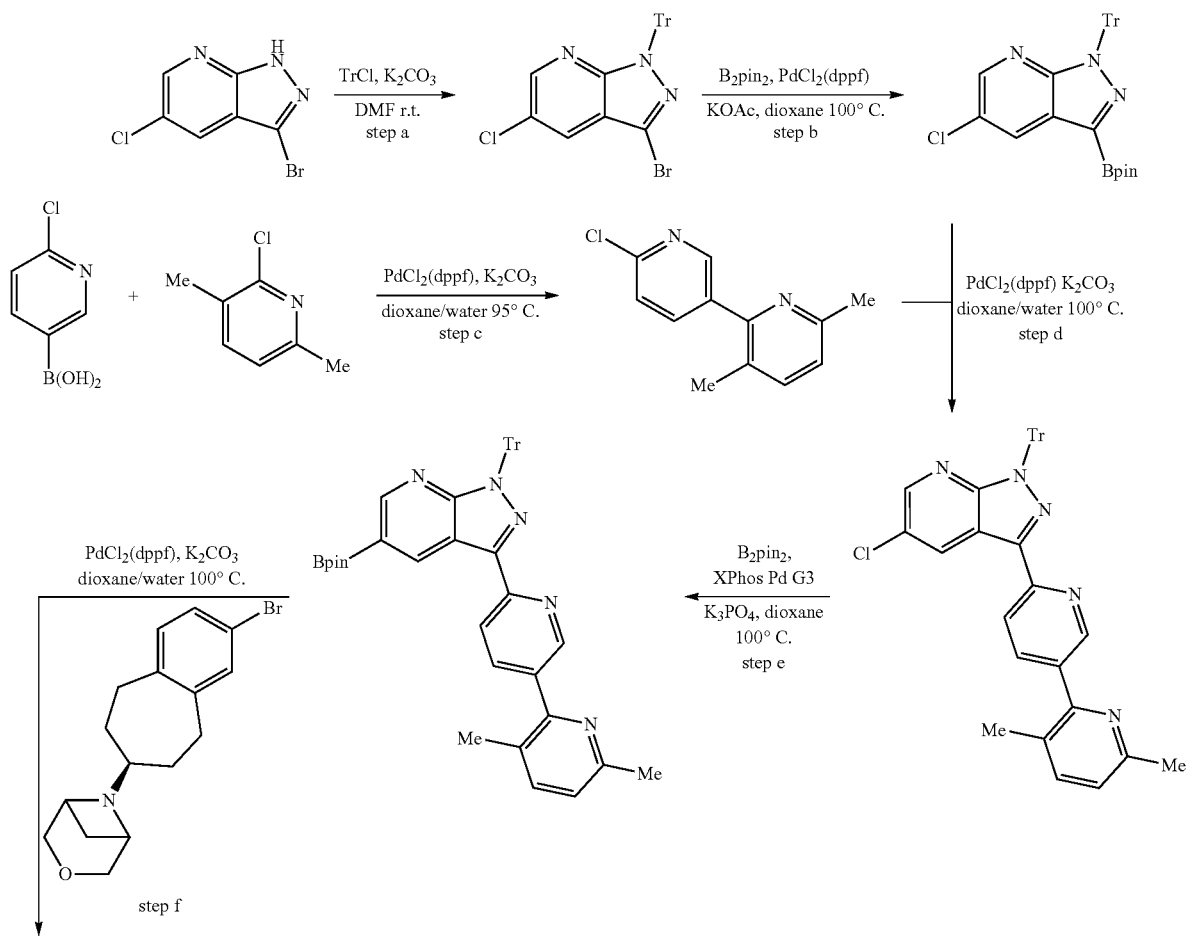

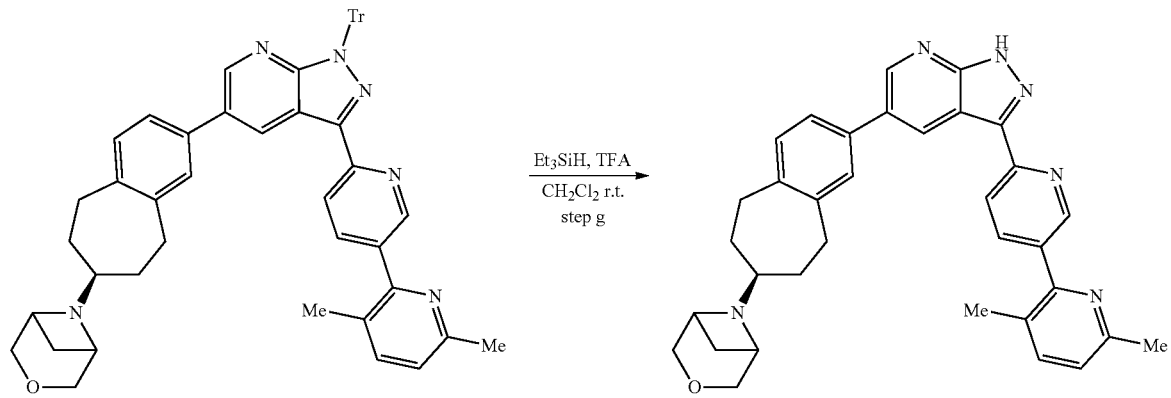

Step a: To a solution of 3-bromo-5-chloro-1H-pyrazolo[3,4-b]pyridine (10 g, 43 mmol) in DMF (150 mL) at 0° C. was added K₂CO₃ (17.88 g, 129.6 mmol). The mixture was stirred at 0° C. for 30 minutes. Triphenylchloromethane (14.45 g, 51.84 mmol) was added to the above reaction mixture at 0° C. The mixture was stirred at r.t. for 16 hours and water (100 mL) was added. The aqueous phase was extracted with EtOAc (3×60 mL). The combined organic phases were washed with brine (50 mL), dried over MgSO₄, concentrated, and purified by silica gel chromatography (hexanes:EtOAc 0 to 20% gradient) to afford the desired product as a white solid (15.98 g, 78%).

Step b: A mixture of the product from step a (269 mg, 0.566 mmol), B₂pin₂ (144 mg, 0.566 mmol), PdCl₂(dppf) (20.7 mg, 0.0283 mmol), and KOAc (111 mg, 1.13 mmol) was placed under nitrogen. Degassed dioxane (20 mL) was added and the reaction mixture was stirred at 100° C. for 4 hours. The mixture was cooled to r.t., concentrated, diluted with CH₂Cl₂ (50 mL), filtered through celite to remove solids, and again concentrated to afford the desired product which was used crude in step d.

Step c: To a mixture of 2-chloro-5-pyridineboronic acid (789 mg, 5.01 mmol), 2-chloro-3,6-dimethylpyridine (708 mg, 5.00 mmol), PdCl₂(dppf) (183 mg, 0.250 mmol), and K₂CO₃ (1.38 g, 10.0 mmol) under nitrogen was added degassed dioxane (20 mL) and degassed water (5 mL). The reaction mixture was stirred at 95° C. for 16 hours, cooled, concentrated, diluted with CH₂Cl₂ (25 mL), dried over MgSO₄, and concentrated. The crude material was purified by silica gel chromatography (hexanes:EtOAc 0 to 20% gradient) to afford the desired product as a white solid (547 mg, 50%).

Step d: To a mixture of the product from step b (0.566 mmol assumed), the product from step c (103 mg, 0.471 mmol), PdCl₂(dppf) (17.2 mg, 0.0236 mmol), and K₂CO₃ (130 mg, 0.942 mmol) was added degassed dioxane (2.4 mL) and degassed water (0.48 mL). The reaction mixture was stirred at 100° C. for 16 hours, cooled, concentrated, diluted with CH₂Cl₂ (25 mL), dried over MgSO₄, and concentrated. The crude material was purified by silica gel chromatography (hexanes:EtOAc 0 to 20% gradient) to afford the desired product as a white solid (81.2 mg, 30%).

Step e: A mixture of the product from step d (81.2 mg, 0.140 mmol), $B_{2p}in_2$ (42.7 mg, 0.168 mmol), K₃PO₄ (59.4 mg, 0.280 mmol), and XPhos Pd G³ (5.9 mg, 0.0070 mmol) was placed under nitrogen. Degassed dioxane (0.7 mL) was added and the mixture was sparged with nitrogen for 10 minutes. The reaction mixture was stirred at 100° C. for 2 hours, cooled, concentrated, diluted with CH₂Cl₂ (10 mL), filtered through celite to remove solids, and again concentrated to afford the desired product which was used crude in step f.

Step f: To a mixture of the product from step e (0.140 mmol assumed), 6-[(7S)-3-bromo-6,7,8,9-tetrahydro-5H-benzo[7]annulen-7-yl]-3-oxa-6-azabicyclo[3.1.1]heptane (45.1 mg, 0.140 mmol), PdCl₂(dppf) (5.1 mg, 0.0070 mmol), and K₂CO₃ (38.7 mg, 0.280 mmol) under nitrogen was added degassed dioxane (0.7 mL) and degassed water (0.14 mL). The reaction mixture was stirred at 95° C. for 16 hours, cooled, concentrated, diluted with CH₂Cl₂ (10 mL), dried over MgSO₄, and concentrated. The crude material was purified by silica gel chromatography (CH₂Cl₂:MeOH 0 to 15% gradient) to afford the desired product as a grey solid (89 mg, 81%).

Step g: To a mixture of the product from step f (89 mg, 0.11 mmol) and CH₂Cl₂ (10 mL) at 0° C. was added triethylsilane (66.3 mg, 0.570 mmol) followed by slow dropwise addition of TFA (65.0 mg, 0.570 mmol). The reaction mixture was stirred at room temperature for 1 hours and concentrated. The crude material was purified by silica gel chromatography (CH₂Cl₂:MeOH 0 to 15% gradient) to afford the desired product as a white solid (42.3 mg, 69% yield). ¹H NMR (400 MHz, DMSO-d₆) δ 9.03 (d, J=2.2 Hz, 1H), 8.92 (dd, J=2.3, 0.9 Hz, 1H), 8.85 (d, J=2.2 Hz, 1H), 8.26 (dd, J=8.3, 0.9 Hz, 1H), 8.09 (dd, J=8.2, 2.3 Hz, 1H), 7.64 (d, J=7.8 Hz, 1H), 7.51 (s, 1H), 7.48-7.43 (m, 1H), 7.24 (d, J=7.8 Hz, 1H), 7.20 (d, J=7.8 Hz, 1H), 4.13 (d, J=10.7 Hz, 2H), 3.53 (dd, J=18.8, 8.3 Hz, 4H), 3.21-3.10 (m, 1H), 3.04-2.85 (m, 2H), 2.77 (q, J=14.4 Hz, 2H), 2.48-2.45 (m, 3H), 2.40-2.26 (m, 4H), 1.91-1.75 (m, 2H), 1.65 (d, J=8.0 Hz, 1H), 1.26-1.08 (m, 2H). ESI MS [M+H]⁺ for C₃₄H₃₅N₆O, calcd. 543.3, found 543.3.

Example 10: 2-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]propan-2-ol Steps d-g: The title compound was prepared in a similar manner to example 2. $^1$H NMR (400 MHz, Chloroform-d) δ 11.53 (s, 1H), 8.83 (d, J=2.0 Hz, 1H), 8.55 (dd, J=4.7, 1.6 Hz, 1H), 8.48 (d, J=2.0 Hz, 1H), 8.09-8.02 (m, 2H), 7.59-7.52 (m, 2H), 7.40-7.35 (m, 2H), 7.32 (dd, J=8.1, 4.7 Hz,

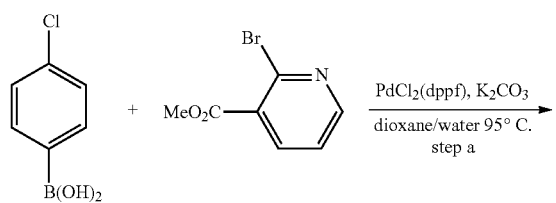

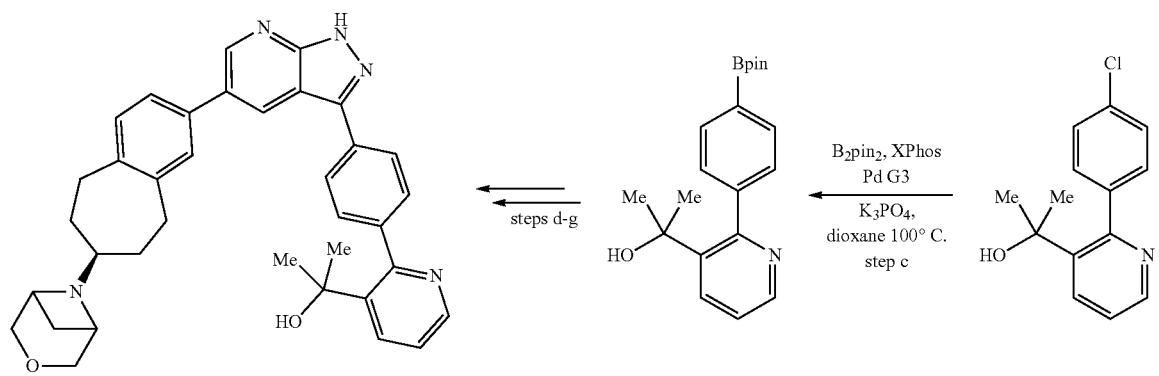

Step a: A mixture of methyl 2-bromonicotinate (1.71 g, 10.0 mmol), 4-chlorophenylboronic acid (1.56 g, 10.0 mmol), K$_2$CO$_3$ (2.76 g, 20.0 mmol), and PdCl$_2$(dppf) (365 mg, 0.500 mmol) was placed under nitrogen. Degassed dioxane (25 mL) and degassed water (25 mL) were added and the reaction mixture was stirred at 95° C. for 4 hours. The mixture was cooled to r.t., concentrated, diluted with CH$_2$Cl$_2$ (25 mL), dried over MgSO$_4$, and concentrated. The crude material was purified by silica gel chromatography (hexanes:EtOAc 0 to 20% gradient) to afford the desired product as a colorless liquid (2 g, 80%).

Step b: To a solution of the product from step a (2 g, 8 mmol) in THF (20 mL) at 0° C. was added methylmagnesium bromide (8.0 mL, 24 mmol, 3 M in diethyl ether) dropwise. The mixture was stirred at r.t. for 16 hours. Sat. NH$_4$Cl$_{(aq)}$ (20 mL) was added and the mixture extracted with EtOAc (2×20 mL). The combined organic phases were washed with brine (20 mL), dried over Na$_2$SO$_4$, filtered, and concentrated to afford the desired product (1.6 g, 65%).

Step c: A mixture of the product from step b (1.3 g, 5.2 mmol), B$_2$pin$_2$ (2.66 g, 10.4 mmol), K$_3$PO$_4$ (2.77 g, 13.1 mmol), XPhos Pd G$^3$ (221 mg, 0.260 mmol), and dioxane (50 mL) was sparged with nitrogen for 10 minutes. The reaction mixture stirred at 100° C. for 16 hours, cooled to r.t., concentrated, diluted with CH$_2$Cl$_2$ (50 mL), filtered through celite to remove solids, and again concentrated to afford the desired product which was used crude in the next step.

1H), 7.22 (s, 1H), 4.30 (d, J=10.7 Hz, 2H), 3.72 (d, J=10.7 Hz, 2H), 3.64 (d, J=6.1 Hz, 2H), 3.25 (t, J=9.6 Hz, 1H), 3.03-2.94 (m, 2H), 2.85 (q, J=13.1 Hz, 2H), 2.56 (q, J=6.8 Hz, 1H), 1.94 (brs, 2H), 1.85-1.83 (m, 2H), 1.52 (s, 6H), 1.41-1.23 (m, 2H), 0.91-0.82 (m, 1H). ESI MS [M+H]$^+$ for C$_{36}$H$_{38}$N$_5$O$_2$, calcd. 572.3, found 572.3.

Example 11: 6-[(7S)-2-{3-[4-(3-Methyl-4H-1,2,4-triazol-4-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

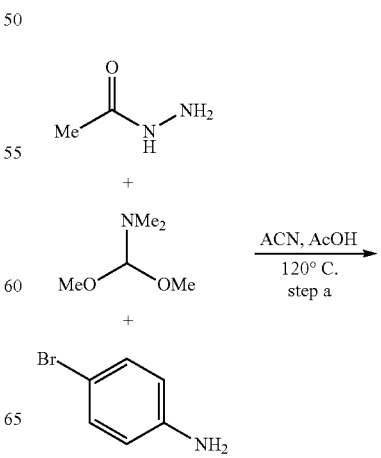

83

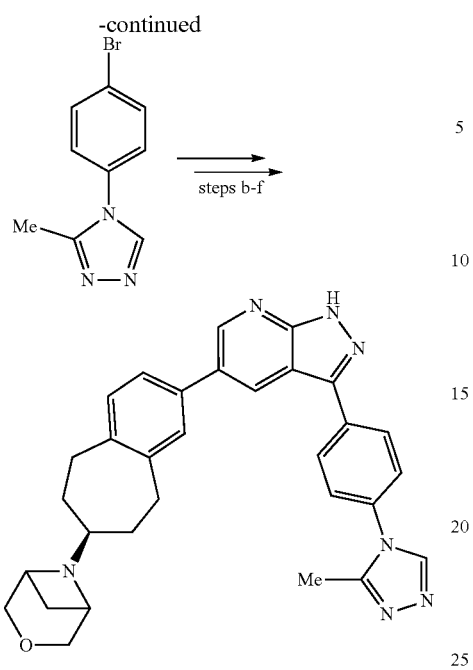

Step a: To a solution of acetic hydrazide (740 mg, 10.0 mmol) and ACN (4 mL) at r.t. was added dimethylacetamide dimethyl acetal (1.2 g, 10 mmol). The reaction mixture was stirred at 50° C. for 30 minutes. A solution of 4-bromoaniline (1.72 mg, 10.0 mmol) in ACN (4 mL) was added followed by acetic acid (3 mL). The reaction mixture was then stirred at 120° C. for 3 hours, cooled, concentrated, and purified by silica gel chromatography (100% EtOAc followed by 95% EtOAc/5% 0.7 M ammonia in methanol) to afford the desired product (832 mg, 35%).

Steps b-f: The title compound was prepared in a similar manner to example 2, steps b-f. $^1$H NMR (400 MHz, Chloroform-d) δ 12.17 (s, 1H), 8.84 (d, J=2.0 Hz, 1H), 8.46 (d, J=2.0 Hz, 1H), 8.28 (s, 1H), 8.24-8.12 (m, 2H), 7.52-7.40 (m, 2H), 7.37 (d, J=7.2 Hz, 2H), 7.24 (s, 1H), 4.30 (d, J=10.8 Hz, 2H), 3.76-3.68 (m, 4H), 3.28 (t, J=9.9 Hz, 1H), 3.04-2.75 (m, 4H), 2.59 (q, J=6.8 Hz, 1H), 2.49 (s, 3H), 1.99 (s, 2H), 1.86 (d, J=8.4 Hz, 1H), 1.43-1.25 (m, 2H). ESI MS [M+H]$^+$ for $C_{31}H_{32}N_7O$, calcd. 518.3, found 518.3.

Example 12: N,N-Dimethyl-4'-{5-[(7S)-7-{3-oxa-6-azabicyclo[3.1.1]heptan-6-yl}-6,7,8,9-tetrahydro-5H-benzo[7]annulen-2-yl]-2H-pyrazolo[3,4-b]pyridin-3-yl}-[1,1'-biphenyl]-2-carboxamide

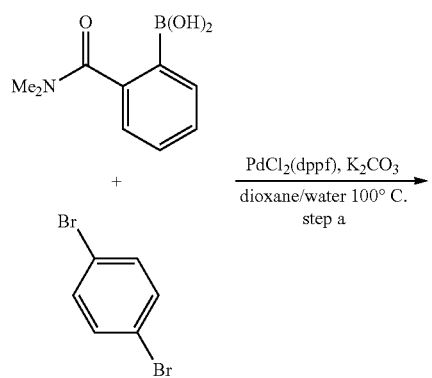

84

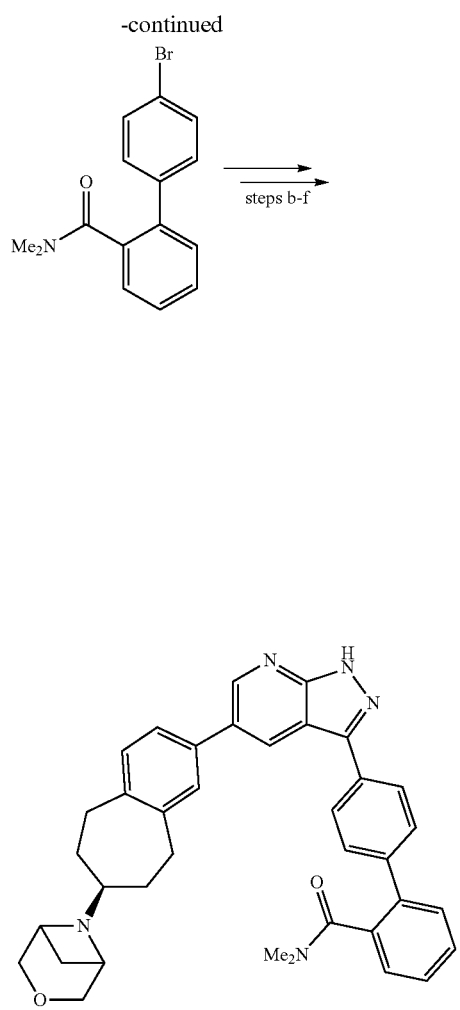

Step a: To a mixture of methyl [2-(dimethylcarbamoyl) phenyl]boronic acid (1.25 g, 6.48 mmol) 1,4-dibromobenzene (1.52 g, 6.44 mmol), K$_2$CO$_3$ (1.76 g, 12.8 mmol), and PdCl$_2$(dppf) (234 mg, 0.324 mmol) under nitrogen was added degassed dioxane (16 mL) and degassed water (16 mL). The reaction mixture was stirred at 70° C. for 4 hours, cooled to r.t., concentrated, diluted with CH$_2$Cl$_2$ (25 mL), dried over MgSO$_4$, and concentrated. The crude material was purified by silica gel chromatography (hexanes:EtOAc 0 to 20% gradient to afford the desired product as a colorless liquid (700 mg, 35%).

Steps b-f: The title compound was prepared in a similar manner to example 2, steps b-f. $^1$H NMR (400 MHz, Chloroform-d) δ 11.30 (brs, 1H), 8.83 (d, J=2.0 Hz, 1H), 8.50 (d, J=2.1 Hz, 1H), 8.15-7.92 (m, 2H), 7.70-7.52 (m, 2H), 7.50-7.45 (m, 1H), 7.43 (dd, J=2.8, 1.5 Hz, 1H), 7.41-7.35 (m, 1H), 7.24 (s, 4H), 4.30 (d, J=10.7 Hz, 2H), 3.73 (d, J=10.8 Hz, 2H), 3.66 (d, J=6.1 Hz, 2H), 3.27 (t, J=9.7 Hz, 1H), 3.06-2.95 (m, 2H), 2.89 (s, 3H), 2.48-2.47 (s, 3H), 2.47 (s, 2H), 2.03-1.88 (m, 2H), 1.84 (d, J=8.3 Hz, 1H), 1.44-1.19 (m, 2H), 0.89-0.75 (m, 1H). ESI MS [M+H]$^+$ for $C_{37}H_{38}N_5O_2$, calcd. 584.3, found 584.4.

Example 13: 6-[(7S)-2-{3-[4-(1-Methyl-1H-1,2,3-triazol-5-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

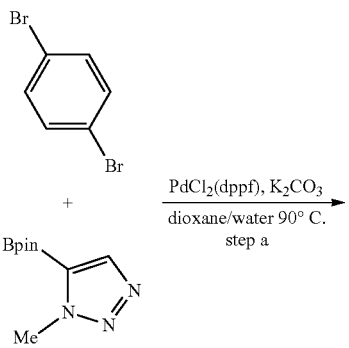

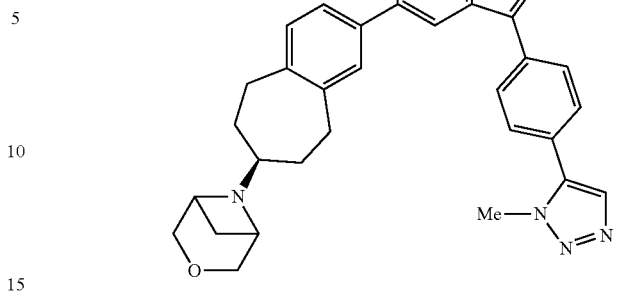

Step a: To a mixture of 1,4-dibromobenzene (944 mg, 4.00 mmol), 1-methyl-5-(4,4,5,5-tetramethyl-1,3,2-dioxaborolan-2-yl)-1H-1,2,3-triazole (836 mg, 4.00 mmol), PdCl$_2$(dppf) (293 mg, 0.400 mmol), and K$_2$CO$_3$ under nitrogen at room temperature was added degassed dioxane (16 mL) and degassed water (4 mL). The reaction mixture was stirred at 90° C. for 14 hours, cooled, diluted with CH$_2$Cl$_2$ (200 mL), dried over Na$_2$SO$_4$, and concentrated. The crude material was purified by silica gel chromatography (hexanes:EtOAc 0 to 100% gradient) to afford the desired product as a pale yellow oil (390 mg, 41%).

Steps b-f: The title compound was prepared in a similar manner to example 2, steps b-f. $^1$H NMR (400 MHz, DMSO-d$_6$, citrate salt) δ 14.03 (s, 1H), 8.91 (d, J=2.0 Hz, 1H), 8.75 (d, J=2.0 Hz, 1H), 8.29 (d, J=8.3 Hz, 2H), 8.02 (s, 1H), 7.80 (d, J=8.3 Hz, 2H), 7.69 (s, 1H), 7.62 (d, J=7.6 Hz, 1H), 7.31 (d, J=7.8 Hz, 1H), 4.40-4.19 (m, 3H), 4.16 (s, 3H), 4.01-3.79 (m, 2H), 3.76-3.59 (m, 1H), 3.51-3.16 (m, 3H), 3.06-2.83 (m, 4H), 2.62 (d, J 15.2 Hz, 2H), 2.54 (d, J=15.3 Hz, 2H), 2.21-1.93 (m, 2H), 1.27-1.13 (m, 2H). ESI MS [M+H]$^+$ for C$_{31}$H$_{32}$N$_7$O, calcd. 518.3, found 518.3.

Example 14: 6-[(7S)-2-{3-[4-(2,5-Dimethyl-2H-1,2,3-triazol-4-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

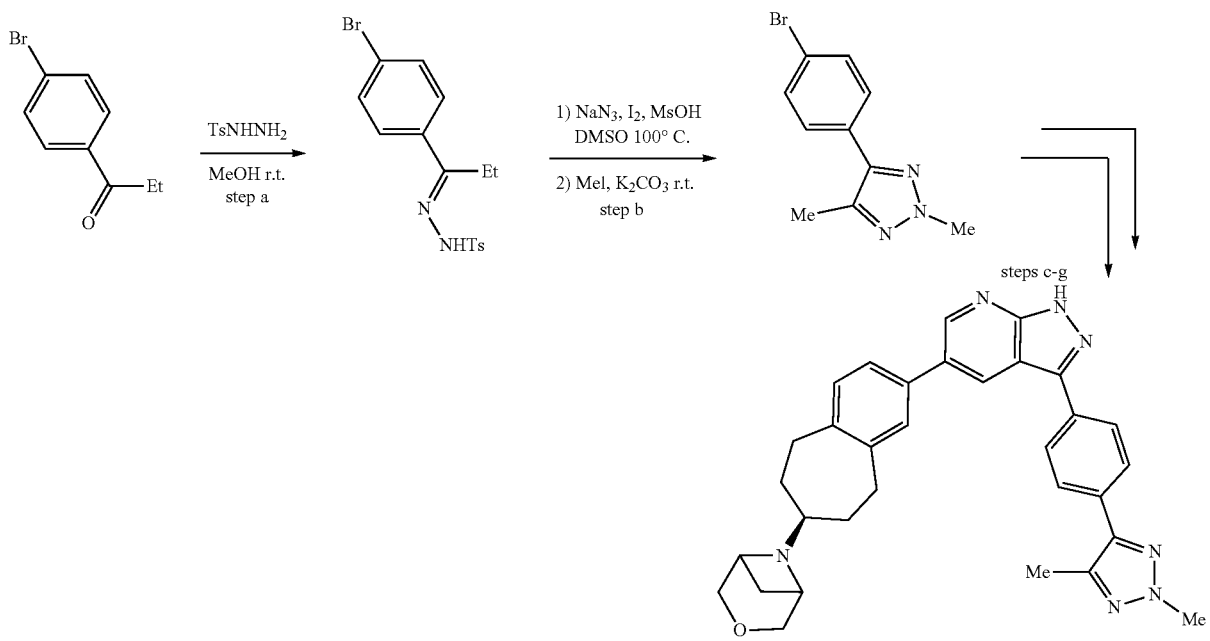

Step a: To a solution of 4-methylbenzenesulfonyl hydrazide (16.4 g, 88.2 mmol) in MeOH (88 mL) at room temperature was added 4'-bromopropiophenone (18.8 g, 88.2 mmol) in one portion. The reaction mixture was stirred at room temperature for 30 minutes and concentrated to afford the desired product as a white solid (33.5 g, 99%).

Step b: To a mixture of the product from step a (7.63 g, 20.0 mmol), sodium azide (1.56 g, 24.0 mmol) and DMSO (100 mL) at room temperature was added iodine (5.08 g, 20.0 mmol). The mixture was stirred at room temperature for 5 minutes and methanesulfonic acid (1.30 mL, 20.0 mmol) was added. The reaction mixture was stirred at 100° C. for 4 hours and cooled. To the mixture was added $K_2CO_3$ (13.8 g, 100 mmol) followed by methyl iodide (2.49 mL, 40.0 mmol). The reaction mixture was stirred at room temperature for 2 hours, diluted with EtOAc (1.0 L), washed with water (1×1.0 L), washed with 3:2 water:brine (2×1.0 L), dried over $Na_2SO_4$, and concentrated. The crude material was purified by silica gel chromatography (hexanes:EtOAc 0 to 100% gradient) to afford the desired product as a pale yellow oil (439 mg, 9%).

Steps c-g: The title compound was prepared in a similar manner to example 2, steps b-f. $^1$H NMR (400 MHz, DMSO-$d_6$, citrate salt) δ 13.93 (s, 1H), 8.89 (d, J=2.0 Hz, 1H), 8.74 (d, J=2.0 Hz, 1H), 8.23 (d, J=8.3 Hz, 2H), 7.88 (d, J=8.3 Hz, 2H), 7.68 (s, 1H), 7.62 (d, J=7.7 Hz, 1H), 7.31 (d, J=7.8 Hz, 1H), 4.29 (d, J=12.1 Hz, 2H), 4.23-4.07 (m, 1H), 4.01 (s, 3H), 3.97-3.79 (m, 2H), 3.72-3.54 (m, 1H), 3.49-3.20 (m, 3H), 3.07-2.83 (m, 4H), 2.61 (d, J=15.2 Hz, 2H), 2.53 (s, 3H), 2.53 (d, J=15.9 Hz, 2H), 2.20-1.91 (m, 2H), 1.28-1.11 (m, 2H). ESI MS [M+H]$^+$ for $C_{32}H_{34}N_7O$, calcd. 532.3, found 532.4.

Example 15: 3-(2-Methoxyethyl)-7-{3-[4-(3-methylpyridin-2-yl)phenyl]-1H-pyrazolo[3,4-b]pyridin-5-yl}-2,3,4,5-tetrahydro-1H-3-benzazepine

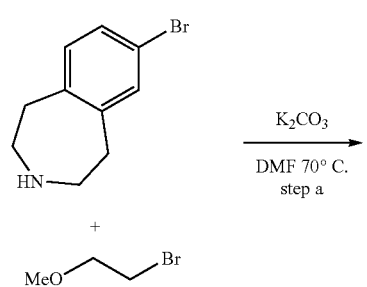

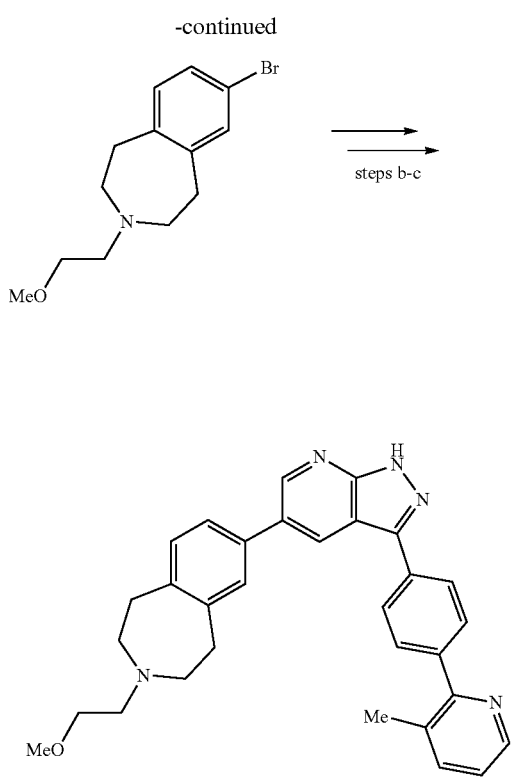

Step a: To a mixture of 7-bromo-2,3,4,5-tetrahydro-1H-3-benzazepine (565 mg, 2.50 mmol), $K_2CO_3$ (691 mg, 5.00 mmol), and DMF (13 mL) at room temperature was added 2-bromoethyl methyl ether (235 μL, 2.50 mmol). The reaction mixture was stirred at 70° C. for 3 hours, stirred at 80° C. for 12 hours, cooled, diluted with EtOAc (125 mL), washed with 0.2 M NaOH$_{(aq)}$ (4×100 mL), dried over $Na_2SO_4$, and concentrated. The crude material was purified by C18 reverse phase chromatography ((water:ACN)+1% TFA 5 to 35% gradient) followed by neutralization with sat. NaHCO$_{3(aq)}$ and partial concentration to remove ACN. The mixture was diluted with EtOAc (200 mL), washed with 0.2 M NaOH$_{(aq)}$ (2×200 mL), dried over $Na_2SO_4$, and concentrated to afford the desired product as a pale yellow oil (342 mg, 48%).

Steps b-c: The title compound was prepared in a similar manner to example 2, steps e and f. $^1$H NMR (400 MHz, DMSO-$d_6$, citrate salt) δ 13.97 (s, 1H), 8.89 (d, J=2.0 Hz, 1H), 8.74 (d, J=2.1 Hz, 1H), 8.53 (dd, J=4.8, 1.0 Hz, 1H), 8.21 (d, J=8.4 Hz, 2H), 7.79-7.69 (m, 4H), 7.66 (dd, J=7.7, 2.0 Hz, 1H), 7.34 (d, J=7.7 Hz, 1H), 7.33 (d, J=7.7 Hz, 1H), 3.61 (t, J=5.2 Hz, 2H), 3.44-3.26 (m, 2H), 3.31 (s, 3H), 3.20-3.00 (m, 8H), 2.64 (d, J=15.2 Hz, 2H), 2.55 (d, J=15.2 Hz, 2H), 2.42 (s, 3H). ESI MS [M+H]$^+$ for $C_{31}H_{32}N_5O$, calcd. 490.3, found 490.3.

Example 16: 3-Methyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridin-1-ium-1-olate

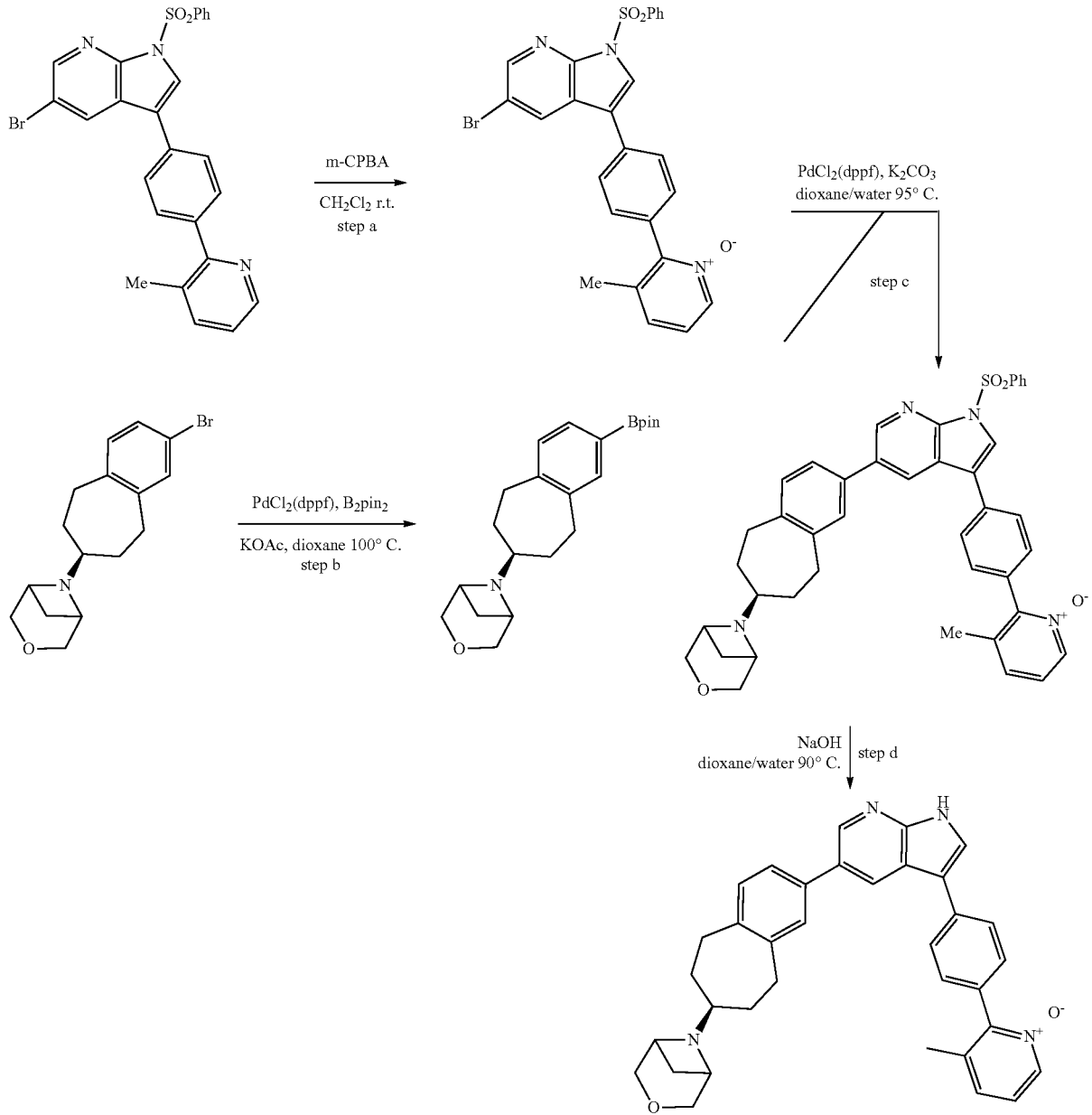

Step a: To a solution of the product from example 1, step d (504 mg, 1.00 mmol) in CH$_2$Cl$_2$ (5.0 mL) at room temperature was added m-CPBA (230 mg, 1.00 mmol, 75% wt. in water). The reaction mixture was stirred at room temperature for 14 hours and additional m-CPBA (115 mg, 0.500 mmol, 75% wt. in water) was added. The reaction mixture was stirred at room temperature for 5 hours and concentrated. The crude material was purified by silica gel chromatography (CH$_2$Cl$_2$:MeOH 0 to 10% gradient) to afford the desired product as a light brown solid (350 mg, 67%).

Step b: To a mixture of the product from example 1, step a (64 mg, 0.20 mmol), B$_2$pin$_2$ (51 mg, 0.20 mmol), PdCl$_2$(dppf) (7 mg, 0.01 mmol), and KOAc (39 mg, 0.40 mmol) under nitrogen at room temperature was added degassed dioxane (1.0 mL). The reaction mixture was stirred at 100° C. for 14 hours, cooled, diluted with EtOAc (10 mL), filtered through celite, and concentrated to afford the desired product which was used crude in step c.

Steps c-d: The title compound was prepared in a similar manner to example 1, steps f and g. $^1$H NMR (400 MHz, DMSO-d$_6$, citrate salt) δ 12.08 (d, J=2.7 Hz, 1H), 8.58 (d, J=2.0 Hz, 1H), 8.47 (d, J=2.1 Hz, 1H), 8.22 (t, J=3.9 Hz, 1H), 8.02 (d, J=2.6 Hz, 1H), 7.91 (d, J=8.3 Hz, 2H), 7.64-7.58 (m, 1H), 7.54 (d, J=7.6 Hz, 1H), 7.42 (d, J=8.3 Hz, 2H), 7.34 (d, J=3.9 Hz, 2H), 7.31-7.24 (m, 1H), 4.37-4.06 (m, 3H), 4.00-3.77 (m, 2H), 3.68-3.49 (m, 1H), 3.46-3.24 (m, 3H), 3.05-2.80 (m, 4H), 2.61 (d, J=15.2 Hz, 2H), 2.53 (d, J=13.5 Hz, 2H), 2.13 (s, 3H), 2.11-1.88 (m, 2H), 1.41-1.09 (m, 2H). ESI MS [M+H]⁺ for $C_{35}H_{35}N_4O_2$, calcd. 543.3, found 543.3.

Example 17: 6-[(7S)-3-[3-[6-(3-Methylpyridin-2-yl)pyridazin-3-yl]-1H-pyrazolo[3,4-b]pyridin-5-yl]-6,7,8,9-tetrahydro-5H-benzo[7]annulen-7-yl]-3-oxa-6-azabicyclo[3.1.1]heptane

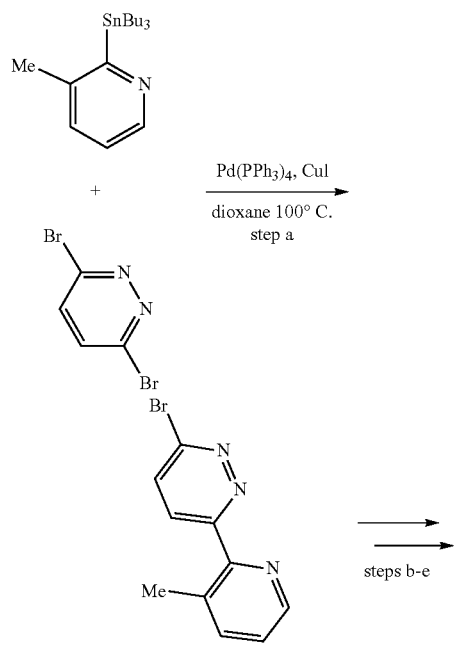

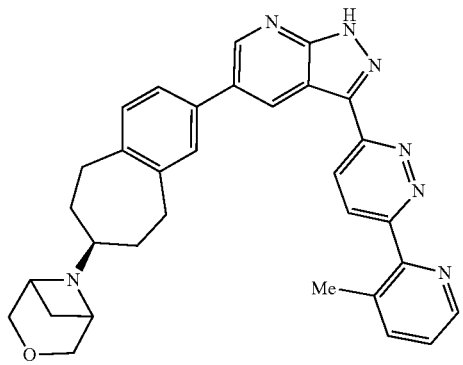

Step a: To a mixture of 3-methyl-2-(tributylstannyl)pyridine (1.91 g, 5.00 mmol), 3,6-dibromopyridazine (1.19 g, 5.00 mmol), CuI (190 mg, 0.997 mmol), and Pd(PPh₃)₄ (578 mg, 0.501 mmol) was added dioxane (25 mL). The mixture was sparged with nitrogen for 10 minutes, stirred at 100° C. for 3.5 hours, cooled, diluted with EtOAc, filtered through celite, and concentrated. The crude material was purified by silica gel chromatography (hexanes:EtOAc 0 to 100% gradient) to afford the desired product (590 mg, 47%).

Steps b-e: The title compound was prepared in a similar manner to example 9, steps d-g. ¹H NMR (400 MHz, Chloroform-d) δ 11.27 (s, 1H), 9.32 (d, J=2.2 Hz, 1H), 8.89 (d, J=2.2 Hz, 1H), 8.65-8.58 (m, 1H), 8.53 (d, J=8.9 Hz, 1H), 8.23 (d, J=8.8 Hz, 1H), 7.76-7.68 (m, 1H), 7.51-7.43 (m, 2H), 7.37-7.20 (m, 2H), 4.33 (d, J=10.7 Hz, 2H), 3.76 (m, 2H), 3.67 (m, 2H), 3.28 (m, 1H), 2.99 (td, J=23.8, 23.0, 14.5 Hz, 2H), 2.91-2.79 (m, 2H), 2.73 (s, 3H), 1.97 (m, 2H), 1.88 (m, 1H), 1.39 (m, 2H), 1.26 (m, 1H). ESI MS [M+H]⁺ for $C_{32}H_{32}N_7O$, calcd. 530.3, found 530.3.

Example 18: 3-[(7S)-7-Methyl-7-[(2R)-2-methylpyrrolidin-1-yl]-5,6,8,9-tetrahydrobenzo[7]annulen-3-yl]-5-[4-(3-methylpyridin-2-yl)phenyl]-7H-pyrrolo[2,3-c]pyridazine

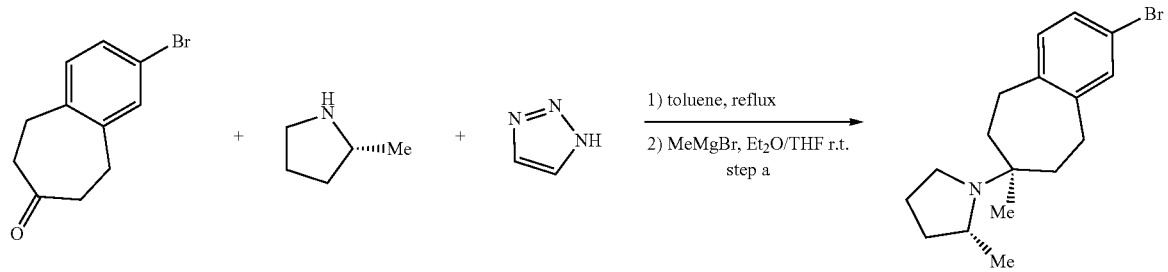

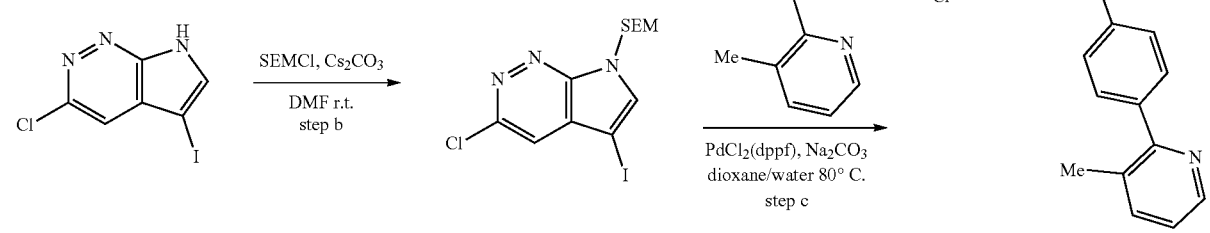

-continued

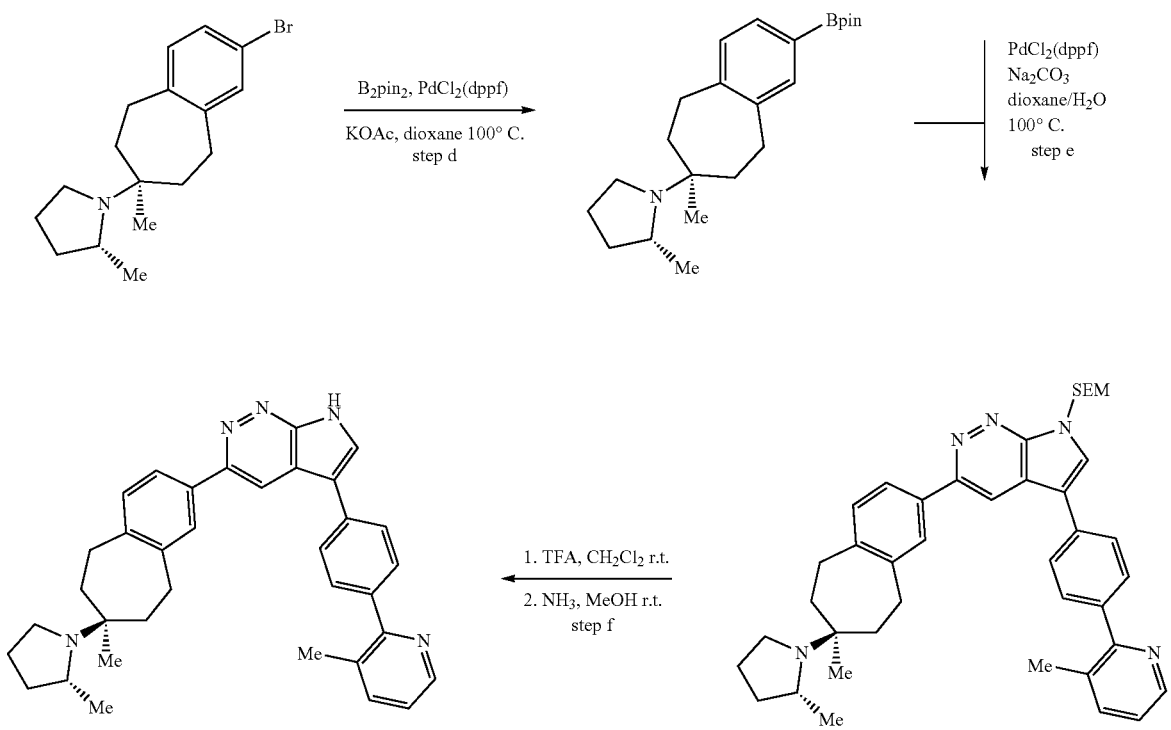

Step a: A flask containing 2-bromo-5,6,8,9-tetrahydrobenzocyclohepten-7-one (23.9 g, 100 mmol), (R)-2-methylpyrrolidine (9.06 mL, 105 mmol), 1,2,3-triazole (7.60 g, 110 mmol), and toluene (100 mL) was fitted with a Dean-Stark trap and heated to reflux with azeotropic removal of water for 18 hours. The mixture was cooled and added dropwise to a mixture of MeMgBr (133 mL, 400 mmol, 3 M in Et$_2$O) and THF (400 mL) at 0° C. The reaction mixture was stirred at 0° C. for 1 hour, stirred at room temperature for 2 hours, quenched carefully with water (7.2 mL). The mixture was diluted with 1 M HCl$_{(aq)}$ (500 mL) and MTBE (250 mL) and agitated. The organic phase was extracted once with 1 M HCl$_{(aq)}$ (500 mL). The acidic aqueous phases were combined and extracted with CH$_2$Cl$_2$ (2×500 mL). The combined organic phases were concentrated. Water (500 mL) was added and the solution basified by addition of 2 M NaOH$_{(aq)}$ (100 mL). MTBE (500 mL) was added and the phases were agitated and separated. The organic phase was washed with 2 M NaOH$_{(aq)}$ (3×250 mL) and dried over Na$_2$SO$_4$ to afford the crude product as a light orange solid (21.2 g, 1:1 d.r. by NMR).

The mixture of diastereomers was dissolved in isopropanol (424 mL) with gradual heating. Once the solids were dissolved, the solution was allowed to cool. The mixture was allowed to stand for 24 hours and the solids were collected by filtration (no washings were performed) to afford diastereomerically enriched product (5.12 g, 24% recovery, 83:17 d.r. by NMR). The enriched material was dissolved in isopropanol (102 mL) with gradual heating. Once the solids were dissolved, the solution was allowed to cool. The mixture was allowed to stand for 24 hours and the solids were collected by filtration (no washings were performed) to afford the desired product as a white solid (3.60 g, 70% recovery, >95:5 d.r. by NMR).

The diastereomeric mixture can also be resolved using chiral HPLC (YMC Amylose-SA; MeOH/DEA 100/0.1 v/v; 0.5 mL/min; UV 227 nm; 10.7 minutes (desired isomer), 12.2 minutes (other isomer)).

Step b: To a mixture of 3-chloro-5-iodo-7H-pyrrolo[2,3-c]pyridazine (1.40 g, 5.01 mmol), Cs$_2$CO$_3$ (3.26 g, 10.0 mmol), and DMF (7 mL) at r.t. was added SEMCl (1.33 mL, 7.51 mmol). The reaction mixture was stirred for 16 hours, diluted with EtOAc (70 mL), washed with water (3×70 mL), washed with brine (70 mL), dried over Na$_2$SO$_4$, and concentrated. The crude material was purified by silica gel chromatography (hexanes:EtOAc 0 to 50% gradient) to afford the desired product (1.44 g, 70%).

Step c: The desired product was prepared in a similar manner to example 1, step d.

Steps d-e: The desired product was prepared in a similar manner to example 16, steps b-c.

Step f: To a solution of the product of step e (129 mg, 0.207 mmol) in CH$_2$Cl$_2$ (1 mL) was added TFA (1 mL). The reaction mixture was stirred at r.t. for 2 hours and concentrated. To the residue was added NH$_3$ (2 mL, 7 M solution in MeOH). The reaction mixture was stirred at r.t. for 16 hours and concentrated. The crude material was purified by C18 reverse phase chromatography ((water:ACN)+1% TFA 20 to 80% gradient) to afford the desired product as a light yellow solid (10 mg, 9%). $^1$H NMR (400 MHz, Chloroform-d) δ 12.07 (s, 1H), 8.63-8.56 (m, 1H), 8.37 (s, 1H), 7.94 (s, 1H), 7.91-7.85 (m, 1H), 7.83-7.72 (m, 3H), 7.74-7.59 (m, 3H), 7.30-7.18 (m, 2H), 3.41 (br s, 1H), 3.29-3.22 (m, 2H), 2.93 (t, J=7.7 Hz, 1H), 2.68 (m, 2H), 2.55 (m, 1H), 2.46 (s, 3H), 1.90 (m, 3H), 1.72 (m, 3H), 1.47 (m, 2H), 1.08 (d, J=6.3 Hz, 3H), 1.00 (s, 3H). ESI MS [M+H]$^+$ for C$_{35}$H$_{38}$N$_5$, calcd. 528.3, found 528.3.

Example 19: 3-Methyl-2-(4-{5-[6-(pyrrolidin-1-yl)-5,6,7,8-tetrahydronaphthalen-2-yl]-1H-pyrazolo[3,4-b]pyridin-3-yl}phenyl)pyridine

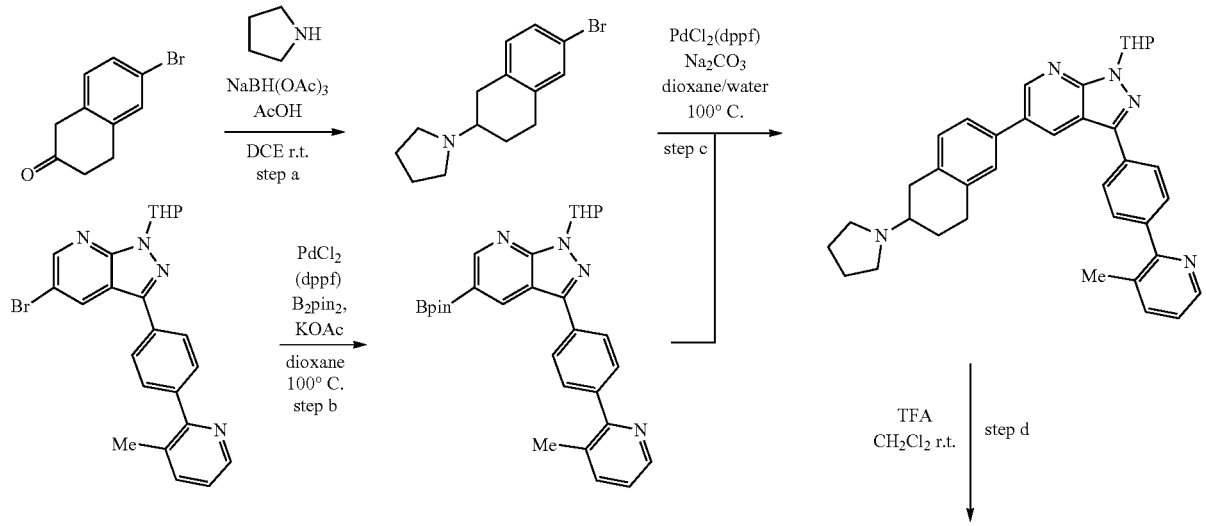

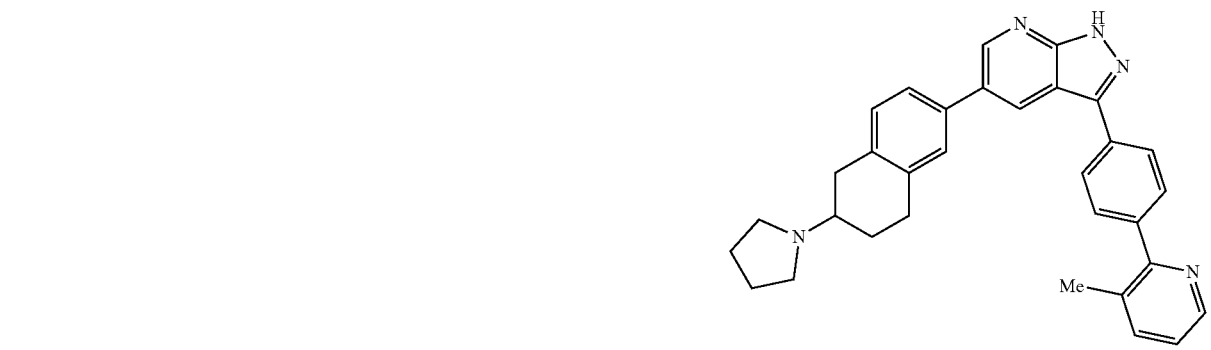

Step a: to a mixture of 6-bromo-3,4-dihydro-2(1h)-naphthalenone (440 mg, 1.95 mmol), pyrrolidine (0.16 ml, 2.0 mmol), and dce (9.8 ml) was added acoh (0.11 ml, 2.0 mmol) followed by nabh(oac)$_3$ (820 mg, 3.90 mmol). The reaction mixture was stirred at room temperature for 20 hours, carefully quenched with water followed by sat. Nahco$_{3(aq)}$. The phases were separated and the aqueous phases was extracted with ch$_2$cl$_2$ (2×15 ml). The combined organic phases were washed with brine, dried over na$_2$so$_4$, and concentrated. The crude material was purified by silica gel chromatography (ch$_2$cl$_2$:meoh 0 to 10% gradient) to afford the desired product as a brown oil (376 mg, 69%).

Step b: To a mixture of the product from example 2, step c (132 mg, 0.294 mmol), B$_2$pin$_2$ (97 mg, 0.83 mmol), and KOAc (37 mg, 0.83 mmol) was added dioxane (2.9 mL). The suspension was degassed with nitrogen for 5 minutes and PdCl$_2$(dppf) (11 mg, 0.015 mmol) was added. The reaction mixture was stirred at 100° C. for 16 hours, cooled, diluted with EtOAc (15 mL), filtered through celite, and concentrated to afford the desired product which was used crude in step c.

Step c: To a mixture of the product from step a (87 mg, 0.30 mmol), the product of step b (0.294 mmol), and Na$_2$CO$_3$ (62 mg, 0.59 mmol) was added dioxane (2.7 mL) and water (0.30 mL). The suspension was degassed with nitrogen for 5 minutes and PdCl$_2$(dppf) (11 mg, 0.015 mmol) was added. The reaction mixture was stirred at 100° C. for 16 hours, cooled, diluted with CH$_2$Cl$_2$ (15 mL), dried over MgSO$_4$, and concentrated. The crude material was purified by silica gel chromatography ((CH$_2$Cl$_2$:MeOH)+ 1% NH$_{3(aq,\ 28\%\ wt.)}$ 0 to 10% gradient) to afford the desired product as a brown solid (64 mg, 38%, 2 steps).

Step d: To a mixture of the product from step c (64 mg, 0.11 mmol) and CH$_2$Cl$_2$ (1.2 mL) was added TFA (1.2 mL). The reaction mixture was stirred for 4 hours at room temperature and concentrated. The crude material was purified by C18 reverse phase chromatography ((water:ACN)+ 1% TFA 5 to 50% gradient) followed by partial concentration and addition of K$_2$CO$_3$. The mixture was extracted with CH$_2$Cl$_2$ (3×10 mL). The combined organic phases were dried over MgSO$_4$ and concentrated to afford the desired product as a white solid (17 mg, 31%). $^1$H NMR (400 MHz, DMSO-d$_6$) δ 8.86 (d, J=2.0 Hz, 1H), 8.72 (d, J=2.1 Hz, 1H), 8.53 (dd, J=4.8, 1.6 Hz, 1H), 8.27-8.10 (m, 2H), 7.85-7.69 (m, 3H), 7.62-7.47 (m, 2H), 7.33 (dd, J=7.7, 4.7 Hz, 1H), 7.22 (d, J=7.8 Hz, 1H), 3.10-2.89 (m, 2H), 2.89-2.70 (m, 2H), 2.70-2.55 (m, 3H), 2.48-2.34 (m, 5H), 2.20-2.00 (m, 1H), 1.81-1.51 (m, 5H). ESI MS [M+H]$^+$ for C$_{32}$H$_{32}$N$_5$, calcd. 486.3, found 486.3.

Example 20: 2,5-Dimethyl-6-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)-2,3-dihydropyridazin-3-one

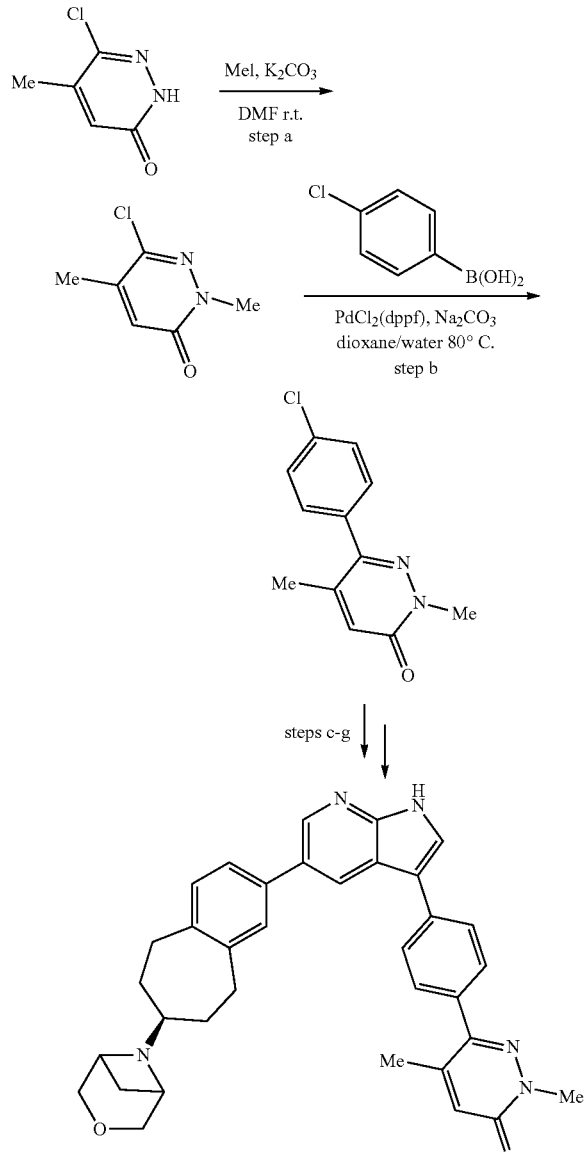

Step a: To a mixture of 6-chloro-5-methyl-3(2H)-pyridazinone (952 mg, 6.59 mmol), $K_2CO_3$ (1.18 g, 8.57 mmol), and DMF (13 mL) was added MeI (0.45 mL, 7.2 mmol). The reaction mixture was stirred at room temperature for 16 hours, diluted with water (30 mL), and extracted with MTBE (3×20 mL) and EtOAc (1×20 mL). The combined organic phases were washed with water (20 mL), washed with brine (20 mL), dried over $MgSO_4$, and concentrated. The crude material was purified by silica gel chromatography (hexanes:EtOAc 0 to 100% gradient) to afford the desired product as a white solid (816 mg, 78%).

Step b: To a mixture of the product from step a (816 mg, 5.15 mmol), (4-chlorophenyl)boronic acid (671 mg, 4.29 mmol), and $Na_2CO_3$ (1.19 g, 8.58 mmol) was added dioxane (17.2 mL) and water (4.3 mL). The suspension was degassed with nitrogen for 10 minutes and $PdCl_2(dppf)$ (157 mg, 0.215 mmol) was added. The reaction mixture was stirred at 80° C. for 16 hours, cooled, diluted with EtOAc (20 mL). The organic phase was dried over $MgSO_4$ and concentrated. The crude material was purified by silica gel chromatography (hexanes:EtOAc 0 to 50% gradient) to afford the desired product as a light yellow solid (1.09 g, 90%).

Steps c-g: The title compound was prepared in a similar manner to example 1, steps c-g. $^1H$ NMR (400 MHz, Chloroform-d) δ 9.71 (s, 1H), 8.62 (s, 1H), 8.40 (s, 1H), 7.78 (dt, J=8.2, 1.6 Hz, 2H), 7.65-7.57 (m, 1H), 7.53 (dt, J=8.2, 1.6 Hz, 2H), 7.44-7.33 (m, 2H), 7.23 (d, J=8.1 Hz, 1H), 6.86 (d, J=1.4 Hz, 1H), 4.31 (d, J=10.7 Hz, 2H), 3.85 (s, 3H), 3.74 (d, J=10.7 Hz, 2H), 3.65 (d, J=6.1 Hz, 2H), 3.26 (t, J=9.8 Hz, 1H), 2.99 (td, J=15.1, 8.5 Hz, 2H), 2.86 (q, J=13.2 Hz, 2H), 2.56 (q, J=8.1, 7.6 Hz, 1H), 2.26 (d, J=1.3 Hz, 3H), 2.03-1.89 (m, 2H), 1.85 (d, J=8.2 Hz, 1H), 1.34 (p, J=10.6 Hz, 2H). ESI MS [M+H]$^+$ for $C_{35}H_{36}N_5O_2$, calcd. 558.3, found 558.3.

Example 21: 2-Methyl-2-[2-[4-[5-[(7S)-7-(3-oxa-6-azabicyclo[3.1.1]heptan-6-yl)-6,7,8,9-tetrahydro-5H-benzo[7]annulen-3-yl]-1H-pyrrolo[2,3-b]pyridin-3-yl]phenyl]pyridin-3-yl]propanenitrile

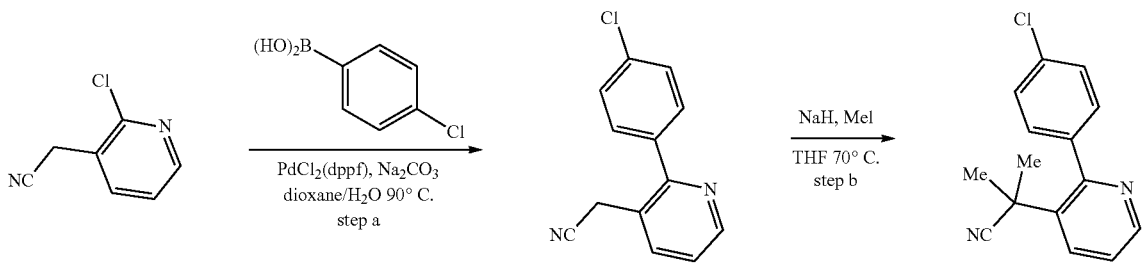

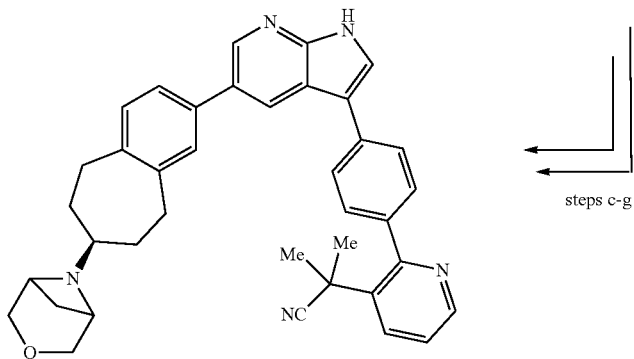

Step a: A mixture of 2-chloro-3-pyridineacetonitrile (5.0 g, 33 mmol), 4-chlorophenyl boronic acid (7.7 g, 49 mmol), 2 M $Na_2CO_{3(aq)}$ (49.2 mL, 98.3 mmol), and dioxane (164 mL) was sparged with nitrogen for ten minutes before the addition of $PdCl_2$(dppf) (2.4 g, 3.3 mmol). The resulting solution was heated to 90° C. The reaction mixture was stirred at 90° C. for 36 hours, cooled, filtered through celite to remove solids, and concentrated. The crude material was purified by silica gel chromatography (hexanes:EtOAc 0 to 100% gradient) to afford the desired product.

Step b: A mixture of the product from step a (1.14 g, 4.98 mmol), methyl iodide (1.09 mL, 17.5 mmol), and THF (8.5 mL) was added dropwise to a refluxing mixture of sodium hydride (0.60 g, 15 mmol, 60% w/w in mineral oil) and THF (8.5 mL). The resulting mixture was heated at reflux for three hours. The reaction was cooled to room temperature and carefully quenched with sat. $NH_4Cl_{(aq)}$. The reaction was extracted with EtOAc and the organics were dried over $MgSO_4$ before concentration. The material was used directly in the next step without further purification.

Steps c-g: The title compound was prepared in a similar manner to example 1, steps c-g. $^1$H NMR (400 MHz, Chloroform-d) δ 9.56 (s, 1H), 8.64 (dd, J=4.7, 1.6 Hz, 1H), 8.58 (d, J=8.58 Hz, 1H), 8.40 (d, J=8.40 Hz, 1H), 8.01 (dd, =8.1, 1.6 Hz, 1H), 7.76-7.73 (m, 2H), 7.57 (d, J=2.2 Hz, 1H), 7.51-7.48 (m, 2H), 7.39-7.34 (m, 3H), 7.21-7.19 (m, 1H), 4.29 (d, J=10.7 Hz, 2H), 3.72 (d, J=10.7 Hz, 2H), 3.64 (d, J=6.1 Hz, 2H), 3.26-3.21 (m, 1H), 3.02-2.77 (m, 4H), 2.54 (dd, J=13.4, 7.1 Hz, 1H), 1.93 (s, 2H), 1.83 (d, J=8.3 Hz, 1H) 1.69 (s, 6H), 1.34-1.25 (m, 2H). ESI MS [M+H]$^+$ for $C_{38}H_{38}N_5O$, calcd. 580.3, found 580.3.

Example 22: 1-[2-[4-[5-[(7S)-7-(3-Oxa-6-azabicyclo [3.1.1]heptan-6-yl)-6,7,8,9-tetrahydro-5H-benzo[7] annulen-3-yl]-1H-pyrrolo[2,3-b]pyridin-3-yl]phenyl] pyridin-3-yl]cyclobutan-1-ol

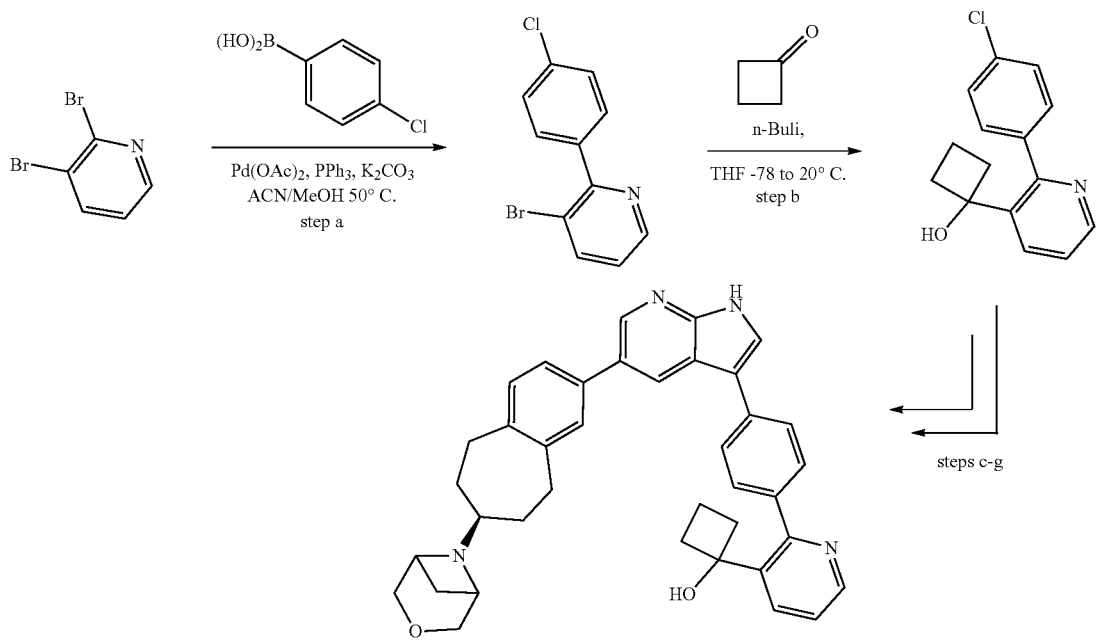

Step a: A mixture of 2,3-dibromopyridine (11.8 g, 49.8 mmol), 4-chlorophenyl boronic acid (8.21 g, 52.5 mmol), triphenylphosphine (1.31 g, 5.00 mmol), K$_2$CO$_3$ (13.8 g, 100 mmol), and 2:1 ACN:water (375 mL) was sparged with nitrogen for ten minutes before the addition of Pd(OAc)$_2$ (561 mg, 2.50 mmol). The reaction was heated to 50° C. for four hours, cooled, filtered over celite, concentrated, and purified by silica gel chromatography (CH$_2$Cl$_2$:EtOAc 0 to 50% gradient) to afford the desired product.

Step b: A mixture of the product from step a (999 mg, 3.72 mmol) and THF (11.2 mL) was cooled to −78° C. n-BuLi (1.63 mL, 4.08 mmol, 2.5 M in hexanes) was added dropwise and the reaction was stirred at −78° C. for 90 minutes. Cyclobutanone (822 µL, 11.2 mmol) was added slowly and the mixture was allowed to warm slowly to room temperature over two hours. The reaction was quenched with sat. NaHCO$_{3(aq)}$, extracted with EtOAc, and dried over Na$_2$SO$_4$. The crude material was purified by silica gel chromatography (CH$_2$Cl$_2$:EtOAc 0 to 50% gradient) to afford the desired product.

Steps c-g: The title compound was prepared in a similar manner to example 1, steps c-g. $^1$H NMR (400 MHz, Chloroform-d) δ 9.97 (s, 1H), 8.62 (dd, J=4.7, 1.7 Hz, 1H), 8.54 (d, J=2.0 Hz, 1H), 8.35 (d, J=2.0 Hz, 1H), 7.75-7.66 (m, 5H), 7.50 (s, 1H), 7.36-7.33 (m, 2H), 7.28 (dd, J=7.8, 4.7 Hz, 1H), 7.18-7.16 (m, 1H), 4.36-4.29 (m, 2H), 3.98-3.82 (m, 4H), 3.37-3.30 (m, 1H), 3.02-2.77 (m, 6H), 2.40-2.30 (m, 2H), 2.12-2.09 (m, 3H), 1.98-1.88 (m, 3H), 1.66-1.57 (m, 3H). ESI MS [M+H]$^+$ for C$_{38}$H$_{39}$N$_4$O$_2$, calcd. 583.3, found 583.3.

Example 23: 6-[(7S)-2-{3-[4-(1,3-Dimethyl-1H-1,2,4-triazol-5-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane Step a: To a solution of 4-bromobenzoic acid (1.01 g, 5.02 mmol) in DMF (18 mL) was added acetamidine hydrochloride (709 mg, 7.50 mmol), HATU (2.09 g, 5.50 mmol), and DIPEA (2.61 mL, 15.0 mmol). The reaction mixture was stirred at room temperature for 2 hours, then methylhydrazine (0.40 mL, 7.5 mmol) and acetic acid (2.86 mL, 50.0 mmol) were added. The reaction mixture was stirred at 80° C. for 3 hours, cooled to room temperature, diluted with EtOAc (200 mL), washed with sat. NaHCO$_{3(aq)}$ (1×200 mL), dried over Na$_2$SO$_4$, and concentrated. The crude material was purified by silica gel chromatography (hexanes:EtOAc 0 to 100% gradient) to afford the desired product as a white solid (895 mg, 71%).

Step b: The desired product was prepared in a similar manner to example 1, step e.

Steps c-f: The desired product was prepared in a similar manner to example 2. $^1$H NMR (400 MHz, DMSO-d$_6$) δ 13.99 (s, 1H), 8.85 (d, J=2.1 Hz, 1H), 8.71 (d, J=2.1 Hz, 1H), 8.31-8.23 (m, 2H), 7.93-7.85 (m, 2H), 7.59 (d, J=2.0 Hz, 1H), 7.53 (dd, J=7.5, 2.0 Hz, 1H), 7.23 (d, J=7.8 Hz, 1H), 4.13 (d, J=10.6 Hz, 2H), 3.93 (s, 3H), 3.53 (dd, J=18.8, 8.3 Hz, 4H), 3.20-3.09 (m, 1H), 3.05-2.85 (m, 2H), 2.77 (q, J=14.7, 14.2 Hz, 2H), 2.37-2.29 (m, 1H), 2.26 (s, 3H), 1.90-1.77 (m, 2H), 1.65 (d, J=7.8 Hz, 1H), 1.25-1.04 (m, 2H). ESI MS [M+H]+ for C$_{32}$H$_{34}$N$_7$O, calcd. 532.3, found 532.3.

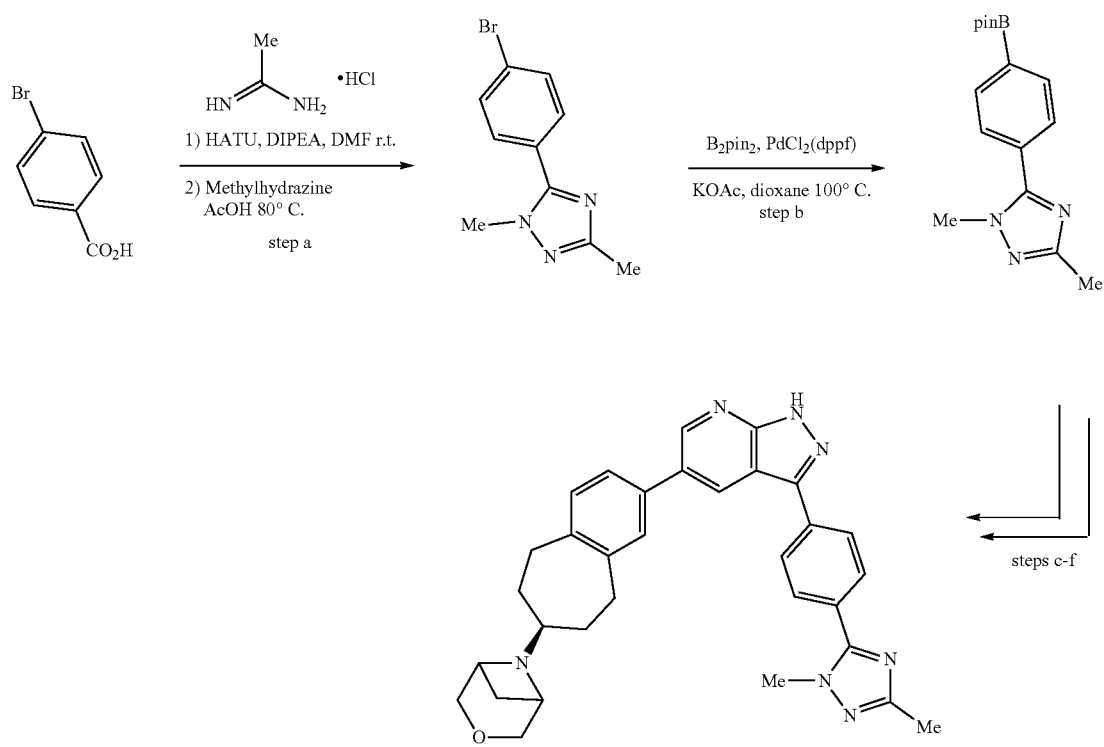

Example 24: 3-Cyclopentyl-7-{3-[4-(3-methylpyridin-2-yl)phenyl]-1H-pyrazolo[3,4-b]pyridin-5-yl}-2,3,4,5-tetrahydro-1H-3-benzazepine

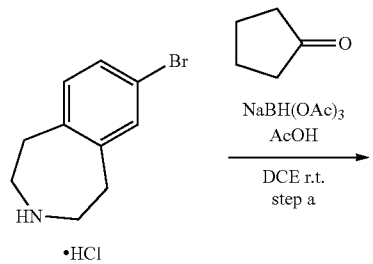

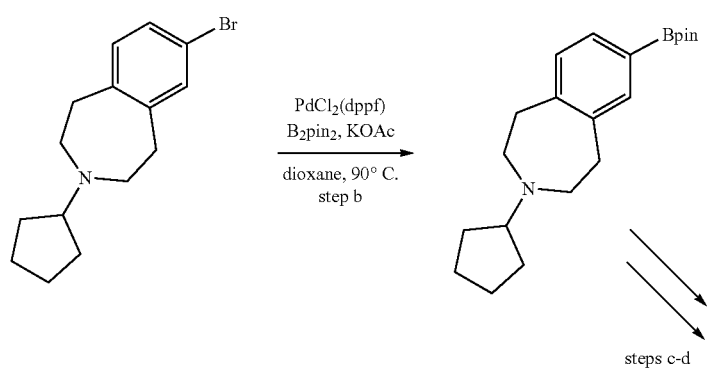

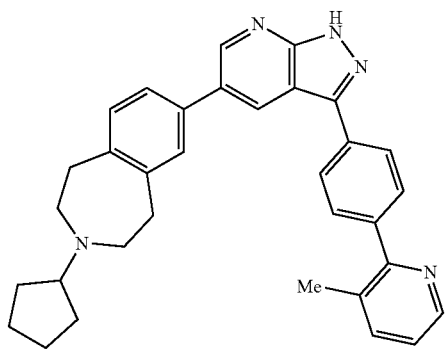

Step a: To a mixture of 7-bromo-2,3,4,5-tetrahydro-1H-3-benzazepine hydrochloride (272 mg, 1.04 mmol), cyclopentanone (0.11 mL, 1.3 mmol), and DCE (5.2 mL) was added AcOH (60 µL, 1.0 mmol) followed by NaBH(OAc)$_3$ (331 mg, 1.56 mmol). The reaction mixture was stirred at room temperature for 17 hours and carefully quenched with sat. NaHCO$_{3(aq)}$. The layers were separated, and the aqueous layer was extracted with CH$_2$Cl$_2$ (2×10 mL). The combined organic layers were washed with brine, dried over MgSO$_4$, and concentrated to afford the desired product as a colorless oil (293 mg, 96%).

Step b: To a mixture of the product from step a (111 mg, 0.377 mmol), B$_2$pin$_2$ (129 mg, 0.490 mmol), and KOAc (48 mg, 0.49 mmol) was added dioxane (3.8 mL). The suspension was degassed with nitrogen for 10 minutes and PdCl$_2$(dppf) (14 mg, 0.019 mmol) was added. The reaction mixture was stirred at 90° C. for 3 hours, cooled, diluted with EtOAc (15 mL), filtered through celite, and concentrated to afford the desired product which was used crude in step c.

Steps c-d: The desired product was prepared in a similar manner to example 2, steps e and f using the bromoazaindazole intermediate formed from example 2, step c. $^1$H NMR (400 MHz, DMSO-d$_6$) δ 13.94 (s, 1H), 8.87 (d, J=2.1 Hz, 1H), 8.73 (d, J=2.1 Hz, 1H), 8.53 (dd, J=5.0, 1.6 Hz, 1H), 8.24-8.17 (m, 2H), 7.80-7.70 (m, 3H), 7.65-7.53 (m, 2H), 7.33 (dd, J=7.7, 4.7 Hz, 1H), 7.25 (d, J=7.7 Hz, 1H), 3.03-2.94 (m, 2H), 2.94-2.88 (m, 2H), 2.88-2.80 (m, 1H), 2.74-2.54 (m, 4H), 2.42 (s, 3H), 1.88-1.70 (m, 2H), 1.67-1.56 (m, 2H), 1.56-1.44 (m, 2H), 1.44-1.33 (m, 2H), 1.31-1.21 (m, 1H). ESI MS [M+H]$^+$ for C$_{33}$H$_{34}$N$_5$, calcd. 500.3, found 500.3.

Example 25: 6-[(7S)-2-{3-[5-(3-Methylpyridin-2-yl)-1,3,4-oxadiazol-2-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane Step c: To a mixture of the product from step b (1.20 g, 3.52 mmol) in 1:1 THF/MeOH (10 mL) was added hydrazine monohydrate (0.86 mL, 18 mmol). The mixture was stirred at 75° C. for 18 hours, cooled, and concentrated. The crude material was purified by silica gel chromatography

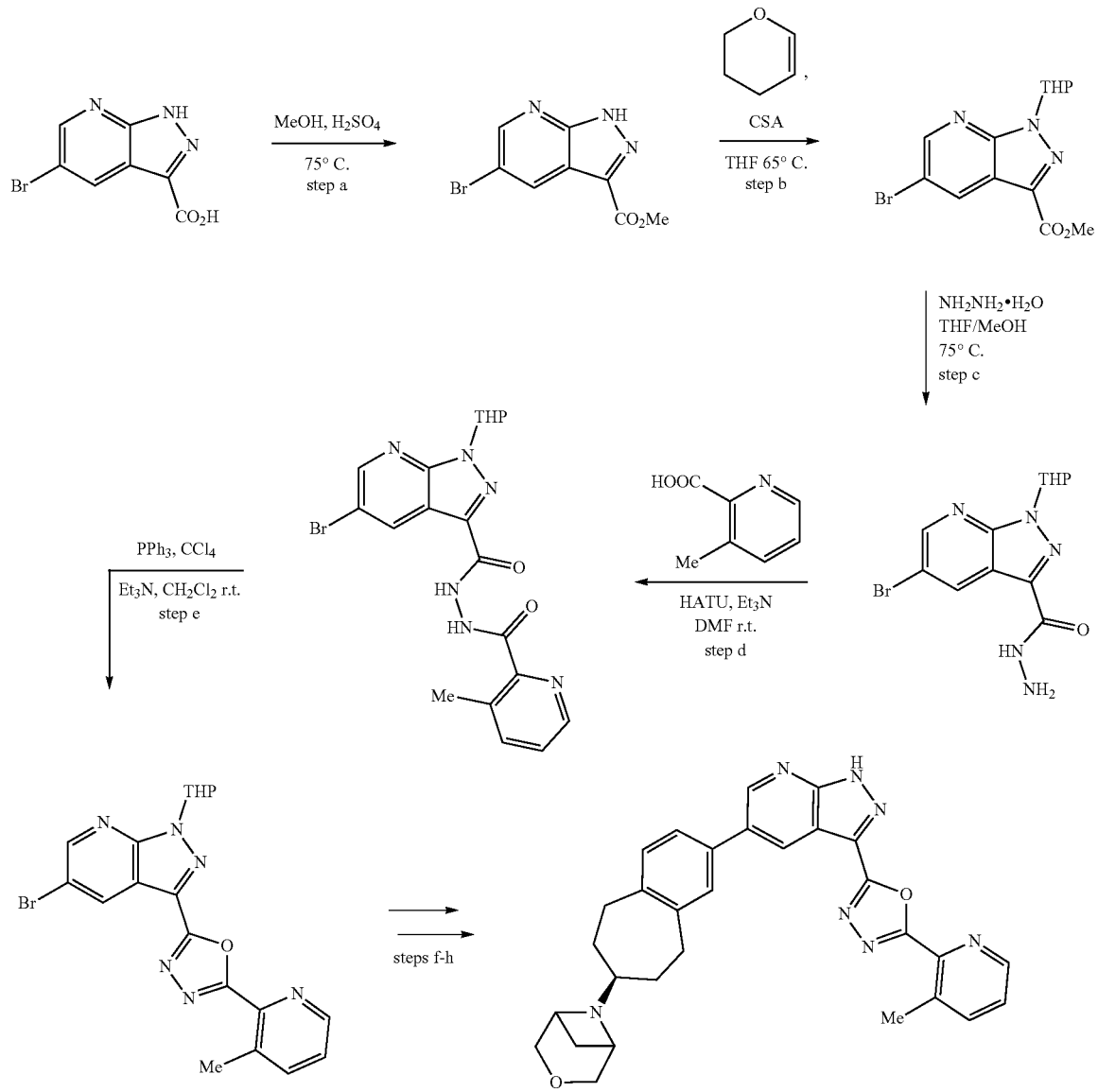

Step a: To a mixture of 5-bromo-1H-pyrazolo[3,4-b]pyridine-3-carboxylic acid (1.21 g, 5.00 mmol) and MeOH (12.5 mL) was added sulfuric acid (0.5 mL, 98% wt.). The reaction mixture was stirred at 75° C. for 18 hours, cooled, and concentrated afford the desired product which was used crude in step b.

Step b: To a mixture of the product from step a (5.00 mmol), camphorsulfonic acid (117 mg, 0.504 mmol), and THF (12.5 mL) at room temperature was added 3,4-dihydro-2H-pyran (0.92 mL, 10 mmol). The reaction mixture was stirred at 65° C. for 4 hours, cooled, and quenched with NH$_{3(aq)}$ (10 mL, 28% wt.), and concentrated. The crude material was purified by silica gel chromatography (hexanes:EtOAc 0 to 50% gradient) to afford the desired product as a white solid (1.20 g, 70%, two steps).

(hexanes:EtOAc 0 to 50% gradient) to afford the desired product as a white solid (1.16 g, 97%).

Step d: To a mixture of the product from step c (579 mg, 1.70 mmol) and DMF (5.1 mL) was added 3-methylpyridine-2-carboxylic acid (280 mg, 2.04 mmol), HATU (2.09 g, 2.55 mmol), and triethylamine (0.47 mL, 3.4 mmol). The mixture was stirred at room temperature for 18 hours, diluted with EtOAc (100 mL), washed with sat. NaHCO$_{3(aq)}$ (1×20 mL), dried over Na$_2$SO$_4$, and concentrated. The crude material was purified by silica gel chromatography (hexanes:EtOAc 0 to 100% gradient) to afford the desired product as a colorless oil (711 mg, 91%).

Step e: To a mixture of the product from step d (711 mg, 1.55 mmol) and CH$_2$Cl$_2$ (20 mL) was added triethylamine (1.08 mL, 7.75 mmol), triphenylphosphine (509 mg, 1.94 mmol), and carbon tetrachloride (0.19 mL, 2.0 mmol). The reaction mixture was stirred at room temperature for 4 hours, diluted with EtOAc (100 mL), washed with sat. NaHCO$_{3(aq)}$ (1×20 mL), dried over Na$_2$SO$_4$, and concentrated. The crude material was purified by silica gel chromatography (hexanes:EtOAc 0 to 100% gradient) to afford the desired product as a colorless oil (499 mg, 73%).

Step f-h: The desired product was prepared in a similar manner to example 2, steps d-f. $^1$H NMR (400 MHz, DMSO-d$_6$) δ 8.96 (s, 1H), 8.71-8.64 (m, 2H), 7.94 (dd, J=7.9, 1.6 Hz, 1H), 7.58-7.54 (m, 2H), 7.50 (dd, J=7.7, 2.0 Hz, 1H), 7.26 (d, J=7.8 Hz, 1H), 4.13 (d, J=10.6 Hz, 2H), 3.59-3.49 (m, 4H), 3.20-2.10 (m, 1H), 3.06-2.86 (m, 2H), 2.85-2.71 (m, 5H), 2.38-2.28 (m, 1H), 1.91-1.78 (m, 2H), 1.65 (d, J=7.9 Hz, 1H), 1.25-1.04 (m, 2H). ESI MS [M+H]$^+$ for C$_{30}$H$_{30}$N$_7$O$_2$, calcd. 520.3, found 520.3.

Example 26: 3-Methyl-6'-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}-2,3'-bipyridine

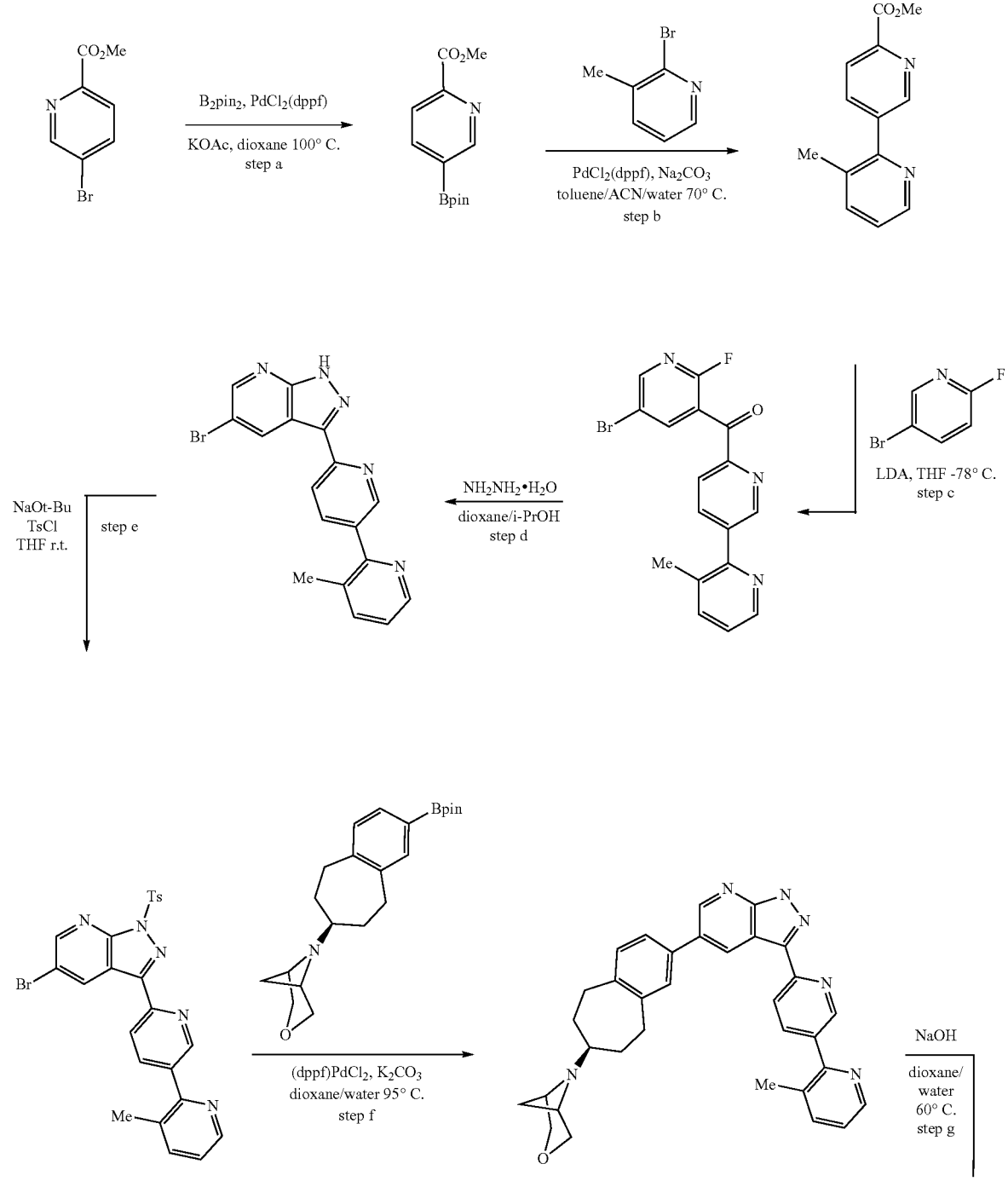

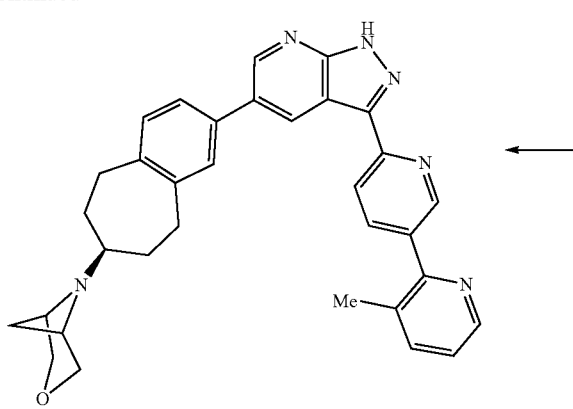

Step a: To a mixture of methyl 5-bromo-2-pyridinecarboxylate (648 mg, 3.00 mmol), B₂pin₂ (762 mg, 3.00 mmol), PdCl₂(dppf) (110 mg, 0.150 mmol), and KOAc (589 mg, 6.00 mmol) under nitrogen at room temperature was added degassed dioxane (15 mL). The reaction mixture was stirred at 100° C. for 1 hour, cooled, diluted with EtOAc (30 mL), filtered through celite, and concentrated to afford the desired product which was used crude in step b.

Step b: To a mixture of the product from step a (3.00 mmol assumed), 2-bromo-3-methylpyridine (774 mg, 4.50 mmol), PdCl₂(dppf) (110 mg, 0.150 mmol), and Na₂CO₃ (636 mg, 6.00 mmol) under nitrogen at room temperature was added degassed toluene (9.0 mL), ACN (6.0 mL), and water (3.0 mL). The reaction mixture was stirred at 70° C. for 2 hours, cooled, diluted with EtOAc (30 mL), washed with water, washed with brine, dried over Na₂SO₄, and concentrated. The crude material was purified by silica gel chromatography (hexanes:EtOAc 0 to 100% gradient) to afford the desired product as a light brown solid (524 mg, 76%).

Step c: To a solution of 2-fluoro-6-bromopyridine (823 μL, 8.00 mmol) in THF (16 mL) at −78° C. was added LDA (4.00 mL, 8.00 mmol, 2 M in ethylbenzene/THF/heptane) dropwise. The reaction mixture was stirred at −78° C. for 30 minutes. To the mixture at −78° C. was added a solution of the product from step b (913 mg, 4.00 mL) in THF (4.0 mL). The reaction mixture was stirred at −78° C. for 1 hour, quenched at −78° C. with sat. NH₄Cl$_{(aq)}$, allowed to warm to room temperature, and diluted with EtOAc (20 mL). The organic phase was dried over Na₂SO₄, concentrated, and triturated with hexane to afford the desired product as a brown solid (872 mg, 59%).

Step d: To a mixture of the product from step c (186 mg, 0.500 mmol) in 1:1 i-PrOH:dioxane (2.5 mL) at room temperature was added hydrazine monohydrate (24 μL, 0.50 mmol). The reaction mixture was stirred at room temperature for 1.5 hours. To the mixture at room temperature was added triethylamine (87 μL, 0.60 mmol) and dioxane (2.5 mL). The reaction mixture was stirred at room temperature for 3 hours, stirred at 60° C. for 1 hour, diluted with water (25 mL). The precipitated solids were collected by filtration, washed with water, dried (149 mg), and recrystallized with EtOAc (5 mL) to afford the desired product as an off-white solid (93 mg, 51%).

Step e: To a mixture of the product from step d (366 mg, 1.00 mmol) and THF (5.0 mL) at room temperature was added sodium tert-butoxide (106 mg, 1.10 mmol) in one portion. The reaction mixture was stirred at room temperature for 15 minutes and 4-methylbenzenesulfonyl chloride (191 mg, 1.00 mmol) was added in one portion. The reaction mixture was stirred at room temperature for 30 minutes, diluted with water (25 mL). The precipitated solid were collected by filtration, washed with water, and dried to afford the desired product as brown solid (458 mg, 88%).

Steps f-g: The title compound was prepared in a similar manner to example 16, steps c and d. ¹H NMR (400 MHz, Chloroform-d) δ 11.66 (s, 1H), 9.17 (d, J=2.1 Hz, 1H), 8.94 (dd, J=2.3, 0.9 Hz, 1H), 8.85 (d, J=2.2 Hz, 1H), 8.58 (ddd, J=4.8, 1.7, 0.7 Hz, 1H), 8.31 (dd, J=8.2, 0.9 Hz, 1H), 8.02 (dd, J=8.2, 2.3 Hz, 1H), 7.63 (ddd, J=7.7, 1.7, 0.8 Hz, 1H), 7.44 (dq, J=3.8, 2.0 Hz, 2H), 7.25 (s, 1H), 7.23-7.20 (m, 1H), 4.30 (d, J=10.7 Hz, 2H), 3.73 (d, J=10.7 Hz, 2H), 3.66 (d, J=6.1 Hz, 1H), 3.26 (t, J=9.6 Hz, 1H), 3.07-2.79 (m, 3H), 2.57 (q, J=6.8 Hz, 1H), 2.46 (s, 3H), 1.94 (s, 2H), 1.84 (d, J=8.3 Hz, 1H), 1.41-1.20 (m, 3H), 0.89-0.72 (m, 1H). ESI MS [M+H]⁺ for C₃₃H₃₃N₆O, calcd. 529.3, found 529.3.

Example 27: 6-[(7S)-2-{3-[1-(3-Methylpyridin-2-yl)-1H-pyrazol-4-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

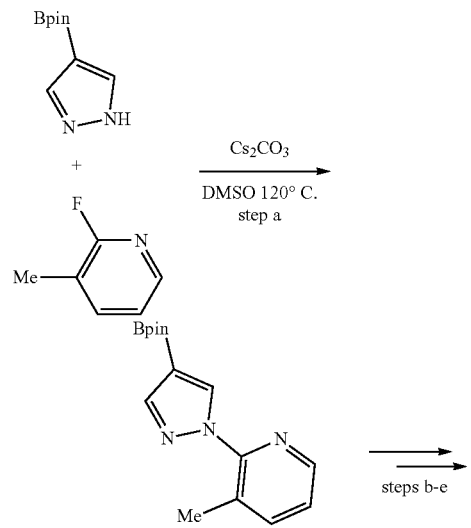

-continued

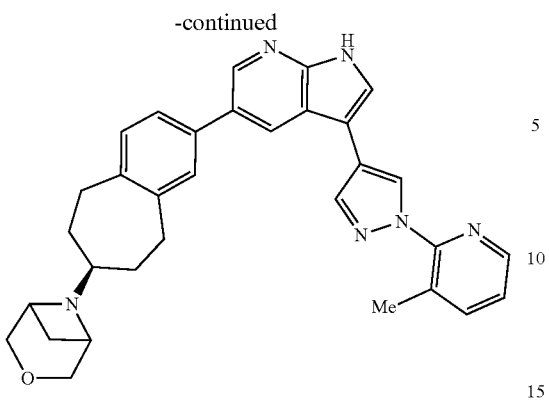

Step a: A mixture of 4-(4,4,5,5-Tetramethyl-1,3,2-dioxaborolan-2-yl)-1H-pyrazole (1.94 g, 10.0 mmol), 2-fluoro-3-methylpyridine (1.11 g, 10.0 mmol), Cs$_2$CO$_3$ (3.58 g, 11.0 mmol), and DMSO (10 mL) was stirred at 120° C. for 15 hours, cooled, diluted with EtOAc (100 mL), washed with 9:1 water:brine (4×200 mL), dried over Na$_2$SO$_4$, and concentrated. The crude material was purified by silica gel chromatography (hexanes:EtOAc 0 to 50% gradient) to afford the desired product as a white solid (515 mg, 18%).

Steps b-e: The title compound (citrate salt) was prepared in a similar manner to example 1, steps d-g. $^1$H NMR (400 MHz, DMSO-d$_6$) δ 11.87 (d, J=2.6 Hz, 1H), 8.84 (d, J=0.8 Hz, 1H), 8.55 (d, J=2.1 Hz, 1H), 8.43 (d, J=2.1 Hz, 1H), 8.41 (dd, J=4.5, 1.3 Hz, 1H), 8.35 (d, J=0.8 Hz, 1H), 7.94 (d, J=2.5 Hz, 1H), 7.91 (dd, J=7.5, 0.9 Hz, 1H), 7.63 (s, 1H), 7.57 (d, J=7.7 Hz, 1H), 7.40 (dd, J=7.6, 4.7 Hz, 1H), 7.27 (d, J=7.8 Hz, 1H), 4.39-4.07 (m, 3H), 4.01-3.79 (m, 2H), 3.73-3.55 (m, 1H), 3.50-3.17 (m, 3H), 3.07-2.80 (m, 4H), 2.61 (d, J=15.2 Hz, 2H), 2.54 (s, 3H), 2.53 (d, J=14.4 Hz, 2H), 2.21-1.90 (m, 2H), 1.30-1.11 (m, 2H). ESI MS [M+H]$^+$ for C$_{32}$H$_{33}$N$_6$O, calcd. 517.3, found 517.3.

Example 28: 6-[(7S)-3-[3-[4-(5-Fluoro-3-methylpyridin-2-yl)phenyl]-1H-pyrazolo[3,4-b]pyridin-5-yl]-6,7,8,9-tetrahydro-5H-benzo[7]annulen-7-yl]-3-oxa-6-azabicyclo[3.1.1]heptane

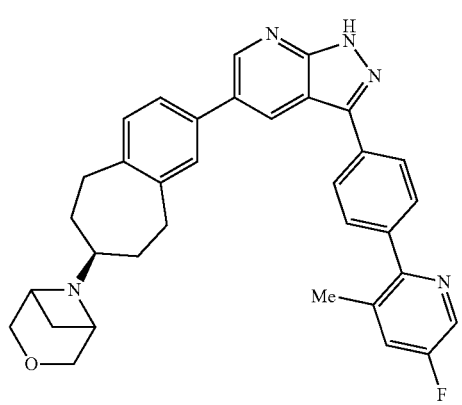 [SMILES: Cc1cc(F)cnc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, Chloroform-d) δ 10.84 (s, 1H), 8.84 (d, J=2.0 Hz, 1H), 8.51 (d, J=2.1 Hz, 1H), 8.43 (dd, J=2.8, 0.6 Hz, 1H), 8.13-8.05 (m, 2H), 7.72-7.64 (m, 2H), 7.43-7.33 (m, 3H), 7.30-7.21 (m, 1H), 4.31 (d, J=10.7 Hz, 2H), 3.74 (d, J=10.9

Hz, 2H), 3.66 (m, 2H), 3.27 (m, 1H), 3.04-2.93 (m, 2H), 2.86 (q, J=13.2 Hz, 2H), 2.57 (m, 1H), 2.46 (t, J=0.7 Hz, 3H), 1.98 (m, 2H), 1.85 (d, J=8.2 Hz, 1H), 1.37-1.22 (m, 2H). ESI MS [M+H]$^+$ for C$_{34}$H$_{33}$FN$_5$O, calcd. 546.3, found 546.3.

Example 29: 6-[(7S)-3-[3-[4-(5-Fluoro-3-methylpyridin-2-yl)phenyl]-1H-pyrrolo[2,3-b]pyridin-5-yl]-6,7,8,9-tetrahydro-5H-benzo[7]annulen-7-yl]-3-oxa-6-azabicyclo[3.1.1]heptane

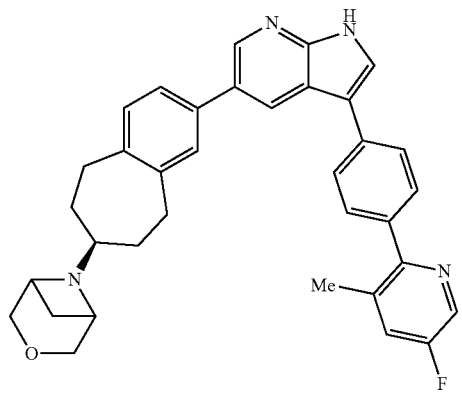 [SMILES: Cc1cc(F)cnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. $^1$H NMR (400 MHz, Chloroform-d) δ 8.89 (s, 1H), 8.61 (d, J=2.0 Hz, 1H), 8.45-8.38 (m, 2H), 7.80-7.72 (m, 2H), 7.65-7.54 (m, 3H), 7.39 (s, 2H), 7.42-7.32 (m, 1H), 7.23-7.20 (m, 1H), 4.31 (d, J=10.7 Hz, 2H), 3.73 (d, J=10.7 Hz, 2H), 3.64 (d, J=6.0 Hz, 2H), 3.25 (m, 1H), 3.01-2.77 (m, 4H), 2.56 (m, 1H), 2.47 (s, 3H), 1.94 (m, 2H), 1.84 (d, J=8.2 Hz, 1H), 1.36-1.24 (m, 2H). ESI MS [M+H]$^+$ for C$_{35}$H$_{34}$FN$_4$O, calcd. 545.3, found 545.3.

Example 30: 6-[(7S)-3-[3-[2-Methyl-4-(3-methylpyridin-2-yl)phenyl]-1H-pyrazolo[3,4-b]pyridin-5-yl]-6,7,8,9-tetrahydro-5H-benzo[7]annulen-7-yl]-3-oxa-6-azabicyclo[3.1.1]heptane

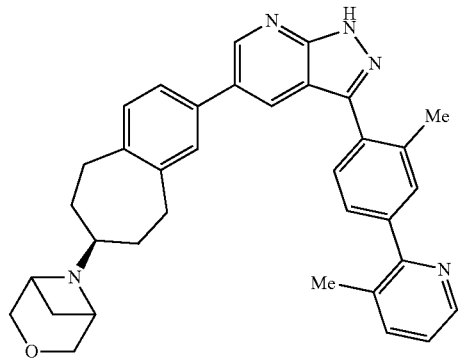 [SMILES: Cc1cc(-c2ncccc2C)ccc1-c1n[nH]c2ncc(-c3ccc4c(c3)CC[C@@H](N3C5COCC3C5)CC4)cc12]

The title compound was prepared in a similar manner to example 2 from the appropriate starting materials. $^1$H NMR (400 MHz, Chloroform-d) δ 11.51 (s, 1H), 8.87 (d, J=2.1 Hz, 1H), 8.56 (ddd, J=4.7, 1.8, 0.7 Hz, 1H), 8.20 (d, J=2.1 Hz, 1H), 7.67-7.60 (m, 2H), 7.57 (dt, J=1.8, 0.6 Hz, 1H), 7.50 (ddd, J=7.8, 1.9, 0.7 Hz, 1H), 7.34 (d, J=11.8 Hz, 2H), 7.21

(dd, J=7.8, 4.8 Hz, 2H), 4.31 (d, J=10.8 Hz, 2H), 3.73 (dd, J=10.6, 4.1 Hz, 2H), 3.66 (d, J=5.8 Hz, 2H), 3.26 (t, J=9.9 Hz, 1H), 3.05-2.80 (m, 4H), 2.57 (q, J=6.8 Hz, 1H), 2.52 (s, 3H), 2.44 (s, 3H), 1.94 (m, 2H), 1.84 (dd, J=8.3, 3.6 Hz, 1H), 1.38-1.28 (m, 2H). ESI MS [M+H]$^+$ for $C_{35}H_{36}N_5O$, calcd. 542.3, found 542.3.

Example 31: 1-[4-[5-[(7S)-7-(3-Oxa-6-azabicyclo[3.1.1]heptan-6-yl)-6,7,8,9-tetrahydro-5H-benzo[7]annulen-3-yl]-1H-pyrazolo[3,4-b]pyridin-3-yl]phenyl]pyridin-2-one

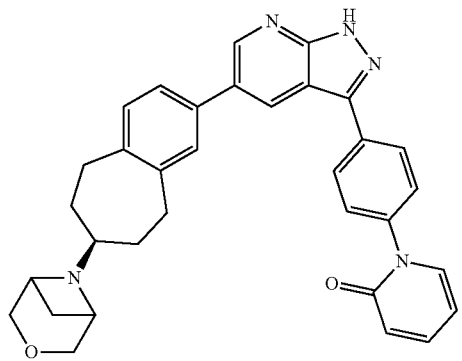 [SMILES: O=c1ccccn1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, Chloroform-d) δ 11.51 (s, 1H), 8.86 (d, J=2.1 Hz, 1H), 8.50 (d, J=2.1 Hz, 1H), 8.16-8.08 (m, 2H), 7.62-7.54 (m, 2H), 7.48-7.36 (m, 4H), 7.30-7.21 (m, 1H), 6.71 (ddd, J=9.2, 1.3, 0.9 Hz, 1H), 6.30 (td, J=6.7, 1.3 Hz, 1H), 4.33 (d, J=10.9 Hz, 2H), 3.78 (m, 3H), 3.30 (m, 1H), 3.01 (td, J=15.5, 7.9 Hz, 2H), 2.86 (q, J=13.4, 13.0 Hz, 2H), 2.64 (m, 1H), 1.97 (m, 2H), 1.88 (d, J=8.4 Hz, 1H), 1.42 (m, 2H), 1.26 (m, 1H). ESI MS [M+H]$^+$ for $C_{33}H_{32}N_5O_2$, calcd. 530.3, found 530.2.

Example 32: (3S)—N-[(7S)-3-[3-(4-Pyridin-2-ylphenyl)-1H-pyrrolo[2,3-b]pyridin-5-yl]-6,7,8,9-tetrahydro-5H-benzo[7]annulen-7-yl]oxan-3-amine

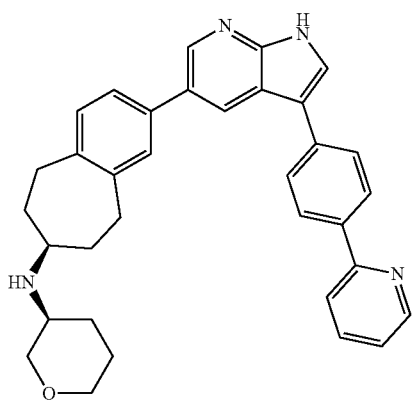 [SMILES: c1ccc(-c2ccc(-c3c[nH]c4ncc(-c5ccc6c(c5)CC[C@@H](N[C@H]5CCCOC5)CC6)cc34)cc2)nc1]

The title compound was prepared in a similar manner to example 1 from the appropriate starting materials. $^1$H NMR (400 MHz, Chloroform-d) δ 9.66 (s, 1H), 8.76-8.69 (m, 1H), 8.61 (d, J=2.0 Hz, 1H), 8.44 (d, J=2.1 Hz, 1H), 8.16-8.08 (m, 2H), 7.84-7.76 (m, 4H), 7.63 (d, J=2.3 Hz, 1H), 7.41 (dq, J=3.5, 2.0 Hz, 2H), 7.29-7.19 (m, 2H), 3.93 (dd, J=11.0, 3.3 Hz, 1H), 3.81 (dt, J=11.2, 4.1 Hz, 1H), 3.48-3.37 (m, 1H), 3.23-3.13 (m, 1H), 3.01-2.86 (m, 3H), 2.83 (t, J=10.3 Hz, 2H), 2.75 (d, J=13.8 Hz, 1H), 2.11 (t, J=12.8 Hz, 2H), 2.01-1.93 (m, 1H), 1.77-1.56 (m, 2H), 1.35 (dq, J=30.8, 18.0, 15.1 Hz, 4H). ESI MS [M+H]$^+$ for $C_{34}H_{35}N_4O$, calcd. 515.3, found 515.3.

Example 33: (1S,4S)-5-[(7S)-3-[3-(4-Pyridin-2-ylphenyl)-1H-pyrrolo[2,3-b]pyridin-5-yl]-6,7,8,9-tetrahydro-5H-benzo[7]annulen-7-yl]-2-oxa-5-azabicyclo[2.2.1]heptane

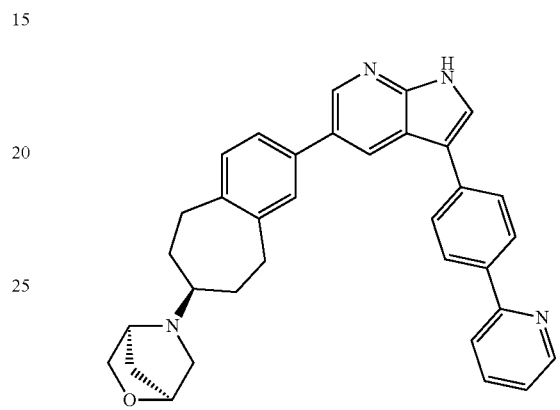

The title compound was prepared in a similar manner to example 1 from the appropriate starting materials. $^1$H NMR (400 MHz, Chloroform-d) δ 9.43 (s, 1H), 8.76-8.69 (m, 1H), 8.61 (d, J=2.0 Hz, 1H), 8.43 (d, J=2.0 Hz, 1H), 8.16-8.08 (m, 2H), 7.84-7.77 (m, 4H), 7.62 (d, J=2.5 Hz, 1H), 7.39 (dq, J=3.5, 2.0 Hz, 2H), 7.29-7.18 (m, 2H), 4.43 (s, 1H), 4.09 (d, J=7.7 Hz, 1H), 3.77 (s, 1H), 3.68 (dd, J=7.5, 1.6 Hz, 1H), 3.15 (m, J=9.7 Hz, 3H), 2.83 (s, 1H), 2.72 (m, 2H), 2.51 (d, J=9.6 Hz, 1H), 1.98 (m, 2H), 1.90 (d, J=9.9 Hz, 1H), 1.78 (d, J=9.8 Hz, 1H), 1.27 (m, J=7.7 Hz, 1H), 0.92-0.81 (m, 1H). ESI MS [M+H]$^+$ for $C_{34}H_{33}N_4O$, calcd. 513.3, found 513.3.

Example 34: 3-[4-(5-Fluoro-3-methylpyridin-2-yl)phenyl]-5-[(7S)-7-methyl-7-[(2R)-2-methylpyrrolidin-1-yl]-5,6,8,9-tetrahydrobenzo[7]annulen-3-yl]-1H-pyrrolo[2,3-b]pyridine

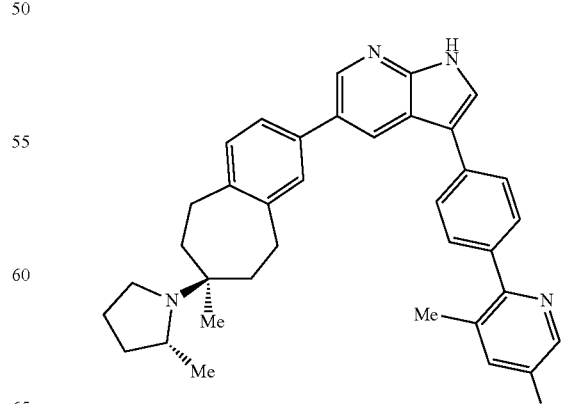

The title compound was prepared in a similar manner to example 1 from the appropriate starting materials. ¹H NMR (400 MHz, Chloroform-d) δ 9.81 (s, 1H), 8.63 (d, J=2.1 Hz, 1H), 8.46-8.39 (m, 2H), 7.81-7.73 (m, 2H), 7.65-7.57 (m, 3H), 7.42-7.32 (m, 3H), 7.21 (d, J=8.2 Hz, 1H), 3.39 (br s, 1H), 3.29-3.20 (m, 2H), 2.92 (t, J=7.6 Hz, 1H), 2.74-2.48 (m, 3H), 2.47 (s, 3H), 1.99-1.83 (m, 3H), 1.79-1.61 (m, 3H), 1.51-1.41 (m, 2H), 1.08 (d, J=6.3 Hz, 3H), 1.00 (s, 3H). ESI MS [M+H]⁺ for $C_{36}H_{38}FN_4$, calcd. 545.3, found 545.3.

Example 35: 6-[(7S)-3-[3-[5-(5-Fluoro-3-methylpyridin-2-yl)pyridin-2-yl]-1H-pyrrolo[2,3-b]pyridin-5-yl]-6,7,8,9-tetrahydro-5H-benzo[7]annulen-7-yl]-3-oxa-6-azabicyclo[3.1.1]heptane

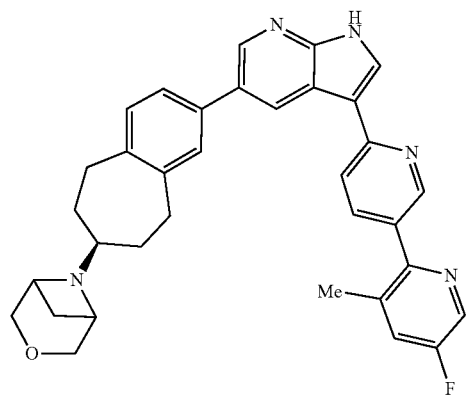 [SMILES: Cc1cc(F)cnc1-c1ccc(-c2c[nH]c3ncc(-c4ccc5c(c4)CC[C@@H](N4C6COCC4C6)CC5)cc23)nc1]

The title compound was prepared in a similar manner to example 9 from the appropriate starting materials. ¹H NMR (400 MHz, Chloroform-d) δ 10.93 (s, 1H), 8.94 (d, J=2.1 Hz, 1H), 8.84 (dd, J=2.3, 0.8 Hz, 1H), 8.63 (d, J=2.1 Hz, 1H), 8.44 (dd, J=2.8, 0.7 Hz, 1H), 8.02 (d, J=1.9 Hz, 1H), 7.91 (dd, J=8.2, 2.3 Hz, 1H), 7.78 (dd, J=8.2, 0.9 Hz, 1H), 7.44 (dq, J=3.7, 2.0 Hz, 2H), 7.37 (ddd, J=9.0, 2.8, 0.8 Hz, 1H), 7.23 (d, J=8.2 Hz, 1H), 4.32 (d, J=10.7 Hz, 2H), 3.71 (dd, J=27.1, 8.4 Hz, 4H), 3.32-3.22 (m, 1H), 2.99 (td, J=19.7, 17.0, 7.8 Hz, 2H), 2.86 (q, J=13.7, 13.1 Hz, 2H), 2.59 (q, J=6.8 Hz, 1H), 2.48 (d, J=0.8 Hz, 3H), 1.96 (m, 2H) 1.85 (d, J=8.3 Hz, 1H), 1.36 (p, J=10.4 Hz, 2H). ESI MS [M+H]⁺ for $C_{34}H_{33}FN_5$, calcd. 546.3, found 546.3.

Example 36: 6-[(7S)-3-[5-[4-(3-Methylpyridin-2-yl)phenyl]-7H-pyrrolo[2,3-c]pyridazin-3-yl]-6,7,8,9-tetrahydro-5H-benzo[7]annulen-7-yl]-3-oxa-6-azabicyclo[3.1.1]heptane

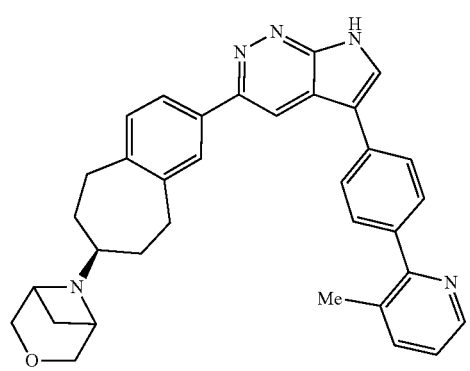 [SMILES: Cc1cccnc1-c1ccc(-c2c[nH]c3nnc(-c4ccc5c(c4)CC[C@@H](N4C6COCC4C6)CC5)cc23)cc1]

The title compound was prepared in a similar manner to example 18 from the appropriate starting materials. ¹H NMR (400 MHz, Chloroform-d) δ 12.27 (s, 1H), 8.65-8.55 (m, 1H), 8.38 (s, 1H), 7.96-7.90 (m, 2H), 7.87-7.71 (m, 3H), 7.72-7.58 (m, 3H), 7.31-7.17 (m, 2H), 4.32 (d, J=10.6 Hz, 2H), 3.74 (d, J=10.7 Hz, 2H), 3.67 (d, J=6.0 Hz, 2H), 3.32-3.22 (m, 1H), 3.06 (dt, J=18.8, 9.6 Hz, 1H), 2.98 (s, 1H), 2.90 (p, J=13.9 Hz, 2H), 2.57 (q, J=6.8 Hz, 1H), 2.45 (s, 3H), 1.96 (t, J=10.7 Hz, 2H), 1.85 (d, J=8.2 Hz, 1H), 1.34 (m, 2H). ESI MS [M+H]⁺ for $C_{34}H_{34}N_5O$, calcd. 528.3, found 528.3.

Example 37: 6-[(7S)-3-[3-[5-(3-Methylpyridin-2-yl)pyrimidin-2-yl]-1H-pyrrolo[2,3-b]pyridin-5-yl]-6,7,8,9-tetrahydro-5H-benzo[7]annulen-7-yl]-3-oxa-6-azabicyclo[3.1.1]heptane

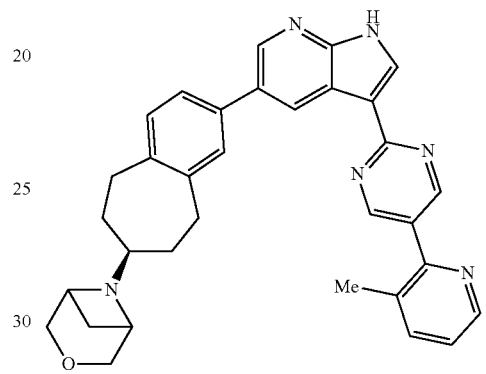

The title compound was prepared in a similar manner to example 9 from the appropriate starting materials. ¹H NMR (400 MHz, Chloroform-d) δ 10.36 (s, 1H), 9.17 (d, J=2.2 Hz, 1H), 8.99 (s, 2H), 8.65-8.57 (m, 2H), 8.40 (d, J=2.5 Hz, 1H), 7.65 (ddd, J=7.7, 1.7, 0.8 Hz, 1H), 7.47 (dq, J=3.4, 1.8 Hz, 2H), 7.30-7.20 (m, 2H), 4.32 (d, J=10.7 Hz, 2H), 3.74 (d, J=10.7 Hz, 2H), 3.70-3.63 (m, 2H), 3.33-3.23 (m, 1H), 3.00 (ddd, J=22.8, 14.3, 7.8 Hz, 2H), 2.90 (d, J=14.8 Hz, 1H), 2.84 (d, J=14.6 Hz, 1H), 2.57 (q, J=6.7 Hz, 1H), 2.49 (s, 3H), 1.96 (s, 2H), 1.85 (d, J=8.3 Hz, 1H), 1.35 (p, J=10.5 Hz, 2H). ESI MS [M+H]⁺ for $C_{33}H_{33}N_6O$, calcd. 529.3, found 529.3.

Example 38: 6-[(7S)-3-[3-[2-(3-Methylpyridin-2-yl)pyrimidin-5-yl]-1H-pyrrolo[2,3-b]pyridin-5-yl]-6,7,8,9-tetrahydro-5H-benzo[7]annulen-7-yl]-3-oxa-6-azabicyclo[3.1.1]heptane

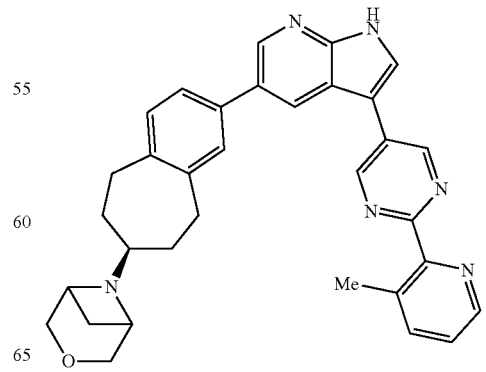

The title compound was prepared in a similar manner to example 17 from the appropriate starting materials. $^1$H NMR (400 MHz, Chloroform-d) δ 10.55 (s, 1H), 9.25 (s, 2H), 8.72-8.63 (m, 2H), 8.42 (d, J=2.0 Hz, 1H), 7.76 (d, J=2.3 Hz, 1H), 7.68 (ddd, J=7.7, 1.7, 0.8 Hz, 1H), 7.40 (dq, J=4.6, 2.1 Hz, 2H), 7.32 (dd, J=7.7, 4.7 Hz, 1H), 7.24 (t, J=8.4 Hz, 1H), 4.32 (dd, J=10.6, 3.2 Hz, 2H), 3.74 (d, J=10.9 Hz, 2H), 3.66 (d, J=6.0 Hz, 2H), 3.26 (t, J=9.7 Hz, 1H), 3.00 (td, J=18.5, 16.6, 7.9 Hz, 2H), 2.89 (d, J=13.4 Hz, 1H), 2.83 (d, J=14.1 Hz, 1H), 2.64 (s, 3H), 2.56 (q, J=6.8 Hz, 1H), 1.96 (d, J=11.2 Hz, 2H), 1.85 (d, J=8.2 Hz, 1H), 1.36 (q, J=11.2, 10.6 Hz, 2H). ESI MS [M+H]$^+$ for $C_{33}H_{33}N_6O$, calcd. 529.3, found 529.3.

Example 39: 1-Methyl-6-[4-[5-[(7S)-7-(3-oxa-6-azabicyclo[3.1.1]heptan-6-yl)-6,7,8,9-tetrahydro-5H-benzo[7]annulen-3-yl]-1H-pyrrolo[2,3-b]pyridin-3-yl]phenyl]pyridin-2-one

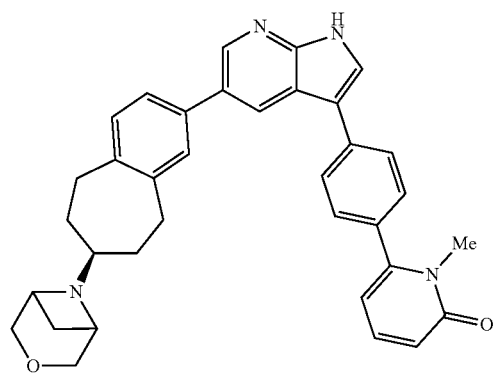 [SMILES: Cn1c(-c2ccc(-c3c[nH]c4ncc(-c5ccc6c(c5)CC[C@@H](N5C7COCC5C7)CC6)cc34)cc2)cccc1=O]

The title compound was prepared in a similar manner to example 1 from the appropriate starting materials. $^1$H NMR (400 MHz, Chloroform-d) δ 9.61 (s, 1H), 8.62 (d, J=2.1 Hz, 1H), 8.40 (d, J=2.0 Hz, 1H), 7.82-7.74 (m, 2H), 7.62 (d, J=2.5 Hz, 1H), 7.49-7.41 (m, 2H), 7.43-7.33 (m, 3H), 7.29-7.19 (m, 1H), 6.63 (dd, J=9.1, 1.4 Hz, 1H), 6.18 (dd, J=6.8, 1.4 Hz, 1H), 4.31 (d, J=10.7 Hz, 2H), 3.74 (d, J=10.7 Hz, 2H), 3.66 (d, J=6.0 Hz, 2H), 3.48 (s, 3H), 3.26 (t, J=9.7 Hz, 2H), 2.99 (td, J=14.9, 7.8 Hz, 2H), 2.86 (q, J=13.5 Hz, 2H), 2.56 (q, J=6.8 Hz, 1H), 1.95 (m, 2H), 1.85 (d, J=8.3 Hz, 1H), 1.33 (m, 2H). ESI MS [M+H]$^+$ for $C_{35}H_{35}N_4O_2$, calcd. 543.3, found 543.3.

Example 40: 6-[(7S)-2-{3-[3-Fluoro-4-(pyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

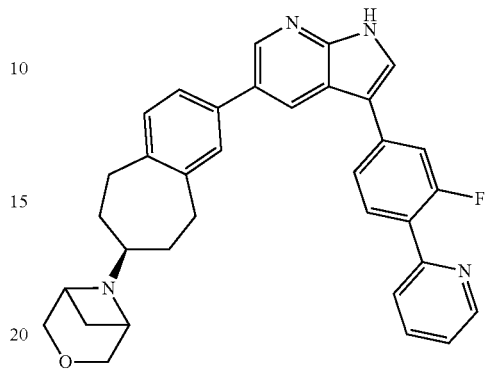

The title compound was prepared in a similar manner to example 1 from the appropriate starting materials. $^1$H NMR (400 MHz, DMSO-d$_6$) δ 12.15 (d, J=2.7 Hz, 1H), 8.77-8.70 (m, 1H), 8.59-8.53 (m, 1H), 8.49 (d, J=2.1 Hz, 1H), 8.12 (d, J=2.7 Hz, 1H), 8.06 (t, J=8.4 Hz, 1H), 7.92 (td, J=7.7, 1.8 Hz, 1H), 7.89-7.78 (m, 2H), 7.80-7.70 (m, 1H), 7.58-7.52 (m, 1H), 7.53-7.46 (m, 1H), 7.40 (ddd, J=7.4, 4.8, 1.2 Hz, 1H), 7.23 (d, J=7.7 Hz, 1H), 4.16 (d, J=10.7 Hz, 2H), 3.62-3.51 (m, 4H), 3.22-3.12 (m, 1H), 3.07-2.88 (m, 2H), 2.87-2.71 (m, 2H), 2.41-2.32 (m, 1H), 1.93-1.79 (m, 2H), 1.68 (d, J=7.8 Hz, 1H), 1.22-1.09 (m, 2H). $^{19}$F NMR (376 MHz, DMSO-d$_6$) δ −116.73−−116.85 (m). ESI MS [M+H]$^+$ for $C_{34}H_{32}FN_4O$, calcd. 531.3, found 531.3.

Example 41: 6-[(7S)-2-{3-[4-(Pyridin-4-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

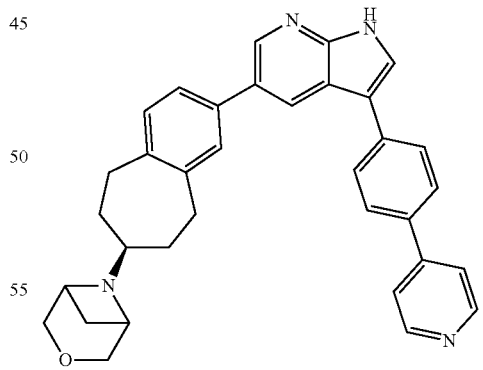

The title compound was prepared in a similar manner to example 1 from the appropriate starting materials. $^1$H NMR (400 MHz, Chloroform-d) δ 9.27 (s, 1H), 8.73-8.63 (m, 2H), 8.60 (d, J=2.1 Hz, 1H), 8.39 (d, J=2.0 Hz, 1H), 7.85-7.71 (m, 4H), 7.59 (d, J=2.5 Hz, 1H), 7.58-7.52 (m, 2H), 7.41-7.34 (m, 2H), 7.21 (d, J=8.3 Hz, 1H), 4.29 (d, J=10.6 Hz, 2H), 3.71 (d, J=10.6 Hz, 2H), 3.62 (d, J=6.1 Hz, 2H), 3.31-3.20 (m, 1H), 2.98 (td, J=14.4, 8.0 Hz, 2H), 2.87 (d, J=12.5 Hz, 1H), 2.80 (d, J=13.2 Hz, 1H), 2.54 (q, J=6.7 Hz, 1H), 2.01-1.88 (m, 2H), 1.83 (d, J=8.1 Hz, 1H), 1.41-1.25 (m, 2H). ESI MS [M+H]$^+$ for $C_{34}H_{33}N_4O$, calcd. 513.3, found 513.3.

Example 42: 6-[(7S)-2-{3-[4-(3-Fluoropyridin-2-yl) phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

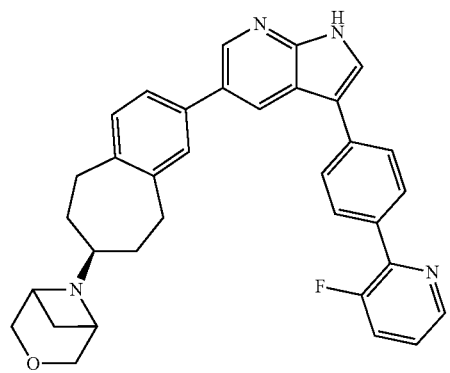 [SMILES: Fc1cccnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. $^1$H NMR (400 MHz, Chloroform-d) δ 9.32 (s, 1H), 8.62 (d, J=2.1 Hz, 1H), 8.55 (dt, J=4.6, 1.6 Hz, 1H), 8.44 (d, J=1.9 Hz, 1H), 8.11 (dq, J=8.4, 1.9 Hz, 2H), 7.85-7.76 (m, 2H), 7.62 (d, J=2.6 Hz, 1H), 7.52 (ddd, J=11.2, 8.2, 1.4 Hz, 1H), 7.44-7.36 (m, 2H), 7.30-7.26 (m, 1H), 7.22 (d, J=8.3 Hz, 1H), 4.31 (d, J=10.7 Hz, 2H), 3.73 (d, J=10.7 Hz, 2H), 3.64 (d, J=6.1 Hz, 2H), 3.32-3.18 (m, 1H), 3.09-2.92 (m, 2H), 2.88 (d, J=12.8 Hz, 1H), 2.82 (d, J=13.6 Hz, 1H), 2.56 (q, J=6.7 Hz, 1H), 2.01-1.88 (m, 2H), 1.84 (d, J=8.2 Hz, 1H), 1.34 (p, J=10.5 Hz, 2H). $^{19}$F NMR (376 MHz, Chloroform-d) δ –122.80-–122.88 (m). ESI MS [M+H]$^+$ for $C_{34}H_{32}FN_4O$, calcd. 531.3, found 531.3.

Example 43: 6-[(7S)-2-{3-[4-(3-Chloropyridin-2-yl) phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

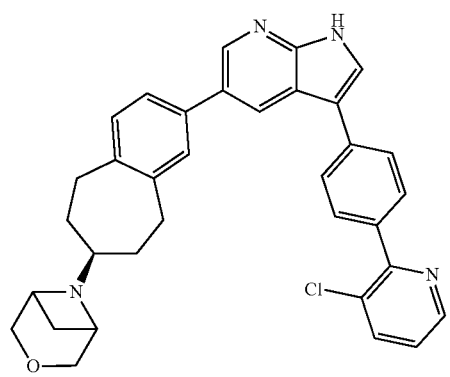 [SMILES: Clc1cccnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. $^1$H NMR (400 MHz, DMSO-d$_6$) δ 12.07 (d, J=2.6 Hz, 1H), 8.66 (dd, J=4.6, 1.5 Hz, 1H), 8.56 (d, J=2.1 Hz, 1H), 8.48 (d, J=2.1 Hz, 1H), 8.07 (dd, J=8.1, 1.5 Hz, 1H), 8.03 (d, J=2.6 Hz, 1H), 7.96-7.87 (m, 2H), 7.83-7.76 (m, 2H), 7.54 (d, J=1.9 Hz, 1H), 7.49 (dd, J=7.6, 1.9 Hz, 1H), 7.44 (dd, J=8.1, 4.6 Hz, 1H), 7.23 (d, J=7.8 Hz, 1H), 4.16 (d, J=10.6 Hz, 2H), 3.65-3.46 (m, 4H), 3.22-3.11 (m, 1H), 3.08-2.87 (m, 2H), 2.78 (q, J=14.4, 13.9 Hz, 2H), 2.36 (q, J=6.5, 5.8 Hz, 1H), 1.93-1.76 (m, 2H), 1.68 (d, J=7.8 Hz, 1H), 1.22-1.08 (m, 2H). ESI MS [M+H]$^+$ for $C_{34}H_{32}C_1N_4O$, calcd. 547.2, found 547.2.

Example 44: 6-[(7S)-2-{3-[3-Chloro-4-(pyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

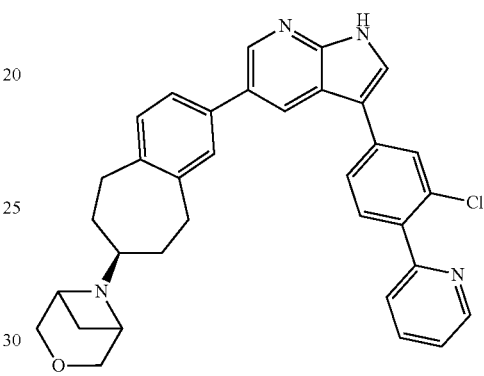

The title compound was prepared in a similar manner to example 1 from the appropriate starting materials. $^1$H NMR (400 MHz, Chloroform-d) δ 9.79 (s, 1H), 8.76 (ddd, J=4.9, 1.8, 1.0 Hz, 1H), 8.63 (s, 1H), 8.39 (d, J=2.0 Hz, 1H), 7.82-7.67 (m, 5H), 7.62 (d, J=2.5 Hz, 1H), 7.43-7.37 (m, 2H), 7.31 (ddd, J=7.2, 4.9, 1.5 Hz, 1H), 7.23 (d, J=8.2 Hz, 1H), 4.31 (d, J=10.6 Hz, 2H), 3.73 (d, J=10.6 Hz, 2H), 3.65 (d, J=6.1 Hz, 2H), 3.26 (t, J=9.6 Hz, 1H), 3.00 (td, J=16.5, 15.9, 7.7 Hz, 2H), 2.86 (q, J=13.3 Hz, 2H), 2.56 (q, J=6.8 Hz, 1H), 2.03-1.88 (m, 2H), 1.85 (d, J=8.2 Hz, 1H), 1.41-1.30 (m, 2H). ESI MS [M+H]$^+$ for $C_{34}H_{32}C_1N_4O$, calcd. 547.2, found 547.2.

Example 45: 6-[(7S)-2-{3-[1-(Pyridin-4-yl)-1H-pyrazol-4-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

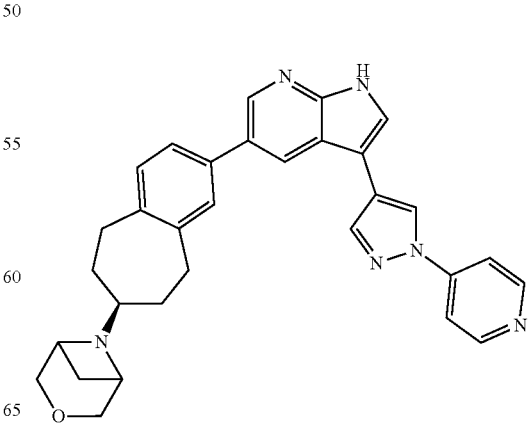

The title compound was prepared in a similar manner to example 1 from the appropriate starting materials. $^1$H NMR (400 MHz, DMSO-d$_6$) δ 11.91 (d, J=2.6 Hz, 1H), 9.16 (s, 1H), 8.73-8.59 (m, 2H), 8.59-8.47 (m, 2H), 8.40 (s, 1H), 8.01-7.97 (m, 2H), 7.96 (d, J=2.6 Hz, 1H), 7.59-7.53 (m, 1H), 7.51 (dd, J=7.6, 1.7 Hz, 1H), 7.25 (d, J=7.7 Hz, 1H), 4.17 (d, J=10.7 Hz, 2H), 3.64-3.47 (m, 4H), 3.24-3.12 (m, 1H), 3.08-2.88 (m, 2H), 2.88-2.72 (m, 2H), 2.42-2.29 (m, 1H), 1.96-1.79 (m, 2H), 1.69 (d, J=7.9 Hz, 1H), 1.25-1.10 (m, 2H). ESI MS [M+H]$^+$ for C$_{31}$H$_{31}$N$_6$O, calcd. 503.3, found 503.2.

Example 46: 2-(4-{5-[(7S)-7-{3-Oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-3-carbonitrile

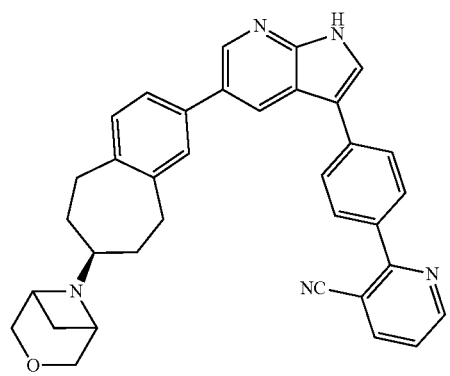

The title compound was prepared in a similar manner to example 1 from the appropriate starting materials. $^1$H NMR (400 MHz, DMSO-d$_6$) δ 12.14 (s, 1H), 8.96 (dd, J=4.8, 1.7 Hz, 1H), 8.57 (d, J=2.0 Hz, 1H), 8.51 (d, J=2.0 Hz, 1H), 8.45 (dd, J=8.0, 1.8 Hz, 1H), 8.10 (d, J=2.7 Hz, 1H), 8.03 (d, J=8.5 Hz, 2H), 7.99 (d, J=8.5 Hz, 2H), 7.61 (dd, J=7.9, 4.8 Hz, 1H), 7.56 (d, J=2.0 Hz, 1H), 7.50 (dd, J=7.7, 1.7 Hz, 1H), 7.23 (d, J=7.7 Hz, 1H), 4.16 (d, J=10.6 Hz, 2H), 3.65-3.48 (m, 4H), 3.22-3.09 (m, 1H), 3.07-2.87 (m, 2H), 2.87-2.70 (m, 2H), 2.41-2.28 (m, 1H), 1.96-1.78 (m, 2H), 1.68 (d, J=7.9 Hz, 1H), 1.24-1.08 (m, 2H). ESI MS [M+H]$^+$ for C$_{35}$H$_{32}$N$_5$O, calcd. 538.3, found 538.2.

Example 47: 6-[(7S)-2-{3-[4-(5-Methylpyrimidin-4-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

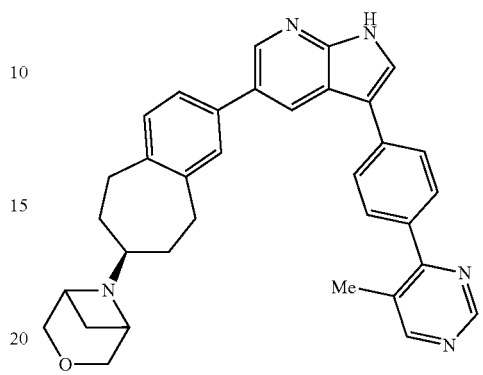

The title compound was prepared in a similar manner to example 1 from the appropriate starting materials. $^1$H NMR (400 MHz, DMSO-d$_6$) δ 12.11 (d, J=2.7 Hz, 1H), 9.10 (s, 1H), 8.74 (s, 1H), 8.57 (d, J=2.1 Hz, 1H), 8.49 (d, J=2.1 Hz, 1H), 8.07 (d, J=2.7 Hz, 1H), 7.97 (dt, J=8.5, 1.9 Hz, 2H), 7.82 (dt, J=8.5, 2.0 Hz, 2H), 7.55 (d, J=2.0 Hz, 1H), 7.49 (dd, J=7.6, 2.0 Hz, 1H), 7.23 (d, J=7.8 Hz, 1H), 4.16 (d, J=10.6 Hz, 2H), 3.59 (d, J=10.6 Hz, 2H), 3.54 (d, J=6.0 Hz, 2H), 3.23-3.09 (m, 1H), 3.09-2.86 (m, 2H), 2.79 (q, J=14.3 Hz, 2H), 2.45 (s, 3H), 2.41-2.26 (m, 1H), 1.95-1.75 (m, 2H), 1.68 (d, J=7.8 Hz, 1H), 1.28-1.05 (m, 2H). ESI MS [M+H]$^+$ for C$_{34}$H$_{34}$N$_5$O, calcd. 528.3, found 528.3.

Example 48: 6-[(7S)-2-{3-[4-(3-Methylpyrazin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

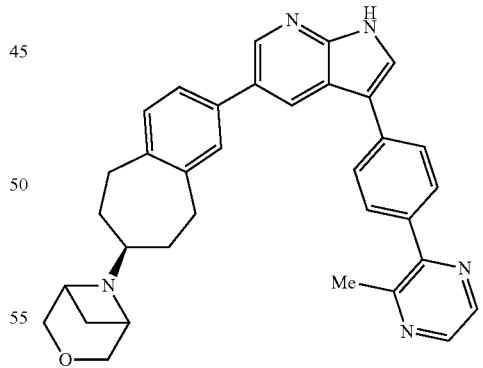

The title compound was prepared in a similar manner to example 1 from the appropriate starting materials. $^1$H NMR (400 MHz, DMSO-d$_6$) δ 12.09 (d, J=2.7 Hz, 1H), 8.59-8.57 (m, 1H), 8.56 (d, J=2.1 Hz, 1H), 8.52 (d, J=2.5 Hz, 1H), 8.48 (d, J=2.1 Hz, 1H), 8.04 (d, J=2.7 Hz, 1H), 7.99-7.91 (m, 2H), 7.78-7.70 (m, 2H), 7.54 (d, J=1.9 Hz, 1H), 7.48 (dd, J=7.9, 1.8 Hz, 1H), 7.23 (d, J=7.8 Hz, 1H), 4.15 (d, J=10.5 Hz, 2H), 3.58 (d, J=10.6 Hz, 2H), 3.54 (d, J=6.0 Hz, 2H), 3.22-3.09 (m, 1H), 3.09-2.85 (m, 2H), 2.78 (q, J=13.8 Hz, 2H), 2.66 (s, 3H), 2.36 (q, J=7.2, 6.7 Hz, 1H), 1.94-1.73 (m, 2H), 1.68 (d, J=7.8 Hz, 1H), 1.29-1.02 (m, 2H). ESI MS [M+H]+ for C34H34N5O, calcd. 528.3, found 528.3.

Example 49: 6-[(7S)-2-{3-[4-(4-Methylpyridazin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

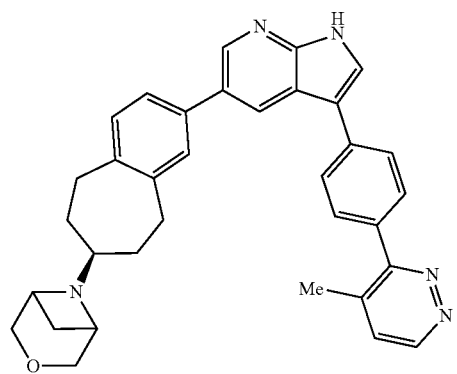 [SMILES: Cc1ccnnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. 1H NMR (400 MHz, DMSO-d6) δ 12.09 (d, J=2.8 Hz, 1H), 9.08 (d, J=5.2 Hz, 1H), 8.57 (d, J=2.0 Hz, 1H), 8.49 (d, J=2.1 Hz, 1H), 8.05 (d, J=2.6 Hz, 1H), 8.00-7.90 (m, 2H), 7.80-7.68 (m, 2H), 7.66 (dd, J=5.2, 1.0 Hz, 1H), 7.55 (d, J=1.8 Hz, 1H), 7.49 (dd, J=7.5, 2.0 Hz, 1H), 7.23 (d, J=7.8 Hz, 1H), 4.16 (d, J=10.6 Hz, 2H), 3.68-3.46 (m, 4H), 3.24-3.07 (m, 1H), 3.06-2.87 (m, 2H), 2.79 (q, J=14.4, 13.9 Hz, 2H), 2.42 (s, 3H), 2.41-2.28 (m, 1H), 1.93-1.80 (m, 2H), 1.68 (d, J=7.9 Hz, 1H), 1.26-1.00 (m, 2H). ESI MS [M+H]+ for C34H34N5O, calcd. 528.3, found 528.3.

Example 50: 6-[(7S)-2-{3-[4-(3,5-Dimethylpyrazin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

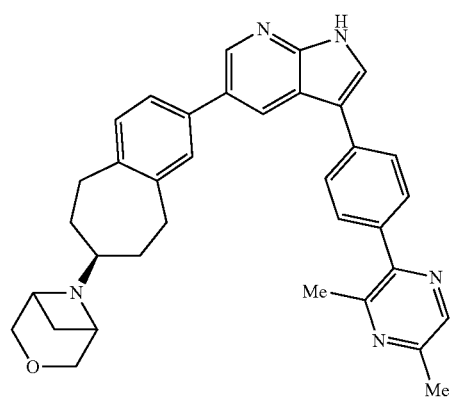 [SMILES: Cc1cnc(-c2ccc(-c3c[nH]c4ncc(-c5ccc6c(c5)CC[C@@H](N5C7COCC5C7)CC6)cc34)cc2)c(C)n1]

The title compound was prepared in a similar manner to example 1 from the appropriate starting materials. 1H NMR (400 MHz, Chloroform-d) δ 10.21 (s, 1H), 8.64 (d, J=2.0 Hz, 1H), 8.44 (d, J=2.0 Hz, 1H), 8.40 (s, 1H), 7.87-7.75 (m, 2H), 7.75-7.66 (m, 2H), 7.63 (d, J=2.5 Hz, 1H), 7.47-7.35 (m, 2H), 7.23 (d, J=8.3 Hz, 1H), 4.31 (d, J=10.6 Hz, 2H), 3.73 (d, J=10.7 Hz, 2H), 3.65 (d, J=6.1 Hz, 2H), 3.32-3.17 (m, 1H), 3.00 (td, J=17.1, 16.1, 7.9 Hz, 2H), 2.86 (q, J=13.6 Hz, 2H), 2.70 (s, 3H), 2.60 (s, 3H), 2.56 (q, J=6.4 Hz, 1H), 2.04-1.89 (m, 2H), 1.85 (d, J=8.2 Hz, 1H), 1.34 (p, J=10.1 Hz, 2H). ESI MS [M+H]+ for C35H36N5O, calcd. 542.3, found 542.3.

Example 51: 4-methyl-3-(4-{5-[(7S)-7-Methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyridazine

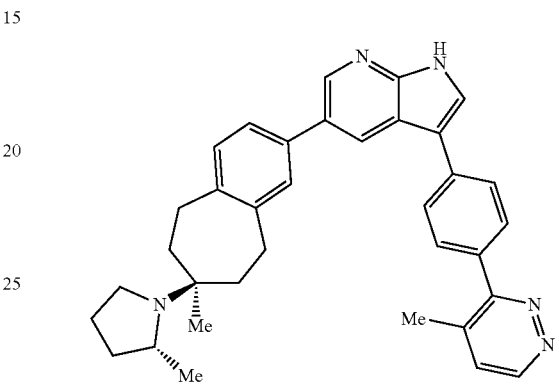

The title compound was prepared in a similar manner to example 1 from the appropriate starting materials. 1H NMR (400 MHz, DMSO-d6) δ 12.08 (s, 1H), 9.08 (d, J=5.1 Hz, 1H), 8.56 (d, J=2.1 Hz, 1H), 8.48 (d, J=2.0 Hz, 1H), 8.05 (d, J=2.7 Hz, 1H), 8.00-7.84 (m, 2H), 7.78-7.68 (m, 2H), 7.66 (dt, J=5.1, 0.7 Hz, 1H), 7.51 (s, 1H), 7.46 (d, J=7.8 Hz, 1H), 7.20 (d, J=7.7 Hz, 1H), 3.29-3.09 (m, 3H), 2.83 (t, J=7.6 Hz, 1H), 2.71-2.52 (m, 3H), 2.42 (s, 3H), 1.96-1.57 (m, 5H), 1.46-1.20 (m, 3H), 1.03 (d, J=6.2 Hz, 3H), 0.92 (s, 3H). ESI MS [M+H]+ for C35H38N5, calcd. 528.3, found 528.3.

Example 52: 2-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridine-3-carbonitrile

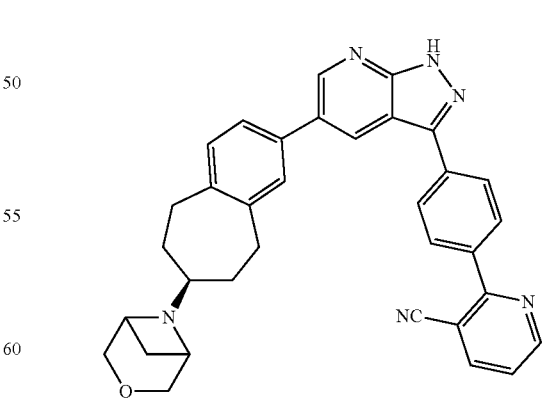

The title compound was prepared in a similar manner to example 2 from the appropriate starting materials. 1H NMR (400 MHz, DMSO-d6) δ 9.03-8.93 (m, 1H), 8.89 (d, J=2.0 Hz, 1H), 8.78 (d, J=2.1 Hz, 1H), 8.48 (dd, J=7.9, 1.7 Hz, 1H), 8.42-8.26 (m, 2H), 8.18-7.96 (m, 2H), 7.70-7.59 (m, 2H), 7.58 (d, J=7.7 Hz, 1H), 7.26 (d, J=7.7 Hz, 1H), 4.16 (d, J=11.0 Hz, 2H), 3.71-3.44 (m, 4H), 3.23-3.10 (m, 1H), 3.10-2.89 (m, 2H), 2.89-2.71 (m, 2H), 2.42-2.28 (m, 1H), 2.00-1.79 (m, 2H), 1.68 (d, J=7.7 Hz, 1H), 1.24-1.09 (m, 2H). ESI MS [M+H]$^+$ for $C_{34}H_{31}N_6O$, calcd. 539.3, found 539.3.

Example 53: 6-[(7S)-2-{3-[4-(3,6-Dimethylpyrazin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

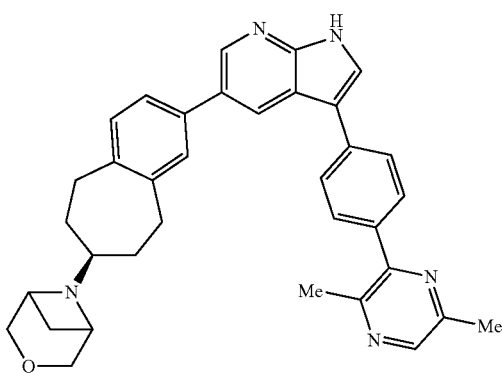 [SMILES: Cc1cnc(C)c(-c2ccc(-c3c[nH]c4ncc(-c5ccc6c(c5)CC[C@@H](N5C7COCC5C7)CC6)cc34)cc2)n1]

The title compound was prepared in a similar manner to example 1 from the appropriate starting materials. $^1$H NMR (400 MHz, DMSO-d$_6$) δ 12.08 (d, J=2.7 Hz, 1H), 8.56 (d, J=2.1 Hz, 1H), 8.48 (d, J=2.0 Hz, 1H), 8.41 (s, 1H), 8.03 (d, J=2.7 Hz, 1H), 7.97-7.88 (m, 2H), 7.77-7.65 (m, 2H), 7.54 (d, J=1.9 Hz, 1H), 7.48 (dd, J=7.7, 2.0 Hz, 1H), 7.23 (d, J=7.8 Hz, 1H), 4.15 (d, J=10.6 Hz, 2H), 3.58 (d, J=10.6 Hz, 2H), 3.54 (d, J=6.0 Hz, 2H), 3.17 (t, J=8.5 Hz, 1H), 2.97 (ddd, J=33.5, 13.7, 8.6 Hz, 2H), 2.78 (q, J=13.8 Hz, 2H), 2.60 (s, 3H), 2.52 (s, 3H), 2.36 (q, J=6.9 Hz, 1H), 1.94-1.76 (m, 2H), 1.68 (d, J=7.9 Hz, 1H), 1.26-1.07 (m, 2H). ESI MS [M+H]$^+$ for $C_{35}H_{36}N_5O$, calcd. 542.3, found 542.3.

Example 54: 6-[(7S)-2-{3-[5-(3-Methylpyrazin-2-yl)pyridin-2-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

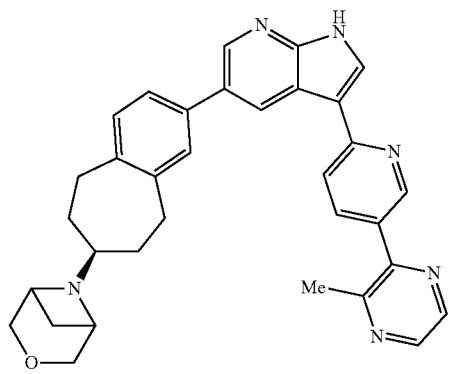 [SMILES: Cc1nccnc1-c1ccc(-c2c[nH]c3ncc(-c4ccc5c(c4)CC[C@@H](N4C6COCC4C6)CC5)cc23)nc1]

The title compound was prepared in a similar manner to example 9 from the appropriate starting materials. $^1$H NMR (400 MHz, Chloroform-d) δ 10.75 (d, J=13.3 Hz, 1H), 8.97 (d, J=1.7 Hz, 1H), 8.95 (dt, J=2.3, 0.7 Hz, 1H), 8.64 (s, 1H), 8.55 (dt, J=2.5, 0.7 Hz, 1H), 8.50 (d, J=2.4 Hz, 1H), 8.05 (s, 1H), 8.01 (dd, J=8.2, 2.5 Hz, 1H), 7.83 (dt, J=8.3, 0.7 Hz, 1H), 7.49-7.41 (m, 2H), 7.24 (d, J=8.2 Hz, 1H), 4.32 (d, J=10.7 Hz, 2H), 3.75 (d, J=10.7 Hz, 2H), 3.68 (d, J=6.1 Hz, 2H), 3.27 (t, J=9.7 Hz, 1H), 3.00 (ddd, J=20.7, 14.4, 7.8 Hz, 2H), 2.95-2.79 (m, 2H), 2.76 (s, 3H), 2.58 (q, J=6.6 Hz, 1H), 2.03-1.91 (m, 2H), 1.86 (d, J=8.3 Hz, 1H), 1.36 (p, J=9.8 Hz, 2H). ESI MS [M+H]$^+$ for $C_{33}H_{33}N_6O$, calcd. 529.3, found 529.3.

Example 55: 6-[(7S)-2-{3-[5-(3-Methylpyrazin-2-yl)pyridin-2-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

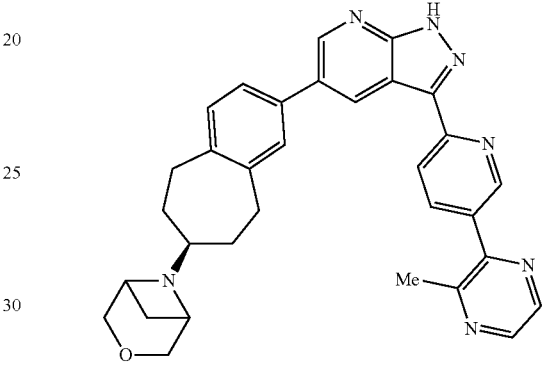

The title compound was prepared in a similar manner to example 9 from the appropriate starting materials. $^1$H NMR (400 MHz, Chloroform-d) δ 12.16 (s, 1H), 9.19 (s, 1H), 9.11-8.96 (m, 1H), 8.88 (s, 1H), 8.58-8.55 (m, 1H), 8.53 (d, J=2.4 Hz, 1H), 8.38 (dt, J=8.2, 0.9 Hz, 1H), 8.09 (ddd, J=8.3, 2.3, 0.8 Hz, 1H), 7.51-7.36 (m, 2H), 7.26-7.22 (m, 1H), 4.33 (d, J=10.7 Hz, 2H), 3.75 (d, J=10.7 Hz, 2H), 3.68 (d, J=6.1 Hz, 2H), 3.35-3.20 (m, 1H), 3.08-2.78 (m, 4H), 2.76 (s, 3H), 2.60 (q, J=6.9 Hz, 1H), 2.08-1.89 (m, 2H), 1.87 (d, J=8.2 Hz, 1H), 1.46-1.28 (m, 2H). ESI MS [M+H]$^+$ for $C_{32}H_{32}N_7O$, calcd. 530.3, found 530.3.

Example 56: 6-[(7S)-2-{3-[5-(4-Methylpyridazin-3-yl)pyridin-2-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

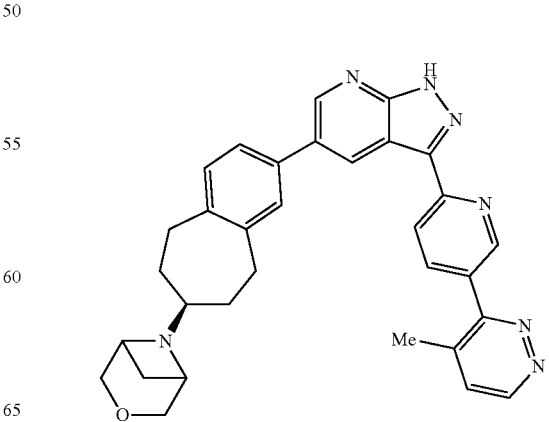

The title compound was prepared in a similar manner to example 9 from the appropriate starting materials. ¹H NMR (400 MHz, DMSO-d₆) δ 9.15 (d, J=5.2 Hz, 1H), 9.07 (d, J=2.2 Hz, 1H), 9.06-9.03 (m, 1H), 8.90 (d, J=2.2 Hz, 1H), 8.36 (dd, J=8.2, 0.8 Hz, 1H), 8.25 (dd, J=8.3, 2.2 Hz, 1H), 7.73 (dt, J=5.1, 0.7 Hz, 1H), 7.54 (s, 1H), 7.48 (dd, J=7.7, 1.9 Hz, 1H), 7.28 (d, J=7.7 Hz, 1H), 4.16 (d, J=10.6 Hz, 2H), 3.66-3.44 (m, 4H), 3.25-3.09 (m, 1H), 3.09-2.88 (m, 2H), 2.80 (q, J=13.9 Hz, 2H), 2.46 (s, 3H), 2.36 (q, J=7.2 Hz, 1H), 2.03-1.78 (m, 2H), 1.68 (d, J=7.9 Hz, 1H), 1.29-0.97 (m, 2H). ESI MS [M+H]⁺ for $C_{32}H_{32}N_7O$, calcd. 530.3, found 530.3.

Example 57: 3,5-Dimethyl-2-(4-{5-[(7S)-7-methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyrazine

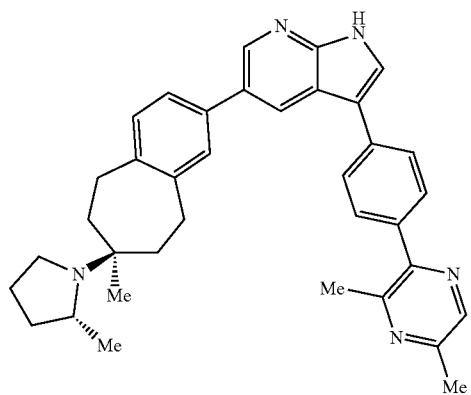 [SMILES: Cc1cnc(-c2ccc(-c3c[nH]c4ncc(-c5ccc6c(c5)CC[C@@](C)(N5CCC[C@H]5C)CC6)cc34)cc2)c(C)n1]

The title compound was prepared in a similar manner to example 1 from the appropriate starting materials. ¹H NMR (400 MHz, Chloroform-d) δ 9.27 (s, 1H), 8.62 (d, J=2.0 Hz, 1H), 8.42 (d, J=1.8 Hz, 1H), 8.40 (s, 1H), 7.87-7.73 (m, 2H), 7.73-7.64 (m, 2H), 7.60 (d, J=2.5 Hz, 1H), 7.42-7.34 (m, 2H), 7.21 (d, J=8.1 Hz, 1H), 3.52-3.29 (m, 1H), 3.24 (p, J=6.5 Hz, 2H), 2.92 (t, J=7.6 Hz, 1H), 2.77-2.44 (m, 9H), 2.01-1.78 (m, 3H), 1.79-1.62 (m, 2H), 1.55-1.37 (m, 3H), 1.08 (d, J=6.3 Hz, 3H), 1.00 (s, 3H). ESI MS [M+H]⁺ for $C_{36}H_{40}N_5$, calcd. 542.3, found 542.3.

Example 58: 2,5-Dimethyl-3-(4-{5-[(7S)-7-methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyrazine

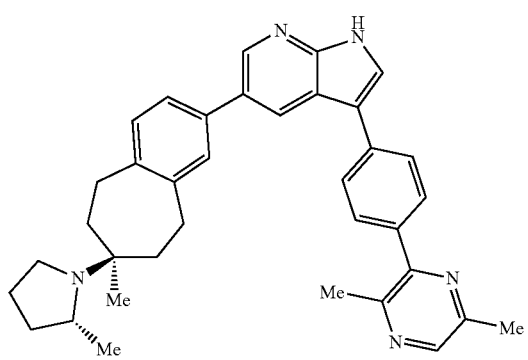 [SMILES: Cc1cnc(C)c(-c2ccc(-c3c[nH]c4ncc(-c5ccc6c(c5)CC[C@@](C)(N5CCC[C@H]5C)CC6)cc34)cc2)n1]

The title compound was prepared in a similar manner to example 1 from the appropriate starting materials. ¹H NMR (400 MHz, Chloroform-d) δ 9.32 (s, 1H), 8.62 (d, J=2.0 Hz, 1H), 8.42 (d, J=2.0 Hz, 1H), 8.35 (s, 1H), 7.89-7.74 (m, 2H), 7.74-7.65 (m, 2H), 7.60 (d, J=2.5 Hz, 1H), 7.42-7.33 (m, 2H), 7.21 (d, J=8.2 Hz, 1H), 3.52-3.30 (m, 1H), 3.30-3.17 (m, 2H), 2.92 (t, J=7.6 Hz, 1H), 2.74-2.63 (m, 4H), 2.64-2.45 (m, 5H), 1.99-1.80 (m, 3H), 1.79-1.62 (m, 2H), 1.56-1.39 (m, 3H), 1.08 (d, J=6.3 Hz, 3H), 1.00 (s, 3H). ESI MS [M+H]⁺ for $C_{36}H_{40}N_5$, calcd. 542.3, found 542.3.

Example 59: 3,5-Dimethyl-2-(4-{5-[(7S)-7-(pyrrolidin-1-yl)-6,7,8,9-tetrahydro-5H-benzo[7]annulen-2-yl]-1H-pyrrolo[2,3-b]pyridin-3-yl}phenyl)pyrazine

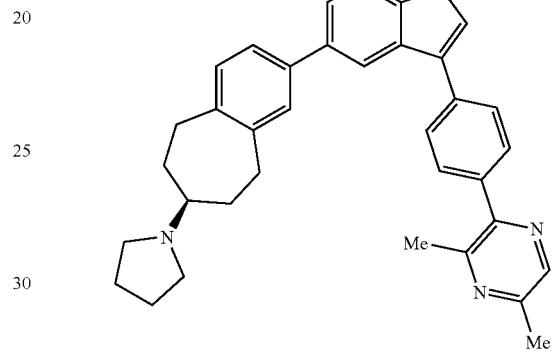

The title compound was prepared in a similar manner to example 1 from the appropriate starting materials. ¹H NMR (400 MHz, Chloroform-d) δ 9.20 (s, 1H), 8.62 (s, 1H), 8.43 (d, J=1.3 Hz, 1H), 8.40 (s, 1H), 7.83-7.75 (m, 2H), 7.70 (dt, J=8.3, 0.7 Hz, 2H), 7.60 (d, J=2.3 Hz, 1H), 7.42-7.37 (m, 2H), 7.23 (d, J=7.8 Hz, 1H), 3.15-2.95 (m, 2H), 2.82-2.68 (m, 5H), 2.69-2.50 (m, 8H), 2.19-2.01 (m, 2H), 1.87-1.73 (m, 4H), 1.68-1.60 (m, 2H). ESI MS [M+H]⁺ for $C_{34}H_{36}N_5$, calcd. 514.3, found 514.3.

Example 60: 3,5-Dimethyl-2-(6-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}pyridin-3-yl)pyrazine

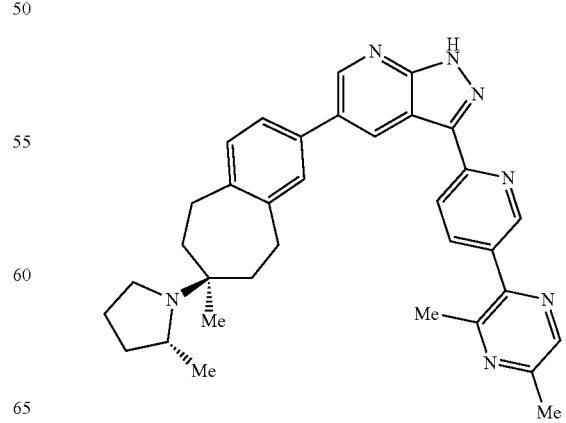

The title compound was prepared in a similar manner to example 9 from the appropriate starting materials. ¹H NMR (400 MHz, Chloroform-d) δ 11.62 (s, 1H), 9.20 (d, J=1.9 Hz, 1H), 8.99 (dd, J=2.3, 0.9 Hz, 1H), 8.90 (s, 1H), 8.44 (s, 1H), 8.36 (dd, J=8.2, 0.9 Hz, 1H), 8.07 (dd, J=8.2, 2.3 Hz, 1H), 7.49-7.37 (m, 2H), 7.23 (d, J=8.1 Hz, 1H), 3.48-3.33 (m, 1H), 3.33-3.17 (m, 2H), 2.93 (t, J=7.7 Hz, 1H), 2.77-2.57 (m, 8H), 2.58-2.45 (m, 1H), 2.02-1.79 (m, 3H), 1.80-1.64 (m, 2H), 1.56-1.39 (m, 3H), 1.09 (d, J=6.5 Hz, 3H), 1.00 (s, 3H). ESI MS [M+H]⁺ for $C_{34}H_{38}N_7$, calcd. 544.3, found 544.3.

Example 61: 2,5-Dimethyl-3-(6-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}pyridin-3-yl)pyrazine

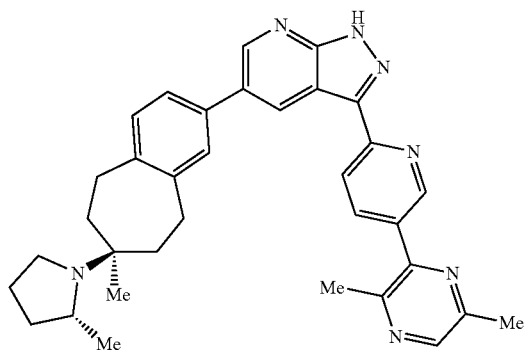 [SMILES: Cc1cnc(C)c(-c2ccc(-c3n[nH]c4ncc(-c5ccc6c(c5)CC[C@@](C)(N5CCC[C@H]5C)CC6)cc34)nc2)n1]

The title compound was prepared in a similar manner to example 9 from the appropriate starting materials. ¹H NMR (400 MHz, Chloroform-d) δ 11.68 (s, 1H), 9.20 (s, 1H), 9.00 (dt, J=2.3, 0.7 Hz, 1H), 8.91 (s, 1H), 8.41 (s, 1H), 8.36 (dt, J=8.3, 0.7 Hz, 1H), 8.08 (dd, J=8.1, 2.1 Hz, 1H), 7.48-7.39 (m, 2H), 7.24 (d, J=8.2 Hz, 1H), 3.53-3.34 (m, 1H), 3.34-3.16 (m, 2H), 2.93 (t, J=7.6 Hz, 1H), 2.76-2.58 (m, 8H), 2.59-2.44 (m, 1H), 2.03-1.80 (m, 3H), 1.80-1.63 (m, 2H), 1.58-1.37 (m, 3H), 1.09 (d, J=6.3 Hz, 3H), 1.01 (s, 3H). ESI MS [M+H]⁺ for $C_{34}H_{38}N_7$, calcd. 544.3, found 544.3.

Example 62: (1S,4S)-5-[(7S)-2-{3-[4-(3,6-Dimethylpyrazin-2-yl)phenyl]-1H-pyrrolo[2,3-b]pyridin-5-yl}-6,7,8,9-tetrahydro-5H-benzo[7]annulen-7-yl]-2-oxa-5-azabicyclo[2.2.1]heptane

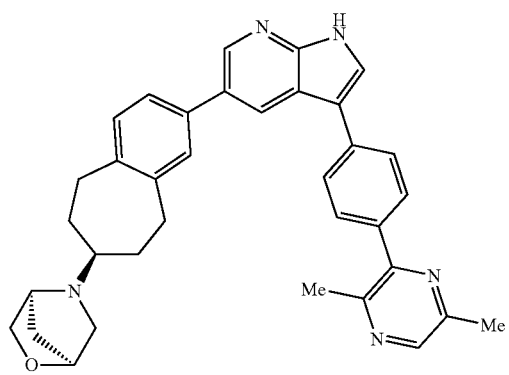 [SMILES: Cc1cnc(C)c(-c2ccc(-c3c[nH]c4ncc(-c5ccc6c(c5)CC[C@@H](N5C[C@@H]7C[C@H]5CO7)CC6)cc34)cc2)n1]

The title compound was prepared in a similar manner to example 1 from the appropriate starting materials. ¹H NMR (400 MHz, DMSO-d₆) δ 12.07 (s, 1H), 8.56 (d, J=2.1 Hz, 1H), 8.47 (d, J=2.1 Hz, 1H), 8.41 (s, 1H), 8.02 (d, J=2.6 Hz, 1H), 7.97-7.86 (m, 2H), 7.79-7.61 (m, 2H), 7.54 (s, 1H), 7.48 (d, J=8.0 Hz, 1H), 7.22 (d, J=7.7 Hz, 1H), 4.34 (s, 1H), 3.91 (d, J=7.5 Hz, 1H), 3.71 (s, 1H), 3.54 (d, J=7.4 Hz, 1H), 3.18-2.93 (m, 3H), 2.80-2.61 (m, 3H), 2.60 (s, 3H), 2.52 (s, 3H), 2.35 (d, J=9.8 Hz, 1H), 2.00-1.76 (m, 2H), 1.73 (d, J=9.3 Hz, 1H), 1.62 (d, J=9.3 Hz, 1H), 1.58-1.30 (m, 2H). ESI MS [M+H]⁺ for $C_{35}H_{36}N_5O$, calcd. 542.3, found 542.3.

Example 63: 3-(4-{5-[(7S)-7-[(3S)-3-(Methoxymethyl)pyrrolidin-1-yl]-6,7,8,9-tetrahydro-5H-benzo[7]annulen-2-yl]-1H-pyrrolo[2,3-b]pyridin-3-yl}phenyl)-2,5-dimethylpyrazine

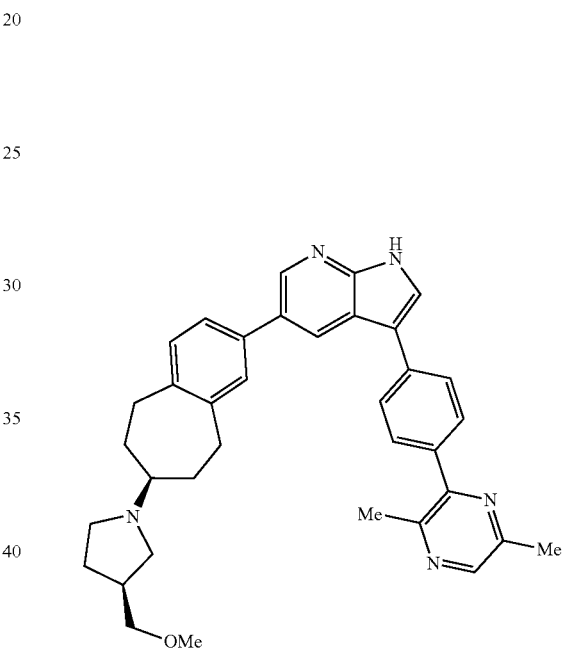

The title compound was prepared in a similar manner to example 1 from the appropriate starting materials. ¹H NMR (400 MHz, Chloroform-d) δ 9.29 (s, 1H), 8.62 (d, J=2.0 Hz, 1H), 8.42 (d, J=2.1 Hz, 1H), 8.35 (s, 1H), 7.83-7.74 (m, 2H), 7.73-7.65 (m, 2H), 7.60 (d, J=2.5 Hz, 1H), 7.43-7.34 (m, 2H), 7.22 (d, J=7.7 Hz, 1H), 3.35 (s, 3H), 3.32 (dd, J=7.0, 4.0 Hz, 2H), 3.21-3.00 (m, 2H), 2.88-2.77 (m, 1H), 2.77-2.62 (m, 7H), 2.61 (s, 3H), 2.57-2.49 (m, 1H), 2.49-2.36 (m, 2H), 2.13-1.83 (m, 3H), 1.75-1.61 (m, 2H), 1.54-1.36 (m, 1H). ESI MS [M+H]⁺ for $C_{36}H_{40}N_5O$, calcd. 558.3, found 558.3.

Example 64: 2,5-Dimethyl-3-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyrazine

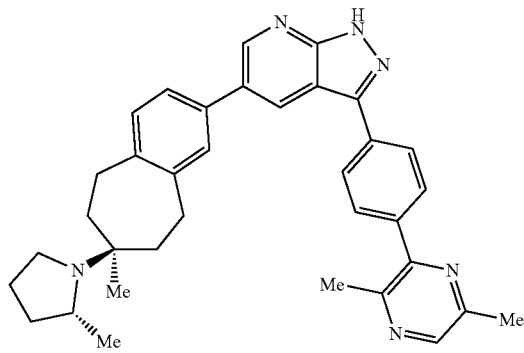

The title compound was prepared in a similar manner to example 2 from the appropriate starting materials. ¹H NMR (400 MHz, Chloroform-d) δ 11.62 (s, 1H), 8.90 (d, J=2.0 Hz, 1H), 8.53 (d, J=2.0 Hz, 1H), 8.38 (s, 1H), 8.20-8.03 (m, 2H), 7.82-7.70 (m, 2H), 7.46-7.33 (m, 2H), 7.24 (d, J=8.2 Hz, 1H), 3.55-3.33 (m, 1H), 3.33-3.16 (m, 2H), 2.93 (t, J=7.4 Hz, 1H), 2.74-2.48 (m, 9H), 2.02-1.80 (m, 3H), 1.80-1.63 (m, 2H), 1.58-1.39 (m, 3H), 1.09 (d, J=6.3 Hz, 3H), 1.00 (s, 3H). ESI MS [M+H]⁺ for $C_{35}H_{39}N_6$, calcd. 543.3, found 543.3.

Example 65: 6-[(7S)-2-{3-[4-(3,6-Dimethylpyrazin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

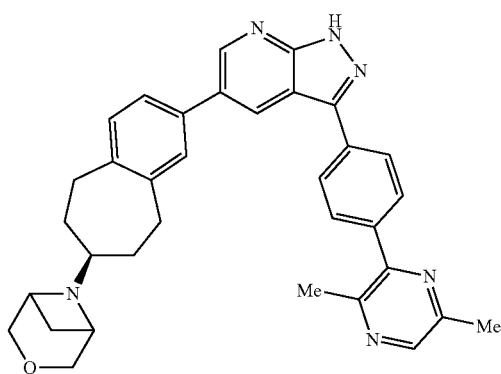 [SMILES: Cc1cnc(C)c(-c2ccc(-c3n[nH]c4ncc(-c5ccc6c(c5)CC[C@@H](N5C7COCC5C7)CC6)cc34)cc2)n1]

The title compound was prepared in a similar manner to example 2 from the appropriate starting materials. ¹H NMR (400 MHz, DMSO-d₆) δ 13.97 (s, 1H), 8.88 (d, J=2.0 Hz, 1H), 8.74 (d, J=2.0 Hz, 1H), 8.44 (s, 1H), 8.25 (d, J=8.3 Hz, 2H), 7.81 (d, J=8.2 Hz, 2H), 7.63 (s, 1H), 7.56 (d, J=7.9 Hz, 1H), 7.26 (d, J=7.8 Hz, 1H), 4.16 (d, J=10.6 Hz, 2H), 3.66-3.42 (m, 4H), 3.24-3.11 (m, 1H), 3.11-2.87 (m, 2H), 2.88-2.71 (m, 2H), 2.61 (s, 3H), 2.53 (s, 3H), 2.41-2.30 (m, 1H), 2.01-1.76 (m, 2H), 1.69 (d, J=8.1 Hz, 1H), 1.26-0.98 (m, 2H). ESI MS [M+H]⁺ for $C_{34}H_{35}N_6O$, calcd. 543.3, found 543.3.

Example 66: 2-(4-{5-[(7S)-7-Methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyridine-3-carbonitrile

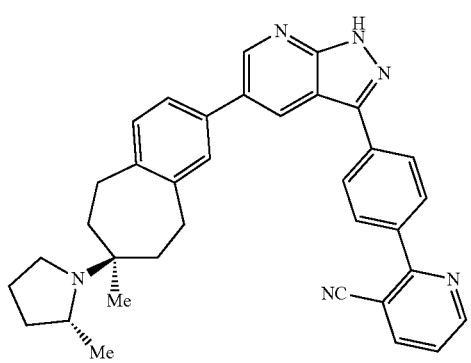 [SMILES: C[C@@H]1CCCN1[C@@]1(C)CCc2ccc(-c3cnc4[nH]nc(-c5ccc(-c6ncccc6C#N)cc5)c4c3)cc2CC1]

The title compound was prepared in a similar manner to example 2 from the appropriate starting materials. ¹H NMR (400 MHz, Chloroform-d) δ 11.68 (s, 1H), 8.93 (dd, J=4.8, 1.8 Hz, 1H), 8.91 (d, J=2.0 Hz, 1H), 8.56 (d, J=2.0 Hz, 1H), 8.26-8.19 (m, 2H), 8.18-8.11 (m, 3H), 7.48-7.36 (m, 3H), 7.24 (d, J=7.9 Hz, 1H), 3.49-3.34 (m, 1H), 3.34-3.12 (m, 2H), 2.93 (t, J=7.7 Hz, 1H), 2.77-2.43 (m, 3H), 2.02-1.80 (m, 3H), 1.79-1.66 (m, 2H), 1.58-1.41 (m, 3H), 1.09 (d, J=6.3 Hz, 3H), 1.01 (s, 3H). ESI MS [M+H]⁺ for $C_{35}H_{35}N_6$, calcd. 539.3, found 539.3.

Example 67: 3-Methyl-2-(4-{5-[7-(pyrrolidin-1-yl)-5,6,7,8-tetrahydronaphthalen-2-yl]-1H-pyrazolo[3,4-b]pyridin-3-yl}phenyl)pyridine

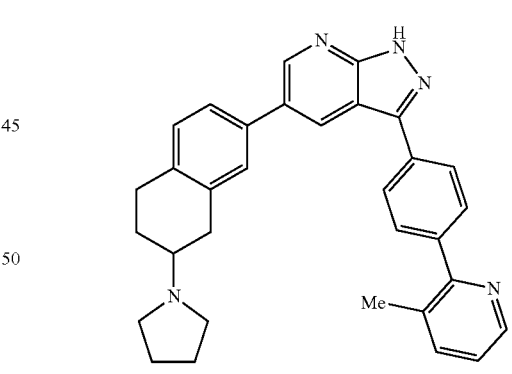

The title compound was prepared in a similar manner to example 19 from the appropriate starting materials. ¹H NMR (400 MHz, Chloroform-d) δ 11.28 (s, 1H), 8.86 (dd, J=2.1, 1.0 Hz, 1H), 8.58 (d, J=4.8 Hz, 1H), 8.54-8.43 (m, 1H), 8.19-8.01 (m, 2H), 7.73 (d, J=8.1 Hz, 2H), 7.63 (d, J=7.7 Hz, 1H), 7.45-7.32 (m, 2H), 7.25-7.20 (m, 2H), 3.19 (dd, J=16.4, 4.4 Hz, 1H), 3.05-2.82 (m, 3H), 2.83-2.63 (m, 4H), 2.60-2.47 (m, 1H), 2.45 (s, 3H), 2.35-2.19 (m, 1H), 1.99-1.81 (m, 4H), 1.83-1.69 (m, 1H). ESI MS [M+H]⁺ for $C_{32}H_{32}N_5$, calcd. 486.3, found 486.3.

Example 68: 2,5-Dimethyl-3-(6-{5-[(7S)-7-methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}pyridin-3-yl)pyrazine

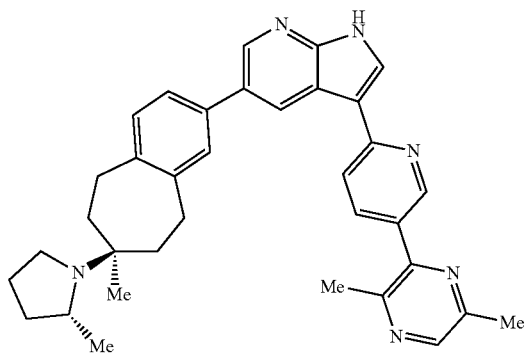 [SMILES: Cc1cnc(C)c(-c2ccc(-c3c[nH]c4ncc(-c5ccc6c(c5)CC[C@@](C)(N5CCC[C@H]5C)CC6)cc34)nc2)n1]

The title compound was prepared in a similar manner to example 9 from the appropriate starting materials. $^1$H NMR (400 MHz, Chloroform-d) δ 10.09 (s, 1H), 8.94 (d, J=2.1 Hz, 1H), 8.92 (dd, J=2.4, 0.8 Hz, 1H), 8.64 (d, J=2.1 Hz, 1H), 8.38 (s, 1H), 8.02 (d, J=2.6 Hz, 1H), 7.99 (dd, J=8.2, 2.3 Hz, 1H), 7.82 (dd, J=8.2, 0.9 Hz, 1H), 7.47-7.37 (m, 2H), 7.22 (d, J=8.2 Hz, 1H), 3.52-3.34 (m, 1H), 3.25 (p, J=7.0, 6.5 Hz, 2H), 2.98-2.88 (m, 1H), 2.74-2.57 (m, 8H), 2.57-2.48 (m, 1H), 2.02-1.80 (m, 3H), 1.80-1.64 (m, 2H), 1.59-1.39 (m, 3H), 1.08 (d, J=6.3 Hz, 3H), 1.01 (s, 3H). ESI MS [M+H]$^+$ for $C_{35}H_{39}N_6$, calcd. 543.3, found 543.3.

Example 69: 6-[(7S)-2-{3-[5-(3,6-Dimethylpyrazin-2-yl)pyridin-2-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

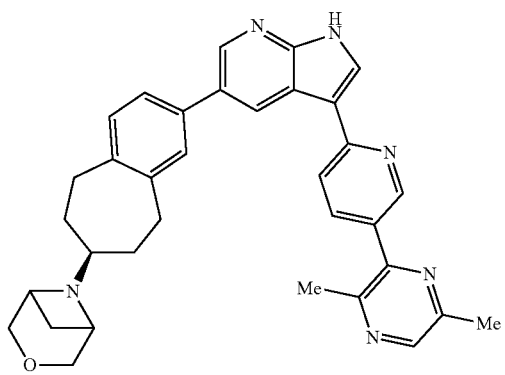 [SMILES: Cc1cnc(C)c(-c2ccc(-c3c[nH]c4ncc(-c5ccc6c(c5)CC[C@@H](N5C7COCC5C7)CC6)cc34)nc2)n1]

The title compound was prepared in a similar manner to example 9 from the appropriate starting materials. $^1$H NMR (400 MHz, Chloroform-d) δ 10.38 (s, 1H), 9.03-8.79 (m, 2H), 8.63 (s, 1H), 8.42-8.26 (m, 1H), 8.11-7.90 (m, 2H), 7.81 (dd, J=8.2, 4.0 Hz, 1H), 7.48-7.30 (m, 2H), 7.25-7.20 (m, 1H), 4.32 (d, J=9.8 Hz, 2H), 3.73 (dd, J=11.3, 3.7 Hz, 2H), 3.66 (d, J=5.9 Hz, 2H), 3.33-3.17 (m, 1H), 3.09-2.76 (m, 4H), 2.70 (s, 3H), 2.62 (s, 3H), 2.58-2.50 (m, 1H), 2.06-1.88 (m, 2H), 1.85 (d, J=8.3 Hz, 1H), 1.41-1.24 (m, 2H). ESI MS [M+H]$^+$ for $C_{34}H_{35}N_6O$, calcd. 543.3, found 543.3.

Example 70: 6-Methyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridine-3-carbonitrile

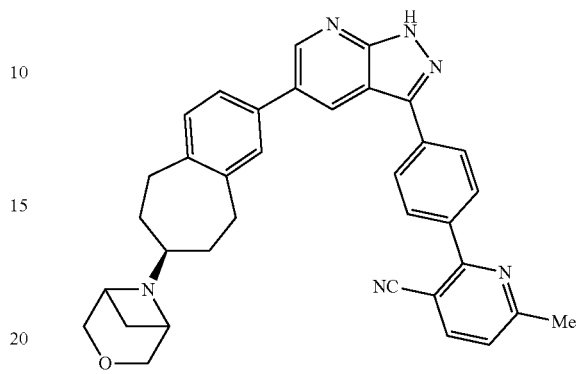

The title compound was prepared in a similar manner to example 2 from the appropriate starting materials. $^1$H NMR (400 MHz, DMSO-d$_6$) δ 8.89 (d, J=2.0 Hz, 1H), 8.77 (d, J=2.0 Hz, 1H), 8.42-8.24 (m, 3H), 8.05 (d, J=8.4 Hz, 2H), 7.64 (s, 1H), 7.58 (d, J=7.7 Hz, 1H), 7.51 (d, J=8.1 Hz, 1H), 7.26 (d, J=7.7 Hz, 1H), 4.16 (d, J=10.7 Hz, 2H), 3.70-3.43 (m, 4H), 3.25-3.08 (m, 1H), 3.08-2.88 (m, 2H), 2.88-2.68 (m, 2H), 2.66 (s, 3H), 2.43-2.27 (m, 1H), 2.00-1.76 (m, 2H), 1.69 (d, J=7.9 Hz, 1H), 1.25-1.08 (m, 2H). ESI MS [M+H]$^+$ for $C_{35}H_{33}N_6O$, calcd. 553.3, found 553.3.

Example 71: 6-Methyl-2-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyridine-3-carbonitrile

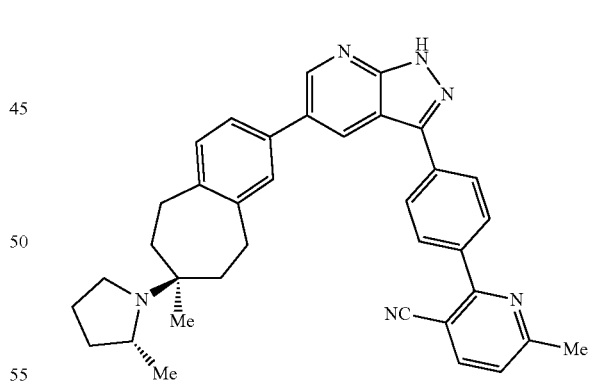

The title compound was prepared in a similar manner to example 2 from the appropriate starting materials. $^1$H NMR (400 MHz, Chloroform-d) δ 11.44 (s, 1H), 8.89 (d, J=2.0 Hz, 1H), 8.55 (d, J=2.0 Hz, 1H), 8.26-8.17 (m, 2H), 8.17-8.09 (m, 2H), 7.99 (d, J=8.0 Hz, 1H), 7.43-7.34 (m, 2H), 7.29-7.26 (m, 1H), 7.24 (d, J=8.2 Hz, 1H), 3.56-3.35 (m, 1H), 3.32-3.16 (m, 2H), 2.93 (t, J=7.6 Hz, 1H), 2.73 (s, 3H), 2.72-2.45 (m, 3H), 2.02-1.80 (m, 3H), 1.80-1.63 (m, 2H), 1.55-1.39 (m, 3H), 1.09 (d, J=6.3 Hz, 3H), 1.01 (s, 3H). ESI MS [M+H]$^+$ for $C_{36}H_{37}N_6$, calcd. 553.3, found 553.3.

Example 72: 6-Methyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-3-carbonitrile

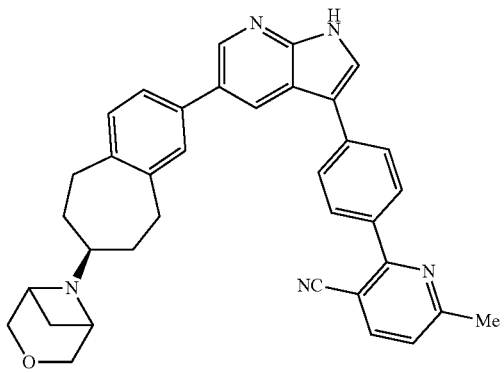 [SMILES: Cc1ccc(C#N)c(-c2ccc(-c3c[nH]c4ncc(-c5ccc6c(c5)CC[C@@H](N5C7COCC5C7)CC6)cc34)cc2)n1]

The title compound was prepared in a similar manner to example 1 from the appropriate starting materials. $^1$H NMR (400 MHz, Chloroform-d) δ 10.27 (s, 1H), 8.64 (d, J=2.0 Hz, 1H), 8.45 (d, J=2.0 Hz, 1H), 8.10-8.00 (m, 2H), 7.97 (d, J=8.0 Hz, 1H), 7.88-7.82 (m, 2H), 7.66 (d, J=2.5 Hz, 1H), 7.45-7.35 (m, 2H), 7.24 (d, J=7.9 Hz, 2H), 4.32 (d, J=10.7 Hz, 2H), 3.74 (d, J=10.7 Hz, 2H), 3.66 (d, J=6.1 Hz, 2H), 3.27 (t, J=9.6 Hz, 1H), 3.01 (ddd, J=22.5, 14.4, 8.0 Hz, 2H), 2.86 (q, J=14.1 Hz, 2H), 2.72 (s, 3H), 2.57 (q, J=6.7 Hz, 1H), 2.02-1.89 (m, 2H), 1.85 (d, J=8.2 Hz, 1H), 1.35 (p, J=10.6 Hz, 2H). ESI MS [M+H]$^+$ for C$_{36}$H$_{34}$N$_5$O, calcd. 552.3, found 552.3.

Example 73: 6-[(7S)-2-{3-[4-(2,6-Dimethylpyridin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

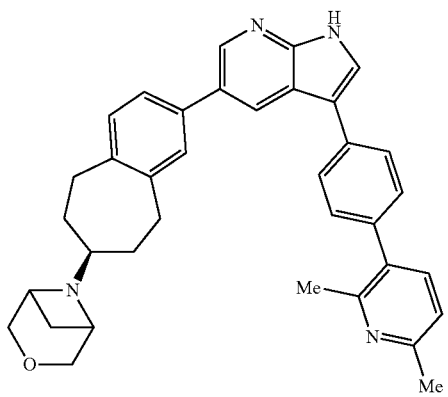 [SMILES: Cc1ccc(-c2ccc(-c3c[nH]c4ncc(-c5ccc6c(c5)CC[C@@H](N5C7COCC5C7)CC6)cc34)cc2)c(C)n1]

The title compound was prepared in a similar manner to example 1 from the appropriate starting materials. $^1$H NMR (400 MHz, DMSO-d$_6$) δ 12.04 (d, J=2.5 Hz, 1H), 8.55 (d, J=2.1 Hz, 1H), 8.45 (d, J=2.1 Hz, 1H), 7.98 (d, J=2.7 Hz, 1H), 7.92-7.80 (m, 2H), 7.60-7.52 (m, 2H), 7.52-7.41 (m, 3H), 7.22 (d, J=7.8 Hz, 1H), 7.17 (d, J=7.8 Hz, 1H), 4.15 (d, J=10.6 Hz, 2H), 3.58 (d, J=10.6 Hz, 2H), 3.54 (d, J=6.0 Hz, 2H), 3.17 (t, J=10.2 Hz, 1H), 2.96 (ddd, J=33.1, 14.0, 8.5 Hz, 2H), 2.78 (q, J=14.4 Hz, 2H), 2.48 (s, 3H), 2.47 (s, 3H), 2.36 (q, J=6.9 Hz, 1H), 1.93-1.79 (m, 2H), 1.68 (d, J=7.9 Hz, 1H), 1.26-1.04 (m, 2H). ESI MS [M+H]$^+$ for C$_{36}$H$_{37}$N$_4$O, calcd. 541.3, found 541.3.

Example 74: 6-[(7S)-2-{3-[4-(2-Methylpyridin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

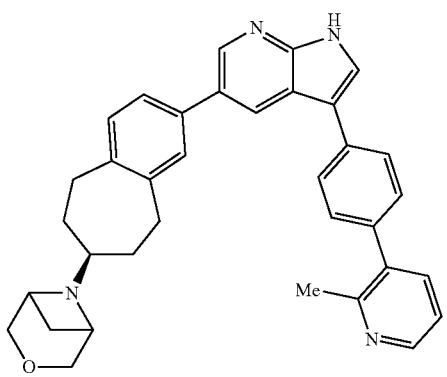 [SMILES: Cc1ncccc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. $^1$H NMR (400 MHz, Chloroform-d) δ 9.25 (s, 1H), 8.61 (d, J=2.0 Hz, 1H), 8.53 (dd, J=5.0, 1.7 Hz, 1H), 8.43 (d, J=2.0 Hz, 1H), 7.81-7.72 (m, 2H), 7.62-7.54 (m, 2H), 7.48-7.42 (m, 2H), 7.42-7.36 (m, 2H), 7.24-7.18 (m, 2H), 4.31 (d, J=10.7 Hz, 2H), 3.73 (d, J=10.7 Hz, 2H), 3.65 (d, J=6.1 Hz, 2H), 3.32-3.19 (m, 1H), 2.99 (td, J=15.8, 15.3, 9.5 Hz, 2H), 2.85 (q, J=13.3 Hz, 2H), 2.60 (s, 3H), 2.59-2.51 (m, 1H), 2.01-1.88 (m, 2H), 1.85 (d, J=8.3 Hz, 1H), 1.39-1.26 (m, 2H). ESI MS [M+H]$^+$ for C$_{35}$H$_{35}$N$_4$O, calcd. 527.3, found 527.2.

Example 75: 5-Methyl-6-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-2-carbonitrile

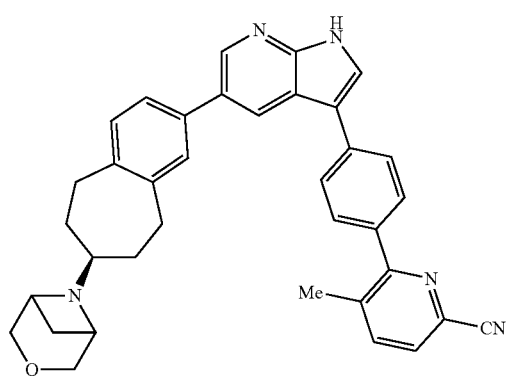 [SMILES: Cc1ccc(C#N)nc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. $^1$H NMR (400 MHz, Chloroform-d) δ 10.30 (s, 1H), 8.64 (d, J=2.0 Hz, 1H), 8.44 (d, J=2.0 Hz, 1H), 7.84-7.77 (m, 2H), 7.78-7.71 (m, 1H), 7.70-7.62 (m, 3H), 7.60 (d, J=7.8 Hz, 1H), 7.45-7.37 (m, 2H), 7.23 (d, J=8.2 Hz, 1H), 4.32 (d, J=10.7 Hz, 2H), 3.74 (d, J=10.7 Hz, 2H), 3.66 (d, J=6.1 Hz, 2H), 3.27

(t, J=9.7 Hz, 1H), 3.00 (td, J=18.6, 16.5, 7.8 Hz, 2H), 2.86 (q, J=13.5 Hz, 2H), 2.58 (q, J=5.8, 4.6 Hz, 1H), 2.54 (s, 3H), 2.03-1.89 (m, 2H), 1.85 (d, J=8.2 Hz, 1H), 1.35 (p, J=10.2 Hz, 2H). ESI MS [M+H]$^+$ for $C_{36}H_{34}N_5O$, calcd. 552.3, found 552.3.

Example 76: 5-Methyl-6-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-2-carboxamide

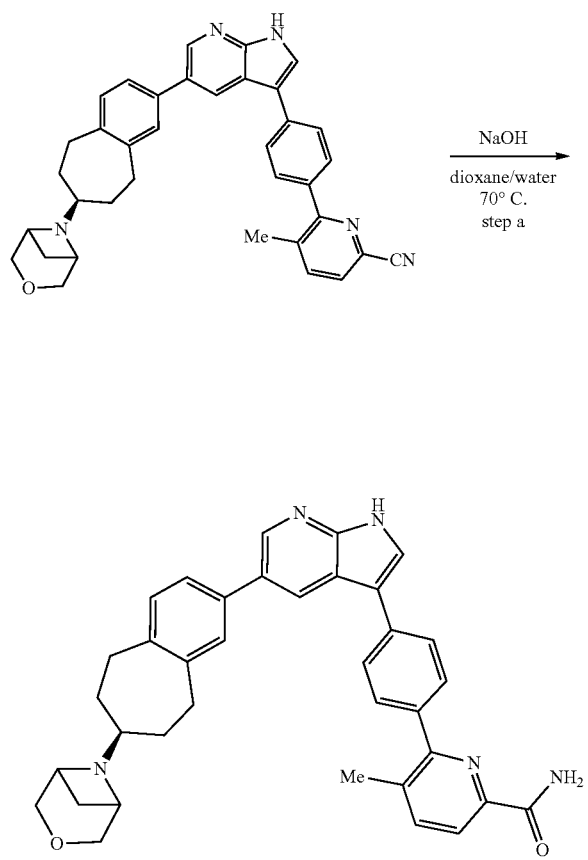

Step a: The title compound was formed from the azaindole deprotection conditions (5 eq. of 6 N NaOH$_{(aq)}$ in dioxane stirred at 70° C. for 1 hour) (see example 1, step g) during the preparation of example 75. $^1$H NMR (400 MHz, Chloroform-d) δ 10.27 (s, 1H), 8.63 (d, J=2.0 Hz, 1H), 8.45 (d, J=2.0 Hz, 1H), 8.12 (d, J=7.8 Hz, 1H), 7.96 (d, J=4.6 Hz, 1H), 7.85-7.74 (m, 3H), 7.70-7.66 (m, 2H), 7.65 (d, J=2.5 Hz, 1H), 7.46-7.37 (m, 2H), 7.23 (d, J=8.2 Hz, 1H), 5.82 (d, J=4.6 Hz, 1H), 4.31 (d, J=10.6 Hz, 2H), 3.73 (d, J=10.7 Hz, 2H), 3.65 (d, J=6.1 Hz, 2H), 3.34-3.19 (m, 1H), 2.99 (td, J=15.1, 7.8 Hz, 2H), 2.86 (q, J=13.4 Hz, 2H), 2.56 (q, J=6.8 Hz, 1H), 2.52 (s, 3H), 2.03-1.88 (m, 2H), 1.85 (d, J=8.2 Hz, 1H), 1.33 (p, J=10.0 Hz, 2H). ESI MS [M+H]$^+$ for $C_{36}H_{36}N_5O_2$, calcd. 570.3, found 570.3.

Example 77: 6-[(7S)-2-{3-[4-(4,6-Dimethylpyridazin-3-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

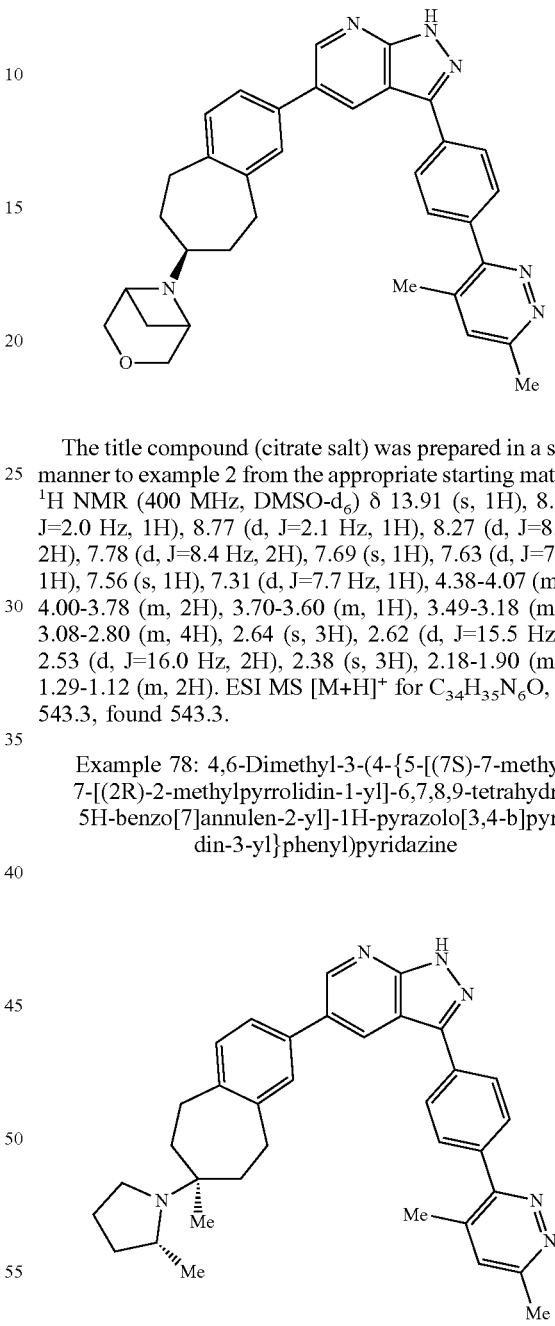

The title compound (citrate salt) was prepared in a similar manner to example 2 from the appropriate starting materials. $^1$H NMR (400 MHz, DMSO-d$_6$) δ 13.91 (s, 1H), 8.90 (d, J=2.0 Hz, 1H), 8.77 (d, J=2.1 Hz, 1H), 8.27 (d, J=8.3 Hz, 2H), 7.78 (d, J=8.4 Hz, 2H), 7.69 (s, 1H), 7.63 (d, J=7.7 Hz, 1H), 7.56 (s, 1H), 7.31 (d, J=7.7 Hz, 1H), 4.38-4.07 (m, 3H), 4.00-3.78 (m, 2H), 3.70-3.60 (m, 1H), 3.49-3.18 (m, 3H), 3.08-2.80 (m, 4H), 2.64 (s, 3H), 2.62 (d, J=15.5 Hz, 2H), 2.53 (d, J=16.0 Hz, 2H), 2.38 (s, 3H), 2.18-1.90 (m, 2H), 1.29-1.12 (m, 2H). ESI MS [M+H]$^+$ for $C_{34}H_{35}N_6O$, calcd. 543.3, found 543.3.

Example 78: 4,6-Dimethyl-3-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyridazine The title compound (citrate salt) was prepared in a similar manner to example 2 from the appropriate starting materials. $^1$H NMR (400 MHz, DMSO-d$_6$) δ 14.00 (s, 1H), 8.90 (d, J=2.0 Hz, 1H), 8.75 (d, J=2.1 Hz, 1H), 8.27 (d, J=8.4 Hz, 2H), 7.79 (d, J=8.4 Hz, 2H), 7.72 (s, 1H), 7.65 (d, J=7.7 Hz, 1H), 7.56 (s, 1H), 7.33 (d, J=7.8 Hz, 1H), 3.34 (s, 4H), 3.04-2.75 (m, 4H), 2.65 (s, 3H), 2.57 (d, J=15.2 Hz, 2H), 2.49 (d, J=14.9 Hz, 2H), 2.38 (s, 3H), 2.23-2.11 (m, 1H), 2.11-1.99 (m, 1H), 1.99-1.83 (m, 3H), 1.83-1.73 (m, 1H), 1.73-1.59 (m, 2H), 1.59-1.40 (m, 2H), 1.26 (d, J=6.5 Hz, 3H). ESI MS [M+H]+ for C35H39N6, calcd. 543.3, found 543.3.

Example 79: 6-[(7S)-2-{3-[1-(3-Methylpyridin-2-yl)-1H-pyrazol-4-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

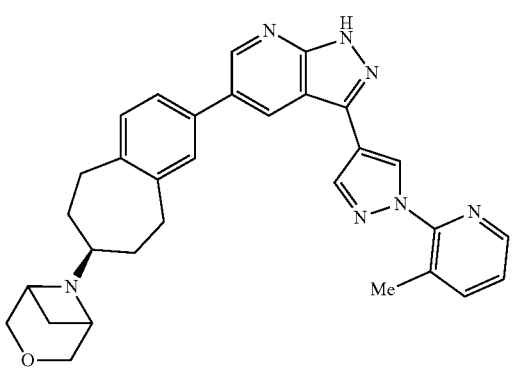 [SMILES: Cc1cccnc1-n1cc(-c2n[nH]c3ncc(-c4ccc5c(c4)CC[C@@H](N4C6COCC4C6)CC5)cc23)cn1]

The title compound (citrate salt) was prepared in a similar manner to example 27 from the appropriate starting materials. 1H NMR (400 MHz, DMSO-d6) δ 13.73 (s, 1H), 9.10 (d, J=0.8 Hz, 1H), 8.87 (d, J=2.0 Hz, 1H), 8.75 (d, J=2.1 Hz, 1H), 8.49 (d, J=0.8 Hz, 1H), 8.44 (dd, J=4.8, 1.1 Hz, 1H), 7.95 (dd, J=7.5, 1.0 Hz, 1H), 7.69 (s, 1H), 7.64 (d, J=7.7 Hz, 1H), 7.45 (dd, J=7.6, 4.8 Hz, 1H), 7.29 (d, J=7.8 Hz, 1H), 4.40-4.07 (m, 3H), 3.99-3.79 (m, 2H), 3.74-3.54 (m, 1H), 3.50-3.20 (m, 3H), 3.07-2.81 (m, 4H), 2.62 (d, J=15.2 Hz, 2H), 2.54 (d, J=12.6 Hz, 2H), 2.51 (s, 3H), 2.04 (t, J=17.5 Hz, 2H), 1.20 (d, J=16.8 Hz, 2H). ESI MS [M+H]+ for C31H32N7O, calcd. 518.3, found 518.3.

Example 80: 6-[(7S)-2-{3-[4-(4,6-Dimethylpyridazin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

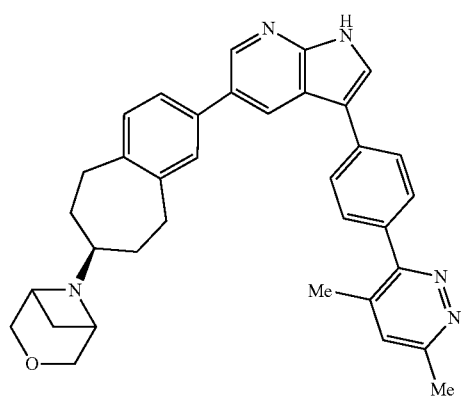 [SMILES: Cc1cc(C)c(-c2ccc(-c3c[nH]c4ncc(-c5ccc6c(c5)CC[C@@H](N5C7COCC5C7)CC6)cc34)cc2)nn1]

The title compound (citrate salt) was prepared in a similar manner to example 1 from the appropriate starting materials. 1H NMR (400 MHz, DMSO-d6) δ 12.10 (d, J=2.7 Hz, 1H), 8.58 (d, J=2.1 Hz, 1H), 8.50 (d, J=2.1 Hz, 1H), 8.05 (d, J=2.7 Hz, 1H), 7.95 (d, J=8.3 Hz, 2H), 7.70 (d, J=8.3 Hz, 2H), 7.61 (s, 1H), 7.55 (d, J=7.3 Hz, 1H), 7.53 (s, 1H), 7.28 (d, J=7.7 Hz, 1H), 4.39-4.07 (m, 3H), 4.00-3.78 (m, 2H), 3.76-3.55 (m, 1H), 3.48-3.18 (m, 3H), 3.08-2.78 (m, 4H), 2.63 (s, 3H), 2.61 (d, J=14.8 Hz, 2H), 2.53 (d, J=14.9 Hz, 2H), 2.38 (s, 3H), 2.18-1.93 (m, 2H), 1.30-1.09 (m, 2H). ESI MS [M+H]+ for C35H36N5O, calcd. 542.3, found 542.3.

Example 81: 6-[(7S)-2-{3-[3-(3-Methylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

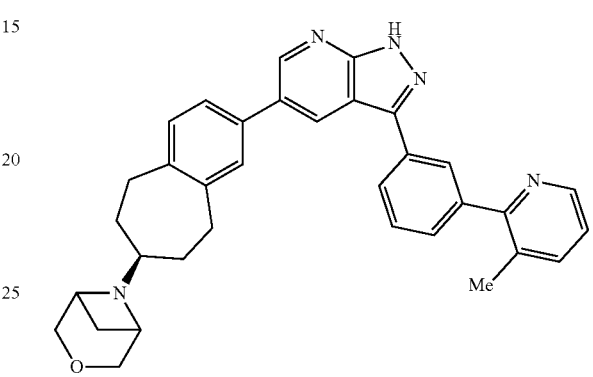

The title compound (citrate salt) was prepared in a similar manner to example 2 from the appropriate starting materials. 1H NMR (400 MHz, DMSO-d6) δ 13.93 (s, 1H), 8.88 (d, J=2.0 Hz, 1H), 8.67 (d, J=2.1 Hz, 1H), 8.53 (ddd, J=4.8, 1.7, 0.7 Hz, 1H), 8.23-8.20 (m, 1H), 8.17 (dt, J=7.0, 1.9 Hz, 1H), 7.77 (ddd, J=7.7, 1.7, 0.8 Hz, 1H), 7.69-7.61 (m, 3H), 7.59 (d, J=7.8 Hz, 1H), 7.34 (dd, J=7.7, 4.7 Hz, 1H), 7.30 (d, J=7.8 Hz, 1H), 4.38-4.03 (m, 3H), 4.00-3.77 (m, 2H), 3.72-3.53 (m, 1H), 3.45-3.22 (m, 3H), 3.05-2.82 (m, 4H), 2.61 (d, J=15.2 Hz, 2H), 2.53 (d, J=15.0 Hz, 2H), 2.43 (s, 3H), 2.14-1.93 (m, 2H), 1.29-1.11 (m, 2H). ESI MS [M+H]+ for C34H34N5O, calcd. 528.3, found 528.3.

Example 82: 6-[(7S)-2-{3-[3-(3-Methylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

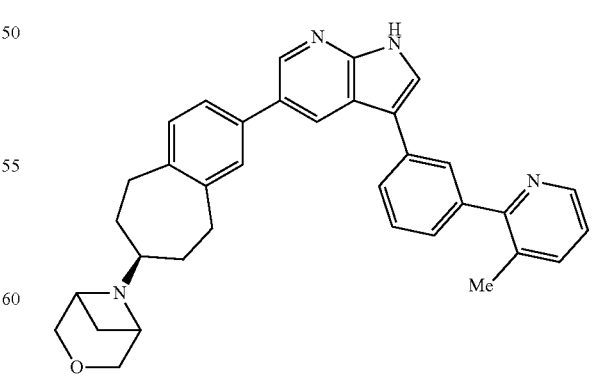

The title compound (citrate salt) was prepared in a similar manner to example 1 from the appropriate starting materials. 1H NMR (400 MHz, DMSO-d6) δ 12.03 (d, J=2.7 Hz, 1H), 8.56 (d, J=2.0 Hz, 1H), 8.51 (dd, J=4.7, 1.0 Hz, 1H), 8.41 (d, J=2.1 Hz, 1H), 7.97 (d, J=2.6 Hz, 1H), 7.90-7.87 (m, 1H), 7.85 (dt, J=7.7, 1.4 Hz, 1H), 7.75 (dd, J=7.7, 0.9 Hz, 1H), 7.61-7.53 (m, 2H), 7.50 (d, J=7.0 Hz, 1H), 7.44 (dt, J=7.6, 1.4 Hz, 1H), 7.32 (dd, J=7.7, 4.7 Hz, 1H), 7.27 (d, J=7.8 Hz, 1H), 4.39-4.07 (m, 3H), 4.00-3.79 (m, 2H), 3.72-3.55 (m, 1H), 3.47-3.22 (m, 3H), 3.04-2.81 (m, 4H), 2.61 (d, J=15.2 Hz, 2H), 2.53 (d, J=14.4 Hz, 2H), 2.43 (s, 3H), 2.16-1.91 (m, 2H), 1.33-1.10 (m, 2H). ESI MS [M+H]$^+$ for $C_{35}H_{35}N_4O$, calcd. 527.3, found 527.3.

Example 83: 3-Methyl-2'-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}-2,4'-bipyridine

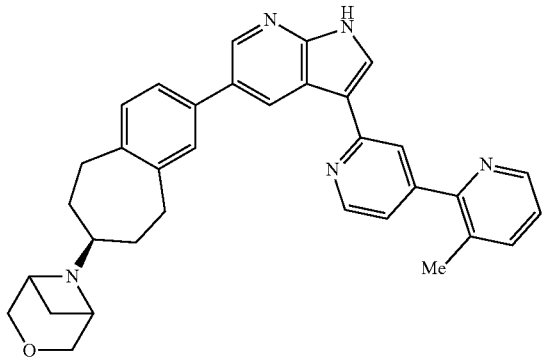 [SMILES: Cc1cccnc1-c1ccnc(-c2c[nH]c3ncc(-c4ccc5c(c4)CC[C@@H](N4C6COCC4C6)CC5)cc23)c1]

The title compound (citrate salt) was prepared in a similar manner to example 9 from the appropriate starting materials. $^1$H NMR (400 MHz, DMSO-d$_6$) δ 12.15 (d, J=2.6 Hz, 1H), 9.03 (d, J=2.2 Hz, 1H), 8.73 (dd, J=5.1, 0.9 Hz, 1H), 8.59-8.54 (m, 2H), 8.41 (d, J=2.8 Hz, 1H), 8.07-8.05 (m, 1H), 7.82 (dd, J=7.8, 0.9 Hz, 1H), 7.55 (s, 1H), 7.48 (d, J=7.6 Hz, 1H), 7.41 (dd, J=7.7, 4.7 Hz, 1H), 7.35-7.28 (m, 2H), 4.41-4.12 (m, 3H), 4.03-3.81 (m, 2H), 3.76-3.58 (m, 1H), 3.49-3.21 (m, 3H), 3.07-2.83 (m, 4H), 2.62 (d, J=15.2 Hz, 2H), 2.53 (d, J=17.0 Hz, 2H), 2.42 (s, 3H), 2.17-1.96 (m, 2H), 1.29-1.12 (m, 2H). ESI MS [M+H]$^+$ for $C_{34}H_{34}N_5O$, calcd. 528.3, found 528.3.

Example 84: 6-[(7S)-2-(3-{2'-Fluoro-6'-methyl-[1,1'-biphenyl]-4-yl}-1H-pyrrolo[2,3-b]pyridin-5-yl)-6,7,8,9-tetrahydro-5H-benzo[7]annulen-7-yl]-3-oxa-6-azabicyclo[3.1.1]heptane

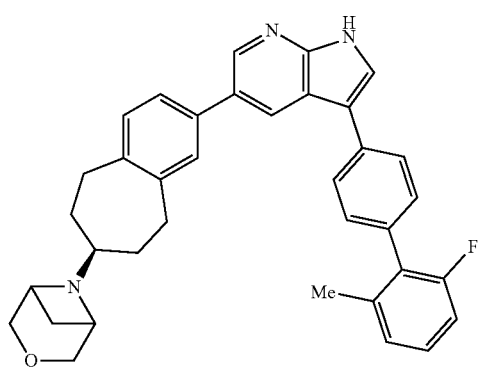 [SMILES: Cc1cccc(F)c1-c1ccc(-c2c[nH]c3ncc(-c4ccc5c(c4)CC[C@@H](N4C6COCC4C6)CC5)cc23)cc1]

The title compound (citrate salt) was prepared in a similar manner to example 1 from the appropriate starting materials. $^1$H NMR (400 MHz, DMSO-d$_6$) δ 12.06 (d, J=2.7 Hz, 1H), 8.57 (d, J=2.1 Hz, 1H), 8.48 (d, J=2.1 Hz, 1H), 8.01 (d, J=2.6 Hz, 1H), 7.90 (d, J=8.2 Hz, 2H), 7.61 (s, 1H), 7.54 (d, J=8.2 Hz, 1H), 7.37 (d, J=7.7 Hz, 2H), 7.36-7.24 (m, 2H), 7.19 (d, J=7.7 Hz, 1H), 7.14 (t, J=9.0 Hz, 1H), 4.39-4.08 (m, 3H), 4.01-3.78 (m, 2H), 3.72-3.58 (m, 1H), 3.48-3.21 (m, 3H), 3.06-2.81 (m, 4H), 2.61 (d, J=15.2 Hz, 2H), 2.53 (d, J=14.7 Hz, 2H), 2.21 (s, 3H), 2.16-1.93 (m, 2H), 1.28-1.11 (m, 2H). ESI MS [M+H]$^+$ for $C_{36}H_{35}FN_3O$, calcd. 544.3, found 544.3.

Example 85: 2-Methyl-2-[2-[4-[5-[(7S)-7-(3-oxa-6-azabicyclo[3.1.1]heptan-6-yl)-6,7,8,9-tetrahydro-5H-benzo[7]annulen-3-yl]-1H-pyrazolo[3,4-b]pyridine-3-yl]phenyl]pyridine-3-yl]propanenitrile

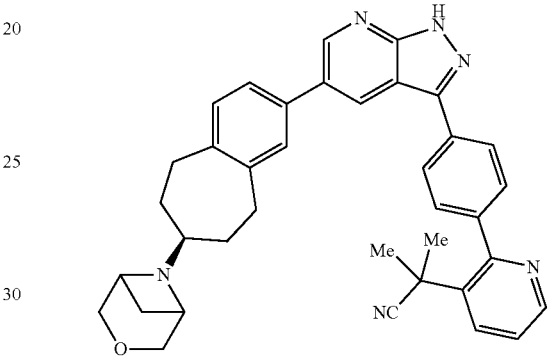

The title compound was prepared in a similar manner to example 21 from the appropriate starting materials. $^1$H NMR (400 MHz, Chloroform-d) δ 11.62 (s, 1H), 8.83 (d, J=2.1 Hz, 1H), 8.64 (dd, J=4.7, 1.6 Hz, 1H), 8.50 (d, J=2.1 Hz, 1H), 8.12-8.09 (m, 2H), 8.03 (dd, J=8.2, 1.6 Hz, 1H), 7.59-7.56 (m, 2H), 7.39-7.36 (m, 3H), 7.24-7.22 (m, 1H), 4.31 (d, J=10.8 Hz, 2H), 3.77-3.68 (m, 4H), 3.3-3.25 (m, 1H), 2.99 (td, J=15.4, 7.7 Hz, 2H), 2.90-2.80 (m, 2H), 2.62-2.56 (m, 1H), 1.95 (s, 2H), 1.85 (d, 1H), 1.67 (s, 6H), 1.40-1.33 (m, 2H). ESI MS [M+H]$^+$ for $C_{37}H_{37}N_6O$, calcd. 581.3, found 581.3.

Example 86: 6-[(7S)-3-[3-[4-(4-Methoxy-3-methylpyridin-2-yl)phenyl]-1H-pyrrolo[2,3-b]pyridin-5-yl]-6,7,8,9-tetrahydro-5H-benzo[7]annulen-7-yl]-3-oxa-6-azabicyclo[3.1.1]heptane

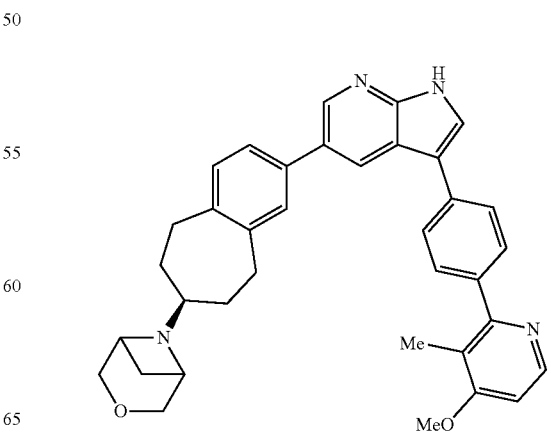

The title compound was prepared in a similar manner to example 1 from the appropriate starting materials. $^1$H NMR (400 MHz, Chloroform-d) δ 10.48 (s, 1H), 8.59 (s, 1H), 8.46 (d, J=5.6 Hz, 1H), 8.41 (s, 1H), 7.77-7.68 (m, 2H), 7.63-7.57 (m, 2H), 7.55 (s, 1H), 7.42-7.34 (m, 2H), 7.19 (d, J=7.5 Hz, 1H), 6.76 (d, J=5.6 Hz, 1H), 4.32 (d, J=11.1 Hz, 2H), 3.92 (s, 3H), 3.79-3.77 (m, 4H), 3.34-3.23 (m, 1H), 3.02-2.68 (m, 5H), 2.25 (s, 3H), 1.95 (s, 2H), 1.87 (d, J=8.5 Hz, 1H), 1.47-1.37 (m, 2H). ESI MS [M+H]$^+$ for $C_{36}H_{37}N_4O_2$, calcd. 557.3, found 557.3.

Example 87: 6-[(7S)-3-[3-[4-(4-Methoxy-3-methylpyridin-2-yl)phenyl]-1H-pyrazolo[3,4-b]pyridin-5-yl]-6,7,8,9-tetrahydro-5H-benzo[7]annulen-7-yl]-3-oxa-6-azabicyclo[3.1.1]heptane

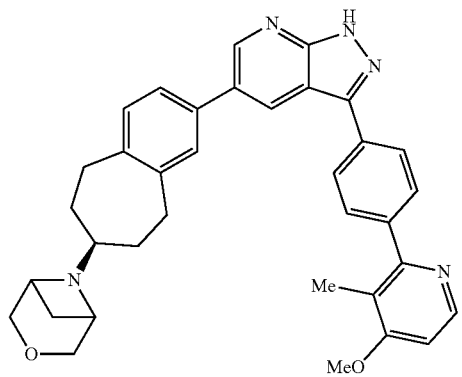 [SMILES: COc1ccnc(-c2ccc(-c3n[nH]c4ncc(-c5ccc6c(c5)CC[C@@H](N5C7COCC5C7)CC6)cc34)cc2)c1C]

The title compound was prepared in a similar manner to example 2 from the appropriate starting materials. $^1$H NMR (400 MHz, Chloroform-d) δ 11.26 (s, 1H), 8.83 (d, J=2.0 Hz, 1H), 8.50 (d, J=2.0 Hz, 1H), 8.45 (d, J=5.7 Hz, 1H), 8.08-8.05 (m, 2H), 7.69-7.66 (m, 2H), 7.41-7.376 (m, 2H), 7.24-7.22 (m, 1H), 6.78 (d, J=5.7 Hz, 1H), 4.35 (d, J=11.4 Hz, 2H), 3.96-3.78 (m, 6H), 3.35 (s, 1H), 3.04-2.68 (m, 6H), 2.24 (s, 3H), 2.02-1.89 (m, 3H), 1.48 (s, 2H). ESI MS [M+H]$^+$ for $C_{35}H_{36}N_5O_2$, calcd. 558.3, found 558.3.

Example 88: 6-[(7S)-3-[3-[4-[3-(Trifluoromethyl)pyridin-2-yl]phenyl]-1H-pyrazolo[3,4-b]pyridin-5-yl]-6,7,8,9-tetrahydro-5H-benzo[7]annulen-7-yl]-3-oxa-6-azabicyclo[3.1.1]heptane

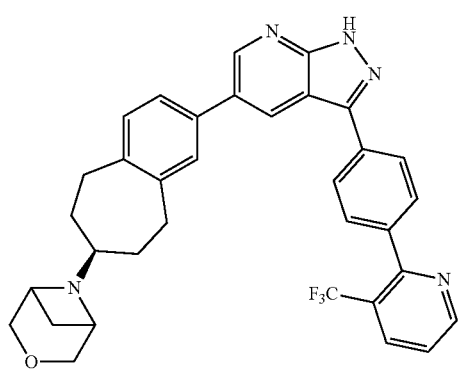 [SMILES: FC(F)(F)c1cccnc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, Chloroform-d) δ 12.94 (s, 1H), 8.87-8.84 (m, 2H), 8.51 (d, J=2.1 Hz, 1H), 8.12-8.02 (m, 3H), 7.68 (d, J=8.2 Hz, 2H), 7.45-7.42 (m, 1H), 7.39-7.37 (m, 2H), 7.22 (d, J=8.2 Hz, 1H), 4.31 (d, J=10.7 Hz, 2H), 3.77-3.67 (m, 4H), 3.27 (t, J=9.7 Hz, 1H), 3.13-2.80 (m, 4H), 2.60 (q, J=6.7 Hz, 1H), 1.99-1.91 (m, 2H), 1.85 (d, J=8.3 Hz, 1H), 1.39 (q, J=11.4 Hz, 2H). ESI MS [M+H]$^+$ for $C_{34}H_{31}F_3N_5O$, calcd. 582.2, found 582.3.

Example 89: 6-[(7S)-3-[3-[4-[3-(Difluoromethyl)pyridin-2-yl]phenyl]-1H-pyrazolo[3,4-b]pyridin-5-yl]-6,7,8,9-tetrahydro-5H-benzo[7]annulen-7-yl]-3-oxa-6-azabicyclo[3.1.1]heptane

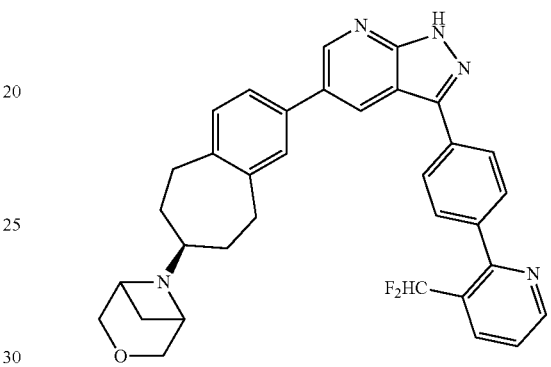

The title compound was prepared in a similar manner to example 2 from the appropriate starting materials. $^1$H NMR (400 MHz, Chloroform-d) δ 12.05 (s, 1H), 8.85 (d, J=2.1 Hz, 1H), 8.83 (m, J=5.0 Hz, 1H), 8.51 (d, J=2.1 Hz, 1H), 8.17-8.13 (m, 3H), 7.76-7.72 (m, 2H), 7.45 (dd, J=7.9, 4.8 Hz, 1H), 7.41-7.37 (m, 2H), 7.24-7.23 (m, 1H), 6.72 (t, J=54.3 Hz, 1H), 4.33 (d, J=11.0 Hz, 2H), 3.87-3.74 (m, 4H), 3.30 (t, J=10.3 Hz, 1H), 3.11-2.80 (m, 4H), 2.66 (s, 1H), 2.02-1.92 (m, 2H), 1.89 (d, J=8.6 Hz, 1H), 1.49-1.38 (m, 2H). ESI MS [M+H]$^+$ for $C_{34}H_{32}F_2N_5O$, calcd. 564.3, found 564.3.

Example 90: 2-(4-{5-[(7S)-7-Methyl-7-[(2R)-2-methylpyrrolidin-1-yl]-6,7,8,9-tetrahydro-5H-benzo[7]annulen-2-yl]-2H-pyrazolo[3,4-b]pyridin-3-yl}phenyl)-1,3-oxazole

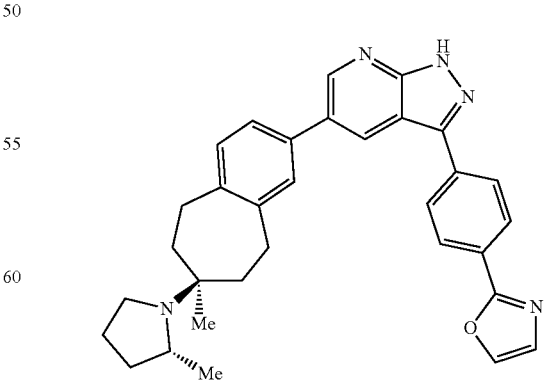

The title compound was prepared in a similar manner to example 2 from the appropriate starting materials. $^1$H NMR (400 MHz, Chloroform-d) δ 11.37 (s, 1H), 8.86 (d, J=2.0 Hz, 1H), 8.50 (d, J=2.0 Hz, 1H), 8.26-8.17 (m, 2H), 8.17-8.06 (m, 2H), 7.75 (d, J=0.8 Hz, 1H), 7.36 (dt, J=3.8, 2.2 Hz, 2H), 7.28 (d, J=0.8 Hz, 1H), 7.23 (td, J=0.4 Hz, 1H), 3.41 (s, 1H), 3.32-3.15 (m, 2H), 2.91 (t, J=7.6 Hz, 1H), 2.72-2.45 (m, 4H), 2.00-1.81 (m, 3H), 1.71 (tt, J=12.2, 6.4 Hz, 2H), 1.51-1.38 (m, 2H), 1.07 (d, J=6.3 Hz, 3H), 0.98 (s, 3H). ESI MS [M+H]⁺ for C₃₂H₃₄N₅O, calcd. 504.3, found 504.3.

Example 91: 2-(4-{5-[(7S)-7-Methyl-7-[(2R)-2-methylpyrrolidin-1-yl]-6,7,8,9-tetrahydro-5H-benzo[7]annulen-2-yl]-2H-pyrazolo[3,4-b]pyridin-3-yl}phenyl)-1,3-thiazole

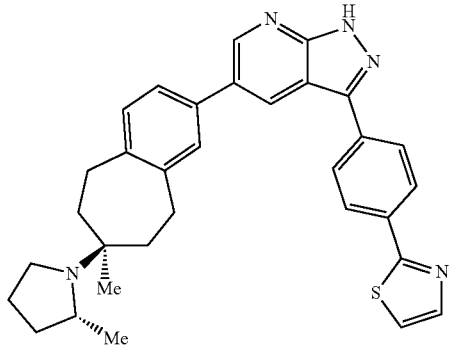 [SMILES: C[C@@H]1CCCN1[C@@]1(C)CCc2ccc(-c3cnc4[nH]nc(-c5ccc(-c6ncco6)cc5)c4c3)cc2CC1]

The title compound was prepared in a similar manner to example 2 from the appropriate starting materials. ¹H NMR (400 MHz, Chloroform-d) δ 11.30 (s, 1H), 8.86 (d, J=2.0 Hz, 1H), 8.50 (d, J=2.1 Hz, 1H), 8.16-8.05 (m, 4H), 7.90 (d, J=3.3 Hz, 1H), 7.38-7.32 (m, 3H), 7.24-7.19 (m, 1H), 3.46-3.41 (m, 1H), 3.24 (d, J=10.4 Hz, 2H), 2.90 (d, J=7.9 Hz, 2H), 2.68-2.5 (m, 3H), 1.95-1.87 (m, 3H), 1.74-1.71 (m, 2H), 1.50-1.41 (m, 2H), 1.07 (d, J=6.3 Hz, 3H), 0.99 (s, 3H). ESI MS [M+H]⁺ for C₃₂H₃₄N₅S, calcd. 520.3, found 520.3.

Example 92: N,N-Dimethyl-4'-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}-[1,1'-biphenyl]-2-carboxamide

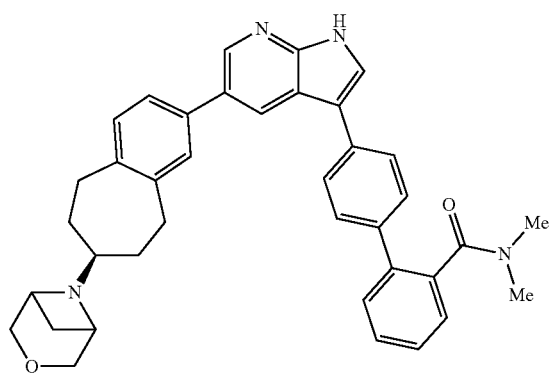 [SMILES: CN(C)C(=O)c1ccccc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. ¹H NMR (400 MHz, Chloroform-d) δ 9.24 (s, 1H), 8.58 (d, J=2.1 Hz, 1H), 8.40 (d, J=2.0 Hz, 1H), 7.74-7.67 (m, 2H), 7.60-7.53 (m, 3H), 7.48-7.44 (m, 2H), 7.44-7.36 (m, 3H), 7.23-7.15 (m, 2H), 4.29 (d, J=10.7 Hz, 2H), 3.71 (d, J=10.8 Hz, 2H), 3.63 (d, J=6.1 Hz, 2H), 3.27-3.22 (m, 1H), 3.07-2.93 (m, 2H), 2.90 (s, 3H), 2.54 (d, J=7.1 Hz, 1H), 2.49 (s, 3H), 1.93 (d, J=11.2 Hz, 2H), 1.83 (d, J=8.2 Hz, 1H), 1.43-1.10 (m, 2H), 0.91-0.75 (m, 2H). ESI MS [M+H]⁺ for C₃₈H₃₉N₄O₂, calcd. 583.3, found 584.3.

Example 93: 6-[(7S)-2-(3-{2'-Methanesulfonyl-[1,1'-biphenyl]-4-yl}-1H-pyrrolo[2,3-b]pyridin-5-yl)-6,7,8,9-tetrahydro-5H-benzo[7]annulen-7-yl]-3-oxa-6-azabicyclo[3.1.1]heptane

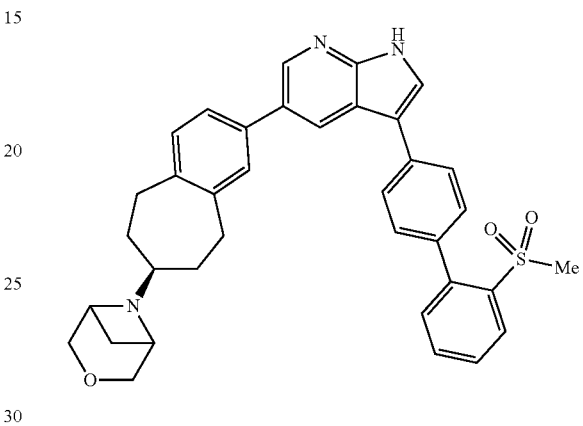

The title compound was prepared in a similar manner to example 1 from the appropriate starting materials. ¹H NMR (400 MHz, Chloroform-d) δ 10.00 (s, 1H), 8.58 (s, 1H), 8.42 (d, J=1.8 Hz, 1H), 8.25 (dd, J=8.0, 1.4 Hz, 1H), 7.83-7.75 (m, 2H), 7.68-7.62 (m, 2H), 7.61-7.54 (m, 2H), 7.44-7.40 (m, 2H), 7.21 (d, J=7.7 Hz, 1H), 4.39 (d, J=12.0 Hz, 2H), 4.27 (s, 2H), 3.99 (d, J=12.0 Hz, 2H), 3.44 (t, J=11.1 Hz, 1H), 3.03-2.79 (m, 4H), 2.72 (s, 3H), 2.03-1.99 (m, 2H), 1.62-1.56 (m, 1H), 1.33-1.21 (m, 2H), 0.94 (d, J=6.6 Hz, 1H), 0.90-0.80 (m, 2H). ESI MS [M+H]⁺ for C₃₆H₃₆N₃O₃S, calcd. 590.25, found 590.3.

Example 94: N,N-Dimethyl-6-(4-{5-[(7S)-7-{3-oxa-6-azabicyclo[3.1.1]heptan-6-yl}-6,7,8,9-tetrahydro-5H-benzo[7]annulen-2-yl]-2H-pyrazolo[3,4-b]pyridin-3-yl}phenyl)pyridine-2-carboxamide

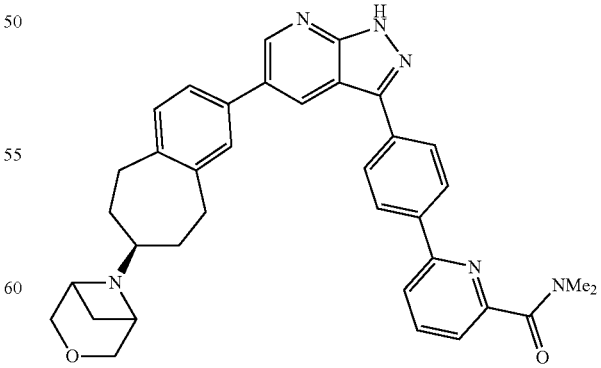

The title compound was prepared in a similar manner to example 2 from the appropriate starting materials. ¹H NMR (400 MHz, Chloroform-d) δ 11.87 (s, 1H), 8.84 (d, J=2.0 Hz, 1H), 8.51 (d, J=2.0 Hz, 1H), 8.19 (d, J=8.5 Hz, 2H), 8.16-8.08 (m, 2H), 7.92-7.81 (m, 2H), 7.62 (dd, J=7.2, 1.4 Hz, 1H), 7.38 (d, J=6.8 Hz, 2H), 7.24 (s, 1H), 4.31 (d, J=10.8 Hz, 2H), 3.74 (dd, J=17.0, 8.3 Hz, 3H), 3.28 (t, J=9.8 Hz, 1H), 3.22 (s, 3H), 3.18 (s, 3H), 3.01-2.81 (m, 3H), 1.96-1.93 (m, 2H), 1.86 (d, J=8.4 Hz, 2H), 1.46-1.31 (m, 2H), 1.31-1.15 (m, 1H), 0.90-0.81 (m, 1H). ESI MS [M+H]⁺ for $C_{36}H_{37}N_6O_2$, calcd. 585.3, found 585.3.

Example 95: 2-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridin-3-yl]propan-2-ol

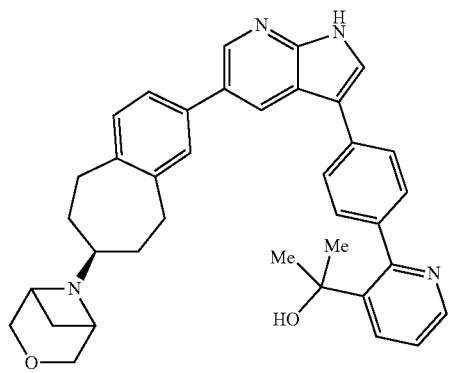 [SMILES: CC(C)(O)c1cccnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. ¹H NMR (400 MHz, Chloroform-d) δ 9.41 (s, 1H), 8.59 (d, J=2.1 Hz, 1H), 8.56 (dd, J=4.7, 1.6 Hz, 1H), 8.40-8.37 (m, 1H), 8.02 (dd, J=8.1, 1.7 Hz, 1H), 7.75-7.68 (m, 2H), 7.52 (d, J=2.5 Hz, 1H), 7.49-7.45 (m, 2H), 7.38 (dq, J=4.2, 2.0 Hz, 2H), 7.30 (dd, J=8.1, 4.7 Hz, 1H), 7.20 (d, J=8.3 Hz, 1H), 4.29 (d, J=10.7 Hz, 2H), 3.71 (d, J=10.7 Hz, 2H), 3.63 (d, J=6.1 Hz, 2H), 3.23 (d, J=9.9 Hz, 1H), 2.98 (ddd, J=21.6, 14.5, 8.0 Hz, 2H), 2.83 (q, J=13.7 Hz, 2H), 2.54 (d, J=7.2 Hz, 1H), 1.93 (brs, 2H), 1.83 (d, J=8.2 Hz, 1H), 1.54 (s, 6H), 1.41-1.20 (m, 2H), 0.95 (d, J=6.6 Hz, 1H). ESI MS [M+H]⁺ for $C_{37}H_{39}N_4O_2$, calcd. 571.3, found 571.3.

Example 96: 3-Methyl-6'-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}-2,3'-bipyridine

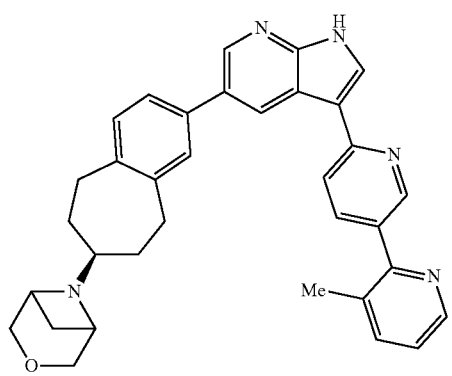 [SMILES: Cc1cccnc1-c1ccc(-c2c[nH]c3ncc(-c4ccc5c(c4)CC[C@@H](N4C6COCC4C6)CC5)cc23)nc1]

The title compound was prepared in a similar manner to example 9 from the appropriate starting materials. ¹H NMR (400 MHz, Chloroform-d) δ 10.16 (s, 1H), 8.92 (d, J=2.1 Hz, 1H), 8.87 (dt, J=2.4, 0.8 Hz, 1H), 8.61 (d, J=2.1 Hz, 1H), 8.59-8.55 (m, 1H), 7.98 (d, J=2.5 Hz, 1H), 7.95 (ddd, J=8.1, 2.3, 0.6 Hz, 1H), 7.78 (dt, J=8.2, 0.8 Hz, 1H), 7.62 (ddt, J=7.7, 1.6, 0.8 Hz, 1H), 7.43 (dq, J=4.6, 2.0 Hz, 2H), 7.24-7.17 (m, 2H), 4.30 (d, J=10.7 Hz, 2H), 3.72 (d, J=10.7 Hz, 2H), 3.63 (d, J=6.1 Hz, 2H), 3.31-3.19 (m, 1H), 2.98 (ddd, J=21.3, 14.3, 7.8 Hz, 2H), 2.85 (q, J=13.7 Hz, 2H), 2.54 (q, J=6.8 Hz, 1H), 2.46 (s, 3H), 1.94 (brs, 2H), 1.83 (d, J=8.2 Hz, 1H), 1.37-1.24 (m, 2H). ESI MS [M+H]⁺ for $C_{34}H_{34}N_5O$, calcd. 528.3, found 528.3.

Example 97: 6-[(7S)-2-{3-[5-(2-Methylphenyl)pyridin-2-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

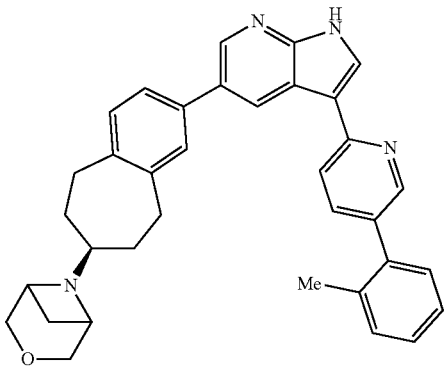 [SMILES: Cc1ccccc1-c1ccc(-c2c[nH]c3ncc(-c4ccc5c(c4)CC[C@@H](N4C6COCC4C6)CC5)cc23)nc1]

The title compound was prepared in a similar manner to example 9 from the appropriate starting materials. ¹H NMR (400 MHz, Chloroform-d) δ 9.82 (s, 1H), 8.90 (d, J=2.1 Hz, 2H), 8.66 (dd, J=2.3, 0.8 Hz, 1H), 8.60 (d, J=2.1 Hz, 1H), 7.97 (d, J=2.5 Hz, 1H), 7.75 (dd, J=8.2, 0.9 Hz, 1H), 7.69 (dd, J=8.1, 2.3 Hz, 1H), 7.43 (dq, J=4.6, 2.1 Hz, 2H), 7.33-7.26 (m, 3H), 7.21 (d, J=8.2 Hz, 1H), 4.30 (d, J=10.7 Hz, 2H), 3.72 (d, J=10.7 Hz, 2H), 3.64 (d, J=6.1 Hz, 2H), 3.24 (t, J=9.6 Hz, 1H), 3.07-2.77 (m, 3H), 2.54 (q, J=6.8 Hz, 1H), 2.35 (s, 3H), 1.94 (s, 2H), 1.83 (d, J=8.3 Hz, 1H), 1.42-1.22 (m, 2H), 0.91-0.77 (m, 1H). ESI MS [M+H]⁺ for $C_{35}H_{35}N_4O$, calcd. 527.3, found 527.3.

Example 98: 6-[(7S)-2-{3-[5-(2-Methylphenyl)pyridin-2-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

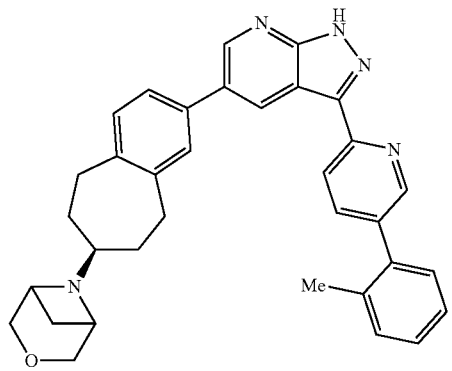 [SMILES: Cc1ccccc1-c1ccc(-c2n[nH]c3ncc(-c4ccc5c(c4)CC[C@@H](N4C6COCC4C6)CC5)cc23)nc1]

The title compound was prepared in a similar manner to example 9 from the appropriate starting materials. ¹H NMR (400 MHz, Chloroform-d) δ 9.85 (s, 1H), 8.90 (d, J=2.0 Hz, 1H), 8.66 (dt, J=2.0, 0.9 Hz, 1H), 8.60 (d, J=2.0 Hz, 1H), 8.01-7.94 (m, 1H), 7.78-7.67 (m, 2H), 7.46-7.39 (m, 2H), 7.35-7.26 (m, 3H), 7.21 (d, J=8.2 Hz, 1H), 4.30 (d, J=10.6 Hz, 2H), 3.72 (d, J=10.7 Hz, 2H), 3.63 (d, J=6.1 Hz, 2H), 3.24 (t, J=9.6 Hz, 1H), 3.08-2.77 (m, 4H), 2.57 (s, 1H), 2.35 (s, 3H), 1.94 (s, 2H), 1.40-1.16 (m, 3H). ESI MS [M+H]⁺ for $C_{34}H_{34}N_5O$, calcd. 528.3, found 528.3.

Example 99: 6-[(7S)-2-(3-{4-[3-(Difluoromethoxy)pyridin-2-yl]phenyl}-1H-pyrazolo[3,4-b]pyridin-5-yl)-6,7,8,9-tetrahydro-5H-benzo[7]annulen-7-yl]-3-oxa-6-azabicyclo[3.1.1]heptane

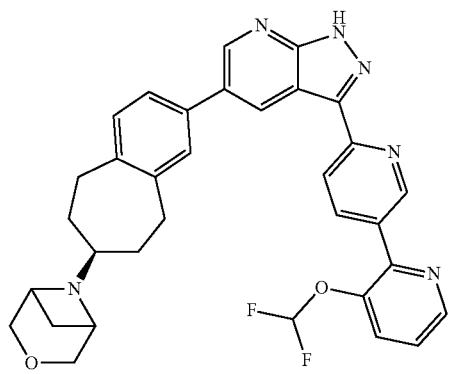 [SMILES: FC(F)Oc1cccnc1-c1ccc(-c2n[nH]c3ncc(-c4ccc5c(c4)CC[C@@H](N4C6COCC4C6)CC5)cc23)nc1]

The title compound was prepared in a similar manner to example 2 from the appropriate starting materials. ¹H NMR (400 MHz, Chloroform-d) δ 11.48 (s, 1H), 8.84 (d, J=2.0 Hz, 1H), 8.61 (dd, J=4.6, 1.4 Hz, 1H), 8.52 (d, J=2.0 Hz, 1H), 8.17-8.08 (m, 2H), 8.08-7.99 (m, 2H), 7.63 (dd, J=8.3, 1.2 Hz, 1H), 7.39 (d, J=7.3 Hz, 2H), 7.31 (dd, J=8.3, 4.6 Hz, 1H), 7.23 (dq, J=0.4 Hz, 1H), 6.45 (t, J=73.1 Hz, 1H), 4.32 (d, J=11.0 Hz, 2H), 3.78 (d, J=10.9 Hz, 2H), 3.30 (s, 1H), 2.99 (td, J=14.8, 7.7 Hz, 2H), 2.85 (q, J=13.1 Hz, 2H), 2.64 (brs, 2H), 1.96 (brs, 2H), 1.88 (d, J=8.5 Hz, 1H), 1.41 (brs, 3H). ESI MS [M+H]⁺ for $C_{34}H_{32}F_2N_5O_2$, calcd. 580.3, found 580.3.

Example 100: 2-(6'-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}-[2,3'-bipyridin]-3-yl)propan-2-ol

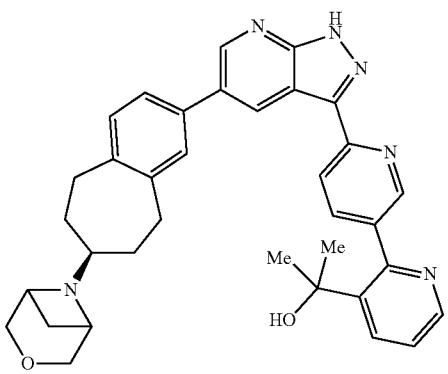 [SMILES: CC(C)(O)c1cccnc1-c1ccc(-c2n[nH]c3ncc(-c4ccc5c(c4)CC[C@@H](N4C6COCC4C6)CC5)cc23)nc1]

The title compound was prepared in a similar manner to example 9 from the appropriate starting materials. ¹H NMR (400 MHz, Chloroform-d) δ 9.13 (d, J=2.0 Hz, 1H), 8.82 (s, 1H), 8.75 (s, 1H), 8.58 (dd, J=4.7, 1.6 Hz, 1H), 8.24 (d, J=8.1 Hz, 1H), 8.07 (dd, J=8.2, 1.6 Hz, 1H), 7.83 (d, J=8.1 Hz, 1H), 7.42 (dt, J=4.5, 2.3 Hz, 1H), 7.34 (dd, J=8.2, 4.7 Hz, 1H), 7.21 (d, J=8.2 Hz, 1H), 4.30 (d, J=10.6 Hz, 2H), 3.72 (d, J=10.7 Hz, 2H), 3.64 (d, J=6.1 Hz, 2H), 3.25 (s, 1H), 3.06-2.73 (m, 4H), 2.56 (d, J=7.1 Hz, 1H), 1.93 (s, 2H), 1.83 (d, J=8.2 Hz, 2H), 1.52 (s, 6H), 1.42-1.27 (m, 3H), 0.93-0.68 (m, 1H). ESI MS [M+H]⁺ for $C_{35}H_{37}N_6O_2$, calcd. 573.3, found 573.3.

Example 101: 6-[(7S)-2-{3-[4-(3-Methanesulfonylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

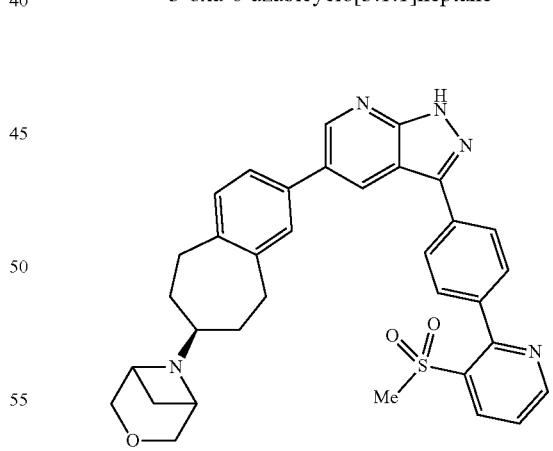

The title compound was prepared in a similar manner to example 2 from the appropriate starting materials. ¹H NMR (400 MHz, Chloroform-d) δ 11.64 (s, 1H), 8.92 (ddd, J=4.8, 1.8, 0.9 Hz, 1H), 8.85 (dd, J=2.1, 0.9 Hz, 1H), 8.59 (ddd, J=8.0, 1.7, 0.9 Hz, 1H), 8.53 (dd, J=2.0, 0.9 Hz, 1H), 8.20-8.12 (m, 2H), 7.93-7.84 (m, 2H), 7.55 (ddd, J=8.2, 4.8, 0.9 Hz, 1H), 7.39 (d, J=6.2 Hz, 2H), 7.24 (d, J=1.0 Hz, 1H), 4.31 (d, J=10.8 Hz, 2H), 3.75 (d, J=10.8 Hz, 2H), 3.69 (s, 2H), 3.27 (s, 1H), 3.09-2.93 (m, 2H), 2.89 (d, J=13.6 Hz, 2H), 2.75 (s, 3H), 2.59 (d, J=7.5 Hz, 1H), 1.95 (s, 2H), 1.85 (d, J=8.3 Hz, 1H), 1.41-1.34 (m, 1H), 0.94-0.72 (m, 1H). ESI MS [M+H]+ for $C_{34}H_{34}N_5O_3S$, calcd. 592.3, found 592.3.

Example 102: 6-[(7S)-2-{3-[4-(3-Methanesulfonylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

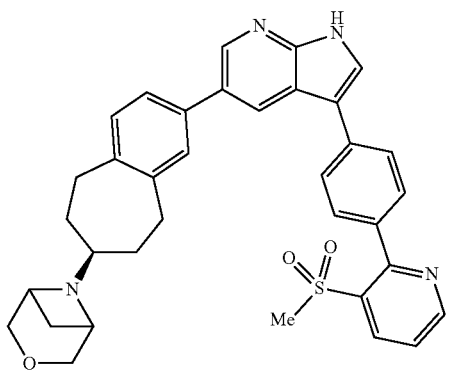 [SMILES: CS(=O)(=O)c1cccnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. 1H NMR (400 MHz, Chloroform-d) δ 9.99 (s, 1H), 8.91 (dd, J=4.8, 1.7 Hz, 1H), 8.61 (d, J=2.1 Hz, 1H), 8.58 (dd, J=8.1, 1.7 Hz, 1H), 8.43 (d, J=2.0 Hz, 1H), 7.87-7.76 (m, 4H), 7.64 (d, J=2.4 Hz, 1H), 7.53 (dd, J=8.1, 4.8 Hz, 1H), 7.39 (dt, J=4.3, 2.0 Hz, 2H), 7.21 (d, J=8.2 Hz, 1H), 4.30 (d, J=10.7 Hz, 2H), 3.72 (d, J=10.7 Hz, 2H), 3.64 (d, J=6.1 Hz, 2H), 3.30-3.18 (m, 1H), 2.98 (ddd, J=22.5, 14.5, 7.9 Hz, 2H), 2.84 (q, J=14.6 Hz, 2H), 2.77 (s, 3H), 2.55 (q, J=6.8 Hz, 1H), 1.94 (d, J=11.8 Hz, 2H), 1.84 (s, 1H), 1.39-1.21 (m, 2H). ESI MS [M+H]+ for $C_{35}H_{35}N_4O_3S$, calcd. 591.3, found 591.3.

Example 103: 6-[(7S)-2-(3-{4-[3-(Trifluoromethoxy)pyridin-2-yl]phenyl}-1H-pyrrolo[2,3-b]pyridin-5-yl)-6,7,8,9-tetrahydro-5H-benzo[7]annulen-7-yl]-3-oxa-6-azabicyclo[3.1.1]heptane

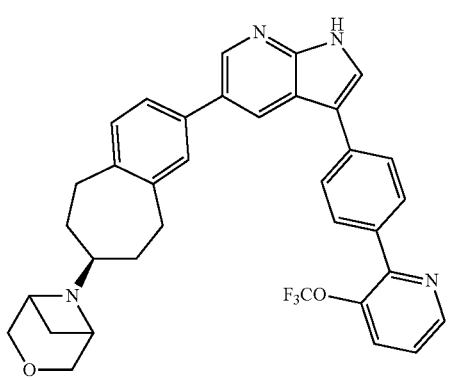 [SMILES: FC(F)(F)Oc1cccnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. 1H NMR (400 MHz, Chloroform-d) δ 9.76 (s, 1H), 8.66 (dd, J=4.6, 1.4 Hz, 1H), 8.58 (d, J=1.9 Hz, 1H), 8.44 (d, J=1.9 Hz, 1H), 8.00-7.92 (m, 2H), 7.82-7.76 (m, 2H), 7.69 (dt, J=8.3, 1.5 Hz, 1H), 7.62 (d, J=2.0 Hz, 1H), 7.42-7.37 (m, 2H), 7.32 (dd, J=8.3, 4.6 Hz, 1H), 7.21 (d, J=8.3 Hz, 1H), 4.30 (d, J=10.8 Hz, 2H), 3.76-3.63 (m, 4H), 3.25 (t, J=9.6 Hz, 1H), 2.98 (td, J=17.4, 16.2, 7.8 Hz, 2H), 2.83 (q, J=13.2 Hz, 2H), 2.57 (d, J=7.6 Hz, 1H), 1.94 (s, 2H), 1.83 (d, J=8.3 Hz, 1H), 1.44-1.25 (m, 2H). ESI MS [M+H]+ for $C_{35}H_{32}F_3N_4O_2$, calcd. 597.3, found 597.3.

Example 104: 6-[(7S)-2-[3-(4-{3-[(3R)—Oxolan-3-yloxy]pyridin-2-yl}phenyl)-1H-pyrazolo[3,4-b]pyridin-5-yl]-6,7,8,9-tetrahydro-5H-benzo[7]annulen-7-yl]-3-oxa-6-azabicyclo[3.1.1]heptane

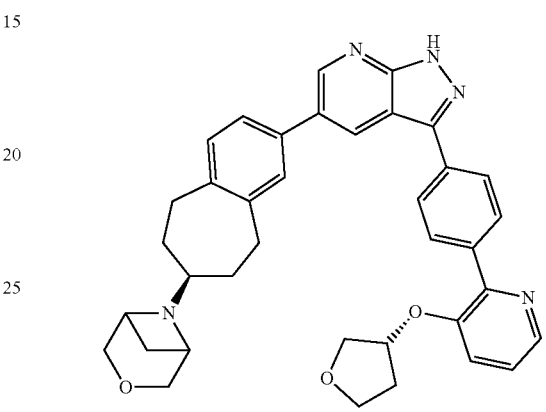

The title compound was prepared in a similar manner to example 2 from the appropriate starting materials. 1H NMR (400 MHz, Chloroform-d) δ 11.84 (s, 1H), 8.84 (d, J=2.0 Hz, 1H), 8.53 (d, J=2.0 Hz, 1H), 8.37 (dd, J=3.7, 2.2 Hz, 1H), 8.18-8.02 (m, 3H), 7.39 (d, J=6.8 Hz, 2H), 7.26-7.21 (m, 3H), 7.08 (s, 1H), 5.02-4.91 (m, 1H), 4.31 (d, J 10.8 Hz, 2H), 4.02 (d, J=3.3 Hz, 2H), 4.00-3.87 (m, 2H), 3.82-3.65 (m, 4H), 3.28 (s, 1H), 2.99 (td, J=15.1, 7.9 Hz, 2H), 2.85 (q, J=13.8, 13.3 Hz, 2H), 2.60 (s, 2H), 2.24-2.15 (m, 2H), 1.95 (s, 2H), 1.47-1.28 (m, 2H). ESI MS [M+H]+ for $C_{37}H_{38}N_5O_3$, calcd. 600.3, found 600.3.

Example 105: 3-Methyl-6'-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}-2,3'-bipyridine

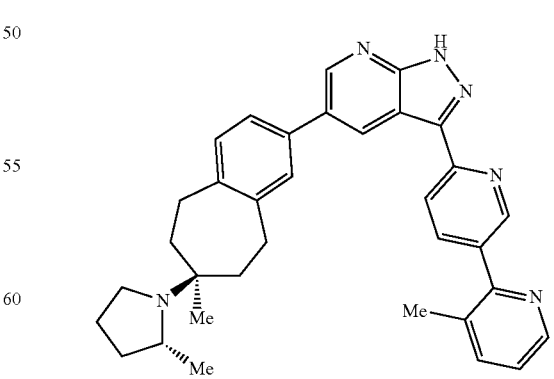

The title compound was prepared in a similar manner to example 9 from the appropriate starting materials. 1H NMR (400 MHz, Chloroform-d) δ 11.5 (s, 1H), 9.18 (d, J=2.0 Hz, 1H), 8.94 (dd, J=2.3, 0.8 Hz, 1H), 8.87 (s, 1H), 8.62-8.56 (m, 1H), 8.31 (dd, J=8.2, 0.8 Hz, 1H), 8.03 (dd, J=8.1, 2.2 Hz, 1H), 7.67-7.62 (m, 1H), 7.45-7.39 (m, 2H), 7.25 (d, J=4.4 Hz, 1H), 7.23-7.19 (m, 1H), 3.39 (s, 1H), 3.30-3.18 (m, 2H), 2.91 (t, J=7.6 Hz, 1H), 2.71-2.47 (m, 3H), 2.46 (s, 3H), 2.00-1.77 (m, 3H), 1.77-1.38 (m, 8H), 1.07 (d, J=6.3 Hz, 3H). ESI MS [M+H]$^+$ for $C_{34}H_{37}N_6$, calcd. 529.3, found 529.3.

Example 106: (3S)—N-[(7S)-2-(3-{3-Methyl-[2,3'-bipyridin]-6'-yl}-1H-pyrazolo[3,4-b]pyridin-5-yl)-6,7,8,9-tetrahydro-5H-benzo[7]annulen-7-yl]oxan-3-amine

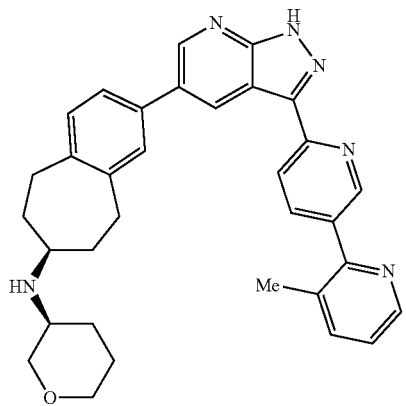 [SMILES: Cc1cccnc1-c1ccc(-c2n[nH]c3ncc(-c4ccc5c(c4)CC[C@@H](N[C@H]4CCCOC4)CC5)cc23)nc1]

The title compound was prepared in a similar manner to example 9 from the appropriate starting materials. $^1$H NMR (400 MHz, Chloroform-d) δ 11.55 (s, 1H), 9.18 (d, J=2.2 Hz, 1H), 8.95 (dd, J=2.3, 0.8 Hz, 1H), 8.85 (d, J=2.1 Hz, 1H), 8.59 (ddd, J=4.8, 1.6, 0.7 Hz, 1H), 8.32 (dd, J=8.2, 0.9 Hz, 1H), 8.03 (dd, J=8.2, 2.3 Hz, 1H), 7.64 (ddd, J=7.7, 1.7, 0.7 Hz, 1H), 7.49-7.41 (m, 2H), 7.26-7.22 (m, 2H), 4.52 (s, 1H), 4.15 (d, J=9.1 Hz, 1H), 3.79 (d, J=9.0 Hz, 2H), 3.08 (d, J=16.2 Hz, 3H), 2.93-2.68 (m, 2H), 2.46 (s, 2H), 2.16 (brs, 3H), 2.00 (d, J=21.3 Hz, 1H), 1.55 (dd, J=91.0, 45.9 Hz, 6H), 1.26 (d, J=7.9 Hz, 1H). ESI MS [M+H]$^+$ for $C_{33}H_{35}N_6O$, calcd. 531.3, found 531.3.

Example 107: (3S)—N-[(7S)-2-(3-{3-Methyl-[2,3'-bipyridin]-6'-yl}-1H-pyrazolo[3,4-b]pyridin-5-yl)-6,7,8,9-tetrahydro-5H-benzo[7]annulen-7-yl]oxan-3-amine

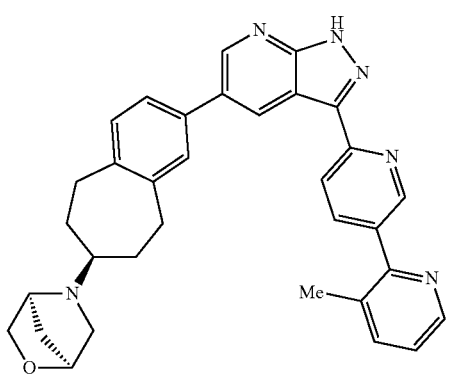 [SMILES: Cc1cccnc1-c1ccc(-c2n[nH]c3ncc(-c4ccc5c(c4)CC[C@@H](N4C[C@@H]6C[C@H]4CO6)CC5)cc23)nc1]

The title compound was prepared in a similar manner to example 9 from the appropriate starting materials. $^1$H NMR (400 MHz, Chloroform-d) δ 11.75 (s, 1H), 9.14 (d, J=2.2 Hz, 1H), 8.92 (dd, J=2.2, 0.8 Hz, 1H), 8.82 (d, J=2.1 Hz, 1H), 8.64-8.53 (m, 1H), 8.29 (dd, J=8.1, 0.8 Hz, 1H), 8.01 (dd, J=8.2, 2.2 Hz, 1H), 7.63 (ddd, J=7.7, 1.7, 0.8 Hz, 1H), 7.47-7.34 (m, 2H), 7.26-7.18 (m, 2H), 4.00-3.88 (m, 1H), 3.80 (dt, J=11.3, 4.0 Hz, 1H), 3.48-3.35 (m, 1H), 3.25 (t, J=9.9 Hz, 1H), 2.93 (ddd, J=22.4, 15.0, 8.3 Hz, 3H), 2.78 (q, J=14.5 Hz, 2H), 2.45 (s, 3H), 2.19-1.98 (m, 2H), 1.99 (d, J=12.6 Hz, 1H), 1.83-1.57 (m, 3H), 1.42 (d, J=13.7 Hz, 2H). ESI MS [M+H]$^+$ for $C_{33}H_{33}N_6O$, calcd. 529.3, found 529.3.

Example 108: (7S)-2-(3-{3-Methyl-[2,3'-bipyridin]-6'-yl}-1H-pyrazolo[3,4-b]pyridin-5-yl)-N-[cis-3-methoxycyclobutyl]-6,7,8,9-tetrahydro-5H-benzo[7]annulen-7-amine

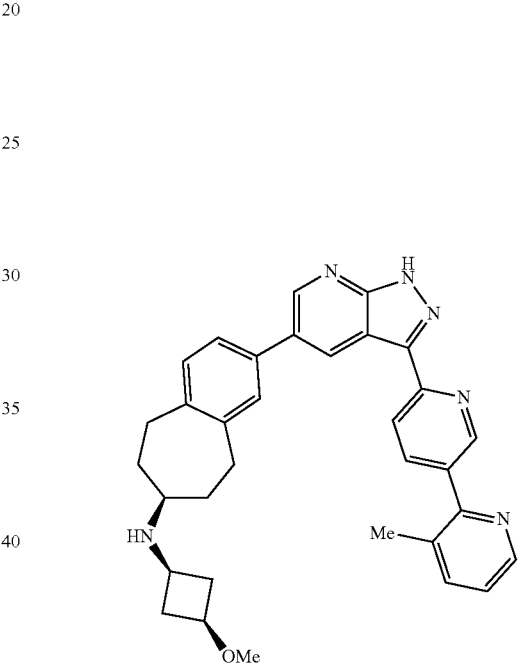

The title compound was prepared in a similar manner to example 9 from the appropriate starting materials. $^1$H NMR (400 MHz, Chloroform-d) δ 9.06 (d, J=2.2 Hz, 1H), 8.90 (dd, J=2.2, 0.8 Hz, 1H), 8.72 (d, J=2.2 Hz, 1H), 8.58 (dd, J=4.8, 1.6 Hz, 1H), 8.25 (dd, J=8.2, 0.9 Hz, 1H), 7.98 (dd, J=8.2, 2.2 Hz, 1H), 7.67-7.60 (m, 1H), 7.35 (dd, J=5.4, 2.1 Hz, 2H), 7.24-7.14 (m, 3H), 3.66 (t, J=7.0 Hz, 2H), 3.25 (t, J=7.9 Hz, 1H), 3.21 (s, 3H), 3.17-3.04 (m, 1H), 2.93 (td, J=14.2, 7.6 Hz, 2H), 2.83-2.57 (m, 4H), 2.43 (s, 2H), 2.25 (s, 2H), 2.10 (d, J=9.3 Hz, 2H), 2.06 (s, 2H), 1.70-1.42 (m, 1H). ESI MS [M+H]$^+$ for $C_{33}H_{35}N_6O$, calcd. 531.3, found 531.3.

Example 109: 6-[(7S)-2-{3-[4-(1-Methyl-1H-pyrazol-5-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

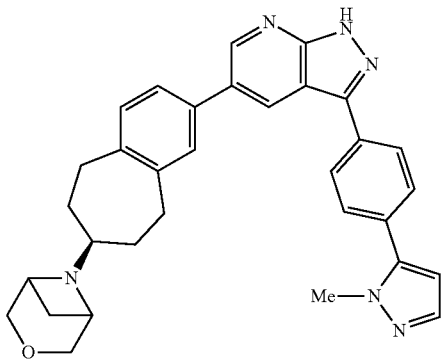 [SMILES: Cn1nccc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, DMSO-$d_6$) δ 13.93 (s, 1H), 8.84 (d, J=2.1 Hz, 1H), 8.69 (d, J=2.1 Hz, 1H), 8.25-8.17 (m, 2H), 7.70-7.64 (m, 2H), 7.58 (d, J=2.0 Hz, 1H), 7.52 (dd, J=7.7, 2.0 Hz, 1H), 7.47 (d, J=1.9 Hz, 1H), 7.22 (d, J=7.8 Hz, 1H), 6.46 (d, J=1.9 Hz, 1H), 4.12 (d, J=10.6 Hz, 2H), 3.90 (s, 3H), 3.53 (dd, J=18.0, 8.3 Hz, 4H), 3.18-3.09 (m, 1H), 3.04-2.86 (m, 2H), 2.83-2.66 (m, 2H), 2.32 (q, J=6.9 Hz, 1H), 1.90-1.75 (m, 2H), 1.64 (d, J=7.9 Hz, 1H), 1.30-1.03 (m, 2H). ESI MS [M+H]$^+$ for $C_{32}H_{33}N_6O$, calcd. 517.3, found 517.3.

Example 110: 6-[(7S)-2-{3-[4-(1-Methyl-1H-1,2,4-triazol-5-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

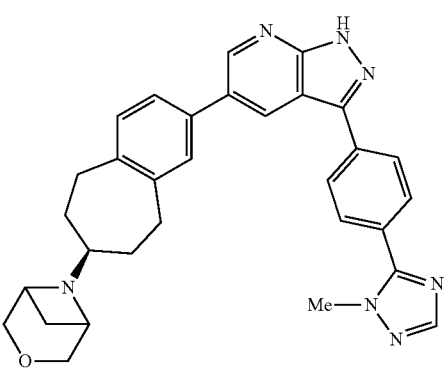 [SMILES: Cn1ccnc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, DMSO-$d_6$) δ 14.00 (s, 1H), 8.85 (d, J=2.1 Hz, 1H), 8.72 (d, J=2.0 Hz, 1H), 8.32-8.24 (m, 2H), 8.01 (s, 1H), 7.97-7.88 (m, 2H), 7.59 (d, J=2.0 Hz, 1H), 7.53 (dd, J=7.7, 2.0 Hz, 1H), 7.22 (d, J=7.7 Hz, 1H), 4.12 (d, J=10.6 Hz, 2H), 4.02 (s, 3H), 3.53 (dd, J=18.4, 8.3 Hz, 4H), 3.19-3.10 (m, 1H), 3.05-2.86 (m, 2H), 2.83-2.68 (m, 2H), 2.39-2.26 (m, 1H), 1.90-1.75 (m, 2H), 1.64 (d, J=7.9 Hz, 1H), 1.27-1.06 (m, 2H). ESI MS [M+H]$^+$ for $C_{31}H_{32}N_7O$, calcd. 518.3, found 518.2.

Example 111: 6-[(7S)-2-{3-[4-(1-Methyl-1H-imidazol-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

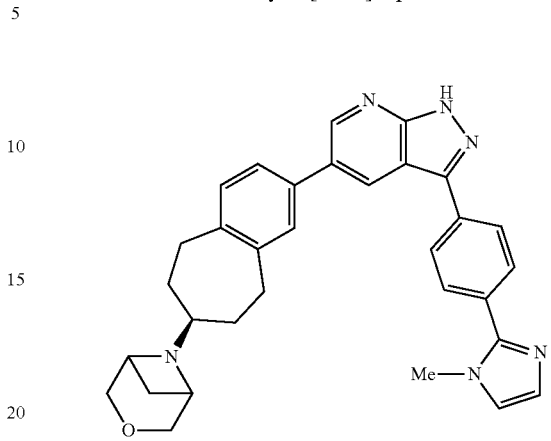

The title compound was prepared in a similar manner to example 2 from the appropriate starting materials. $^1$H NMR (400 MHz, DMSO-$d_6$) δ 13.92 (s, 1H), 8.84 (d, J=2.0 Hz, 1H), 8.70 (d, J=2.1 Hz, 1H), 8.19 (d, J=8.4 Hz, 2H), 7.84 (d, J=8.5 Hz, 2H), 7.59 (d, J=1.9 Hz, 1H), 7.52 (dd, J=7.7, 2.0 Hz, 1H), 7.27 (d, J=1.1 Hz, 1H), 7.22 (d, J=7.8 Hz, 1H), 6.99 (d, J=1.1 Hz, 1H), 4.12 (d, J=10.6 Hz, 2H), 3.80 (s, 3H), 3.53 (dd, J=17.8, 8.3 Hz, 4H), 3.18-3.07 (m, 1H), 3.04-2.84 (m, 2H), 2.84-2.67 (m, 2H), 2.39-2.24 (m, 1H), 1.89-1.74 (m, 2H), 1.64 (d, J=7.9 Hz, 1H), 1.25-1.03 (m, 2H). ESI MS [M+H]$^+$ for $C_{32}H_{33}N_6O$, calcd. 517.3, found 517.3.

Example 112: 1-Methyl-5-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)-1H-1,2,4-triazole

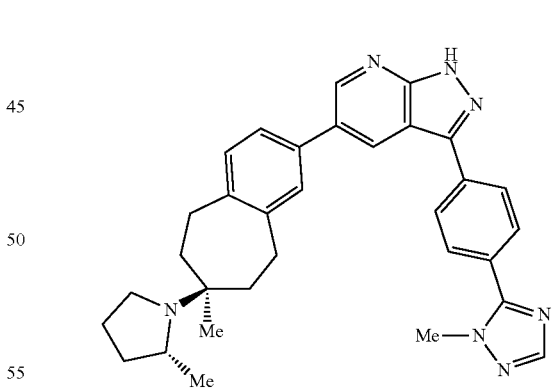

The title compound was prepared in a similar manner to example 18 from the appropriate starting materials. $^1$H NMR (400 MHz, DMSO-$d_6$) δ 13.99 (s, 1H), 8.84 (d, J=2.1 Hz, 1H), 8.70 (d, J=2.1 Hz, 1H), 8.38-8.21 (m, 2H), 8.01 (s, 1H), 7.95-7.89 (m, 2H), 7.55 (d, J=2.0 Hz, 1H), 7.50 (dd, J=7.7, 2.0 Hz, 1H), 7.20 (d, J=7.8 Hz, 1H), 4.02 (s, 3H), 3.40-3.10 (m, 3H), 2.80 (t, J=7.4 Hz, 1H), 2.69-2.39 (m, 3H), 1.91-1.79 (m, 1H), 1.79-1.72 (m, 1H), 1.71-1.56 (m, 2H), 1.46-1.14 (m, 3H), 1.00 (d, J=6.2 Hz, 3H), 0.89 (s, 3H). ESI MS [M+H]$^+$ for $C_{32}H_{36}N_7$, calcd. 518.3, found 518.3.

Example 113: 2-[2-(5-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}pyridin-2-yl)phenyl]propan-2-ol

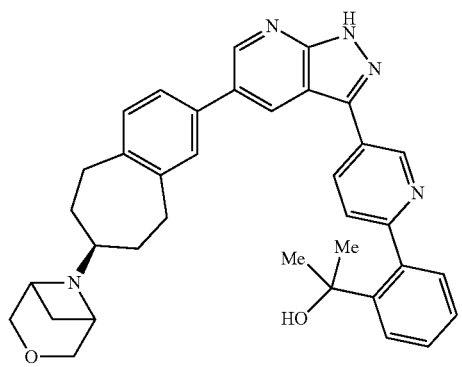 [SMILES: CC(C)(O)c1ccccc1-c1ccc(-c2n[nH]c3ncc(-c4ccc5c(c4)CC[C@@H](N4C6COCC4C6)CC5)cc23)cn1]

The title compound was prepared in a similar manner to example 10 from the appropriate starting materials. $^1$H NMR (400 MHz, DMSO-$d_6$) δ 9.32 (dd, J=2.4, 0.9 Hz, 1H), 8.87 (d, J=2.1 Hz, 1H), 8.78 (d, J=2.0 Hz, 1H), 8.60 (dd, J=8.2, 2.3 Hz, 1H), 7.68 (dd, J=7.8, 1.4 Hz, 1H), 7.65-7.60 (m, 2H), 7.55 (dd, J=7.6, 2.0 Hz, 1H), 7.41 (td, J=7.6, 1.7 Hz, 1H), 7.34 (td, J=7.4, 1.3 Hz, 1H), 7.28 (dd, J=7.6, 1.6 Hz, 1H), 7.22 (d, J=7.8 Hz, 1H), 6.05 (s, 1H), 4.12 (d, J=10.6 Hz, 2H), 3.60-3.46 (m, 4H), 3.19-3.11 (m, 1H), 3.04-2.85 (m, 2H), 2.84-2.66 (m, 2H), 2.38-2.26 (m, 1H), 1.89-1.74 (m, 2H), 1.65 (d, J=7.9 Hz, 1H), 1.31 (s, 6H), 1.25-1.07 (m, 2H). ESI MS [M+H]$^+$ for $C_{36}H_{38}N_5O_2$, calcd. 572.3, found 572.3.

Example 114: 2-[2-(5-{5-[(7S)-7-{3-Oxa-6-azabicyclo[3.1.1]heptan-6-yl}-6,7,8,9-tetrahydro-5H-benzo[7]annulen-2-yl]-1H-pyrrolo[2,3-b]pyridin-3-yl}pyridin-2-yl)phenyl]propan-2-ol

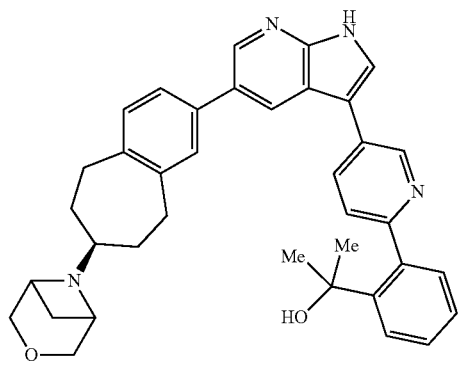 [SMILES: CC(C)(O)c1ccccc1-c1ccc(-c2c[nH]c3ncc(-c4ccc5c(c4)CC[C@@H](N4C6COCC4C6)CC5)cc23)cn1]

The title compound was prepared in a similar manner to example 10 from the appropriate starting materials. $^1$H NMR (400 MHz, DMSO-$d_6$) δ 12.17 (d, J=2.7 Hz, 1H), 9.06 (dd, J=2.4, 0.8 Hz, 1H), 8.55 (d, J=2.1 Hz, 1H), 8.48 (d, J=2.1 Hz, 1H), 8.37 (dd, J=8.2, 2.4 Hz, 1H), 8.15 (d, J=2.7 Hz, 1H), 7.66 (dd, J=7.8, 1.4 Hz, 1H), 7.59-7.52 (m, 2H), 7.47 (dd, J=7.7, 1.9 Hz, 1H), 7.41-7.29 (m, 3H), 7.19 (d, J=7.8 Hz, 1H), 6.48 (s, 1H), 4.12 (d, J=10.5 Hz, 2H), 3.59-3.46 (m, 4H), 3.19-3.08 (m, 1H), 3.04-2.83 (m, 2H), 2.82-2.67 (m, 2H), 2.36-2.27 (m, 1H), 1.91-1.76 (m, 2H), 1.65 (d, J=7.9 Hz, 1H), 1.30 (s, 6H), 1.25-1.03 (m, 2H). ESI MS [M+H]$^+$ for $C_{37}H_{39}N_4O_2$, calcd. 571.3, found 571.3.

Example 115: 6-[(7S)-2-{3-[4-(5-Methylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

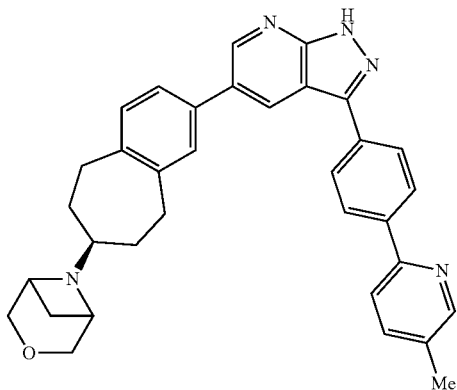 [SMILES: Cc1ccc(-c2ccc(-c3n[nH]c4ncc(-c5ccc6c(c5)CC[C@@H](N5C7COCC5C7)CC6)cc34)cc2)nc1]

The title compound was prepared in a similar manner to example 1 from the appropriate starting materials. $^1$H NMR (400 MHz, DMSO-$d_6$) δ 13.91 (s, 1H), 8.84 (d, J=2.1 Hz, 1H), 8.69 (d, J=2.1 Hz, 1H), 8.51 (dt, J=2.4, 0.8 Hz, 1H), 8.24-8.16 (m, 4H), 7.92 (d, J=8.1 Hz, 1H), 7.70 (ddd, J=8.1, 2.3, 0.8 Hz, 1H), 7.59 (d, J=2.0 Hz, 1H), 7.52 (dd, J=7.7, 2.0 Hz, 1H), 7.23 (d, J=7.8 Hz, 1H), 4.13 (d, J=10.6 Hz, 2H), 3.53 (dd, J=18.0, 8.3 Hz, 4H), 3.19-3.09 (m, 1H), 2.95 (dt, J=31.4, 11.1 Hz, 2H), 2.77 (q, J=14.2 Hz, 2H), 2.36-2.27 (m, 4H), 1.87-1.76 (m, 2H), 1.65 (d, J=7.9 Hz, 1H), 1.21-1.04 (m, 2H). ESI MS [M+H]$^+$ for $C_{34}H_{34}N_5O$, calcd. 528.3, found 528.3.

Example 116: 6-[(7S)-2-{3-[4-(6-Methylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

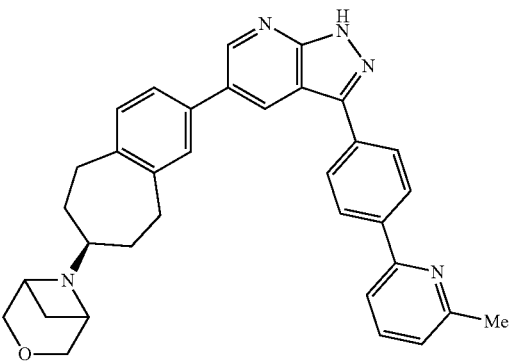 [SMILES: Cc1cccc(-c2ccc(-c3n[nH]c4ncc(-c5ccc6c(c5)CC[C@@H](N5C7COCC5C7)CC6)cc34)cc2)n1]

The title compound was prepared in a similar manner to example 1 from the appropriate starting materials. $^1$H NMR (400 MHz, DMSO-$d_6$) δ 13.91 (s, 1H), 8.85 (d, J=2.1 Hz, 1H), 8.70 (d, J=2.1 Hz, 1H), 8.28-8.16 (m, 4H), 7.85-7.72 (m, 2H), 7.59 (d, J=2.0 Hz, 1H), 7.53 (dd, J=7.7, 2.0 Hz, 1H), 7.27-7.19 (m, 2H), 4.13 (d, J=10.6 Hz, 2H), 3.53 (dd, J=18.1, 8.3 Hz, 4H), 3.20-3.10 (m, 1H), 3.05-2.86 (m, 2H), 2.77 (q, J=14.2 Hz, 2H), 2.54 (s, 3H), 2.38-2.27 (m, 1H), 1.90-1.77 (m, 2H), 1.65 (d, J=7.8 Hz, 1H), 1.23-1.03 (m, 2H). ESI MS [M+H]$^+$ for C$_{34}$H$_{34}$N$_5$O, calcd. 528.3, found 528.3.

Example 117: 6-[(7S)-2-{3-[4-(4-Methylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

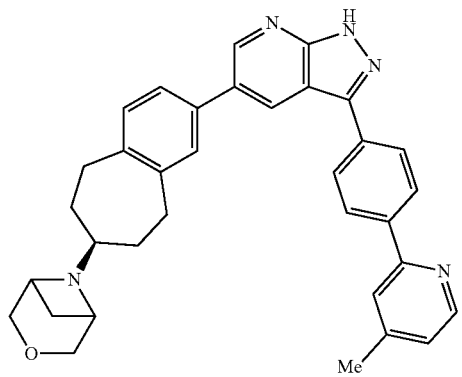 [SMILES: Cc1ccnc(-c2ccc(-c3n[nH]c4ncc(-c5ccc6c(c5)CC[C@@H](N5C7COCC5C7)CC6)cc34)cc2)c1]

The title compound was prepared in a similar manner to example 2 from the appropriate starting materials. $^1$H NMR (400 MHz, DMSO-d$_6$) δ 13.92 (s, 1H), 8.84 (d, J=2.1 Hz, 1H), 8.69 (d, J=2.1 Hz, 1H), 8.52 (d, J=5.0 Hz, 1H), 8.25-8.18 (m, 4H), 7.87 (d, J=1.5 Hz, 1H), 7.59 (d, J=2.0 Hz, 1H), 7.52 (dd, J=7.7, 2.0 Hz, 1H), 7.23 (d, J=7.8 Hz, 1H), 7.19 (dd, J=5.3, 1.1 Hz, 1H), 4.13 (d, J=10.7 Hz, 2H), 3.53 (dd, J=17.9, 8.3 Hz, 4H), 3.20-3.10 (m, 1H), 3.05-2.85 (m, 2H), 2.77 (q, J=14.6, 14.1 Hz, 2H), 2.39 (s, 3H), 2.36-2.26 (m, 1H), 1.89-1.76 (m, 2H), 1.65 (d, J=7.9 Hz, 1H), 1.22-1.01 (m, 2H). ESI MS [M+H]$^+$ for C$_{34}$H$_{34}$N$_5$O, calcd. 528.3, found 528.3.

Example 118: 6-[(7S)-2-{3-[4-(3,4-Dimethylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

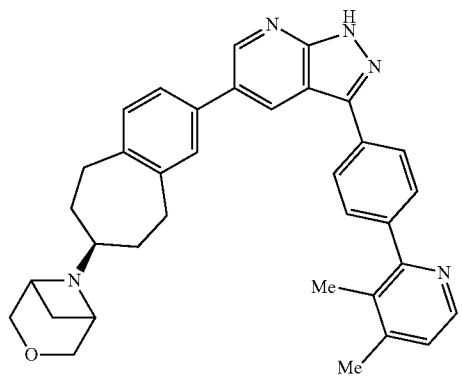 [SMILES: Cc1ccnc(-c2ccc(-c3n[nH]c4ncc(-c5ccc6c(c5)CC[C@@H](N5C7COCC5C7)CC6)cc34)cc2)c1C]

The title compound was prepared in a similar manner to example 2 from the appropriate starting materials. $^1$H NMR (400 MHz, DMSO-d$_6$) δ 13.89 (s, 1H), 8.84 (d, J=2.1 Hz, 1H), 8.70 (d, J=2.1 Hz, 1H), 8.34 (d, J=4.8 Hz, 1H), 8.23-8.10 (m, 2H), 7.65-7.57 (m, 3H), 7.52 (dd, J=7.7, 2.0 Hz, 1H), 7.25-7.17 (m, 2H), 4.12 (d, J=10.6 Hz, 2H), 3.53 (dd, J=18.2, 8.3 Hz, 4H), 3.19-3.09 (m, 1H), 3.04-2.84 (m, 2H), 2.76 (q, J=13.9 Hz, 2H), 2.36-2.28 (m, 4H), 2.26 (s, 3H), 1.91-1.78 (m, 2H), 1.64 (d, J=7.8 Hz, 1H), 1.22-1.01 (m, 2H). ESI MS [M+H]$^+$ for C$_{35}$H$_{36}$N$_5$O, calcd. 542.3, found 542.3.

Example 119: 6-[(7S)-2-{3-[4-(3,5-Dimethylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

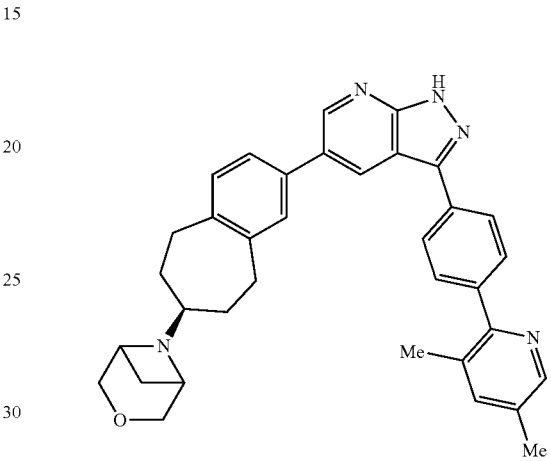

The title compound was prepared in a similar manner to example 2 from the appropriate starting materials. $^1$H NMR (400 MHz, DMSO-d$_6$) δ 13.89 (s, 1H), 8.84 (d, J=2.0 Hz, 1H), 8.69 (d, J=2.1 Hz, 1H), 8.40-8.30 (m, 1H), 8.21-8.10 (m, 2H), 7.72-7.64 (m, 2H), 7.59 (d, J=2.0 Hz, 1H), 7.56-7.49 (m, 2H), 7.22 (d, J=7.8 Hz, 1H), 4.12 (d, J=10.6 Hz, 2H), 3.53 (dd, J=18.2, 8.3 Hz, 4H), 3.19-3.08 (m, 1H), 3.05-2.84 (m, 2H), 2.76 (q, J=14.5, 14.0 Hz, 2H), 2.39-2.27 (m, 7H), 1.89-1.77 (m, 2H), 1.64 (d, J=7.8 Hz, 1H), 1.21-1.02 (m, 2H). ESI MS [M+H]$^+$ for C$_{35}$H$_{36}$N$_5$O, calcd. 542.3, found 542.3.

Example 120: 6-[(7S)-2-{3-[4-(3,6-Dimethylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

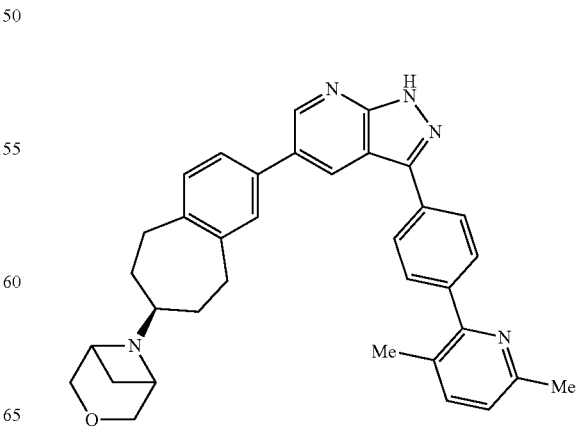

The title compound was prepared in a similar manner to example 2 from the appropriate starting materials. ¹H NMR (400 MHz, DMSO-d₆) δ 13.89 (s, 1H), 8.84 (d, J=2.1 Hz, 1H), 8.69 (d, J=2.1 Hz, 1H), 8.17 (d, J=8.4 Hz, 2H), 7.70-7.65 (m, 2H), 7.62-7.57 (m, 2H), 7.52 (dd, J=7.7, 2.0 Hz, 1H), 7.22 (d, J=7.8 Hz, 1H), 7.15 (d, J=7.8 Hz, 1H), 4.12 (d, J=10.6 Hz, 2H), 3.53 (dd, J=18.2, 8.3 Hz, 4H), 3.20-3.09 (m, 1H), 3.05-2.85 (m, 2H), 2.76 (q, J=14.1 Hz, 2H), 2.48-2.44 (m, 3H), 2.37-2.25 (m, 4H), 1.89-1.76 (m, 2H), 1.64 (d, J=7.9 Hz, 1H), 1.22-1.02 (m, 2H). ESI MS [M+H]⁺ for C₃₅H₃₆N₅O, calcd. 542.3, found 542.3.

Example 121: 3-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]-1,3-oxazolidin-2-one

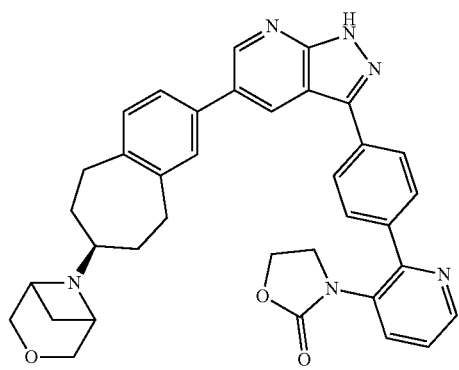 [SMILES: O=C1OCCN1c1cccnc1-c1ccc(-c2n[nH]c3ncc(-c4ccc5c(c4)CC[C@@H](N4C6COCC4C6)CC5)cc23)cc1]

The title compound was prepared in a similar manner to example 7 from the appropriate starting materials. ¹H NMR (400 MHz, DMSO-d₆) δ 13.93 (s, 1H), 8.84 (d, J=2.0 Hz, 1H), 8.73 (d, J=2.0 Hz, 1H), 8.65 (dd, J=4.7, 1.6 Hz, 1H), 8.27-8.20 (m, 2H), 7.98 (dd, J=8.0, 1.6 Hz, 1H), 7.81-7.72 (m, 2H), 7.59 (s, 1H), 7.56-7.48 (m, 2H), 7.23 (d, J=7.8 Hz, 1H), 4.35 (dd, J=8.8, 7.0 Hz, 2H), 4.12 (d, J=10.6 Hz, 2H), 3.79-3.71 (m, 2H), 3.53 (dd, J=17.9, 8.3 Hz, 4H), 3.19-3.09 (m, 1H), 3.05-2.85 (m, 2H), 2.77 (q, J=14.0 Hz, 2H), 2.37-2.24 (m, 1H), 1.89-1.75 (m, 2H), 1.65 (d, J=7.8 Hz, 1H), 1.25-0.98 (m, 2H). ESI MS [M+H]⁺ for C₃₆H₃₅N₆O₃, calcd. 599.3, found 599.3.

Example 122: 6-[(7S)-2-{3-[4-(2,5-Dimethylpyrimidin-4-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

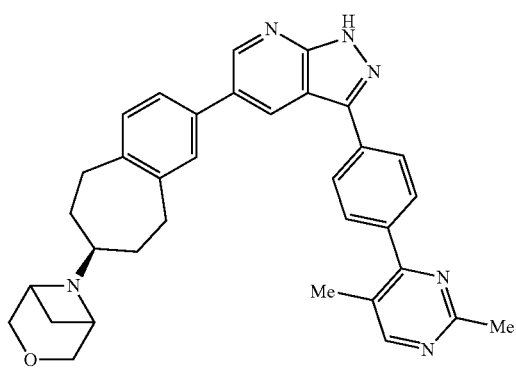 [SMILES: Cc1ncc(C)c(-c2ccc(-c3n[nH]c4ncc(-c5ccc6c(c5)CC[C@@H](N5C7COCC5C7)CC6)cc34)cc2)n1]

The title compound was prepared in a similar manner to example 2 from the appropriate starting materials. ¹H NMR (400 MHz, DMSO-d₆) δ 13.96 (s, 1H), 8.85 (d, J=2.0 Hz, 1H), 8.71 (d, J=2.1 Hz, 1H), 8.61 (d, J=0.8 Hz, 1H), 8.26-8.21 (m, 2H), 7.84-7.79 (m, 2H), 7.59 (d, J=2.0 Hz, 1H), 7.53 (dd, J=7.8, 2.0 Hz, 1H), 7.23 (d, J=7.8 Hz, 1H), 4.13 (d, J=10.6 Hz, 2H), 3.53 (dd, J=18.8, 8.3 Hz, 4H), 3.21-3.10 (m, 1H), 3.05-2.85 (m, 2H), 2.77 (q, J=14.3 Hz, 2H), 2.61 (s, 3H), 2.39-2.27 (m, 4H), 1.90-1.77 (m, 2H), 1.65 (d, J=7.9 Hz, 1H), 1.27-1.08 (m, 2H). ESI MS [M+H]⁺ for C₃₄H₃₅N₆O, calcd. 543.3, found 543.3.

Example 123: 6-[(7S)-2-{3-[4-(2,5-Dimethylpyrimidin-4-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

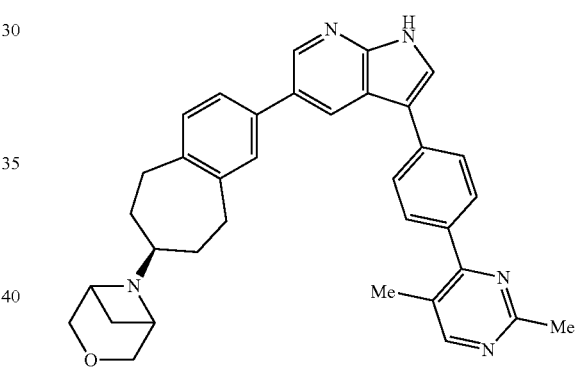

The title compound was prepared in a similar manner to example 1 from the appropriate starting materials. ¹H NMR (400 MHz, DMSO-d₆) δ 12.06 (d, J=2.7 Hz, 1H), 8.58 (d, J=0.8 Hz, 1H), 8.53 (d, J=2.1 Hz, 1H), 8.45 (d, J=2.1 Hz, 1H), 8.01 (d, J=2.7 Hz, 1H), 7.94-7.89 (m, 2H), 7.77-7.72 (m, 2H), 7.51 (d, J=2.0 Hz, 1H), 7.45 (dd, J=7.7, 2.0 Hz, 1H), 7.19 (d, J=7.8 Hz, 1H), 4.12 (d, J=10.6 Hz, 2H), 3.53 (dd, J 18.6, 8.3 Hz, 4H), 3.19-3.09 (m, 1H), 3.03-2.84 (m, 2H), 2.75 (q, J=14.1 Hz, 2H), 2.60 (s, 3H), 2.38-2.28 (m, 4H), 1.89-1.77 (m, 2H), 1.64 (d, J=7.8 Hz, 1H), 1.27-1.06 (m, 2H). ESI MS [M+H]⁺ for C₃₅H₃₆N₅O, calcd. 542.3, found 542.3.

Example 124: (4R)-4-Methyl-3-[2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]-1,3-oxazolidin-2-one

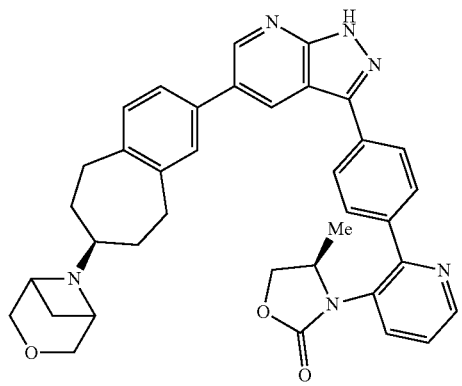 [SMILES: C[C@@H]1COC(=O)N1c1cccnc1-c1ccc(-c2n[nH]c3ncc(-c4ccc5c(c4)CC[C@@H](N4C6COCC4C6)CC5)cc23)cc1]

The title compound was prepared in a similar manner to example 7 from the appropriate starting materials. $^1$H NMR (400 MHz, DMSO-$d_6$) δ 13.94 (s, 1H), 8.84 (d, J=2.1 Hz, 1H), 8.74 (d, J=2.0 Hz, 1H), 8.68 (dd, J=4.7, 1.6 Hz, 1H), 8.27-8.21 (m, 2H), 7.92 (dd, J=8.0, 1.6 Hz, 1H), 7.77-7.71 (m, 2H), 7.59 (d, J=2.0 Hz, 1H), 7.56-7.49 (m, 2H), 7.23 (d, J=7.8 Hz, 1H), 4.49-4.39 (m, 1H), 4.12 (d, J=10.6 Hz, 2H), 3.94-3.83 (m, 2H), 3.53 (dd, J=17.7, 8.3 Hz, 4H), 3.19-3.09 (m, 1H), 3.04-2.85 (m, 2H), 2.84-2.69 (m, 2H), 2.38-2.27 (m, 1H), 1.89-1.76 (m, 2H), 1.65 (d, J=7.9 Hz, 1H), 1.28-1.07 (m, 2H), 0.94-0.87 (m, 3H). ESI MS [M+H]$^+$ for $C_{37}H_{37}N_6O_3$, calcd. 613.3, found 613.3.

Example 125: (4S)-4-Methyl-3-[2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]-1,3-oxazolidin-2-one

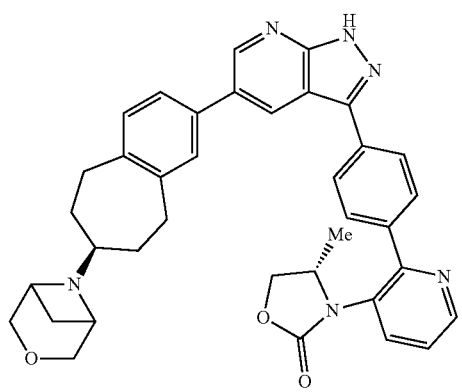 [SMILES: C[C@H]1COC(=O)N1c1cccnc1-c1ccc(-c2n[nH]c3ncc(-c4ccc5c(c4)CC[C@@H](N4C6COCC4C6)CC5)cc23)cc1]

The title compound was prepared in a similar manner to example 7 from the appropriate starting materials. $^1$H NMR (400 MHz, DMSO-$d_6$) δ 13.94 (s, 1H), 8.84 (d, J=2.1 Hz, 1H), 8.74 (d, J=2.1 Hz, 1H), 8.68 (dd, J=4.7, 1.6 Hz, 1H), 8.27-8.22 (m, 2H), 7.92 (dd, J=8.1, 1.6 Hz, 1H), 7.75-7.71 (m, 2H), 7.59 (s, 1H), 7.52 (dt, J=8.0, 4.5 Hz, 2H), 7.23 (d, J=7.8 Hz, 1H), 4.53-4.36 (m, 1H), 4.13 (d, J=10.6 Hz, 2H), 3.95-3.84 (m, 2H), 3.63-3.45 (m, 4H), 3.20-3.09 (m, 1H), 3.06-2.84 (m, 2H), 2.77 (q, J=14.0 Hz, 2H), 2.39-2.25 (m, 1H), 1.92-1.77 (m, 2H), 1.65 (d, J=7.8 Hz, 1H), 1.28-1.04 (m, 2H), 0.91 (dd, J=6.2, 1.8 Hz, 3H). ESI MS [M+H]$^+$ for $C_{37}H_{37}N_6O_3$, calcd. 613.3, found 613.3.

Example 126: 3-[3-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyrazin-2-yl]-1,3-oxazolidin-2-one

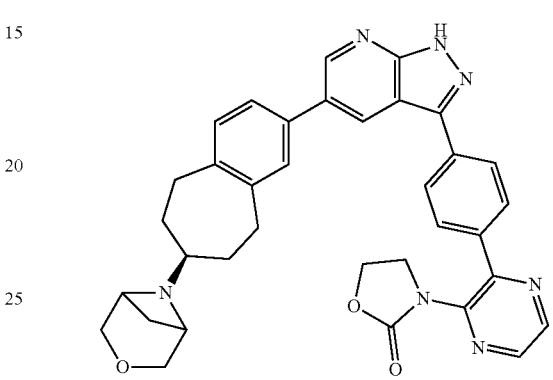

The title compound was prepared in a similar manner to example 7 from the appropriate starting materials. $^1$H NMR (400 MHz, DMSO-$d_6$) δ 8.74 (s, 1H), 8.69 (dd, J=2.5, 0.6 Hz, 1H), 8.63 (s, 1H), 8.50 (d, J=2.4 Hz, 1H), 8.17 (d, J=8.3 Hz, 2H), 7.88 (d, J=8.1 Hz, 2H), 7.56 (s, 1H), 7.50 (d, J=7.7 Hz, 1H), 7.21 (d, J=7.8 Hz, 1H), 4.51 (t, J=7.7 Hz, 2H), 4.26 (t, J=7.8 Hz, 2H), 4.13 (d, J=10.6 Hz, 2H), 3.53 (dd, J=17.5, 8.3 Hz, 4H), 3.20-3.09 (m, 1H), 3.04-2.83 (m, 2H), 2.76 (q, J=14.4, 14.0 Hz, 2H), 2.37-2.25 (m, 1H), 1.89-1.77 (m, 2H), 1.65 (d, J=7.8 Hz, 1H), 1.25-1.01 (m, 2H). ESI MS [M+H]$^+$ for $C_{35}H_{34}N_7O_3$, calcd. 600.3, found 600.3.

Example 127: 1-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]piperidin-2-one

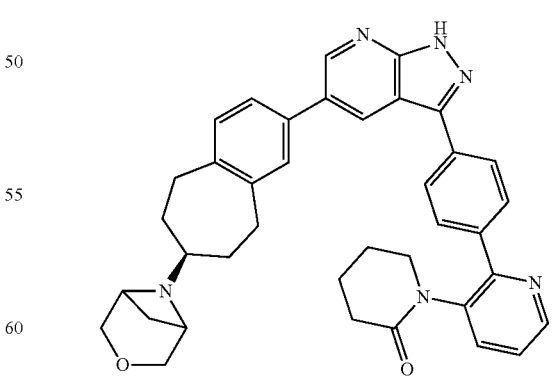

The title compound was prepared in a similar manner to example 7 from the appropriate starting materials. $^1$H NMR (400 MHz, DMSO-$d_6$) δ 13.92 (s, 1H), 8.84 (d, J=2.1 Hz, 1H), 8.71 (d, J=2.1 Hz, 1H), 8.62 (dd, J=4.7, 1.6 Hz, 1H), 8.25-8.18 (m, 2H), 7.77 (dd, J=7.9, 1.6 Hz, 1H), 7.72-7.66 (m, 2H), 7.58 (d, J=2.0 Hz, 1H), 7.52 (dd, J=7.7, 2.0 Hz, 1H), 7.46 (dd, J=7.9, 4.7 Hz, 1H), 7.23 (d, J=7.8 Hz, 1H), 4.12 (d, J=10.6 Hz, 2H), 3.59-3.37 (m, 6H), 3.18-3.05 (m, 1H), 3.04-2.86 (m, 2H), 2.76 (q, J=14.0 Hz, 2H), 2.40-2.21 (m, 3H), 1.90-1.78 (m, 2H), 1.78-1.62 (m, 4H), 1.60-1.39 (m, 1H), 1.27-1.07 (m, 2H). ESI MS [M+H]+ for $C_{38}H_{39}N_6O_2$, calcd. 611.3, found 611.3.

Example 128: N-Methyl-N-[2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]cyclopropanecarboxamide

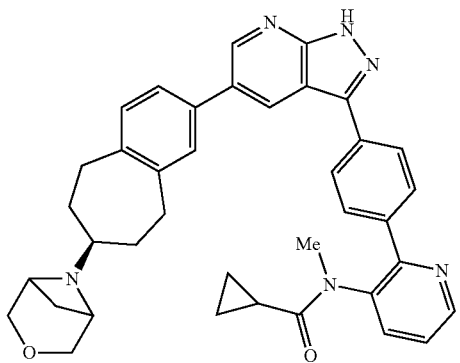 [SMILES: CN(C(=O)C1CC1)c1cccnc1-c1ccc(-c2n[nH]c3ncc(-c4ccc5c(c4)CC[C@@H](N4C6COCC4C6)CC5)cc23)cc1]

The title compound was prepared in a similar manner to example 7 from the appropriate starting materials. $^1$H NMR (400 MHz, DMSO-$d_6$) δ 13.94 (s, 1H), 8.83 (d, J=2.0 Hz, 1H), 8.73-8.68 (m, 2H), 8.25-8.19 (m, 2H), 7.96 (dd, J=8.0, 1.6 Hz, 1H), 7.76-7.71 (m, 2H), 7.59 (d, J=2.0 Hz, 1H), 7.56-7.50 (m, 2H), 7.22 (d, J=7.8 Hz, 1H), 4.12 (d, J=10.5 Hz, 2H), 3.53 (dd, J=17.8, 8.3 Hz, 4H), 3.18-3.10 (m, 1H), 3.04 (s, 3H), 3.01-2.84 (m, 2H), 2.76 (q, J=14.2 Hz, 2H), 2.37-2.26 (m, 1H), 1.92-1.75 (m, 2H), 1.65 (d, J=7.9 Hz, 1H), 1.29-1.05 (m, 3H), 0.74-0.65 (m, 1H), 0.61-0.51 (m, 1H), 0.48-0.40 (m, 2H). ESI MS [M+H]+ for $C_{38}H_{39}N_6O_2$, calcd. 611.3, found 611.3.

Example 129: (3S)—N-[(7S)-2-{3-[4-(3-Methylpyridin-2-yl)phenyl]-1H-pyrazolo[3,4-b]pyridin-5-yl}-6,7,8,9-tetrahydro-5H-benzo[7]annulen-7-yl]oxan-3-amine

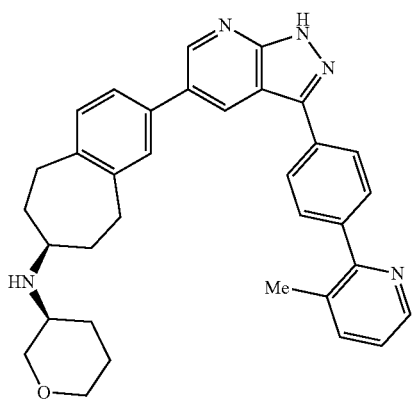 [SMILES: Cc1cccnc1-c1ccc(-c2n[nH]c3ncc(-c4ccc5c(c4)CC[C@@H](N[C@H]4CCCOC4)CC5)cc23)cc1]

The title compound was prepared in a similar manner to example 2 from the appropriate starting materials. $^1$H NMR (400 MHz, DMSO-$d_6$) δ 13.90 (s, 1H), 8.84 (d, J=2.0 Hz, 1H), 8.69 (d, J=2.1 Hz, 1H), 8.49 (ddd, J=4.7, 1.7, 0.7 Hz, 1H), 8.21-8.15 (m, 2H), 7.75-7.68 (m, 3H), 7.59 (d, J=2.0 Hz, 1H), 7.52 (dd, J=7.8, 2.0 Hz, 1H), 7.30 (dd, J=7.6, 4.7 Hz, 1H), 7.21 (d, J=7.8 Hz, 1H), 3.76 (dd, J=10.4, 3.8 Hz, 1H), 3.67 (d, J=11.3 Hz, 1H), 3.20 (td, J=10.9, 2.8 Hz, 1H), 2.93 (dd, J=10.8, 8.9 Hz, 2H), 2.90-2.77 (m, 2H), 2.76-2.53 (m, 3H), 2.39 (s, 3H), 1.98-1.82 (m, 2H), 1.60-1.53 (m, 1H), 1.53-1.39 (m, 1H), 1.27-1.11 (m, 4H). ESI MS [M+H]+ for $C_{34}H_{36}N_5O$, calcd. 530.3, found 530.3.

Example 130: (1S,4S)-5-[(7S)-2-{3-[4-(3-Methylpyridin-2-yl)phenyl]-1H-pyrazolo[3,4-b]pyridin-5-yl}-6,7,8,9-tetrahydro-5H-benzo[7]annulen-7-yl]-2-oxa-5-azabicyclo[2.2.1]heptane

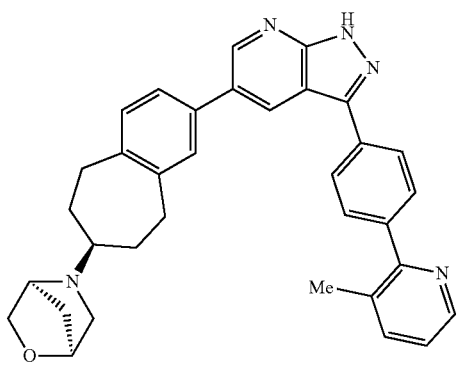

The title compound was prepared in a similar manner to example 2 from the appropriate starting materials. $^1$H NMR (400 MHz, DMSO-$d_6$) δ 8.84 (d, J=2.1 Hz, 1H), 8.69 (d, J=2.1 Hz, 1H), 8.49 (ddd, J=4.8, 1.7, 0.7 Hz, 1H), 8.22-8.13 (m, 2H), 7.76-7.67 (m, 3H), 7.58 (d, J=2.0 Hz, 1H), 7.52 (dd, J=7.7, 2.0 Hz, 1H), 7.29 (dd, J=7.7, 4.7 Hz, 1H), 7.21 (d, J=7.8 Hz, 1H), 4.31 (d, J=2.2 Hz, 1H), 3.88 (d, J=7.5 Hz, 1H), 3.69 (s, 1H), 3.51 (dd, J=7.7, 1.6 Hz, 1H), 3.12-2.90 (m, 3H), 2.76-2.52 (m, 3H), 2.39 (s, 3H), 2.35-2.28 (m, 1H), 1.94-1.74 (m, 2H), 1.70 (d, J=9.2 Hz, 1H), 1.59 (d, J=9.3 Hz, 1H), 1.52-1.39 (m, 1H), 1.27-1.18 (m, 2H). ESI MS [M+H]+ for $C_{34}H_{34}N_5O$, calcd. 528.3, found 528.2.

Example 131: (7S)-2-{3-[4-(3-Methylpyridin-2-yl)phenyl]-1H-pyrazolo[3,4-b]pyridin-5-yl}-N-[cis-3-methoxycyclobutyl]-6,7,8,9-tetrahydro-5H-benzo[7]annulen-7-amine

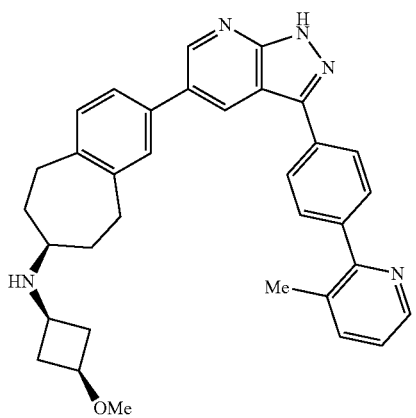 [SMILES: CO[C@H]1C[C@@H](N[C@H]2CCc3ccc(-c4cnc5[nH]nc(-c6ccc(-c7ncccc7C)cc6)c5c4)cc3CC2)C1]

The title compound was prepared in a similar manner to example 2 from the appropriate starting materials. ¹H NMR (400 MHz, DMSO-d₆) δ 13.90 (s, 1H), 8.83 (d, J=2.1 Hz, 1H), 8.69 (d, J=2.1 Hz, 1H), 8.49 (ddd, J=4.7, 1.7, 0.7 Hz, 1H), 8.20-8.16 (m, 2H), 7.75-7.68 (m, 3H), 7.58 (d, J=2.0 Hz, 1H), 7.52 (dd, J=7.7, 2.0 Hz, 1H), 7.29 (dd, J=7.7, 4.7 Hz, 1H), 7.21 (d, J=7.8 Hz, 1H), 3.48 (p, J=7.2 Hz, 1H), 3.07 (s, 3H), 2.98-2.80 (m, 3H), 2.79-2.57 (m, 3H), 2.39 (s, 3H), 1.98-1.81 (m, 2H), 1.59-1.43 (m, 2H), 1.31-1.14 (m, 4H). ESI MS [M+H]⁺ for C₃₄H₃₆N₅O, calcd. 530.3, found 530.3.

Example 132: 2-(4-{5-[(7S)-7-[(3S)-3-(Methoxymethyl)pyrrolidin-1-yl]-6,7,8,9-tetrahydro-5H-benzo[7]annulen-2-yl]-1H-pyrazolo[3,4-b]pyridin-3-yl}phenyl)-3-methylpyridine

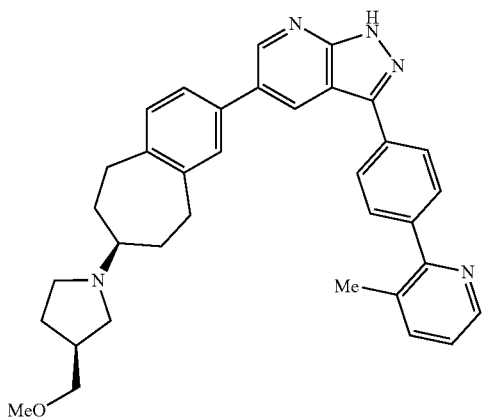 [SMILES: COC[C@H]1CCN([C@H]2CCc3ccc(-c4cnc5[nH]nc(-c6ccc(-c7ncccc7C)cc6)c5c4)cc3CC2)C1]

The title compound was prepared in a similar manner to example 2 from the appropriate starting materials. ¹H NMR (400 MHz, DMSO-d₆) δ 13.91 (s, 1H), 8.84 (d, J=2.1 Hz, 1H), 8.69 (d, J=2.1 Hz, 1H), 8.49 (ddd, J=4.7, 1.7, 0.7 Hz, 1H), 8.21-8.16 (m, 2H), 7.75-7.68 (m, 3H), 7.58 (d, J=2.0 Hz, 1H), 7.51 (dd, J=7.7, 2.0 Hz, 1H), 7.29 (dd, J=7.7, 4.7 Hz, 1H), 7.21 (d, J=7.8 Hz, 1H), 3.23-3.18 (m, 5H), 3.12-2.97 (m, 2H), 2.69-2.59 (m, 2H), 2.58-2.51 (m, 2H), 2.39 (s, 3H), 2.35-2.22 (m, 3H), 1.89-1.75 (m, 2H), 1.71-1.48 (m, 2H), 1.39-1.31 (m, 1H), 1.26-1.18 (m, 2H). ESI MS [M+H]⁺ for C₃₅H₃₈N₅O, calcd. 544.3, found 544.3.

Example 133: 6-[(7S)-2-{3-[4-(1-Methyl-1H-1,2,4-triazol-5-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

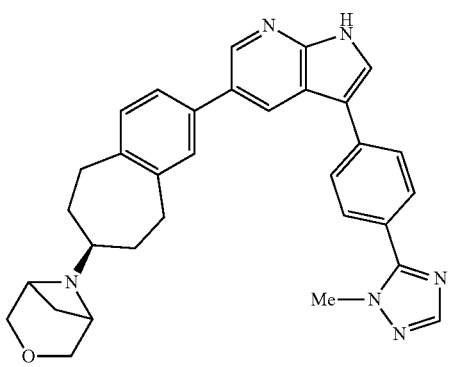 [SMILES: Cn1ncnc1-c1ccc(-c2c[nH]c3ncc(-c4ccc5c(c4)CC[C@@H](N4C6COCC4C6)CC5)cc23)cc1]

The title compound was prepared in a similar manner to example 1 from the appropriate starting materials. ¹H NMR (400 MHz, DMSO-d₆) δ 12.09 (s, 1H), 8.53 (d, J=2.1 Hz, 1H), 8.46 (d, J=2.1 Hz, 1H), 8.04 (d, J=2.7 Hz, 1H), 8.00-7.93 (m, 3H), 7.83 (d, J=8.5 Hz, 2H), 7.51 (d, J=2.0 Hz, 1H), 7.45 (dd, J=7.6, 2.0 Hz, 1H), 7.20 (d, J=7.8 Hz, 1H), 4.12 (d, J=10.5 Hz, 2H), 4.00 (s, 3H), 3.53 (dd, J=18.5, 8.3 Hz, 4H), 3.17-3.09 (m, 1H), 3.04-2.84 (m, 2H), 2.75 (q, J=13.9 Hz, 2H), 2.38-2.27 (m, 1H), 1.89-1.77 (m, 2H), 1.64 (d, J=7.9 Hz, 1H), 1.27-1.18 (m, 1H), 1.18-1.04 (m, 1H). ESI MS [M+H]⁺ for C₃₂H₃₃N₆O, calcd. 517.3, found 517.3.

Example 134: (3S)—N-[(7S)-2-{3-[4-(3-Methylpyridin-2-yl)phenyl]-1H-pyrazolo[3,4-b]pyridin-5-yl}-6,7,8,9-tetrahydro-5H-benzo[7]annulen-7-yl]oxan-3-amine

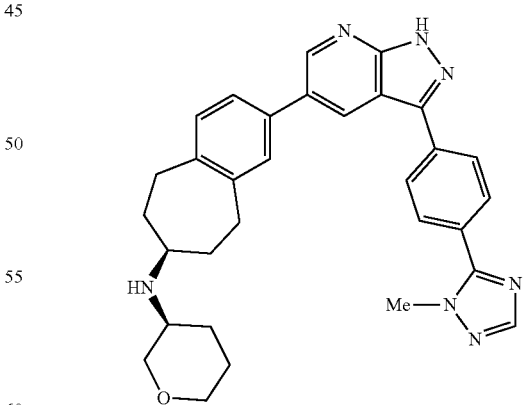

The title compound was prepared in a similar manner to example 2 from the appropriate starting materials. ¹H NMR (400 MHz, DMSO-d₆) δ 13.99 (s, 1H), 8.85 (d, J=2.1 Hz, 1H), 8.72 (d, J=2.0 Hz, 1H), 8.32-8.23 (m, 2H), 8.01 (d, J=0.8 Hz, 1H), 7.98-7.89 (m, 2H), 7.59 (d, J=1.9 Hz, 1H), 7.53 (dd, J=7.8, 1.9 Hz, 1H), 7.22 (d, J=7.8 Hz, 1H), 4.02 (s, 3H), 3.76 (d, J=11.0 Hz, 1H), 3.67 (d, J=11.1 Hz, 1H), 3.25-3.17 (m, 1H), 3.01-2.78 (m, 4H), 2.78-2.53 (m, 3H), 2.06-1.81 (m, 2H), 1.64-1.53 (m, 1H), 1.53-1.38 (m, 1H), 1.32-1.07 (m, 4H). ESI MS [M+H]⁺ for C₃₁H₃₄N₇O, calcd. 520.3, found 520.3.

Example 135: (1S,4S)-5-[(7S)-2-{3-[4-(1-Methyl-1H-1,2,4-triazol-5-yl)phenyl]-1H-pyrazolo[3,4-b]pyridin-5-yl}-6,7,8,9-tetrahydro-5H-benzo[7]annulen-7-yl]-2-oxa-5-azabicyclo[2.2.1]heptane

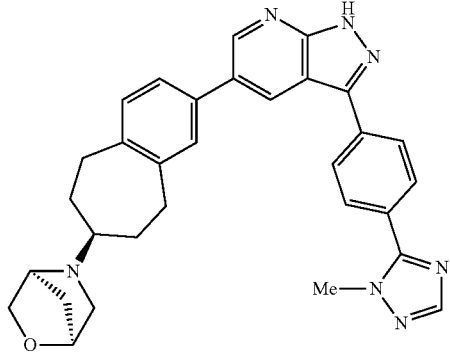

The title compound was prepared in a similar manner to example 2 from the appropriate starting materials. ¹H NMR (400 MHz, DMSO-d₆) δ 13.99 (s, 1H), 8.85 (d, J=2.1 Hz, 1H), 8.72 (d, J=2.0 Hz, 1H), 8.30-8.25 (m, 2H), 8.01 (d, J=0.5 Hz, 1H), 7.96-7.90 (m, 2H), 7.59 (d, J=2.0 Hz, 1H), 7.52 (dd, J=7.7, 2.0 Hz, 1H), 7.22 (d, J=7.8 Hz, 1H), 4.31 (s, 1H), 4.02 (s, 3H), 3.88 (d, J=7.5 Hz, 1H), 3.69 (d, J=2.1 Hz, 1H), 3.51 (d, J=7.5 Hz, 1H), 3.11-2.92 (m, 3H), 2.78-2.54 (m, 3H), 2.35-2.28 (m, 1H), 1.92-1.76 (m, 2H), 1.70 (d, J=9.2 Hz, 1H), 1.59 (d, J=9.3 Hz, 1H), 1.54-1.38 (m, 1H), 1.28-1.18 (m, 1H). ESI MS [M+H]⁺ for C₃₁H₃₂N₇O, calcd. 518.3, found 518.3.

Example 136: 3,6-Dimethyl-2-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyridine

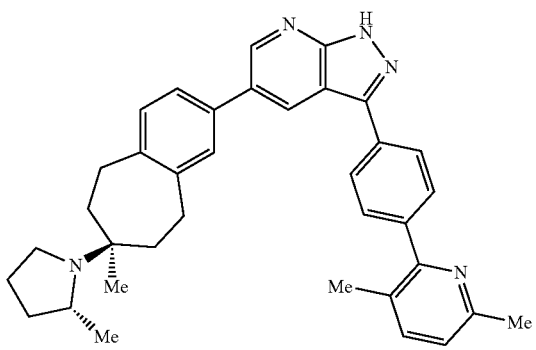 [SMILES: Cc1ccc(C)c(-c2ccc(-c3n[nH]c4ncc(-c5ccc6c(c5)CC[C@@](C)(N5CCC[C@H]5C)CC6)cc34)cc2)n1]

The title compound was prepared in a similar manner to example 18 from the appropriate starting materials. ¹H NMR (400 MHz, DMSO-d₆) δ 13.87 (s, 1H), 8.80 (s, 1H), 8.65 (d, J=2.1 Hz, 1H), 8.18-8.13 (m, 2H), 7.67 (d, J=8.3 Hz, 2H), 7.60 (d, J=7.8 Hz, 1H), 7.54 (d, J=1.9 Hz, 1H), 7.49 (dd, J=7.7, 2.0 Hz, 1H), 7.19 (d, J=7.8 Hz, 1H), 7.14 (d, J=7.8 Hz, 1H), 3.24-3.09 (m, 3H), 2.80 (t, J=7.5 Hz, 1H), 2.67-2.51 (m, 3H), 2.49-2.45 (m, 3H), 2.33 (s, 3H), 1.91-1.80 (m, 2H), 1.80-1.73 (m, 1H), 1.73-1.60 (m, 2H), 1.42-1.22 (m, 3H), 1.00 (d, J=6.2 Hz, 3H), 0.90 (d, J=3.5 Hz, 3H). ESI MS [M+H]⁺ for C₃₆H₄₀N₅, calcd. 542.3, found 542.3.

Example 137: 6-[(7S)-2-{3-[4-(3,6-Dimethylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

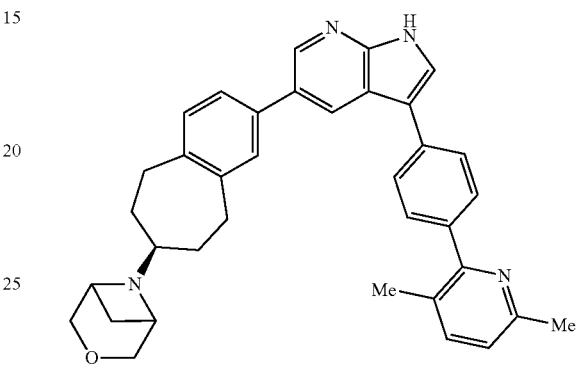

The title compound was prepared in a similar manner to example 1 from the appropriate starting materials. ¹H NMR (400 MHz, DMSO-d₆) δ 12.00 (s, 1H), 8.53 (d, J=2.0 Hz, 1H), 8.43 (d, J=2.1 Hz, 1H), 7.95 (d, J=2.6 Hz, 1H), 7.87-7.81 (m, 2H), 7.58 (dd, J=8.0, 6.0 Hz, 3H), 7.52 (s, 1H), 7.45 (s, 1H), 7.20 (d, J=7.5 Hz, 1H), 7.12 (d, J=7.7 Hz, 1H), 4.22-4.06 (m, 2H), 3.52 (dd, J=18.2, 8.3 Hz, 4H), 3.19-3.07 (m, 1H), 3.04-2.66 (m, 4H), 2.48-2.44 (m, 3H), 2.37-2.27 (m, 4H), 1.89-1.76 (m, 2H), 1.65 (d, J=7.9 Hz, 1H), 1.25-1.02 (m, 2H). ESI MS [M+H]⁺ for C₃₆H₃₇N₄O, calcd. 541.3, found 542.3.

Example 138: 6-[(7S)-2-{3-[4-(1-Ethyl-1H-1,2,4-triazol-5-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

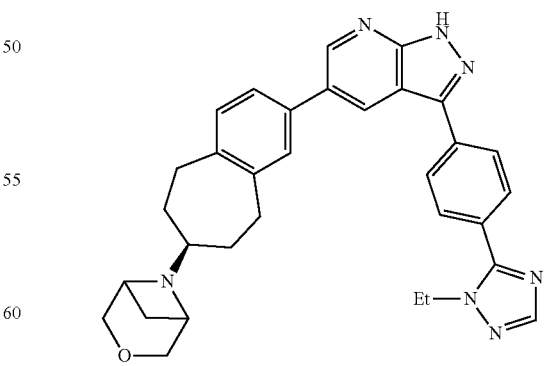

The title compound was prepared in a similar manner to example 23 from the appropriate starting materials. ¹H NMR (400 MHz, DMSO-d₆) δ 14.00 (s, 1H), 8.86 (d, J=2.0 Hz, 1H), 8.73 (d, J=2.0 Hz, 1H), 8.32-8.25 (m, 2H), 8.04 (s, 1H), 7.87-7.80 (m, 2H), 7.59 (d, J=2.0 Hz, 1H), 7.53 (dd, J=7.8, 2.0 Hz, 1H), 7.23 (d, J=7.8 Hz, 1H), 4.31 (q, J=7.2 Hz, 2H), 4.12 (d, J=10.6 Hz, 2H), 3.53 (dd, J=18.2, 8.3 Hz, 4H), 3.20-3.09 (m, 1H), 3.05-2.85 (m, 2H), 2.77 (q, J=14.1 Hz, 2H), 2.38-2.27 (m, 1H), 1.89-1.76 (m, 2H), 1.65 (d, J=7.9 Hz, 1H), 1.41 (t, J=7.2 Hz, 3H), 1.28-1.09 (m, 2H). ESI MS [M+H]+ for $C_{32}H_{34}N_7O$, calcd. 532.3, found 532.3.

Example 139: 3,6-Dimethyl-2-(4-{5-[(7S)-7-(pyrrolidin-1-yl)-6,7,8,9-tetrahydro-5H-benzo[7]annulen-2-yl]-1H-pyrazolo[3,4-b]pyridin-3-yl}phenyl)pyridine

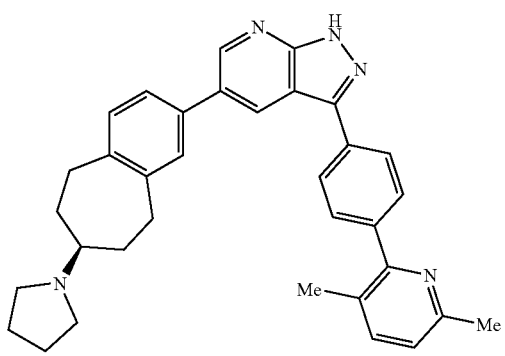 [SMILES: Cc1ccc(C)c(-c2ccc(-c3n[nH]c4ncc(-c5ccc6c(c5)CC[C@@H](N5CCCC5)CC6)cc34)cc2)n1]

The title compound was prepared in a similar manner to example 2 from the appropriate starting materials. 1H NMR (400 MHz, DMSO-d6) δ 13.90 (s, 1H), 8.84 (d, J=2.1 Hz, 1H), 8.69 (d, J=2.0 Hz, 1H), 8.21-8.13 (m, 2H), 7.72-7.64 (m, 2H), 7.64-7.56 (m, 2H), 7.52 (d, J=7.9 Hz, 1H), 7.22 (d, J=7.7 Hz, 1H), 7.15 (d, J=7.8 Hz, 1H), 3.19-2.81 (m, 5H), 2.71-2.49 (m, 4H), 2.49-2.45 (m, 3H), 2.33 (s, 3H), 1.93-1.45 (m, 5H), 1.35-1.07 (m, 3H). ESI MS [M+H]+ for $C_{34}H_{36}N_5$, calcd. 514.3, found 514.3.

Example 140: (3S)—N-[(7S)-2-{3-[4-(3,6-Dimethylpyridin-2-yl)phenyl]-1H-pyrazolo[3,4-b]pyridin-5-yl}-6,7,8,9-tetrahydro-5H-benzo[7]annulen-7-yl]oxan-3-amine

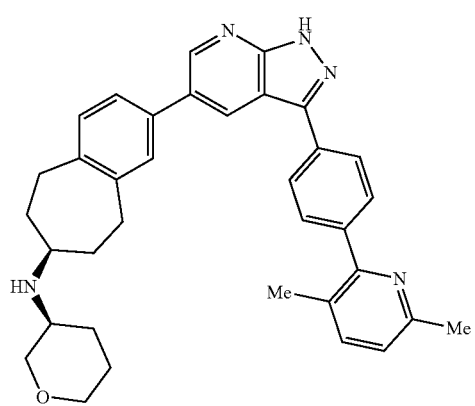 [SMILES: Cc1ccc(C)c(-c2ccc(-c3n[nH]c4ncc(-c5ccc6c(c5)CC[C@@H](N[C@H]5CCCOC5)CC6)cc34)cc2)n1]

The title compound was prepared in a similar manner to example 2 from the appropriate starting materials. 1H NMR (400 MHz, DMSO-d6) δ 13.89 (s, 1H), 8.84 (d, J=2.1 Hz, 1H), 8.69 (d, J=2.1 Hz, 1H), 8.19-8.14 (m, 2H), 7.70-7.65 (m, 2H), 7.62-7.57 (m, 2H), 7.52 (dd, J=7.7, 2.0 Hz, 1H), 7.21 (d, J=7.8 Hz, 1H), 7.15 (d, J=7.8 Hz, 1H), 3.79-3.72 (m, 1H), 3.67 (dt, J=11.0, 3.8 Hz, 1H), 3.21 (td, J=10.8, 2.7 Hz, 1H), 2.99-2.90 (m, 2H), 2.90-2.79 (m, 2H), 2.75-2.55 (m, 3H), 2.48-2.44 (m, 3H), 2.33 (s, 3H), 2.05-1.83 (m, 3H), 1.63-1.53 (m, 1H), 1.52-1.38 (m, 1H), 1.31-1.04 (m, 3H). ESI MS [M+H]+ for $C_{35}H_{38}N_5O$, calcd. 544.3, found 544.3.

Example 141: (1S,4S)-5-[(7S)-2-{3-[4-(3,6-Dimethylpyridin-2-yl)phenyl]-1H-pyrazolo[3,4-b]pyridin-5-yl}-6,7,8,9-tetrahydro-5H-benzo[7]annulen-7-yl]-2-oxa-5-azabicyclo[2.2.1]heptane

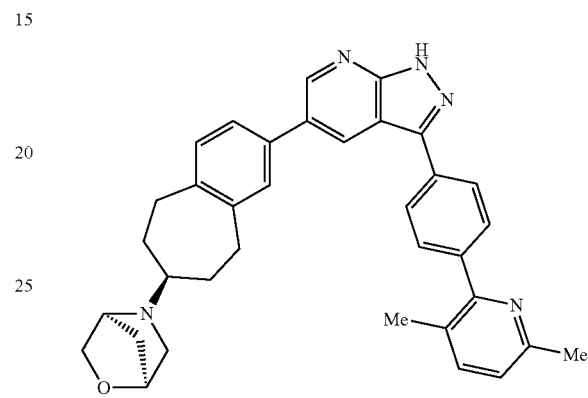

The title compound was prepared in a similar manner to example 2 from the appropriate starting materials. 1H NMR (400 MHz, DMSO-d6) δ 8.79 (s, 1H), 8.65 (s, 1H), 8.18-8.13 (m, 2H), 7.68-7.64 (m, 2H), 7.62-7.55 (m, 2H), 7.50 (dd, J=7.7, 1.9 Hz, 1H), 7.20 (d, J=7.8 Hz, 1H), 7.14 (d, J=7.8 Hz, 1H), 4.30 (s, 1H), 3.88 (d, J=7.5 Hz, 1H), 3.69 (s, 1H), 3.55-3.47 (m, 1H), 3.09-2.92 (m, 3H), 2.77-2.67 (m, 2H), 2.65-2.59 (m, 1H), 2.48-2.45 (m, 3H), 2.33 (s, 3H), 2.31-2.28 (m, 1H), 1.92-1.75 (m, 2H), 1.70 (d, J=9.3 Hz, 1H), 1.59 (d, J=9.3 Hz, 1H), 1.53-1.37 (m, 1H), 1.28-1.18 (m, 1H). ESI MS [M+H]+ for $C_{35}H_{36}N_5O$, calcd. 542.3, found 542.3.

Example 142: 3,6-Dimethyl-6'-{5-[(7S)-7-[(1R)-3-oxa-6-azabicyclo[3.1.1]heptan-6-yl]-6,7,8,9-tetrahydro-5H-benzo[7]annulen-2-yl]-1H-pyrrolo[2,3-b]pyridin-3-yl}-2,3'-bipyridine

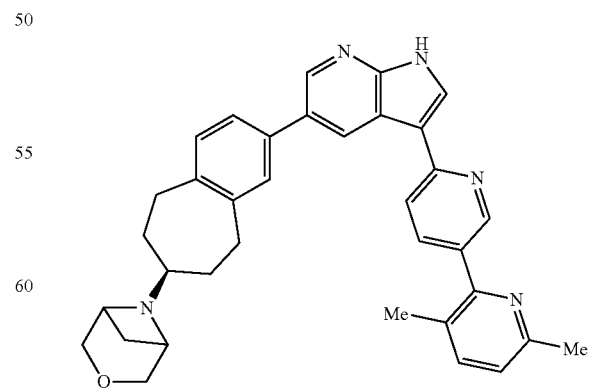

The title compound was prepared in a similar manner to example 9 from the appropriate starting materials. 1H NMR (400 MHz, DMSO-d$_6$) δ 12.15 (s, 1H), 8.96 (d, J=2.2 Hz, 1H), 8.78 (dd, J=2.2, 1.0 Hz, 1H), 8.52 (d, J=2.2 Hz, 1H), 8.34 (d, J=2.8 Hz, 1H), 8.02-7.92 (m, 2H), 7.61 (d, J=7.9 Hz, 1H), 7.47 (s, 1H), 7.41 (d, J=7.7 Hz, 1H), 7.21 (d, J=7.7 Hz, 1H), 7.16 (d, J=7.8 Hz, 1H), 4.13 (d, J=10.6 Hz, 2H), 3.61-3.44 (m, 4H), 3.22-3.07 (m, 1H), 3.04-2.85 (m, 2H), 2.84-2.67 (m, 2H), 2.48-2.45 (m, 3H), 2.38-2.28 (m, 4H), 1.91-1.75 (m, 2H), 1.65 (d, J=7.9 Hz, 1H), 1.29-1.05 (m, 2H). ESI MS [M+H]$^+$ for C$_{35}$H$_{36}$N$_5$O, calcd. 542.3, found 542.3.

Example 143: (1R)-6-[(7S)-2-{3-[4-(3,6-Dimethylpyridin-2-yl)-2-fluorophenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

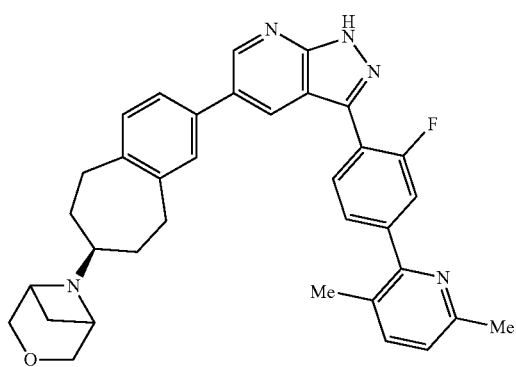 [SMILES: Cc1ccc(C)c(-c2ccc(-c3n[nH]c4ncc(-c5ccc6c(c5)CC[C@@H](N5C7COCC5C7)CC6)cc34)c(F)c2)n1]

The title compound was prepared in a similar manner to example 2 from the appropriate starting materials. $^1$H NMR (400 MHz, DMSO-d$_6$) δ 8.86 (d, J=2.1 Hz, 1H), 8.42 (t, J=2.7 Hz, 1H), 7.96 (t, J=7.8 Hz, 1H), 7.63 (d, J=7.8 Hz, 1H), 7.59-7.51 (m, 3H), 7.46 (d, J=8.3 Hz, 1H), 7.20 (dd, J=10.5, 7.8 Hz, 2H), 4.12 (d, J=10.7 Hz, 2H), 3.57-3.48 (m, 4H), 3.18-3.06 (m, 1H), 3.02-2.84 (m, 2H), 2.84-2.67 (m, 2H), 2.48-2.45 (m, 3H), 2.38-2.28 (m, 4H), 1.89-1.76 (m, 2H), 1.64 (d, J=7.7 Hz, 1H), 1.24-1.07 (m, 2H). ESI MS [M+H]$^+$ for C$_{35}$H$_{35}$FN$_5$O, calcd. 560.3, found 560.3.

Example 144: (1R)-6-[(7S)-2-{3-[4-(3,6-Dimethylpyridin-2-yl)-2-fluorophenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

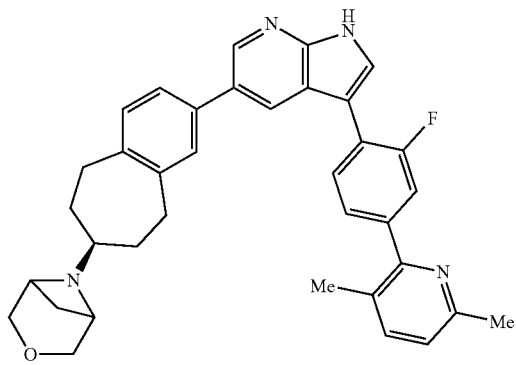 [SMILES: Cc1ccc(C)c(-c2ccc(-c3c[nH]c4ncc(-c5ccc6c(c5)CC[C@@H](N5C7COCC5C7)CC6)cc34)c(F)c2)n1]

The title compound was prepared in a similar manner to example 1 from the appropriate starting materials. $^1$H NMR (400 MHz, DMSO-d$_6$) δ 12.14 (d, J=2.7 Hz, 1H), 8.55 (d, J=2.1 Hz, 1H), 8.27 (s, 1H), 7.88-7.82 (m, 2H), 7.62-7.58 (m, 1H), 7.50-7.44 (m, 3H), 7.42 (d, J=7.7 Hz, 1H), 7.17 (dd, J=12.9, 7.8 Hz, 2H), 4.12 (d, J=10.2 Hz, 2H), 3.60-3.49 (m, 4H), 3.18-3.08 (m, 1H), 3.02-2.82 (m, 2H), 2.81-2.69 (m, 2H), 2.48-2.45 (m, 3H), 2.37-2.27 (m, 4H), 1.90-1.76 (m, 2H), 1.65 (d, J=7.7 Hz, 1H), 1.22-1.06 (m, 2H). ESI MS [M+H]$^+$ for C$_{36}$H$_{36}$FN$_4$O, calcd. 559.3, found 559.3.

Example 145: (1R)-6-[(7S)-2-(3-{4-[3-Methyl-6-(trifluoromethyl)pyridin-2-yl]phenyl}-1H-pyrazolo[3,4-b]pyridin-5-yl)-6,7,8,9-tetrahydro-5H-benzo[7]annulen-7-yl]-3-oxa-6-azabicyclo[3.1.1]heptane

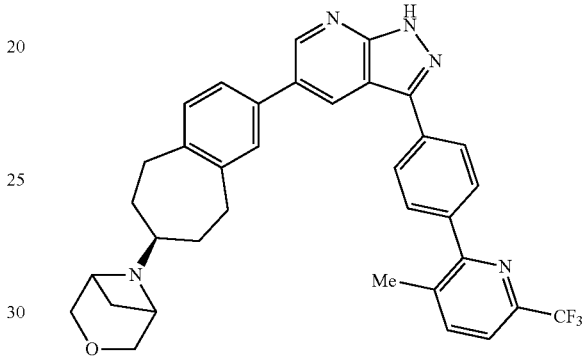

The title compound was prepared in a similar manner to example 2 from the appropriate starting materials. $^1$H NMR (400 MHz, DMSO-d$_6$) δ 13.94 (s, 1H), 8.85 (d, J=2.1 Hz, 1H), 8.72 (d, J=2.0 Hz, 1H), 8.25-8.21 (m, 2H), 8.06-8.01 (m, 1H), 7.81 (d, J=8.0 Hz, 1H), 7.77-7.73 (m, 2H), 7.60 (d, J=2.0 Hz, 1H), 7.53 (dd, J=7.7, 1.9 Hz, 1H), 7.22 (d, J=7.8 Hz, 1H), 4.12 (d, J=10.6 Hz, 2H), 3.53 (dd, J=18.5, 8.3 Hz, 4H), 3.19-3.10 (m, 1H), 3.05-2.86 (m, 2H), 2.77 (q, J=15.0, 14.3 Hz, 2H), 2.49 (s, 3H), 2.38-2.26 (m, 1H), 1.91-1.77 (m, 2H), 1.65 (d, J=7.9 Hz, 1H), 1.24-1.07 (m, 2H). ESI MS [M+H]$^+$ for C$_{35}$H$_{33}$F$_3$N$_5$O, calcd. 596.3, found 596.3.

Example 146: (1R)-6-[(7S)-2-(3-{4-[3-Methyl-6-(trifluoromethyl)pyridin-2-yl]phenyl}-1H-pyrrolo[2,3-b]pyridin-5-yl)-6,7,8,9-tetrahydro-5H-benzo[7]annulen-7-yl]-3-oxa-6-azabicyclo[3.1.1]heptane

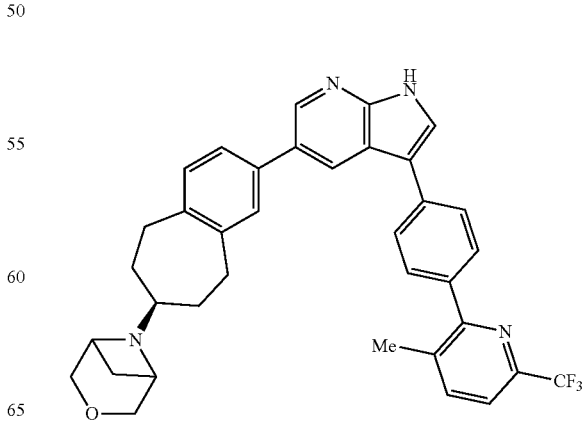

The title compound was prepared in a similar manner to example 1 from the appropriate starting materials. ¹H NMR (400 MHz, DMSO-d₆) δ 12.05 (d, J=2.7 Hz, 1H), 8.53 (d, J=2.1 Hz, 1H), 8.46 (d, J=2.1 Hz, 1H), 8.03-7.98 (m, 2H), 7.94-7.88 (m, 2H), 7.77 (d, J=7.9 Hz, 1H), 7.69-7.64 (m, 2H), 7.52 (s, 1H), 7.46 (d, J=7.6 Hz, 1H), 7.19 (d, J=7.7 Hz, 1H), 4.12 (d, J=10.6 Hz, 2H), 3.53 (dd, J=18.9, 8.2 Hz, 4H), 3.19-3.08 (m, 1H), 3.05-2.83 (m, 2H), 2.75 (q, J=14.6, 13.9 Hz, 2H), 2.50-2.45 (m, 3H), 2.37-2.27 (m, 1H), 1.90-1.77 (m, 2H), 1.64 (d, J=8.1 Hz, 1H), 1.29-1.06 (m, 2H). ESI MS [M+H]⁺ for $C_{36}H_{34}F_3N_4O$, calcd. 595.3, found 595.3.

Example 147: 3,6-Dimethyl-2-(4-{5-[(7S)-7-methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyridine

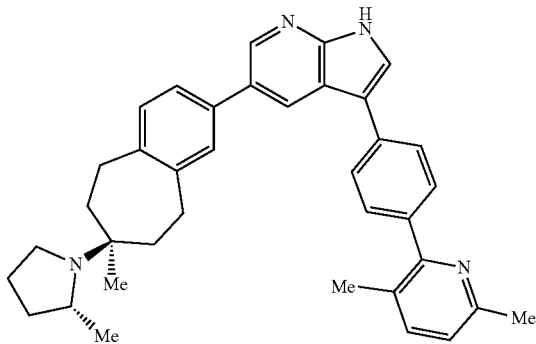 [SMILES: Cc1ccc(C)c(-c2ccc(-c3c[nH]c4ncc(-c5ccc6c(c5)CC[C@@](C)(N5CCC[C@H]5C)CC6)cc34)cc2)n1]

The title compound was prepared in a similar manner to example 18 from the appropriate starting materials. ¹H NMR (400 MHz, DMSO-d₆) δ 12.00 (d, J=2.6 Hz, 1H), 8.51 (d, J=2.0 Hz, 1H), 8.41 (d, J=2.1 Hz, 1H), 7.95 (d, J=2.6 Hz, 1H), 7.86-7.81 (m, 2H), 7.58 (dd, J=7.9, 6.0 Hz, 3H), 7.47 (s, 1H), 7.42 (d, J=8.1 Hz, 1H), 7.16 (d, J=7.7 Hz, 1H), 7.12 (d, J=7.8 Hz, 1H), 3.24-3.08 (m, 3H), 2.79 (t, J=7.4 Hz, 1H), 2.68-2.52 (m, 3H), 2.45 (s, 3H), 2.32 (s, 3H), 1.90-1.59 (m, 5H), 1.43-1.24 (m, 3H), 1.00 (d, J=6.3 Hz, 3H), 0.90 (d, J=5.9 Hz, 3H). ESI MS [M+H]⁺ for $C_{37}H_{41}N_4$, calcd. 541.3, found 541.3.

Example 148: 3,6-Dimethyl-2-(4-{5-[(7S)-7-(pyrrolidin-1-yl)-6,7,8,9-tetrahydro-5H-benzo[7]annulen-2-yl]-1H-pyrrolo[2,3-b]pyridin-3-yl}phenyl)pyridine

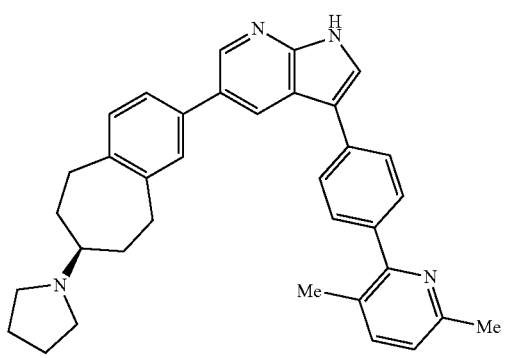 [SMILES: Cc1ccc(C)c(-c2ccc(-c3c[nH]c4ncc(-c5ccc6c(c5)CC[C@@H](N5CCCC5)CC6)cc34)cc2)n1]

The title compound was prepared in a similar manner to example 1 from the appropriate starting materials. ¹H NMR (400 MHz, DMSO-d₆) δ 12.01 (s, 1H), 8.52 (d, J=2.1 Hz, 1H), 8.43 (d, J=2.1 Hz, 1H), 7.96 (d, J=2.6 Hz, 1H), 7.89-7.82 (m, 2H), 7.59 (dd, J=7.9, 5.9 Hz, 3H), 7.51 (s, 1H), 7.44 (s, 1H), 7.19 (d, J=7.6 Hz, 1H), 7.12 (d, J=7.8 Hz, 1H), 3.18-2.79 (m, 5H), 2.73-2.49 (m, 4H), 2.45 (s, 3H), 2.32 (s, 3H), 1.99-1.43 (m, 5H), 1.34-1.11 (m, 3H). ESI MS [M+H]⁺ for $C_{35}H_{37}N_4$, calcd. 513.3, found 513.3.

Example 149: 6-[(7S)-2-(3-{4-[3-(Oxan-4-yl)pyridin-2-yl]phenyl}-1H-pyrazolo[3,4-b]pyridin-5-yl)-6,7,8,9-tetrahydro-5H-benzo[7]annulen-7-yl]-3-oxa-6-azabicyclo[3.1.1]heptane

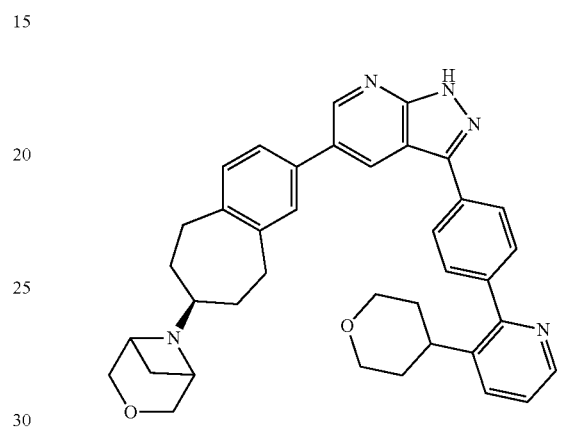

The title compound (trifluoroacetate salt) was prepared in a similar manner to example 5 from the appropriate starting materials. ¹H NMR (400 MHz, DMSO-d₆) δ 9.88-9.76 (m, 1H), 8.88 (t, J=2.0 Hz, 1H), 8.74 (d, J=2.0 Hz, 1H), 8.52 (d, J=4.7 Hz, 1H), 8.25-8.19 (m, 2H), 8.03-7.96 (m, 2H), 7.73-7.58 (m, 4H), 7.49-7.42 (m, 1H), 7.30 (t, J=8.7 Hz, 1H), 4.60 (d, J=6.4 Hz, 1H), 4.51 (s, 2H), 4.38 (d, J=13.0 Hz, 1H), 4.16 (q, J=12.2 Hz, 2H), 4.00 (d, J=13.0 Hz, 2H), 3.90-3.83 (m, 2H), 3.23 (t, J=11.7 Hz, 2H), 3.07-2.88 (m, 2H), 2.86-2.67 (m, 2H), 2.31-2.28 (m, 1H), 2.20-1.99 (m, 3H), 1.84-1.69 (m, 2H), 1.66-1.56 (m, 2H), 1.26-1.02 (m, 2H). ESI MS [M+H]⁺ for $C_{38}H_{40}N_5O_2$, calcd. 598.3, found 598.3.

Example 150: 6-[(7S)-2-[3-(4-{2H,3H,4H-Pyrido[4,3-b][1,4]oxazin-5-yl}phenyl)-1H-pyrazolo[3,4-b]pyridin-5-yl]-6,7,8,9-tetrahydro-5H-benzo[7]annulen-7-yl]-3-oxa-6-azabicyclo[3.1.1]heptane

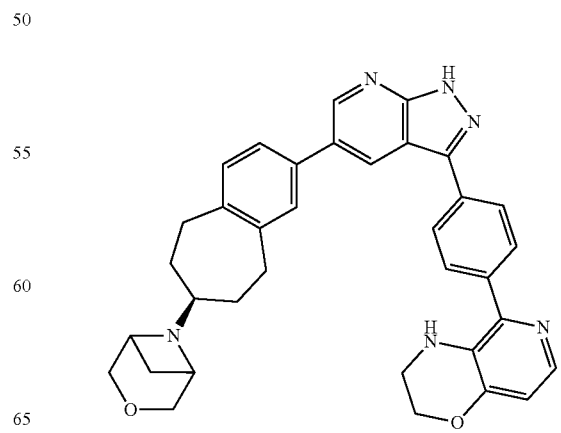

The title compound was prepared in a similar manner to example 2 from the appropriate starting materials. ¹H NMR (400 MHz, DMSO-d₆) δ 13.89 (s, 1H), 8.84 (d, J=2.0 Hz, 1H), 8.71-8.66 (m, 1H), 8.17 (d, J=8.3 Hz, 2H), 7.83 (d, J=8.3 Hz, 2H), 7.79 (d, J=5.2 Hz, 1H), 7.58 (s, 1H), 7.52 (d, J=7.7 Hz, 1H), 7.23 (d, J=7.8 Hz, 1H), 6.69 (dd, J=5.3, 0.6 Hz, 1H), 5.53 (s, 1H), 4.24 (t, J=4.3 Hz, 2H), 4.13 (d, J=10.8 Hz, 2H), 3.53 (dd, J=18.7, 8.2 Hz, 4H), 3.29-3.24 (m, 2H), 3.19-3.10 (m, 1H), 3.05-2.86 (m, 2H), 2.85-2.70 (m, 2H), 2.37-2.28 (m, 1H), 1.90-1.74 (m, 2H), 1.69-1.62 (m, 1H), 1.27-1.08 (m, 2H). ESI MS [M+H]⁺ for $C_{35}H_{35}N_6O_2$, calcd. 571.3, found 571.3.

Example 151: 6-[(7S)-2-[3-(4-{4-Methyl-2H,3H,4H-pyrido[4,3-b][1,4]oxazin-5-yl}phenyl)-1H-pyrazolo[3,4-b]pyridin-5-yl]-6,7,8,9-tetrahydro-5H-benzo[7]annulen-7-yl]-3-oxa-6-azabicyclo[3.1.1]heptane

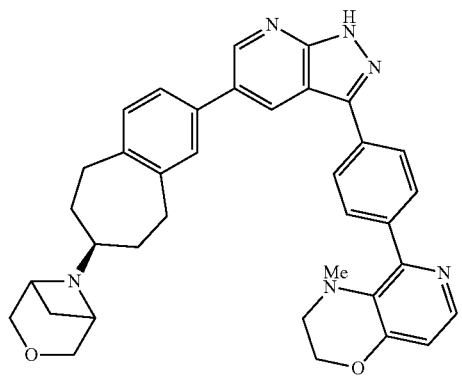 [SMILES: CN1CCOc2ccnc(-c3ccc(-c4n[nH]c5ncc(-c6ccc7c(c6)CC[C@@H](N6C8COCC6C8)CC7)cc45)cc3)c21]

The title compound was prepared in a similar manner to example 2 from the appropriate starting materials. ¹H NMR (400 MHz, DMSO-d₆) δ 13.89 (s, 1H), 8.84 (d, J=2.0 Hz, 1H), 8.71 (d, J=2.0 Hz, 1H), 8.21-8.13 (m, 2H), 8.09-7.99 (m, 3H), 7.60 (s, 1H), 7.57-7.50 (m, 1H), 7.23 (d, J=7.8 Hz, 1H), 6.80 (d, J=5.3 Hz, 1H), 4.22-4.17 (m, 2H), 4.13 (d, J=10.6 Hz, 2H), 3.60-3.47 (m, 4H), 3.22-3.11 (m, 3H), 3.06-2.85 (m, 2H), 2.84-2.68 (m, 2H), 2.39 (s, 3H), 2.36-2.25 (m, 1H), 1.92-1.77 (m, 2H), 1.65 (d, J=7.8 Hz, 1H), 1.27-1.06 (m, 2H). ESI MS [M+H]⁺ for $C_{36}H_{37}N_6O_2$, calcd. 585.3, found 585.3.

Example 152: 6-[(7S)-2-{3-[4-(3,4-Dimethoxypyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

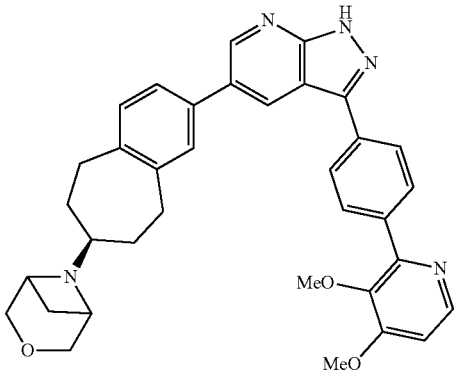 [SMILES: COc1ccnc(-c2ccc(-c3n[nH]c4ncc(-c5ccc6c(c5)CC[C@@H](N5C7COCC5C7)CC6)cc34)cc2)c1OC]

The title compound was prepared in a similar manner to example 2 from the appropriate starting materials. ¹H NMR (400 MHz, DMSO-d₆) δ 13.90 (s, 1H), 8.84 (d, J=2.1 Hz, 1H), 8.71 (d, J=2.1 Hz, 1H), 8.31 (d, J=5.4 Hz, 1H), 8.20-8.15 (m, 2H), 8.06-7.97 (m, 2H), 7.60 (d, J=2.0 Hz, 1H), 7.53 (dd, J=7.8, 2.0 Hz, 1H), 7.23 (d, J=7.8 Hz, 1H), 7.12 (d, J=5.5 Hz, 1H), 4.13 (d, J=10.7 Hz, 2H), 3.91 (s, 3H), 3.66 (s, 3H), 3.53 (dd, J=18.2, 8.3 Hz, 4H), 3.19-3.07 (m, 1H), 3.04-2.86 (m, 2H), 2.77 (q, J=14.2 Hz, 2H), 2.37-2.28 (m, 1H), 1.91-1.76 (m, 2H), 1.65 (d, J=7.8 Hz, 1H), 1.27-1.03 (m, 2H). ESI MS [M+H]⁺ for $C_{35}H_{36}N_5O_3$, calcd. 574.3, found 574.3.

Example 153: 6-[(7S)-2-{3-[2-Fluoro-4-(3-methylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

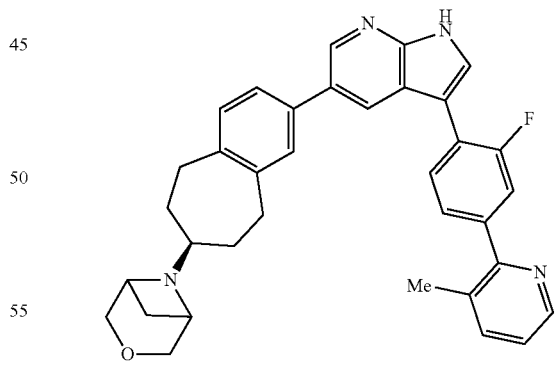

The title compound was prepared in a similar manner to example 1 from the appropriate starting materials. ¹H NMR (400 MHz, DMSO-d₆) δ 12.15 (d, J=2.6 Hz, 1H), 8.54 (d, J=2.1 Hz, 1H), 8.49 (ddd, J=4.7, 1.7, 0.7 Hz, 1H), 8.27 (s, 1H), 7.90-7.85 (m, 2H), 7.73 (ddd, J=7.6, 1.7, 0.8 Hz, 1H), 7.54-7.46 (m, 3H), 7.45-7.39 (m, 1H), 7.30 (dd, J=7.7, 4.7 Hz, 1H), 7.19 (d, J=7.8 Hz, 1H), 4.17-4.07 (m, 2H), 3.61-3.43 (m, 4H), 3.17-3.07 (m, 1H), 3.02-2.82 (m, 2H), 2.81-2.67 (m, 2H), 2.40 (s, 3H), 2.37-2.28 (m, 1H), 1.90-1.74 (m, 2H), 1.64 (d, J=8.0 Hz, 1H), 1.27-1.02 (m, 2H). ESI MS [M+H]+ for C35H34FN4O, calcd. 545.3, found 545.3.

Example 154: 6-[(7S)-2-{3-[4-(Pyridin-2-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

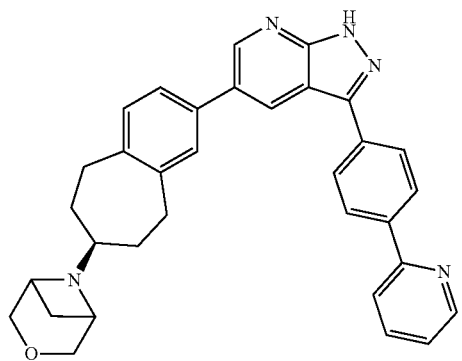 [SMILES: c1ccc(-c2ccc(-c3n[nH]c4ncc(-c5ccc6c(c5)CC[C@@H](N5C7COCC5C7)CC6)cc34)cc2)nc1]

The title compound was prepared in a similar manner to example 2 from the appropriate starting materials. 1H NMR (400 MHz, Chloroform-d) δ 12.16 (s, 1H), 8.84 (d, J=2.0 Hz, 1H), 8.75-8.68 (m, 1H), 8.51 (d, J=2.0 Hz, 1H), 8.21-8.08 (m, 4H), 7.84-7.72 (m, 2H), 7.38 (d, J=6.5 Hz, 2H), 7.29-7.20 (m, 2H), 4.30 (d, J=10.7 Hz, 2H), 3.73 (d, J=10.7 Hz, 2H), 3.65 (d, J=6.1 Hz, 2H), 3.31-3.21 (m, 1H), 3.05-2.92 (m, 2H), 2.85 (q, J=13.5, 12.8 Hz, 2H), 2.57 (q, J=6.7 Hz, 1H), 2.00-1.89 (m, 2H), 1.84 (d, J=8.3 Hz, 1H), 1.36 (q, J=11.5 Hz, 2H). ESI MS [M+H]+ for C33H32N5O, calcd. 514.3, found 514.3.

Example 155: 6-[(7S)-2-{3-[4-(Pyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

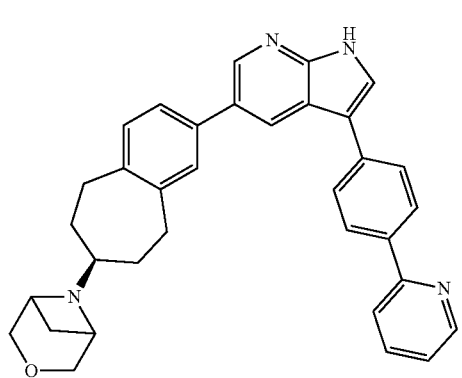 [SMILES: c1ccc(-c2ccc(-c3c[nH]c4ncc(-c5ccc6c(c5)CC[C@@H](N5C7COCC5C7)CC6)cc34)cc2)nc1]

The title compound was prepared in a similar manner to example 1 from the appropriate starting materials. 1H NMR (400 MHz, Chloroform-d) δ 10.09 (s, 1H), 8.74-8.67 (m, 1H), 8.60 (d, J=2.1 Hz, 1H), 8.42 (d, J=2.0 Hz, 1H), 8.14-8.06 (m, 2H), 7.83-7.71 (m, 4H), 7.62 (d, J=2.4 Hz, 1H), 7.42-7.35 (m, 2H), 7.27-7.17 (m, 2H), 4.29 (d, J=10.7 Hz, 2H), 3.71 (d, J 10.7 Hz, 2H), 3.63 (d, J=6.1 Hz, 2H), 3.29-3.19 (m, 1H), 2.97 (td, J=15.0, 7.9 Hz, 2H), 2.84 (q, J=13.1, 12.6 Hz, 2H), 2.54 (q, J=6.7 Hz, 1H), 1.98-1.90 (m, 2H), 1.83 (d, J=8.2 Hz, 1H), 1.40-1.27 (m, 2H). ESI MS [M+H]+ for C34H33N4O, calcd. 513.3, found 513.3.

Example 156: 2-(4-{5-[(7S)-7-Methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyridine

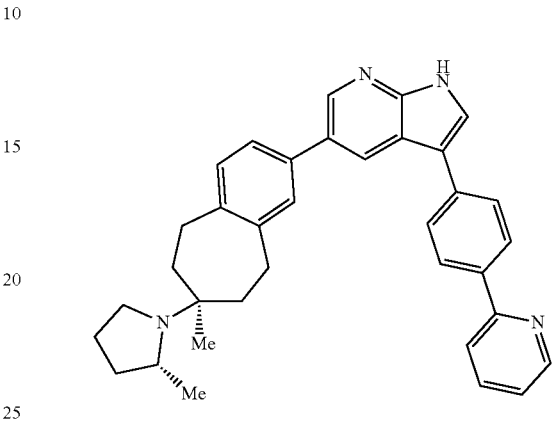

The title compound was prepared in a similar manner to example 1 from the appropriate starting materials. 1H NMR (400 MHz, Chloroform-d) δ 9.57 (s, 1H), 8.74-8.66 (m, 1H), 8.60 (d, J=2.0 Hz, 1H), 8.41 (d, J=2.0 Hz, 1H), 8.14-8.06 (m, 2H), 7.82-7.71 (m, 4H), 7.61 (d, J=2.3 Hz, 1H), 7.37 (s, 2H), 7.26-7.17 (m, 2H), 3.84 (s, 1H), 3.29 (m, 3H), 2.89 (s, 2H), 2.62 (m, 3H), 2.02-1.65 (m, 6H), 1.46 (s, 2H), 1.02 (m, 4H). ESI MS [M+H]+ for C35H37N4, calcd. 513.3, found 513.3.

Example 157: 6-[(7S)-2-{3-[4-(Pyridin-3-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

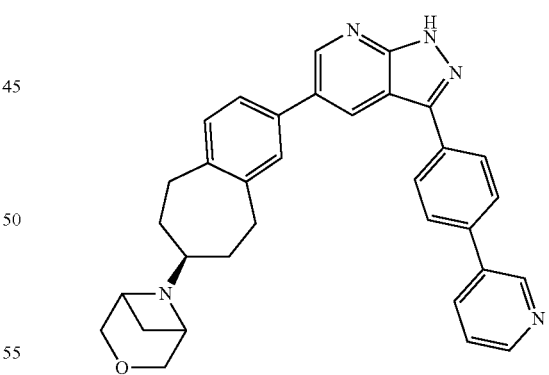

The title compound was prepared in a similar manner to example 2 from the appropriate starting materials. 1H NMR (400 MHz, Chloroform-d) δ 11.05 (s, 1H), 8.93 (s, 1H), 8.82 (d, J=2.0 Hz, 1H), 8.65-8.59 (m, 1H), 8.52-8.47 (m, 1H), 8.18-8.07 (m, 2H), 7.95 (ddd, J=7.9, 2.4, 1.6 Hz, 1H), 7.81-7.73 (m, 2H), 7.44-7.30 (m, 3H), 7.22 (s, 1H), 4.38 (d, J=12.0 Hz, 2H), 4.01 (bs, 1H), 3.47 (bs, 1H), 2.97 (m, 2H), 2.85 (m, 3H), 2.00 (bs, 2H), 1.62 (m, 3H), 1.24 (bs, 2H), 0.90-0.81 (m, 1H). ESI MS [M+H]+ for C33H32N5O, calcd. 514.3, found 514.3.

Example 158: 6-[(7S)-2-{3-[4-(Pyridin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

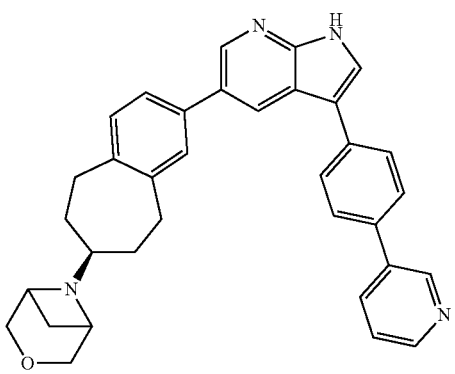 [SMILES: c1cncc(-c2ccc(-c3c[nH]c4ncc(-c5ccc6c(c5)CC[C@@H](N5C7COCC5C7)CC6)cc34)cc2)c1]

The title compound was prepared in a similar manner to example 1 from the appropriate starting materials. ¹H NMR (400 MHz, Chloroform-d) δ 10.81 (s, 1H), 8.91 (dd, J=2.3, 0.9 Hz, 1H), 8.64-8.56 (m, 2H), 8.41 (d, J=2.0 Hz, 1H), 7.92 (ddd, J=7.9, 2.4, 1.6 Hz, 1H), 7.85-7.75 (m, 2H), 7.75-7.60 (m, 3H), 7.41-7.36 (m, 3H), 7.21 (d, J=8.3 Hz, 1H), 4.29 (d, J=10.6 Hz, 2H), 3.72 (d, J=10.6 Hz, 2H), 3.63 (d, J=6.1 Hz, 2H), 3.47 (d, J=4.9 Hz, 1H), 3.24 (d, J=9.5 Hz, 1H), 3.04-2.91 (m, 2H), 2.84 (q, J=12.8, 12.4 Hz, 2H), 2.55 (q, J=6.8 Hz, 1H), 1.93 (t, J=10.8 Hz, 2H), 1.83 (d, J=8.2 Hz, 1H), 1.32 (s, 1H). ESI MS [M+H]⁺ for C₃₄H₃₃N₄O, calcd. 513.3, found 513.3.

Example 159: 6-[(7S)-2-{3-[3-Methyl-4-(pyridin-2-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

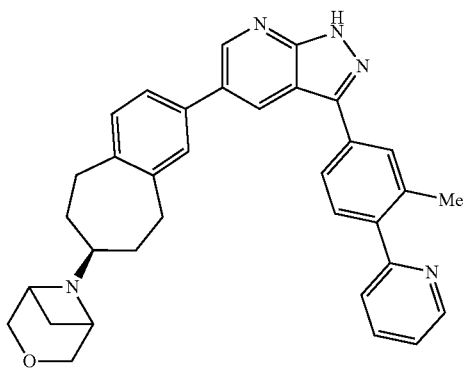 [SMILES: Cc1cc(-c2n[nH]c3ncc(-c4ccc5c(c4)CC[C@@H](N4C6COCC4C6)CC5)cc23)ccc1-c1ccccn1]

The title compound was prepared in a similar manner to example 2 from the appropriate starting materials. ¹H NMR (400 MHz, Chloroform-d) δ 12.50 (s, 1H), 8.84 (d, J=2.1 Hz, 1H), 8.72 (ddd, J=4.8, 1.9, 0.9 Hz, 1H), 8.49 (d, J=2.0 Hz, 1H), 7.95-7.85 (m, 2H), 7.76 (td, J=7.7, 1.8 Hz, 1H), 7.57 (d, J=7.9 Hz, 1H), 7.46 (dt, J=7.8, 1.1 Hz, 1H), 7.37 (d, J=6.3 Hz, 2H), 7.30-7.19 (m, 2H), 4.30 (d, J=10.7 Hz, 2H), 3.73 (d, J=10.7 Hz, 2H), 3.65 (d, J=6.1 Hz, 2H), 3.31-3.21 (m, 1H), 3.05-2.92 (m, 2H), 2.85 (q, J=13.5, 12.8 Hz, 2H), 2.57 (q, J=6.7 Hz, 1H), 2.48 (s, 3H), 2.00-1.89 (m, 2H), 1.84 (d, J=8.3 Hz, 1H), 1.36 (q, J=11.5 Hz, 2H). ESI MS [M+H]⁺ for C₃₄H₃₄N₅O, calcd. 528.3, found 528.3.

Example 160: 6-[(7S)-2-{3-[3-Methoxy-4-(pyridin-2-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

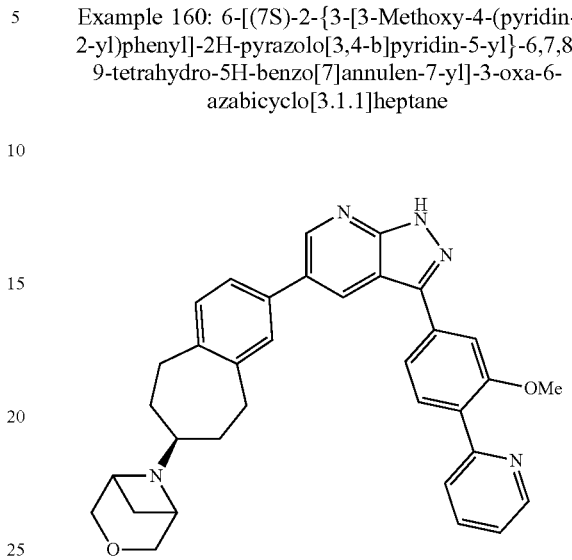

The title compound was prepared in a similar manner to example 2 from the appropriate starting materials. ¹H NMR (400 MHz, Chloroform-d) δ 13.18 (s, 1H), 8.84 (d, J=2.0 Hz, 1H), 8.72 (ddd, J=4.8, 1.9, 1.0 Hz, 1H), 8.48 (d, J=2.1 Hz, 1H), 8.00-7.93 (m, 1H), 7.90 (dt, J=8.0, 1.1 Hz, 1H), 7.75-7.64 (m, 3H), 7.40-7.32 (m, 2H), 7.27-7.17 (m, 2H), 4.30 (d, J=10.7 Hz, 2H), 3.69 (s, 3H), 3.73 (d, J=10.7 Hz, 2H), 3.65 (d, J=6.1 Hz, 2H), 3.31-3.21 (m, 1H), 3.05-2.92 (m, 2H), 2.85 (q, J=13.5, 12.8 Hz, 2H), 2.57 (q, J=6.7 Hz, 1H), 2.00-1.89 (m, 2H), 1.84 (d, J=8.3 Hz, 1H), 1.36 (q, J=11.5 Hz, 2H). ESI MS [M+H]⁺ for C₃₄H₃₄N₅O₂, calcd. 544.3, found 544.3.

Example 161: 6-[(7S)-2-{3-[3-Methoxy-4-(pyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

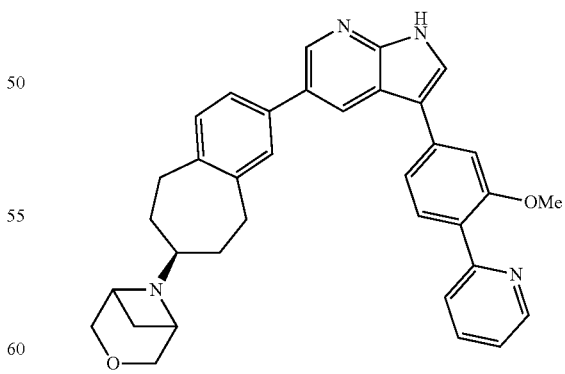

The title compound was prepared in a similar manner to example 1 from the appropriate starting materials. ¹H NMR (400 MHz, Chloroform-d) δ 11.58-11.52 (m, 1H), 8.72 (ddd, J=4.9, 1.9, 1.0 Hz, 1H), 8.62 (d, J=2.1 Hz, 1H), 8.40 (d, J=2.1 Hz, 1H), 7.93-7.84 (m, 2H), 7.70 (ddd, J=8.0, 7.5, 1.9

Hz, 1H), 7.60 (d, J=2.1 Hz, 1H), 7.43-7.34 (m, 3H), 7.27-7.15 (m, 3H), 4.29 (d, J=10.7 Hz, 2H), 3.89 (s, 3H), 3.72 (d, J=10.8 Hz, 2H), 3.64 (d, J=6.1 Hz, 2H), 3.25 (dd, J=11.3, 7.8 Hz, 1H), 2.96 (dt, J=17.0, 8.7 Hz, 2H), 2.89-2.76 (m, 2H), 2.56 (q, J=6.7 Hz, 1H), 1.93 (t, J=10.6 Hz, 2H), 1.83 (d, J=8.3 Hz, 1H), 1.33 (d, J=9.7 Hz, 2H). ESI MS [M+H]$^+$ for $C_{35}H_{35}N_4O_2$, calcd. 543.3, found 543.3.

Example 162: 6-[(7S)-2-{3-[4-(6-Methoxypyridin-2-yl)phenyl]-2H-pyrazolo[3,4-b]pyridin-5-yl}-6,7,8,9-tetrahydro-5H-benzo[7]annulen-7-yl]-3-oxa-6-azabicyclo[3.1.1]heptane

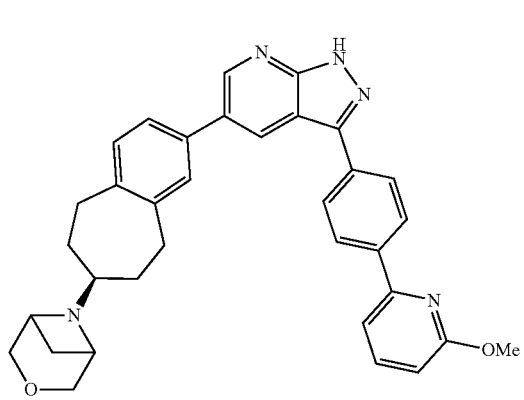 [SMILES: COc1cccc(-c2ccc(-c3n[nH]c4ncc(-c5ccc6c(c5)CC[C@@H](N5C7COCC5C7)CC6)cc34)cc2)n1]

The title compound was prepared in a similar manner to example 2 from the appropriate starting materials. $^1$H NMR (400 MHz, Chloroform-d) δ 10.86 (s, 1H), 8.81 (d, J=2.0 Hz, 1H), 8.50 (dd, J=7.4, 2.0 Hz, 1H), 8.29-8.19 (m, 2H), 8.14-8.04 (m, 2H), 7.65 (dd, J=8.2, 7.4 Hz, 1H), 7.44-7.35 (m, 3H), 7.23 (d, J=7.6 Hz, 1H), 6.71 (dd, J=8.2, 0.6 Hz, 1H), 4.36 (d, J=11.7 Hz, 2H), 4.06 (s, 3H), 3.94 (m, 2H), 3.47 (d, J=5.5 Hz, 2H), 3.06-2.93 (m, 3H), 2.84 (q, J=11.7 Hz, 3H), 1.99 (m, 2H), 1.24 (m, 3H). ESI MS [M+H]$^+$ for $C_{34}H_{34}N_5O_2$, calcd. 544.3, found 544.3.

Example 163: 3-Methyl-2-(4-{5-[(7S)-7-methyl-7-[(2R)-2-methylpyrrolidin-1-yl]-6,7,8,9-tetrahydro-5H-benzo[7]annulen-2-yl]-2H-pyrazolo[3,4-b]pyridin-3-yl}phenyl)pyridine

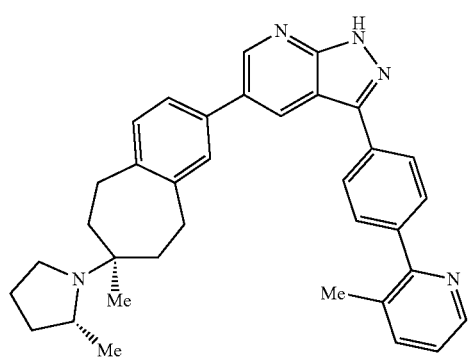 [SMILES: Cc1cccnc1-c1ccc(-c2n[nH]c3ncc(-c4ccc5c(c4)CC[C@@](C)(N4CCC[C@H]4C)CC5)cc23)cc1]

The title compound was prepared in a similar manner to example 2 from the appropriate starting materials. $^1$H NMR (400 MHz, Chloroform-d) δ 12.68 (s, 1H), 8.91 (d, J=2.0 Hz, 1H), 8.56 (ddd, J=4.8, 1.6, 0.7 Hz, 1H), 8.52 (d, J=2.1 Hz, 1H), 8.14-8.06 (m, 2H), 7.76-7.68 (m, 2H), 7.61 (ddt, J=7.7, 1.7, 0.7 Hz, 1H), 7.37 (dq, J=4.8, 2.0 Hz, 2H), 7.25-7.16 (m, 2H), 3.23 (bs, 2H), 2.91 (bs, 1H), 2.73-2.46 (m, 3H), 2.43 (s, 3H), 1.90 (m, 4H), 1.77-1.61 (m, 3H), 1.54 (bs, 3H), 1.03 (m, 5H). ESI MS [M+H]$^+$ for $C_{35}H_{38}N_5$, calcd. 528.3, found 528.3.

Example 164: 6-[(7S)-2-{3-[4-(3-Methoxypyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

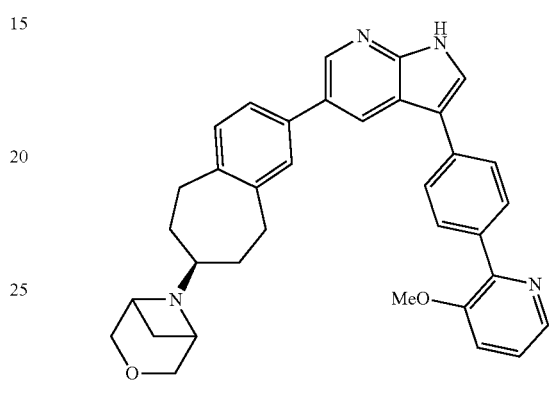

The title compound was prepared in a similar manner to example 1 from the appropriate starting materials. $^1$H NMR (400 MHz, Chloroform-d) δ 10.08 (d, J=2.4 Hz, 1H), 8.60 (d, J=2.0 Hz, 1H), 8.44 (d, J=2.0 Hz, 1H), 8.33 (dd, J=4.6, 1.4 Hz, 1H), 8.07-7.99 (m, 2H), 7.79-7.71 (m, 2H), 7.59 (d, J=2.4 Hz, 1H), 7.39 (dq, J=3.8, 2.0 Hz, 2H), 7.30 (dd, J=8.4, 1.4 Hz, 1H), 7.27-7.17 (m, 2H), 4.29 (d, J=10.7 Hz, 2H), 3.90 (s, 3H), 3.75-3.67 (m, 2H), 3.63 (d, J=6.1 Hz, 2H), 3.29-3.19 (m, 1H), 2.98 (m, 2H), 2.83 (q, J=13.7, 13.3 Hz, 2H), 2.62-2.49 (m, 1H), 1.92 (d, J=8.3 Hz, 2H), 1.83 (d, J=8.2 Hz, 1H), 1.32 (m, 2H). ESI MS [M+H]$^+$ for $C_{35}H_{35}N_4O_2$, calcd. 543.3, found 543.3.

Example 165: N,N-Dimethyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}phenyl)pyridine-3-carboxamide

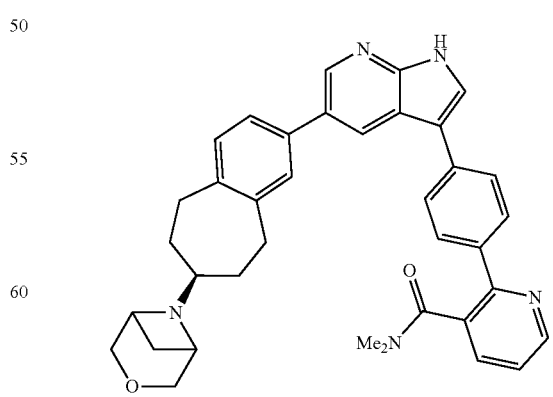

The title compound was prepared in a similar manner to example 1 from the appropriate starting materials. $^1$H NMR (400 MHz, Chloroform-d) δ 10.90 (s, 1H), 8.74 (dd, J=4.8, 1.8 Hz, 1H), 8.58 (s, 1H), 8.41 (d, J=1.6 Hz, 1H), 7.87-7.72 (m, 4H), 7.64 (s, 1H), 7.42-7.34 (m, 2H), 7.31 (dd, J=7.7, 4.8 Hz, 1H), 7.25-7.14 (m, 2H), 4.34 (d, J=11.4 Hz, 2H), 3.97 (bs, 2H), 3.86 (d, J=11.4 Hz, 2H), 3.45 (s, 3H), 3.33 (d, J=10.7 Hz, 1H), 2.96 (s, 3H), 2.93-2.75 (m, 5H), 2.04-1.87 (m, 3H), 1.58-1.39 (m, 2H). ESI MS [M+H]$^+$ for $C_{37}H_{38}N_5O_2$, calcd. 584.3, found 584.3.

Example 166: 6-[(7S)-2-{3-[4-(3-Methoxypyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

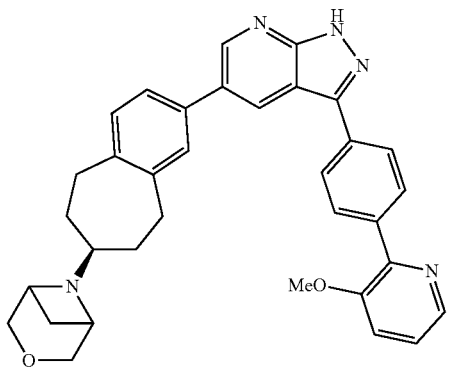

The title compound was prepared in a similar manner to example 2 from the appropriate starting materials. $^1$H NMR (400 MHz, Chloroform-d) δ 12.33 (s, 1H), 8.85 (d, J=2.1 Hz, 1H), 8.52 (d, J=2.0 Hz, 1H), 8.33 (dd, J=4.6, 1.4 Hz, 1H), 8.14-8.04 (m, 4H), 7.41-7.35 (m, 2H), 7.31 (dd, J=8.4, 1.4 Hz, 1H), 7.28-7.19 (m, 2H), 4.30 (d, J=10.7 Hz, 2H), 3.89 (s, 3H), 3.73 (d, J=10.7 Hz, 2H), 3.65 (d, J=6.1 Hz, 2H), 3.25 (t, J=9.9 Hz, 1H), 3.03-2.78 (m, 4H), 2.56 (q, J=7.0 Hz, 1H), 1.98-1.91 (m, 2H), 1.84 (d, J=8.3 Hz, 1H), 1.37 (bs, 2H). ESI MS [M+H]$^+$ for $C_{34}H_{34}N_5O_2$, calcd. 544.3, found 544.3.

Example 167: N,N-Dimethyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridine-3-carboxamide

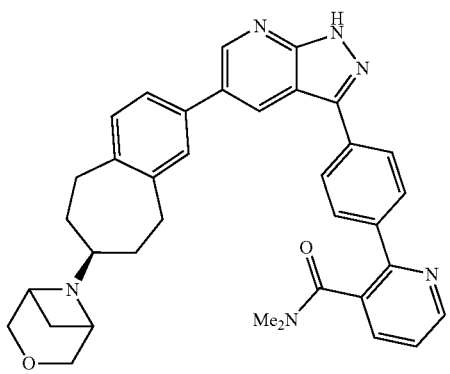 [SMILES: CN(C)C(=O)c1cccnc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. $^1$H NMR (400 MHz, Chloroform-d) δ 12.07 (s, 1H), 8.85 (d, J=2.0 Hz, 1H), 8.76 (dd, J=4.8, 1.7 Hz, 1H), 8.50 (d, J=2.0 Hz, 1H), 8.15-8.07 (m, 2H), 7.96-7.87 (m, 2H), 7.78 (dd, J=7.7, 1.7 Hz, 1H), 7.42-7.31 (m, 3H), 7.24 (d, J=8.3 Hz, 1H), 4.30 (d, J=10.7 Hz, 2H), 3.73 (d, J=10.7 Hz, 2H), 3.65 (d, J=6.1 Hz, 2H), 3.31-3.21 (m, 1H), 2.95 (m, 5H), 2.86 (m, 2H), 2.56 (q, J=6.8 Hz, 1H), 2.47 (s, 3H), 1.94 (bs, 2H), 1.84 (d, J=8.3 Hz, 1H), 1.35 (m, 2H). ESI MS [M+H]$^+$ for $C_{36}H_{37}N_6O_2$, calcd. 585.3, found 585.3.

Example 168: 6-[(7S)-2-{3-[1-(Pyridin-2-yl)-1H-pyrazol-4-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

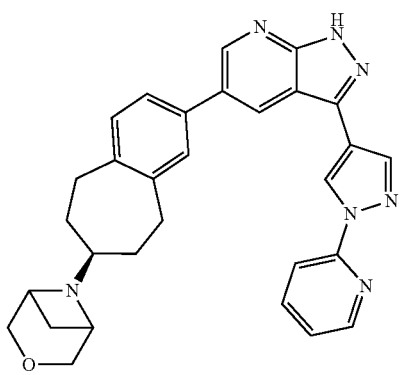 [SMILES: c1ccc(-n2cc(-c3n[nH]c4ncc(-c5ccc6c(c5)CC[C@@H](N5C7COCC5C7)CC6)cc34)cn2)nc1]

The title compound was prepared in a similar manner to example 2 from the appropriate starting materials. $^1$H NMR (400 MHz, Chloroform-d) δ 13.01 (s, 1H), 9.11 (d, J=0.9 Hz, 1H), 8.81 (d, J=2.0 Hz, 1H), 8.48-8.36 (m, 2H), 8.33 (d, J=0.8 Hz, 1H), 8.03 (dt, J=8.2, 1.0 Hz, 1H), 7.82 (ddd, J=8.3, 7.4, 1.8 Hz, 1H), 7.36 (dq, J=3.2, 2.0 Hz, 2H), 7.25-7.16 (m, 2H), 4.31 (d, J=10.7 Hz, 2H), 3.74 (d, J=10.7 Hz, 2H), 3.68 (d, J=6.1 Hz, 2H), 3.32-3.22 (m, 1H), 3.04-2.90 (m, 2H), 2.90-2.77 (m, 2H), 2.65-2.55 (m, 1H), 1.95 (t, J 10.1 Hz, 2H), 1.85 (d, J=8.3 Hz, 1H), 1.39 (q, J=11.3 Hz, 2H). ESI MS [M+H]$^+$ for $C_{30}H_{30}N_7O$, calcd. 504.2, found 504.2.

Example 169: 6-[(7S)-2-{3-[4-(4-Methyl-4H-1,2,4-triazol-3-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

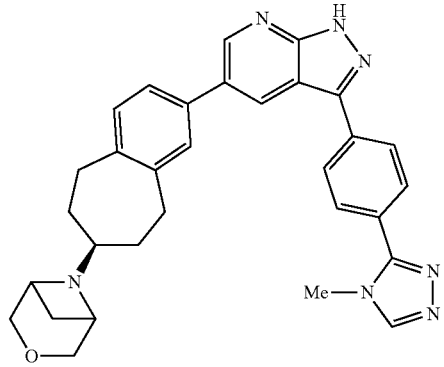 [SMILES: Cn1cnnc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. ¹H NMR (400 MHz, DMSO-d₆) δ 13.98 (s, 1H), 8.85 (d, J=2.1 Hz, 1H), 8.72 (d, J=2.1 Hz, 1H), 8.58 (s, 1H), 8.30-8.22 (m, 2H), 7.93-7.85 (m, 2H), 7.59 (d, J=2.0 Hz, 1H), 7.52 (dd, J=7.7, 2.0 Hz, 1H), 7.22 (d, J=7.8 Hz, 1H), 4.12 (d, J=10.6 Hz, 2H), 3.79 (s, 3H), 3.55 (d, J=10.6 Hz, 2H), 3.50 (d, J=6.1 Hz, 2H), 3.14 (s, 1H), 2.95 (m, 2H), 2.76 (m, 2H), 2.32 (q, J=6.8 Hz, 1H), 1.83 (bs, 2H), 1.64 (d, J=7.9 Hz, 1H), 1.16 (bs, 2H). ESI MS [M+H]⁺ for $C_{31}H_{32}N_7O$, calcd. 518.3, found 518.3.

Example 170: N,N-Dimethyl-2-(5-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}pyridin-2-yl)benzamide

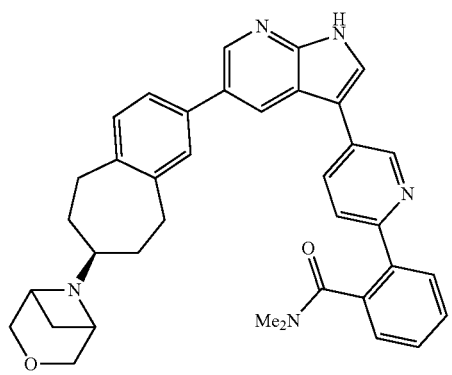 [SMILES: CN(C)C(=O)c1ccccc1-c1ccc(-c2c[nH]c3ncc(-c4ccc5c(c4)CC[C@@H](N4C6COCC4C6)CC5)cc23)cn1]

The title compound was prepared in a similar manner to example 1 from the appropriate starting materials. ¹H NMR (400 MHz, Chloroform-d) δ 10.82 (s, 1H), 9.00 (dd, J=2.3, 0.9 Hz, 1H), 8.60 (d, J=2.1 Hz, 1H), 8.35 (d, J=2.1 Hz, 1H), 7.97 (dd, J=8.2, 2.3 Hz, 1H), 7.80-7.76 (m, 1H), 7.67 (dd, J=8.2, 0.9 Hz, 1H), 7.63 (s, 1H), 7.52-7.34 (m, 5H), 7.18 (dd, J=7.6, 2.2 Hz, 1H), 4.35 (d, J=11.4 Hz, 2H), 3.98 (s, 2H), 3.86 (d, J=11.4 Hz, 2H), 3.46 (d, J=1.4 Hz, 1H), 3.36 (t, J=10.2 Hz, 1H), 3.00 (s, 3H), 2.99-2.76 (m, 4H), 2.64 (s, 3H), 1.93 (d, J=8.9 Hz, 3H), 1.57-1.46 (m, 2H). ESI MS [M+H]⁺ for $C_{37}H_{38}N_5O_2$, calcd. 584.3, found 584.3.

Example 171: 6-[(7S)-2-(3-{4-[3-(Pyrrolidine-1-carbonyl)pyridin-2-yl]phenyl}-1H-pyrrolo[2,3-b]pyridin-5-yl)-6,7,8,9-tetrahydro-5H-benzo[7]annulen-7-yl]-3-oxa-6-azabicyclo[3.1.1]heptane

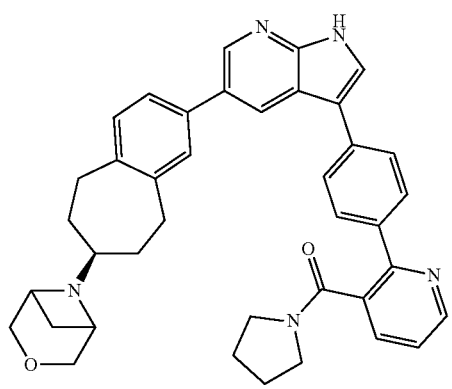 [SMILES: O=C(c1cccnc1-c1ccc(-c2c[nH]c3ncc(-c4ccc5c(c4)CC[C@@H](N4C6COCC4C6)CC5)cc23)cc1)N1CCCC1]

The title compound was prepared in a similar manner to example 1 from the appropriate starting materials. ¹H NMR (400 MHz, Chloroform-d) δ 10.91 (s, 1H), 8.74 (dd, J=4.8, 1.8 Hz, 1H), 8.61 (d, J=2.0 Hz, 1H), 8.41 (d, J=2.0 Hz, 1H), 7.93-7.84 (m, 2H), 7.77 (td, J=7.4, 7.0, 1.8 Hz, 3H), 7.65 (d, J=2.2 Hz, 1H), 7.39 (d, J=6.7 Hz, 2H), 7.31 (dd, J=7.7, 4.8 Hz, 1H), 7.24-7.17 (m, 1H), 4.37-4.29 (m, 2H), 3.82 (d, J=11.5 Hz, 4H), 3.49 (d, J=24.9 Hz, 3H), 3.39-3.29 (m, 1H), 3.07-2.84 (m, 3H), 2.82 (s, 2H), 2.79 (s, 1H), 1.97 (d, J=10.8 Hz, 2H), 1.90 (d, J=8.6 Hz, 1H), 1.74-1.66 (m, 2H), 1.55 (d, J=13.4 Hz, 4H). ESI MS [M+H]⁺ for $C_{39}H_{40}N_5O_2$, calcd. 610.3, found 610.3.

Example 172: 3-Methyl-2-(4-{5-[(7S)-7-methyl-7-[(2R)-2-methylpyrrolidin-1-yl]-6,7,8,9-tetrahydro-5H-benzo[7]annulen-2-yl]-1H-pyrrolo[2,3-b]pyridin-3-yl}phenyl)pyridine

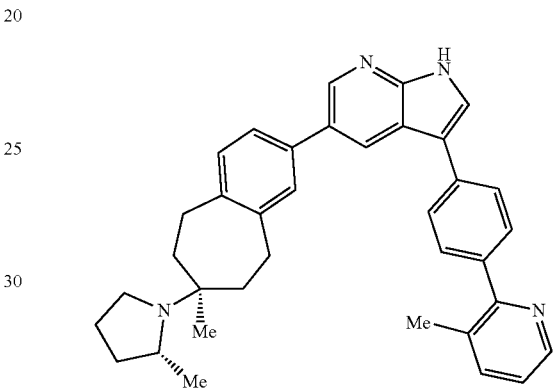

materials. ¹H NMR (400 MHz, Chloroform-d) δ 9.97 (s, 1H), 8.58 (d, J=2.0 Hz, 1H), 8.54 (ddd, J=4.8, 1.7, 0.7 Hz, 1H), 8.42 (d, J=2.1 Hz, 1H), 7.79-7.71 (m, 2H), 7.67-7.54 (m, 4H), 7.40-7.32 (m, 2H), 7.22-7.14 (m, 2H), 3.23 (bs, 2H), 2.91 (bs, 1H), 2.73-2.46 (m, 3H), 2.43 (s, 3H), 1.94-1.82 (m, 3H), 1.77-1.61 (m, 3H), 1.54 (bs, 4H), 1.07-1.00 (m, 5H). ESI MS [M+H]⁺ for $C_{36}H_{39}N_4$, calcd. 527.3, found 527.3.

Example 173: 3-Methyl-2-(4-{5-[(7S)-7-(pyrrolidin-1-yl)-6,7,8,9-tetrahydro-5H-benzo[7]annulen-2-yl]-1H-pyrrolo[2,3-b]pyridin-3-yl}phenyl)pyridine

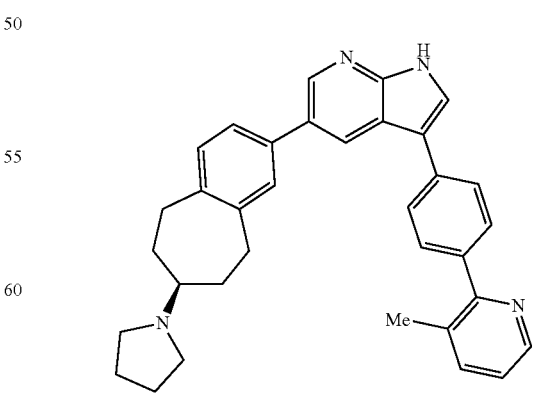

The title compound was prepared in a similar manner to example 1 from the appropriate starting materials. ¹H NMR (400 MHz, Chloroform-d) δ 10.37 (s, 1H), 8.58 (d, J=2.0 Hz, 1H), 8.53 (ddd, J=4.8, 1.7, 0.7 Hz, 1H), 8.42 (d, J=2.1 Hz, 1H), 7.78-7.70 (m, 2H), 7.66-7.54 (m, 4H), 7.37 (d, J=6.6 Hz, 2H), 7.23-7.14 (m, 2H), 3.07-2.93 (m, 2H), 2.80-2.69 (m, 2H), 2.66-2.60 (m, 4H), 2.57-2.52 (m, 1H), 2.43 (s, 3H), 2.14 (d, J=7.2 Hz, 2H), 1.79-1.75 (m, 4H), 1.59-1.56 (m, 2H). ESI MS [M+H]$^+$ for $C_{34}H_{35}N_4$, calcd. 499.3, found 499.5.

Example 174: 6-[(7S)-2-{3-[4-(5-Methylpyrimidin-4-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

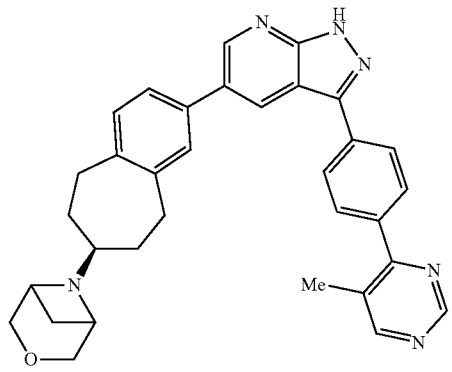

The title compound was prepared in a similar manner to example 2 from the appropriate starting materials. $^1$H NMR (400 MHz, Chloroform-d) δ 13.04-12.99 (m, 1H), 9.15 (t, J=0.5 Hz, 1H), 8.85 (d, J=2.1 Hz, 1H), 8.64 (d, J=0.8 Hz, 1H), 8.50 (d, J=2.0 Hz, 1H), 8.17-8.09 (m, 2H), 7.84-7.76 (m, 2H), 7.38 (d, J=6.7 Hz, 2H), 7.27-7.19 (m, 1H), 4.31 (d, J=10.7 Hz, 2H), 3.74 (d, J=10.7 Hz, 2H), 3.67 (d, J=6.1 Hz, 2H), 3.32-3.22 (m, 1H), 2.96 (dd, J=14.5, 6.9 Hz, 2H), 2.86 (q, J=12.0 Hz, 2H), 2.64-2.54 (m, 1H), 2.45 (t, J=0.7 Hz, 3H), 1.94 (d, J=9.9 Hz, 2H), 1.85 (d, J=8.3 Hz, 1H), 1.38 (q, J=11.3 Hz, 2H). ESI MS [M+H]$^+$ for $C_{33}H_{33}N_6O$, calcd. 529.3, found 529.3.

Example 175: 6-[(7S)-2-{3-[4-(3-Methylpyrazin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

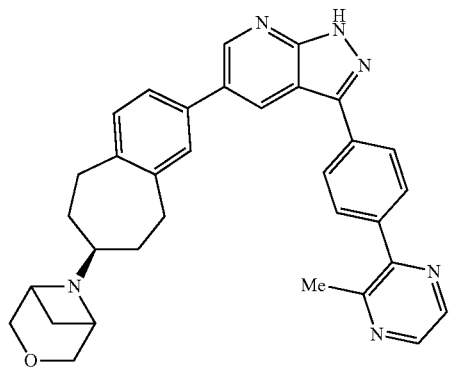

The title compound was prepared in a similar manner to example 2 from the appropriate starting materials. $^1$H NMR (400 MHz, Chloroform-d) δ 13.20 (s, 1H), 8.85 (d, J=2.0 Hz, 1H), 8.52-8.49 (m, 2H), 8.46 (d, J=2.5 Hz, 1H), 8.16-8.08 (m, 2H), 7.79-7.71 (m, 2H), 7.37 (d, J=6.5 Hz, 2H), 7.24-7.20 (m, 1H), 4.31 (d, J=10.6 Hz, 2H), 3.74 (d, J=10.7 Hz, 2H), 3.68 (d, J=6.1 Hz, 2H), 3.26 (dq, J=9.6, 5.2, 3.3 Hz, 1H), 2.97 (dt, J=16.8, 10.0 Hz, 2H), 2.85 (q, J=13.1, 12.2 Hz, 2H), 2.70 (d, J=0.6 Hz, 3H), 2.64-2.54 (m, 1H), 2.01-1.91 (m, 2H), 1.85 (d, J=8.3 Hz, 1H), 1.38 (q, J=11.4 Hz, 2H). ESI MS [M+H]$^+$ for $C_{33}H_{33}N_6O$, calcd. 529.3, found 529.3.

Example 176: 6-[(7S)-2-{3-[4-(4-Methylpyridazin-3-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

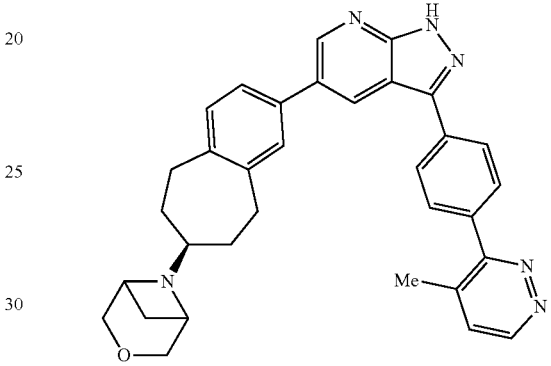

The title compound was prepared in a similar manner to example 2 from the appropriate starting materials. $^1$H NMR (400 MHz, Chloroform-d) δ 13.20 (s, 1H), 8.85 (d, J=2.0 Hz, 1H), 8.52-8.49 (m, 2H), 8.46 (d, J=2.5 Hz, 1H), 8.16-8.08 (m, 2H), 7.79-7.71 (m, 2H), 7.37 (d, J=6.5 Hz, 2H), 7.24-7.20 (m, 1H), 4.31 (d, J=10.6 Hz, 2H), 3.74 (d, J=10.7 Hz, 2H), 3.68 (d, J=6.1 Hz, 2H), 3.26 (dq, J=9.6, 5.2, 3.3 Hz, 1H), 2.97 (dt, J=16.8, 10.0 Hz, 2H), 2.85 (q, J=13.1, 12.2 Hz, 2H), 2.70 (d, J=0.6 Hz, 3H), 2.64-2.54 (m, 1H), 2.01-1.91 (m, 2H), 1.85 (d, J=8.3 Hz, 1H), 1.38 (q, J=11.4 Hz, 2H). ESI MS [M+H]$^+$ for $C_{33}H_{33}N_6O$, calcd. 529.3, found 529.3.

Example 177: 1-[2-(4-{5-[(7S)-7-{3-Oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]pyrrolidin-2-one

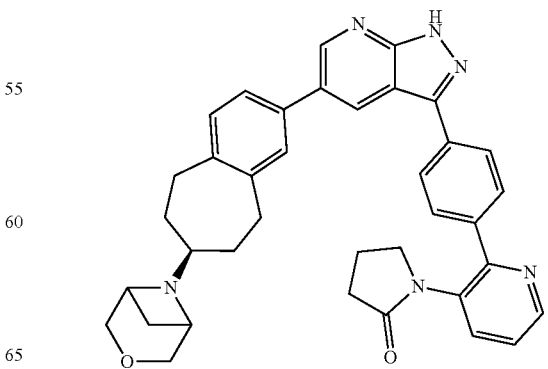

The title compound was prepared in a similar manner to example 2 from the appropriate starting materials. ¹H NMR (400 MHz, Chloroform-d) δ 11.99 (s, 1H), 8.85 (d, J=2.0 Hz, 1H), 8.67 (dd, J=4.7, 1.6 Hz, 1H), 8.50 (d, J=2.1 Hz, 1H), 8.14-8.06 (m, 2H), 7.82-7.70 (m, 3H), 7.42-7.32 (m, 3H), 7.23 (s, 1H), 4.30 (d, J=10.7 Hz, 2H), 3.73 (d, J=10.7 Hz, 2H), 3.65 (d, J=6.1 Hz, 2H), 3.35 (t, J=7.0 Hz, 2H), 3.31-3.21 (m, 1H), 3.06-2.78 (m, 4H), 2.54 (dt, J=26.5, 7.4 Hz, 3H), 1.99 (p, J=9.1, 8.2 Hz, 4H), 1.84 (d, J=8.3 Hz, 1H), 1.35 (q, J=11.7 Hz, 2H). ESI MS [M+H]⁺ for $C_{37}H_{37}N_6O_2$, calcd. 597.3, found 597.3.

Example 178: 6-[(7S)-2-{3-[4-(3-Cyclopropylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

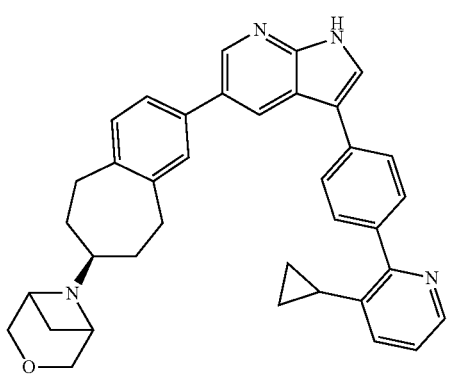 [SMILES: c1cnc(-c2ccc(-c3c[nH]c4ncc(-c5ccc6c(c5)CC[C@@H](N5C7COCC5C7)CC6)cc34)cc2)c(C2CC2)c1]

The title compound was prepared in a similar manner to example 1 from the appropriate starting materials. ¹H NMR (400 MHz, Chloroform-d) δ 10.61 (s, 1H), 8.62 (d, J=2.0 Hz, 1H), 8.51 (dd, J=4.7, 1.7 Hz, 1H), 8.44 (d, J=2.0 Hz, 1H), 7.82-7.72 (m, 4H), 7.59 (d, J=2.4 Hz, 1H), 7.39 (dq, J=4.1, 2.0 Hz, 2H), 7.27 (dd, J=7.9, 1.7 Hz, 1H), 7.23-7.13 (m, 2H), 4.30 (d, J=10.7 Hz, 2H), 3.72 (d, J=10.7 Hz, 2H), 3.64 (d, J=6.1 Hz, 2H), 3.23 (q, J=9.1, 8.6 Hz, 1H), 2.98 (td, J=19.2, 16.8, 7.9 Hz, 2H), 2.84 (q, J=13.4 Hz, 2H), 2.55 (q, J=6.7 Hz, 1H), 2.18-2.05 (m, 1H), 1.92 (bs, 2H), 1.83 (d, J=8.2 Hz, 1H), 1.34 (q, J=11.3, 10.7 Hz, 2H), 1.03-0.93 (m, 2H), 0.82-0.68 (m, 2H). ESI MS [M+H]⁺ for $C_{37}H_{37}N_4O$, calcd. 553.3, found 553.3.

Example 179: 6-[(7S)-2-{3-[4-(3-Cyclopropylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

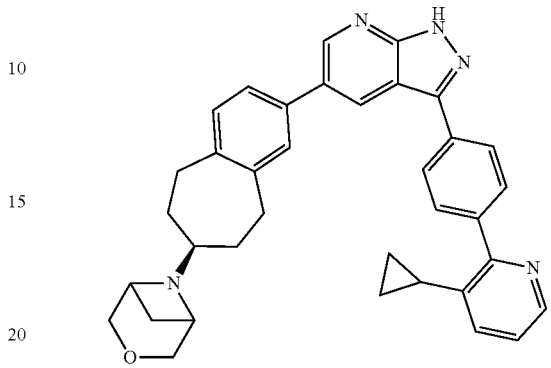

The title compound was prepared in a similar manner to example 2 from the appropriate starting materials. ¹H NMR (400 MHz, Chloroform-d) δ 13.04 (s, 1H), 8.86 (d, J=2.0 Hz, 1H), 8.54-8.48 (m, 2H), 8.13-8.05 (m, 2H), 7.89-7.81 (m, 2H), 7.38 (d, J=6.2 Hz, 2H), 7.28 (ddd, J=7.9, 1.7, 0.5 Hz, 1H), 7.26-7.14 (m, 2H), 4.31 (d, J=10.7 Hz, 2H), 3.73 (d, J=10.7 Hz, 2H), 3.67 (d, J=6.1 Hz, 2H), 3.32-3.22 (m, 1H), 3.04-2.91 (m, 2H), 2.85 (q, J 12.9, 12.4 Hz, 2H), 2.59 (q, J=6.7 Hz, 1H), 2.07 (tt, J=8.4, 5.3 Hz, 1H), 1.98 (bs, 2H), 1.85 (d, J=8.3 Hz, 1H), 1.38 (q, J=11.3 Hz, 2H), 1.02-0.90 (m, 2H), 0.80-0.66 (m, 2H). ESI MS [M+H]⁺ for $C_{36}H_{36}N_5O$, calcd. 554.3, found 554.3.

Example 180: 6-[(7S)-2-(3-{4-[3-(2-Methoxyethoxy)pyridin-2-yl]phenyl}-1H-pyrazolo[3,4-b]pyridin-5-yl)-6,7,8,9-tetrahydro-5H-benzo[7]annulen-7-yl]-3-oxa-6-azabicyclo[3.1.1]heptane

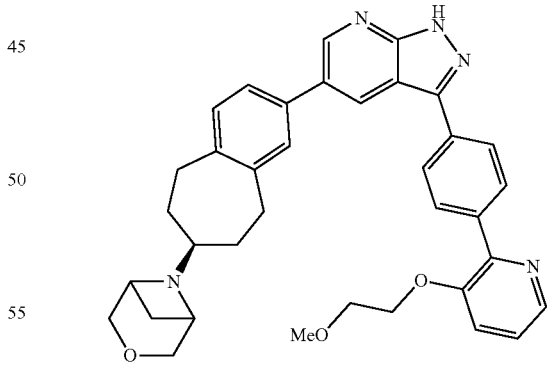

The title compound was prepared in a similar manner to example 2 from the appropriate starting materials. ¹H NMR (400 MHz, Chloroform-d) δ 11.93 (s, 1H), 8.85 (d, J=2.0 Hz, 1H), 8.52 (d, J=2.1 Hz, 1H), 8.35 (dd, J=4.6, 1.4 Hz, 1H), 8.21-8.14 (m, 2H), 8.10-8.04 (m, 2H), 7.41-7.36 (m, 2H), 7.33 (d, J=8.3, 1.4 Hz, 1H), 7.24-7.19 (m, 2H), 4.30 (d, J=10.7 Hz, 2H), 4.22-4.15 (m, 2H), 3.80-3.69 (m, 4H), 3.65 (d, J=6.1 Hz, 2H), 3.42 (s, 3H), 3.31-3.21 (m, 1H), 3.06-2.92 (m, 2H), 2.85 (q, J=13.4, 12.9 Hz, 2H), 2.56 (q, J=6.7 Hz, 1H), 1.94 (bs, 2H), 1.84 (d, J=8.3 Hz, 1H), 1.35 (q, J=11.6 Hz, 2H). ESI MS [M+H]+ for $C_{36}H_{38}N_5O_3$, calcd. 588.3, found 588.3.

Example 181: 6-[(7S)-2-{3-[4-(3-Ethoxypyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

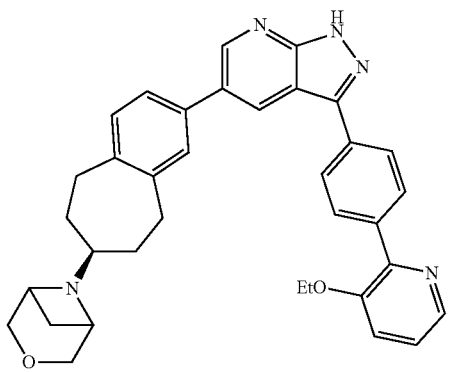

The title compound was prepared in a similar manner to example 2 from the appropriate starting materials. ¹H NMR (400 MHz, Chloroform-d) δ 13.30 (s, 1H), 8.85 (d, J=2.0 Hz, 1H), 8.53 (d, J=2.0 Hz, 1H), 8.32 (dd, J=4.6, 1.4 Hz, 1H), 8.20-8.12 (m, 2H), 8.12-8.04 (m, 2H), 7.38 (d, J=6.5 Hz, 2H), 7.31-7.16 (m, 3H), 4.31 (d, J=10.7 Hz, 2H), 4.09 (q, J=6.9 Hz, 2H), 3.73 (d, J=10.7 Hz, 2H), 3.70-3.64 (m, 2H), 3.31-3.22 (m, 1H), 3.04-2.90 (m, 2H), 2.84 (q, J=12.9, 12.3 Hz, 2H), 2.59 (q, J=6.7 Hz, 1H), 2.01-1.90 (m, 2H), 1.85 (d, J=8.3 Hz, 1H), 1.43 (q, J=8.4, 7.7 Hz, 5H). ESI MS [M+H]+ for $C_{35}H_{36}N_5O_2$, calcd. 588.3, found 588.3.

Example 182: 6-[(7S)-2-{3-[4-(3-Ethylpyridin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

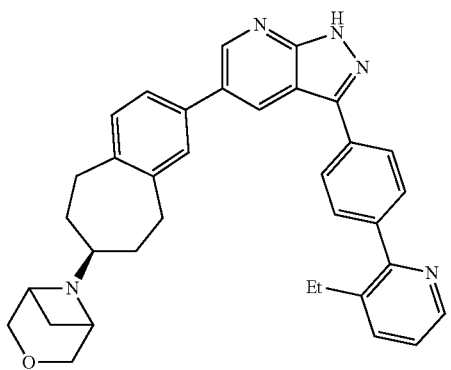

The title compound was prepared in a similar manner to example 2 from the appropriate starting materials. ¹H NMR (400 MHz, Chloroform-d) δ 13.53 (s, 1H), 8.85 (d, J=2.0 Hz, 1H), 8.57-8.47 (m, 2H), 8.11-8.03 (m, 2H), 7.68-7.60 (m, 3H), 7.40-7.33 (m, 2H), 7.21 (td, J=5.8, 2.7 Hz, 2H), 4.31 (d, J=10.7 Hz, 2H), 3.74 (d, J=10.7 Hz, 2H), 3.72-3.66 (m, 2H), 3.31-3.22 (m, 1H), 3.02-2.91 (m, 2H), 2.91-2.78 (m, 2H), 2.73 (q, J=7.5 Hz, 2H), 2.60 (q, J=6.7 Hz, 1H), 2.00-1.90 (m, 2H), 1.84 (d, J=8.3 Hz, 1H), 1.39 (q, J=11.5 Hz, 2H), 1.16 (t, J=7.5 Hz, 3H). ESI MS [M+H]+ for $C_{35}H_{36}N_5O$, calcd. 542.3, found 542.3.

Example 183: 6-[(7S)-2-{3-[4-(3-Ethylpyridin-2-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

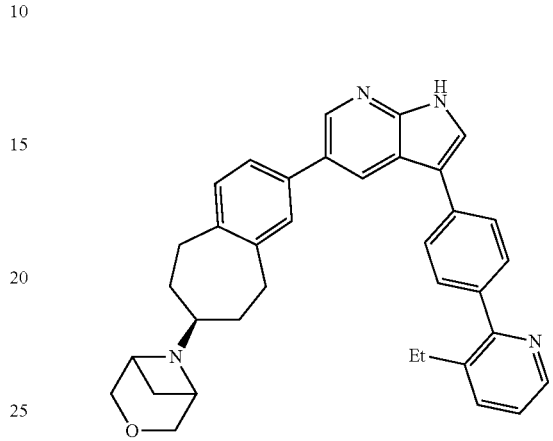

The title compound was prepared in a similar manner to example 1 from the appropriate starting materials. ¹H NMR (400 MHz, Chloroform-d) δ 11.43 (d, J=2.4 Hz, 1H), 8.62 (d, J=1.9 Hz, 1H), 8.55 (dd, J=4.7, 1.7 Hz, 1H), 8.43 (d, J=2.0 Hz, 1H), 7.78-7.70 (m, 2H), 7.67-7.62 (m, 1H), 7.60-7.54 (m, 3H), 7.39 (dq, J=4.0, 2.0 Hz, 2H), 7.27-7.17 (m, 2H), 4.30 (d, J=10.7 Hz, 2H), 3.71 (d, J=10.7 Hz, 2H), 3.70-3.61 (m, 2H), 3.29-3.19 (m, 1H), 2.92 (m, 4H), 2.76 (q, J=7.5 Hz, 2H), 2.60-2.50 (m, 1H), 1.96 (d, J=10.8 Hz, 2H), 1.83 (d, J=8.2 Hz, 1H), 1.34 (q, J=11.4, 10.5 Hz, 2H), 1.19 (t, J=7.5 Hz, 3H). ESI MS [M+H]+ for $C_{36}H_{37}N_4O$, calcd. 541.3, found 541.3.

Example 184: 6-[(7S)-2-{3-[5-(3-Methylpyridin-2-yl)pyrazin-2-yl]-1H-pyrrolo[2,3-b]pyridin-5-yl}-6,7,8,9-tetrahydro-5H-benzo[7]annulen-7-yl]-3-oxa-6-azabicyclo[3.1.1]heptane

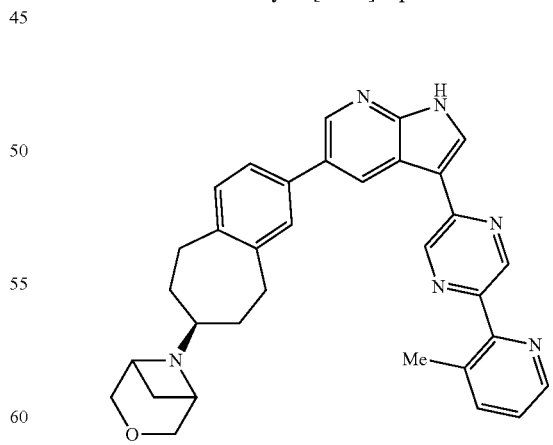

The title compound was prepared in a similar manner to example 17 from the appropriate starting materials. ¹H NMR (400 MHz, Chloroform-d) δ 8.83 (dd, J=2.4, 0.8 Hz, 1H), 8.57 (ddd, J=4.8, 1.7, 0.7 Hz, 1H), 8.36 (d, J=2.3 Hz, 1H), 8.09 (d, J=2.3 Hz, 1H), 8.01 (dd, J=8.4, 2.3 Hz, 1H), 7.88 (dd, J=8.5, 0.8 Hz, 1H), 7.63 (ddt, J=7.7, 1.7, 0.7 Hz, 1H), 7.32-7.18 (m, 2H), 7.15 (d, J=8.2 Hz, 1H), 6.81 (bs, 1H), 3.44-3.12 (m, 3H), 2.89 (dd, J=8.5, 6.7 Hz, 1H), 2.66 (td, J=9.5, 8.7, 5.6 Hz, 1H), 2.61-2.50 (m, 1H), 2.44 (s, 3H), 1.96-1.80 (m, 3H), 1.77-1.60 (m, 2H), 1.55-1.39 (m, 2H), 1.05 (d, J=6.3 Hz, 2H), 0.97 (bs, 2H). ESI MS [M+H]$^+$ for $C_{33}H_{33}N_6O$, calcd. 529.3, found 529.3.

Example 185: 6-[(7S)-2-{3-[4-(3,6-Dimethylpyridin-2-yl)-3-methylphenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

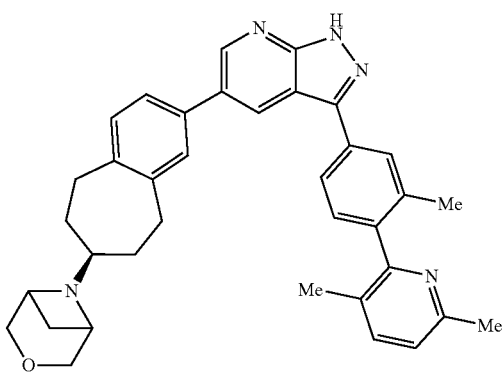 [SMILES: Cc1ccc(C)c(-c2ccc(-c3n[nH]c4ncc(-c5ccc6c(c5)CC[C@@H](N5C7COCC5C7)CC6)cc34)cc2C)n1]

The title compound was prepared in a similar manner to example 2 from the appropriate starting materials. $^1$H NMR (400 MHz, Chloroform-d) δ 12.28 (s, 1H), 8.84 (d, J=2.0 Hz, 1H), 8.48 (d, J=2.0 Hz, 1H), 7.89 (d, J=1.6 Hz, 1H), 7.85 (dd, J=7.7, 1.7 Hz, 1H), 7.48 (d, J=7.8 Hz, 1H), 7.37 (dq, J=3.4, 2.0 Hz, 2H), 7.33 (d, J=7.8 Hz, 1H), 7.23 (d, J=3.9 Hz, 1H), 7.07 (d, J=7.8 Hz, 1H), 4.30 (d, J=10.7 Hz, 2H), 3.73 (d, J=10.7 Hz, 2H), 3.65 (d, J=6.1 Hz, 2H), 3.31-3.21 (m, 1H), 2.98 (td, J=15.0, 7.8 Hz, 2H), 2.85 (q, J=13.2 Hz, 2H), 2.56 (s, 3H), 2.18 (s, 3H), 2.10 (s, 3H), 1.94 (bs, 2H), 1.84 (d, J=8.3 Hz, 2H), 1.35 (q, J=11.5 Hz, 2H). ESI MS [M+H]$^+$ for $C_{36}H_{38}N_5O$, calcd. 556.3, found 556.3.

Example 186: (3S)—N-[(7S)-2-{3-[4-(3-Methylpyridin-2-yl)phenyl]-1H-pyrrolo[2,3-b]pyridin-5-yl}-6,7,8,9-tetrahydro-5H-benzo[7]annulen-7-yl]oxan-3-amine

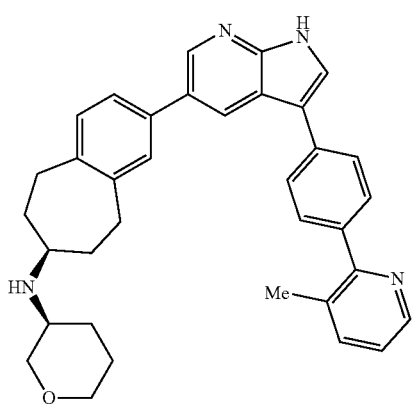 [SMILES: Cc1cccnc1-c1ccc(-c2c[nH]c3ncc(-c4ccc5c(c4)CC[C@@H](N[C@H]4CCCOC4)CC5)cc23)cc1]

The title compound was prepared in a similar manner to example 1 from the appropriate starting materials. $^1$H NMR (400 MHz, Chloroform-d) δ 11.39 (s, 1H), 8.61 (d, J=2.0 Hz, 1H), 8.56 (ddd, J=4.8, 1.7, 0.7 Hz, 1H), 8.43 (d, J=2.0 Hz, 1H), 7.78-7.70 (m, 2H), 7.65-7.61 (m, 2H), 7.58 (ddd, J=8.3, 1.5, 0.7 Hz, 2H), 7.39 (dq, J=4.7, 2.0 Hz, 2H), 7.22-7.15 (m, 2H), 3.91 (ddd, J=11.0, 4.0, 1.7 Hz, 1H), 3.79 (dt, J=11.0, 3.8 Hz, 1H), 3.44-3.36 (m, 1H), 3.17 (dd, J=11.0, 8.4 Hz, 1H), 2.98-2.70 (m, 6H), 2.43 (t, J=0.6 Hz, 3H), 2.18-2.01 (m, 2H), 1.99-1.90 (m, 1H), 1.72-1.57 (m, 2H), 1.41-1.28 (m, 3H). ESI MS [M+H]$^+$ for $C_{35}H_{37}N_4O$, calcd. 529.3, found 529.3.

Example 187: (4S)-5-[(7S)-2-{3-[4-(3-Methylpyridin-2-yl)phenyl]-1H-pyrrolo[2,3-b]pyridin-5-yl}-6,7,8,9-tetrahydro-5H-benzo[7]annulen-7-yl]-2-oxa-5-azabicyclo[2.2.1]heptane

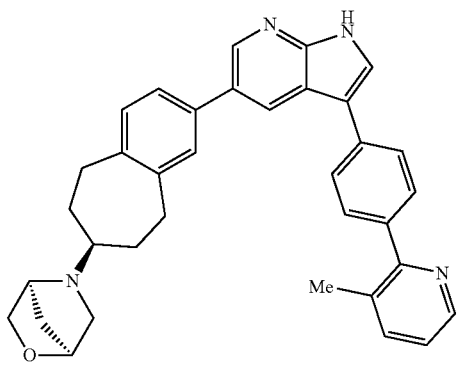 [SMILES: Cc1cccnc1-c1ccc(-c2c[nH]c3ncc(-c4ccc5c(c4)CC[C@@H](N4C[C@@H]6C[C@H]4CO6)CC5)cc23)cc1]

The title compound was prepared in a similar manner to example 1 from the appropriate starting materials. $^1$H NMR (400 MHz, Chloroform-d) δ 11.14 (s, 1H), 8.61 (d, J=2.0 Hz, 1H), 8.57-8.53 (m, 1H), 8.43 (d, J=2.0 Hz, 1H), 7.78-7.69 (m, 2H), 7.66-7.61 (m, 2H), 7.61-7.55 (m, 2H), 7.42-7.35 (m, 2H), 7.21-7.15 (m, 2H), 4.42 (t, J=1.9 Hz, 1H), 4.09 (d, J=7.8 Hz, 1H), 3.80 (s, 1H), 3.67 (dd, J=7.9, 1.6 Hz, 1H), 3.45 (s, 2H), 3.21-3.14 (m, 1H), 3.06 (s, 2H), 2.83 (s, 1H), 2.72 (s, 2H), 2.53 (d, J=9.9 Hz, 1H), 2.43 (s, 3H), 2.04-1.88 (m, 3H), 1.81-1.74 (m, 1H). ESI MS [M+H]$^+$ for $C_{35}H_{35}N_4O$, calcd. 527.3, found 527.3.

Example 188: 3,5-Dimethyl-2-(4-{5-[(7S)-7-methyl-7-[(2R)-2-methylpyrrolidin-1-yl]-6,7,8,9-tetrahydro-5H-benzo[7]annulen-2-yl]-1H-pyrazolo[3,4-b]pyridin-3-yl}phenyl)pyrazine

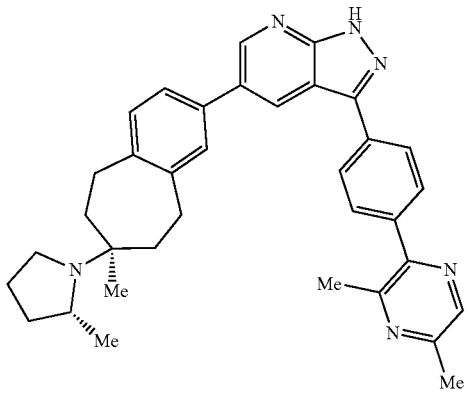 [SMILES: Cc1cnc(-c2ccc(-c3n[nH]c4ncc(-c5ccc6c(c5)CC[C@@](C)(N5CCC[C@H]5C)CC6)cc34)cc2)c(C)n1]

The title compound was prepared in a similar manner to example 2 from the appropriate starting materials. $^1$H NMR (400 MHz, Chloroform-d) δ 13.21 (bs, 1H), 8.91 (d, J=2.0 Hz, 1H), 8.50 (d, J=2.1 Hz, 1H), 8.42-8.36 (m, 1H), 8.16-8.08 (m, 2H), 7.78-7.70 (m, 2H), 7.35 (dq, J=4.0, 2.0 Hz, 2H), 7.20 (d, J=8.3 Hz, 1H), 3.25 (bs, 4H), 2.94 (bs, 1H), 2.67 (d, J=0.7 Hz, 4H), 2.64-2.45 (m, 5H), 1.90 (dt, J=20.4, 11.8 Hz, 3H), 1.74 (d, J=6.1 Hz, 2H), 1.47 (bs, 3H), 1.06 (d, J=33.1 Hz, 5H). ESI MS [M+H]$^+$ for $C_{35}H_{39}N_6$, calcd. 543.3, found 543.3.

Example 189: 3,5-Dimethyl-2-(4-{5-[(7S)-7-(pyrrolidin-1-yl)-6,7,8,9-tetrahydro-5H-benzo[7]annulen-2-yl]-1H-pyrazolo[3,4-b]pyridin-3-yl}phenyl)pyrazine

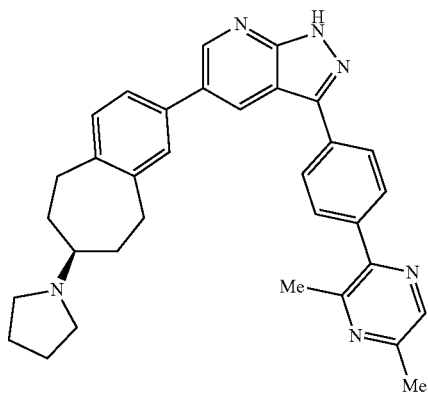 [SMILES: Cc1cnc(-c2ccc(-c3n[nH]c4ncc(-c5ccc6c(c5)CC[C@@H](N5CCCC5)CC6)cc34)cc2)c(C)n1]

The title compound was prepared in a similar manner to example 2 from the appropriate starting materials. $^1$H NMR (400 MHz, Chloroform-d) δ 13.08 (bs, 1H), 8.89 (d, J=2.0 Hz, 1H), 8.51 (d, J=2.1 Hz, 1H), 8.41-8.36 (m, 1H), 8.16-8.07 (m, 2H), 7.78-7.70 (m, 2H), 7.42-7.34 (m, 2H), 7.22 (d, J=8.3 Hz, 1H), 3.11-2.94 (m, 2H), 2.75 (q, J=12.9 Hz, 7H), 2.67 (d, J=0.6 Hz, 3H), 2.59 (s, 3H), 2.17 (d, J=19.6 Hz, 2H), 1.84 (s, 4H), 1.64 (t, J=11.3 Hz, 2H). ESI MS [M+H]$^+$ for $C_{33}H_{35}N_6$, calcd. 515.3, found 515.3.

Example 190: 6-[(7S)-2-{3-[4-(3,5-Dimethylpyrazin-2-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

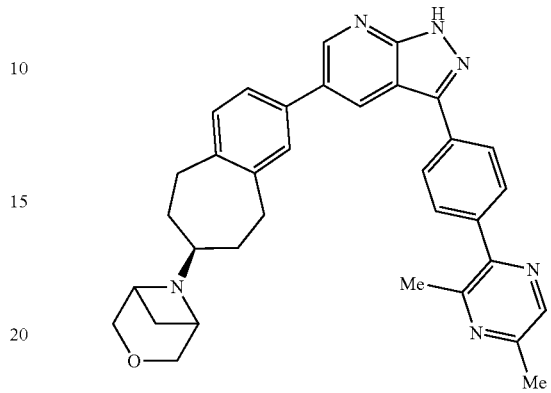

The title compound was prepared in a similar manner to example 2 from the appropriate starting materials. $^1$H NMR (400 MHz, Chloroform-d) δ 12.57 (s, 1H), 8.85 (d, J=2.0 Hz, 1H), 8.51 (d, J=2.0 Hz, 1H), 8.38 (t, J=0.7 Hz, 1H), 8.15-8.07 (m, 2H), 7.78-7.70 (m, 2H), 7.38 (d, J=6.6 Hz, 2H), 7.24-7.21 (m, 1H), 4.31 (d, J=10.7 Hz, 2H), 3.74 (d, J=10.7 Hz, 2H), 3.67 (d, J=6.1 Hz, 2H), 3.32-3.22 (m, 1H), 3.05-2.91 (m, 2H), 2.85 (q, J=12.7, 12.3 Hz, 2H), 2.67 (d, J=0.6 Hz, 3H), 2.59 (s, 4H), 2.01-1.90 (m, 2H), 1.85 (d, J=8.3 Hz, 1H), 1.38 (q, J=11.4 Hz, 2H). ESI MS [M+H]$^+$ for $C_{34}H_{35}N_6O$, calcd. 543.3, found 543.3.

Example 191: 6-[(7S)-2-{3-[4-(3,6-Dimethylpyridin-2-yl)-3-methylphenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

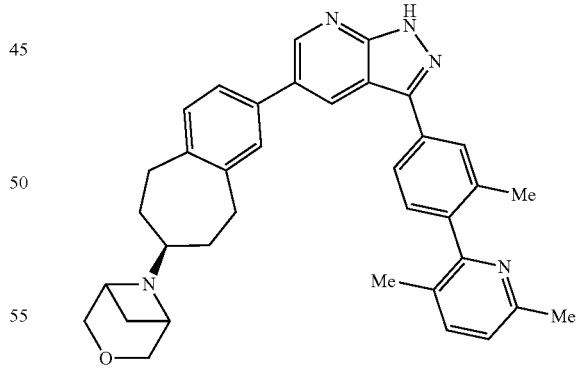

The title compound was prepared in a similar manner to example 1 from the appropriate starting materials. $^1$H NMR (400 MHz, Chloroform-d) δ 11.08-11.03 (m, 1H), 8.59 (d, J=2.0 Hz, 1H), 8.38 (d, J=2.0 Hz, 1H), 7.56-7.44 (m, 3H), 7.42-7.28 (m, 3H), 7.22 (dd, J=15.2, 8.0 Hz, 2H), 7.07 (d, J=7.8 Hz, 1H), 4.30 (d, J=10.8 Hz, 2H), 3.74 (d, J=10.8 Hz, 2H), 3.70 (d, J=6.0 Hz, 2H), 3.31-3.21 (m, 1H), 2.97 (td, J=14.0, 8.5 Hz, 2H), 2.83 (q, J=14.0, 13.5 Hz, 2H), 2.61 (s, 4H), 2.12 (d, J=6.4 Hz, 6H), 1.93 (s, 2H), 1.85 (d, J=8.3 Hz, 1H), 1.38 (p, J=10.6 Hz, 2H). ESI MS [M+H]+ for C37H39N4O, calcd. 555.3, found 555.3.

Example 192: 2-[5-Methyl-6-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-2-yl]propan-2-ol

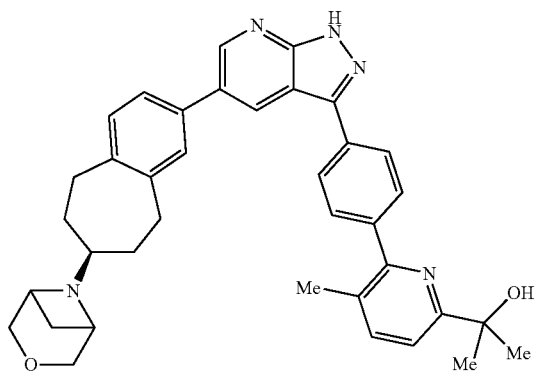 [SMILES: Cc1ccc(C(C)(C)O)nc1-c1ccc(-c2n[nH]c3ncc(-c4ccc5c(c4)CC[C@@H](N4C6COCC4C6)CC5)cc23)cc1]

The title compound was prepared in a similar manner to example 2 from the appropriate starting materials. 1H NMR (400 MHz, Chloroform-d) δ 12.83 (s, 1H), 8.86 (d, J=2.0 Hz, 1H), 8.53 (d, J=2.0 Hz, 1H), 8.15-8.07 (m, 2H), 7.79-7.71 (m, 2H), 7.66-7.58 (m, 1H), 7.39 (d, J=6.7 Hz, 2H), 7.23 (dd, J=9.2, 8.1 Hz, 2H), 5.50 (s, 1H), 4.32 (d, J=10.8 Hz, 2H), 3.81-3.70 (m, 4H), 3.34-3.24 (m, 1H), 2.97 (td, J=14.0, 8.5 Hz, 2H), 2.85 (q, J=12.8, 12.2 Hz, 2H), 2.67 (d, J=7.9 Hz, 1H), 2.43 (d, J=0.6 Hz, 3H), 1.97 (d, J=11.6 Hz, 2H), 1.87 (d, J=8.4 Hz, 1H), 1.56 (s, 6H), 1.43 (d, J=11.8 Hz, 2H). ESI MS [M+H]+ for C37H40N5O2, calcd. 586.3, found 586.3.

Example 193: 6-[(7S)-2-{3-[5-(3-Methylpyridin-2-yl)pyrazin-2-yl]-1H-pyrazolo[3,4-b]pyridin-5-yl}-6,7,8,9-tetrahydro-5H-benzo[7]annulen-7-yl]-3-oxa-6-azabicyclo[3.1.1]heptane

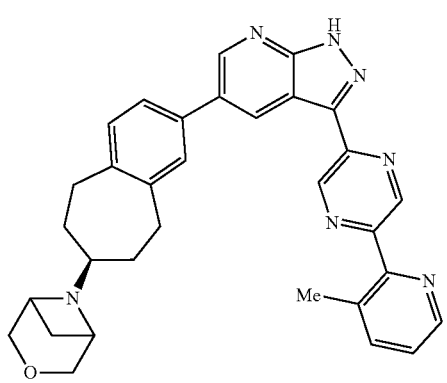 [SMILES: Cc1cccnc1-c1cnc(-c2n[nH]c3ncc(-c4ccc5c(c4)CC[C@@H](N4C6COCC4C6)CC5)cc23)cn1]

The title compound (citrate salt) was prepared in a similar manner to example 17 from the appropriate starting materials. 1H NMR (400 MHz, DMSO-d6) δ 9.43 (d, J=1.5 Hz, 1H), 9.26 (d, J=1.5 Hz, 1H), 8.95 (d, J=2.2 Hz, 1H), 8.91 (d, J=2.2 Hz, 1H), 8.57 (ddd, J=4.7, 1.7, 0.6 Hz, 1H), 7.80 (ddd, J=7.8, 1.7, 0.8 Hz, 1H), 7.59 (s, 1H), 7.52 (d, J=7.7 Hz, 1H), 7.42 (dd, J=7.7, 4.7 Hz, 1H), 7.30 (d, J=7.8 Hz, 1H), 4.26 (bs, 3H), 3.87 (bs, 2H), 2.98-2.82 (m, 4H), 2.56 (d, J=3.1 Hz, 4H), 2.52 (s, 2H), 2.09-1.93 (m, 3H), 1.21-1.10 (m, 2H). ESI MS [M+H]+ for C32H32N7O, calcd. 530.3, found 530.3.

Example 194: 6-[(7S)-2-[3-(4-{2H,3H-[1,4]Dioxino[2,3-c]pyridin-5-yl}phenyl)-1H-pyrrolo[2,3-b]pyridin-5-yl]-6,7,8,9-tetrahydro-5H-benzo[7]annulen-7-yl]-3-oxa-6-azabicyclo[3.1.1]heptane

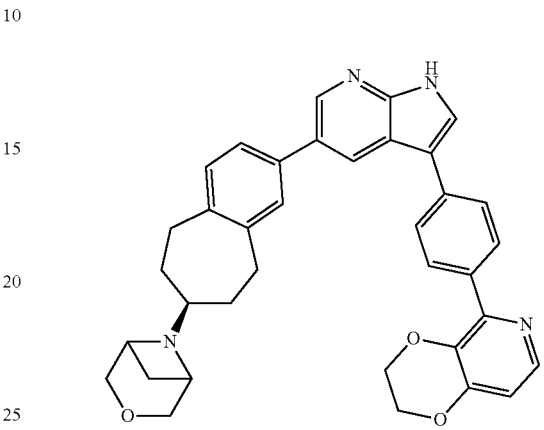

The title compound was prepared in a similar manner to example 1 from the appropriate starting materials. 1H NMR (400 MHz, Chloroform-d) δ 10.17 (d, J=2.4 Hz, 1H), 8.60 (d, J=2.0 Hz, 1H), 8.42 (dd, J=2.1, 0.5 Hz, 1H), 8.14 (d, J=5.3 Hz, 1H), 8.04-7.97 (m, 2H), 7.77-7.69 (m, 2H), 7.59 (d, J=2.4 Hz, 1H), 7.38 (dq, J=3.8, 2.0 Hz, 2H), 7.20 (d, J=8.2 Hz, 1H), 6.79 (d, J=5.3 Hz, 1H), 4.41-4.33 (m, 4H), 4.32-4.25 (m, 2H), 3.75-3.67 (m, 2H), 3.66-3.61 (m, 2H), 3.28-3.19 (m, 1H), 3.03-2.90 (m, 2H), 2.89-2.77 (m, 2H), 2.58-2.51 (m, 1H), 1.97-1.88 (m, 2H), 1.85-1.78 (m, 1H), 1.38-1.27 (m, 2H). ESI MS [M+H]+ for C36H35N4O3, calcd. 571.3, found 571.2.

Example 195: 6-[(7S)-2-{3-[4-(4,6-Dimethylpyridin-3-yl)phenyl]-1H-pyrazolo[3,4-b]pyridin-5-yl}-6,7,8,9-tetrahydro-5H-benzo[7]annulen-7-yl]-3-oxa-6-azabicyclo[3.1.1]heptane

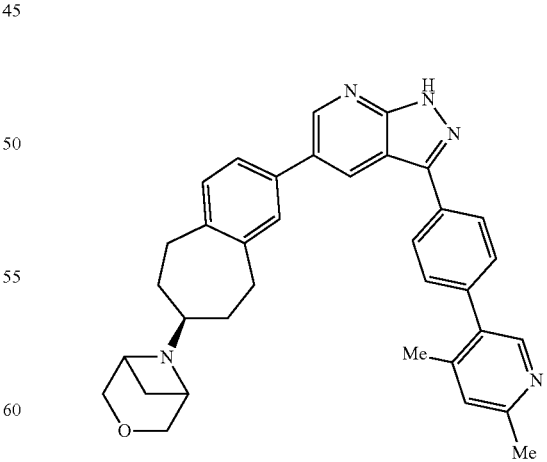

The title compound was prepared in a similar manner to example 2 from the appropriate starting materials. 1H NMR (400 MHz, Chloroform-d) δ 13.85 (s, 1H), 8.83 (d, J=2.0 Hz, 1H), 8.49 (d, J=2.0 Hz, 1H), 8.39 (s, 1H), 8.10-8.02 (m, 2H), 7.48-7.40 (m, 2H), 7.35 (dq, J=4.2, 2.0 Hz, 2H), 7.19 (d, J=8.3 Hz, 1H), 7.09-7.03 (m, 1H), 4.34-4.24 (m, 2H), 3.73 (dt, J=10.6, 1.6 Hz, 2H), 3.68 (d, J=6.1 Hz, 2H), 3.26 (td, J=9.9, 4.4 Hz, 1H), 3.01-2.74 (m, 4H), 2.57 (s, 4H), 2.28 (d, J=0.7 Hz, 3H), 2.00-1.89 (m, 2H), 1.84 (d, J=8.3 Hz, 1H), 1.37 (q, J=11.4 Hz, 2H). ESI MS [M+H]$^+$ for $C_{35}H_{36}N_5O$, calcd. 542.3, found 542.3.

Example 196: 6-[(7S)-2-{3-[4-(4,6-Dimethylpyridin-3-yl)phenyl]-1H-pyrrolo[2,3-b]pyridin-5-yl}-6,7,8,9-tetrahydro-5H-benzo[7]annulen-7-yl]-3-oxa-6-azabicyclo[3.1.1]heptane

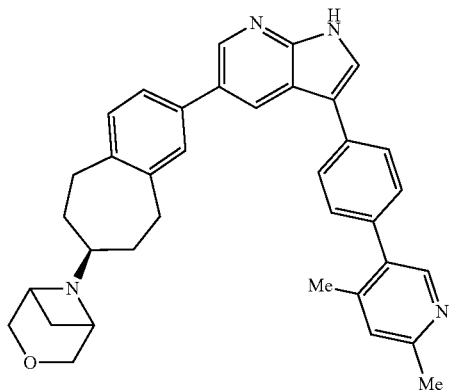 [SMILES: Cc1cc(C)c(-c2ccc(-c3c[nH]c4ncc(-c5ccc6c(c5)CC[C@@H](N5C7COCC5C7)CC6)cc34)cc2)cn1]

The title compound was prepared in a similar manner to example 1 from the appropriate starting materials. $^1$H NMR (400 MHz, Chloroform-d) δ 10.88-10.82 (m, 1H), 8.62 (d, J=2.1 Hz, 1H), 8.43 (d, J=2.1 Hz, 1H), 8.39 (s, 1H), 7.79-7.71 (m, 2H), 7.62 (d, J=2.4 Hz, 1H), 7.45-7.35 (m, 4H), 7.20 (d, J=8.3 Hz, 1H), 7.10-7.05 (m, 1H), 4.29 (d, J=10.6 Hz, 2H), 3.72 (d, J=10.7 Hz, 2H), 3.63 (d, J=6.1 Hz, 2H), 3.29-3.19 (m, 1H), 2.97 (td, J=15.5, 7.8 Hz, 2H), 2.84 (q, J=13.6, 13.1 Hz, 2H), 2.56 (s, 4H), 2.32 (d, J=0.6 Hz, 3H), 1.94 (d, J=8.7 Hz, 2H), 1.83 (d, J=8.2 Hz, 1H), 1.31 (q, J=10.6, 10.1 Hz, 2H). ESI MS [M+H]$^+$ for $C_{36}H_{37}N_4O$, calcd. 541.3, found 541.3.

Example 197: 3-Methyl-2-(6-{5-[(7S)-7-{3-oxa-6-azabicyclo[3.1.1]heptan-6-yl}-6,7,8,9-tetrahydro-5H-benzo[7]annulen-2-yl]-1H-pyrrolo[2,3-b]pyridin-3-yl}pyridin-3-yl)benzonitrile

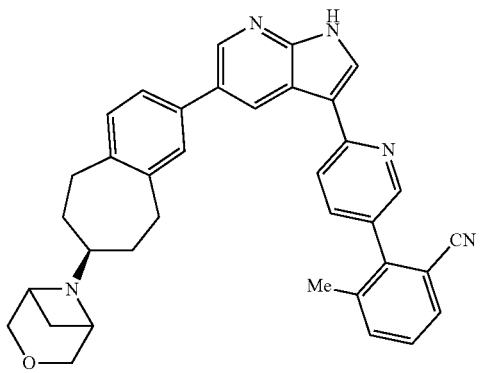 [SMILES: Cc1cccc(C#N)c1-c1ccc(-c2c[nH]c3ncc(-c4ccc5c(c4)CC[C@@H](N4C6COCC4C6)CC5)cc23)nc1]

The title compound was prepared in a similar manner to example 9 from the appropriate starting materials. $^1$H NMR (400 MHz, Chloroform-d) δ 11.46 (s, 1H), 8.96 (d, J=2.1 Hz, 1H), 8.62 (d, J=2.1 Hz, 1H), 8.60 (dd, J=2.4, 0.9 Hz, 1H), 8.04 (d, J=2.3 Hz, 1H), 7.80 (dd, J=8.2, 0.9 Hz, 1H), 7.67 (dd, J=8.2, 2.3 Hz, 1H), 7.62 (ddd, J=7.7, 1.4, 0.7 Hz, 1H), 7.52 (ddd, J=7.8, 1.4, 0.7 Hz, 1H), 7.47-7.41 (m, 2H), 7.38 (t, J=7.8 Hz, 1H), 7.23-7.19 (m, 1H), 4.30 (d, J=10.6 Hz, 2H), 3.71 (d, J=10.8 Hz, 2H), 3.64 (d, J=6.1 Hz, 2H), 3.29-3.19 (m, 1H), 3.04-2.93 (m, 2H), 2.90-2.77 (m, 2H), 2.54 (td, J=7.6, 7.1, 3.6 Hz, 1H), 2.25 (d, J=0.8 Hz, 3H), 2.02-1.91 (m, 2H), 1.83 (d, J=8.2 Hz, 1H), 1.40-1.21 (m, 2H). ESI MS [M+H]$^+$ for $C_{36}H_{34}N_5O$, calcd. 552.3, found 552.3.

Example 198: 1-[6-Methyl-2-(4-{5-[(7S)-7-{3-oxa-6-azabicyclo[3.1.1]heptan-6-yl}-6,7,8,9-tetrahydro-5H-benzo[7]annulen-2-yl]-1H-pyrazolo[3,4-b]pyridin-3-yl}phenyl)pyridin-3-yl]pyrrolidin-2-one

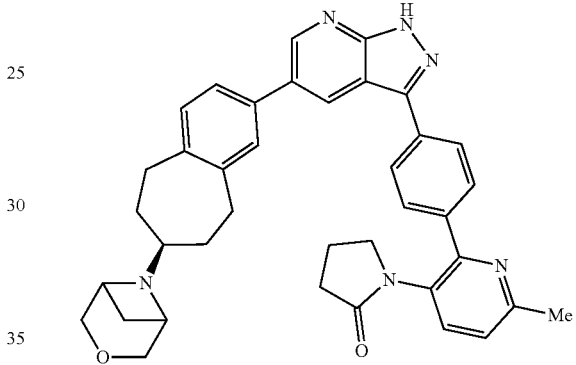

The title compound was prepared in a similar manner to example 2 from the appropriate starting materials. $^1$H NMR (400 MHz, Chloroform-d) δ 12.35 (s, 1H), 8.86 (d, J=2.0 Hz, 1H), 8.50 (d, J=2.0 Hz, 1H), 8.12-8.04 (m, 2H), 7.79-7.71 (m, 2H), 7.59 (d, J=8.1 Hz, 1H), 7.38 (dq, J=3.1, 2.0 Hz, 2H), 7.23 (dd, J=9.7, 8.2 Hz, 2H), 4.31 (d, J=10.8 Hz, 2H), 3.74 (d, J=10.8 Hz, 2H), 3.68 (d, J=6.1 Hz, 2H), 3.33-3.25 (m, 3H), 3.04-2.94 (m, 2H), 2.86 (q, J=13.7 Hz, 2H), 2.63 (s, 3H), 2.58 (q, J=6.8 Hz, 1H), 2.48 (t, J=8.0 Hz, 2H), 1.96 (p, J=7.6 Hz, 4H), 1.85 (d, J=8.3 Hz, 1H), 1.37 (q, J=11.7 Hz, 2H). ESI MS [M+H]$^+$ for $C_{38}H_{39}N_6O_2$, calcd. 611.3, found 611.3.

Biological Example

Measuring Intracellular Binding of Axl Inhibitors

Axl NanoBRET™ intracellular kinase assay (Promega, N2540) was performed according to manufacturer's recommendation. In brief, HEK-293 cells are transiently transfected with Axl-NanoLuc fusion vector (Promega, NV1071), utilizing Fugene HD transfection reagent (Promega, E2311) a day before experiment following manufacturer's recommendation.

The day of the assay, the cells were collected and resuspended in Opti-MEM media (ThermoFisher, 31985070) at 2e5 cells/mL concentration. Testing compounds were serial diluted and dispensed into a white 384 well polystyrene plate at 200 nL in 100% DMSO. 40 μL of resuspended cells is then added per well for a final condition of 8K cells/well with 0.5% DMSO. After one-hour compound pre-incubation at 37° C. and 5% $CO_2$, cells were further incubated with 0.35 µM K-5 NanoBRET tracer for two-hours at 37° C. and 5% $CO_2$. 20 ml of 3× substrate plus Inhibitor solution was prepared according to kits manual and added to the cells followed by a 30 second pulse centrifugation spin. The plate was then immediately read utilizing an Envision (Perkin Elmer) plate reader. The BRET signal is measured by taking the ratio of the emissions reading at 610 nm and 450 nm. Compound binding is based on the decrease BRET signal caused by the displacement of the K-5 tracer. DMSO treated activity was used as neutral control and normalized to 100% activity, and CEP-40783 control compound at 20 µM which reaches 100% inhibition was used as positive control and normalized to 0% activity. ICso value of compounds was determined by 4-parameter non-linear regression fitting of percent activity in GraphPad Prism software. Values are reported in Table 1 (Cell Binding).

Measurement of Biochemical Compound Potency of Axl Inhibitors

Purified recombinant human AXL, TYRO3 and MER proteins were purchased from Invitrogen™. 10 nM AXL, 2 nM TYRO3 or MER were incubated with varying concentrations of compounds in 50 mM HEPES, pH 7.4, 10 mM $MgCl_2$, 0.01% BSA, 1 mM DTT and 2% DMSO in a total volume of 20 µl in a 384-well microplate (Corning™ #3640) at RT for 1 h. The AXL, TYRO3 and MER enzymatic reaction was initiated by transferring 10 µl of enzyme and compound mixture into 10 µl of 1.6 µM TK Substrate-biotin (HTRF® KinEASE-TK kit, Cisbio) and 1400 µM ATP pre-incubated in 50 mM HEPES, pH 7.4, 10 mM $MgCl_2$, 0.01% BSA, 1 mM DTT in a 384-well microplate (Corning™ #3640) at RT, giving the final reaction conditions: 5 nM AXL, 1 nM TYRO3 or MER, 800 nM TK Substrate-biotin and 700 µM ATP in 50 mM HEPES, pH 7.4, 10 mM $MgCl_2$, 0.01% BSA, 1 mM DTT and 1% DMSO with varying concentrations of compounds. Following 2 h incubation at RT, the AXL, TYRO3 and MER enzymatic reaction was stopped by transfer of 10 µl of reaction into 10 µl of detection mix (400 nM Streptavidin-XL665, 200-fold dilution TK Antibody-Cryptate and detection buffer, HTRF® KinEASE-TK kit, Cisbio) in a white 384-well microplate (Perkin Elmer, OptiPlate 384). After 1 h incubation at RT, the plate was put into a plate reader (Evision) to read at 665/620 nm (acceptor/donor) for HTRF. The value of the DMSO blank (MIN inhibition=100% activity) was used as a negative control. The positive control was established by adding 5 µl of enzyme and DMSO mixture into 10 µl of detection mix followed by addition of 5 µl of TK Substrate-biotin and ATP mixture (MAX inhibition=0% activity). To calculate the percent activity, Equation 1 was used. $Ratio_{665/620}$ is the value at a given compound concentration:

$$\% \text{ Activity} = \frac{Ratio_{665/620} - MAX}{MIN - MAX} \times 100 \quad (1)$$

The concentration of compound that resulted in 50% loss of the enzyme activity ($IC_{50}$) was calculated by GraphPad Prism using Equation 2 where N is the Hill coefficient:

$$\% \text{ Activity} = \text{Bottom} + \frac{\text{Top} - \text{Bottom}}{1 + \left(\frac{[I]}{IC_{50}}\right)^N} \quad (2)$$

Values are reported in Table 1 (Biochemical Potency).

Measurement of Axl Phosphorylation Inhibition

The dose-response assays were performed in S-Bio PrimeSurface® 3D culture: Ultra-low Attachment Plates: 384 well, U bottom (#MS-9384UZ) containing 400 nL of 22 serial 2-fold compound dilutions using Bravo and Echo. ELISA assay was performed on Pierce™ streptavidin coated high capacity 384-well white plates (Thermofisher Cat #15505). The plates were coated overnight at 4° C. with 50 µl/well of biotinlyated phospho-tyrosine mouse mAb (Cell Signaling Technology, 9417s).

HEK293T cells were grown in DMEM containing 10% FBS, 1% Pen/Strep, 1% G-Max. A day before the assay, cells were transiently transfected with 6.8 µg of NanoLuc-tagged AXL plasmid DNA and 8 µg of carrier DNA using FuGENE® HD Transfection Reagent (Promega) according to manufacturer's instructions. On the day of the assay, transfected cells were harvested and resuspended in OptiMEM. 70,000 cells/well were added to the compounds containing assay plates. After a gentle mix and a short spin, the plates were incubated at 37° C. After 1 h, the cells were lysed followed by a brief centrifugation and 30 min of shaking at 300 rpm. Meanwhile, the antibody coated plates were brought to room temperature and then were washed ten times in PBS with 0.05% Tween 20 (ELISA-wash buffer). 50 µl/well of cell lysate was transferred to the ELISA plates and shaken for 2 hours. After washing again with the ELISA wash buffer, the samples were diluted with 25 µl of PBS. The captured NanoLuc tagged p-AXL was detected using Nano-Glo® Luciferase Assay System (Promega) and manufacturer's instruction. The luminescence signal was measured using Envision plate reader. IC50 values were determined by fitting the data to a standard 4-parameter logistic equation. Values are reported in Table 1 (p-AXL inhibition).

TABLE 1

Biochemical and cellular potency, and inhibition of Axl phosphorylation of specific examples ($IC_{50}$: + means > 1 µM, ++ means 100 nM to 1 µM, +++ means < 100 nM)

| | Cell Binding | p-AXL Inhibition | Biochemical Potency | | |
|---|---|---|---|---|---|
| Ex. | AXL | p-AXL (media) | AXL | MER | TYRO3 |
| 1 | +++ | +++ | +++ | +++ | +++ |
| 2 | +++ | +++ | +++ | ++ | +++ |
| 3 | | +++ | +++ | +++ | +++ |
| 4 | | ++ | +++ | ++ | ++ |
| 5 | | +++ | +++ | ++ | +++ |
| 6 | | +++ | +++ | ++ | ++ |
| 7 | | +++ | +++ | ++ | +++ |
| 8 | | ++ | +++ | | |
| 9 | | +++ | +++ | ++ | |
| 10 | +++ | +++ | +++ | ++ | +++ |

TABLE 1-continued

Biochemical and cellular potency, and inhibition of Ax1 phosphorylation of specific examples (IC$_{50}$: + means > 1 μM, ++ means 100 nM to 1 μM, +++ means < 100 nM)

| | Cell Binding | p-AXL Inhibition | Biochemical Potency | | |
|---|---|---|---|---|---|
| Ex. | AXL | p-AXL (media) | AXL | MER | TYRO3 |
| 11 | ++ | | +++ | + | + |
| 12 | +++ | +++ | +++ | ++ | ++ |
| 13 | +++ | ++ | +++ | + | + |
| 14 | | +++ | +++ | ++ | +++ |
| 15 | | ++ | +++ | | |
| 16 | | +++ | +++ | | |
| 17 | | +++ | +++ | ++ | |
| 18 | | +++ | +++ | | |
| 19 | | ++ | +++ | | |
| 20 | | +++ | +++ | | |
| 21 | | +++ | +++ | ++ | +++ |
| 22 | | +++ | +++ | +++ | +++ |
| 23 | | +++ | +++ | ++ | +++ |
| 24 | | ++ | +++ | | |
| 25 | | +++ | +++ | | |
| 26 | | +++ | +++ | ++ | ++ |
| 27 | | +++ | +++ | | |
| 28 | | ++ | +++ | ++ | +++ |
| 29 | | ++ | +++ | ++ | ++ |
| 30 | | ++ | + | + | +++ |
| 31 | | ++ | +++ | + | + |
| 32 | | ++ | +++ | ++ | ++ |
| 33 | | ++ | +++ | ++ | ++ |
| 34 | | +++ | +++ | | |
| 35 | | +++ | +++ | | |
| 36 | | + | +++ | | |
| 37 | | +++ | +++ | | |
| 38 | | +++ | +++ | | |
| 39 | | +++ | +++ | | |
| 40 | ++ | | +++ | ++ | ++ |
| 41 | ++ | ++ | +++ | ++ | + |
| 42 | ++ | | +++ | ++ | ++ |
| 43 | ++ | | +++ | ++ | ++ |
| 44 | +++ | ++ | +++ | ++ | ++ |
| 45 | +++ | ++ | +++ | + | + |
| 46 | +++ | +++ | +++ | ++ | ++ |
| 47 | +++ | +++ | +++ | +++ | +++ |
| 48 | +++ | +++ | +++ | ++ | ++ |
| 49 | +++ | +++ | +++ | +++ | +++ |
| 50 | | +++ | +++ | ++ | ++ |
| 51 | | +++ | +++ | +++ | +++ |
| 52 | | +++ | +++ | ++ | ++ |
| 53 | | +++ | +++ | ++ | ++ |
| 54 | | +++ | +++ | + | ++ |
| 55 | | +++ | +++ | + | |
| 56 | | +++ | +++ | ++ | ++ |
| 57 | | +++ | +++ | ++ | ++ |
| 58 | | +++ | +++ | ++ | ++ |
| 59 | | ++ | +++ | ++ | ++ |
| 60 | | ++ | +++ | | |
| 61 | | +++ | +++ | | |
| 62 | | +++ | +++ | | |
| 63 | | +++ | +++ | | |
| 64 | | +++ | +++ | | |
| 65 | | +++ | +++ | | |
| 66 | | +++ | +++ | | |
| 67 | | ++ | +++ | | |
| 68 | | +++ | +++ | | |
| 69 | | ++ | +++ | | |
| 70 | | +++ | +++ | | |
| 71 | | +++ | +++ | | |
| 72 | | ++ | +++ | | |
| 73 | | ++ | +++ | | |
| 74 | | ++ | +++ | | |
| 75 | | +++ | +++ | | |
| 76 | | +++ | +++ | | |
| 77 | | +++ | +++ | ++ | +++ |
| 78 | | +++ | +++ | +++ | +++ |
| 79 | | +++ | +++ | ++ | |
| 80 | | +++ | +++ | +++ | ++ |
| 81 | | +++ | +++ | | |
| 82 | | +++ | +++ | | |
| 83 | | +++ | +++ | | |

TABLE 1-continued

Biochemical and cellular potency, and inhibition of Axl phosphorylation of specific examples (IC$_{50}$: + means > 1 µM, ++ means 100 nM to 1 µM, +++ means < 100 nM)

| | Cell Binding | p-AXL Inhibition | Biochemical Potency | | |
|---|---|---|---|---|---|
| Ex. | AXL | p-AXL (media) | AXL | MER | TYRO3 |
| 84 | | + | +++ | | |
| 85 | | +++ | +++ | ++ | ++ |
| 86 | | ++ | +++ | ++ | ++ |
| 87 | | ++ | +++ | ++ | ++ |
| 88 | | ++ | +++ | ++ | ++ |
| 89 | | ++ | +++ | ++ | ++ |
| 90 | +++ | +++ | +++ | ++ | ++ |
| 91 | +++ | ++ | +++ | ++ | ++ |
| 92 | +++ | +++ | +++ | ++ | +++ |
| 93 | +++ | ++ | +++ | ++ | ++ |
| 94 | +++ | ++ | +++ | + | + |
| 95 | +++ | +++ | +++ | +++ | +++ |
| 96 | | +++ | +++ | ++ | +++ |
| 97 | | + | +++ | + | + |
| 98 | | ++ | +++ | + | + |
| 99 | | +++ | +++ | ++ | ++ |
| 100 | | +++ | +++ | + | ++ |
| 101 | | +++ | +++ | ++ | +++ |
| 102 | | +++ | +++ | ++ | +++ |
| 103 | | + | +++ | + | + |
| 104 | | +++ | +++ | ++ | ++ |
| 105 | | +++ | +++ | +++ | +++ |
| 106 | | +++ | +++ | | |
| 107 | | +++ | +++ | | |
| 108 | | +++ | +++ | | |
| 109 | +++ | +++ | +++ | ++ | ++ |
| 110 | +++ | +++ | +++ | ++ | +++ |
| 111 | +++ | +++ | +++ | +++ | +++ |
| 112 | +++ | +++ | +++ | +++ | +++ |
| 113 | | +++ | +++ | ++ | ++ |
| 114 | | +++ | +++ | ++ | ++ |
| 115 | | ++ | +++ | ++ | + |
| 116 | | ++ | +++ | ++ | ++ |
| 117 | | ++ | +++ | + | ++ |
| 118 | | +++ | +++ | ++ | +++ |
| 119 | | +++ | +++ | +++ | +++ |
| 120 | | +++ | +++ | ++ | +++ |
| 121 | | +++ | +++ | +++ | +++ |
| 122 | | +++ | +++ | ++ | +++ |
| 123 | | +++ | +++ | +++ | +++ |
| 124 | | +++ | +++ | +++ | +++ |
| 125 | | +++ | +++ | +++ | +++ |
| 126 | | ++ | +++ | ++ | |
| 127 | | +++ | +++ | ++ | +++ |
| 128 | | +++ | +++ | ++ | +++ |
| 129 | | +++ | +++ | +++ | +++ |
| 130 | | +++ | +++ | +++ | +++ |
| 131 | | ++ | +++ | +++ | +++ |
| 132 | | +++ | +++ | +++ | +++ |
| 133 | | +++ | +++ | | |
| 134 | | +++ | +++ | | |
| 135 | | +++ | +++ | | |
| 136 | | +++ | +++ | | |
| 137 | | +++ | +++ | | |
| 138 | | +++ | +++ | | |
| 139 | | +++ | +++ | | |
| 140 | | +++ | +++ | | |
| 141 | | +++ | +++ | | |
| 142 | | +++ | +++ | | |
| 143 | | ++ | +++ | | |
| 144 | | +++ | +++ | | |
| 145 | | ++ | +++ | | |
| 146 | | ++ | +++ | | |
| 147 | | +++ | +++ | | |
| 148 | | ++ | +++ | | |
| 149 | | +++ | +++ | | |
| 150 | | ++ | +++ | | |
| 151 | | +++ | +++ | | |
| 152 | | +++ | +++ | | |
| 153 | | +++ | +++ | | |
| 154 | +++ | +++ | +++ | ++ | ++ |
| 155 | +++ | ++ | +++ | + | ++ |
| 156 | +++ | ++ | +++ | ++ | ++ |

TABLE 1-continued

Biochemical and cellular potency, and inhibition of Axl phosphorylation of specific examples (IC$_{50}$: + means > 1 µM, ++ means 100 nM to 1 µM, +++ means < 100 nM)

| | Cell Binding | p-AXL Inhibition | Biochemical Potency | | |
|---|---|---|---|---|---|
| Ex. | AXL | p-AXL (media) | AXL | MER | TYRO3 |
| 157 | ++ | | +++ | + | + |
| 158 | ++ | ++ | +++ | + | + |
| 159 | ++ | ++ | +++ | ++ | ++ |
| 160 | ++ | | +++ | ++ | ++ |
| 161 | ++ | | +++ | ++ | ++ |
| 162 | + | | +++ | + | + |
| 163 | +++ | +++ | +++ | +++ | +++ |
| 164 | +++ | +++ | +++ | ++ | +++ |
| 165 | +++ | +++ | +++ | ++ | +++ |
| 166 | +++ | +++ | +++ | ++ | +++ |
| 167 | +++ | +++ | +++ | ++ | +++ |
| 168 | +++ | ++ | +++ | ++ | ++ |
| 169 | +++ | +++ | +++ | +++ | +++ |
| 170 | +++ | ++ | +++ | ++ | ++ |
| 171 | +++ | +++ | +++ | ++ | ++ |
| 172 | +++ | +++ | +++ | +++ | +++ |
| 173 | +++ | +++ | +++ | +++ | +++ |
| 174 | +++ | +++ | +++ | +++ | +++ |
| 175 | +++ | +++ | +++ | ++ | ++ |
| 176 | +++ | +++ | +++ | +++ | +++ |
| 177 | | +++ | +++ | ++ | ++ |
| 178 | | +++ | +++ | ++ | ++ |
| 179 | | ++ | +++ | ++ | ++ |
| 180 | | +++ | +++ | ++ | +++ |
| 181 | | ++ | +++ | ++ | ++ |
| 182 | | +++ | +++ | ++ | +++ |
| 183 | | +++ | +++ | ++ | +++ |
| 184 | | +++ | +++ | | |
| 185 | | ++ | +++ | | |
| 186 | | ++ | +++ | +++ | +++ |
| 187 | | +++ | +++ | ++ | +++ |
| 188 | | +++ | +++ | | |
| 189 | | ++ | +++ | | |
| 190 | | ++ | +++ | | |
| 191 | | +++ | +++ | | |
| 192 | | ++ | +++ | | |
| 193 | | +++ | +++ | | |
| 194 | | +++ | +++ | | |
| 195 | | ++ | +++ | | |
| 196 | | ++ | +++ | | |
| 197 | | ++ | +++ | | |
| 198 | | ++ | +++ | | |

Particular embodiments of this disclosure are described herein, including the best mode known to the inventors for carrying out the disclosure. Upon reading the foregoing description, variations of the disclosed embodiments may become apparent to individuals working in the art, and it is expected that those skilled artisans may employ such variations as appropriate. Accordingly, it is intended that the disclosure be practiced otherwise than as specifically described herein, and that the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

2. A compound having the structure
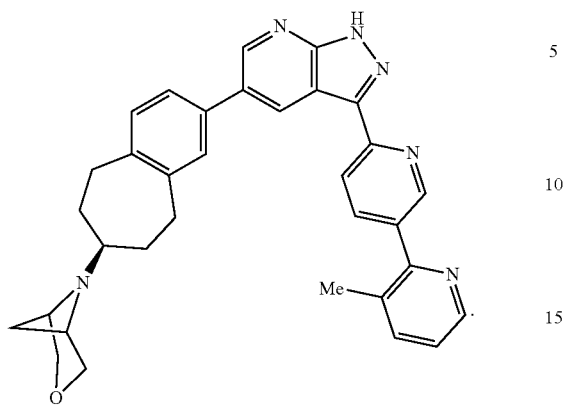

What is claimed is:
1. A compound having the structure

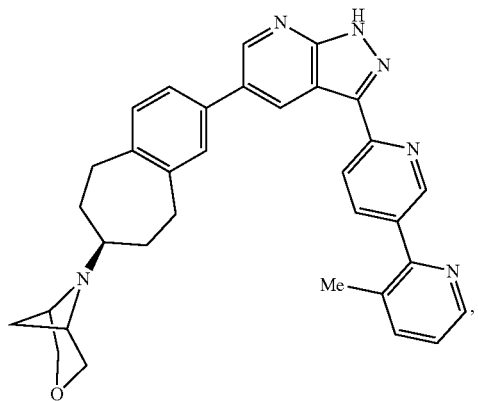 [SMILES: Cc1cccnc1-c1ccc(-c2n[nH]c3ncc(-c4ccc5c(c4)CC[C@@H](N4C6COCC4C6)CC5)cc23)nc1]

or a pharmaceutically acceptable salt thereof.